United States Patent
Boyle et al.

(10) Patent No.: US 12,397,036 B2
(45) Date of Patent: Aug. 26, 2025

(54) PEPTIDE EXCHANGE PROTEIN

(71) Applicant: Cambridge Enterprise Limited, Cambridgeshire (GB)

(72) Inventors: Louise Helen Boyle, Cambridgeshire (GB); Andreas Heinrich Neerincx, Cambridgeshire (GB); Florin Tudor Ilca, Cambridgeshire (GB)

(73) Assignee: Cambridge Enterprise Limited, Cambridgeshire (GB)

( * ) Notice: Subject to any disclaimer, the term of this patent is extended or adjusted under 35 U.S.C. 154(b) by 894 days.

(21) Appl. No.: 16/964,695

(22) PCT Filed: Jan. 25, 2019

(86) PCT No.: PCT/EP2019/051907
§ 371 (c)(1),
(2) Date: Jul. 24, 2020

(87) PCT Pub. No.: WO2019/145509
PCT Pub. Date: Aug. 1, 2019

(65) Prior Publication Data
US 2021/0052695 A1    Feb. 25, 2021

(30) Foreign Application Priority Data

Jan. 26, 2018 (GB) ................................ 1801323
Aug. 23, 2018 (GB) ................................ 1813737

(51) Int. Cl.
| | | |
|---|---|---|
| A61K 38/16 | (2006.01) | |
| A61K 39/00 | (2006.01) | |
| A61K 40/11 | (2025.01) | |
| A61K 40/32 | (2025.01) | |
| A61K 40/42 | (2025.01) | |
| C07K 14/74 | (2006.01) | |
| C12N 5/0783 | (2010.01) | |
| C12N 5/0784 | (2010.01) | |

(52) U.S. Cl.
CPC .......... *A61K 38/16* (2013.01); *A61K 39/0011* (2013.01); *A61K 40/11* (2025.01); *A61K 40/32* (2025.01); *A61K 40/4205* (2025.01); *C07K 14/70539* (2013.01); *C12N 5/0636* (2013.01); *C12N 5/0639* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 2002/0106664 A1* | 8/2002 | Lal | C07K 14/47 435/7.1 |
| 2003/0152921 A1* | 8/2003 | Dumas Milne Edwards | C07K 14/47 435/6.16 |
| 2012/0308561 A1 | 12/2012 | Sooknanan et al. | |
| 2020/0087377 A1* | 3/2020 | Yue | C07K 14/70521 |

FOREIGN PATENT DOCUMENTS

| | | |
|---|---|---|
| JP | 2017509317 A | 4/2017 |
| WO | 1992020356 A1 | 11/1992 |
| WO | 1994005304 A1 | 3/1994 |
| WO | 1994023031 A1 | 10/1994 |
| WO | 1995020974 A1 | 8/1995 |
| WO | 1995023874 A1 | 9/1995 |
| WO | 1996026214 A1 | 8/1996 |
| WO | 2001090357 A1 | 11/2001 |
| WO | 2009095796 A2 | 8/2009 |
| WO | 2015113005 A1 | 7/2015 |
| WO | 2020014097 A1 | 1/2020 |

OTHER PUBLICATIONS

Whisstock et al., 2003, Quart. Rev. Bioph. vol. 3: 307-340 NCBI Sequence NP_060479, 2016, pp. 1-5.*
Rabia et al. 2018, Biochem. Eng. J. vol. 137: 365-374.*
Hall, 1992, J. Immunol. vol. 149: 1605-1612.*
Wang, 2001, J. Biol. Chem. vol. 276: 49213-49220.*
Leone, 2013, J. Nationl. Cancer Inst. vol. 105: 1172-1187.*
Gavilondo, 2000, Biotechniques vol. 29: 128-145.*
Q546GO Accession, 2005, pp. 1-4.*
Altman et al., "Phenotypic Analysis of Antigen-Specific T Lymphocytes," Science, Oct. 4, 1996, vol. 274, pp. 94-96.
Andrade et al., "Prognostic impact of cancer/testis antigen expression in advanced stage multiple myeloma patients," Cancer Immunity, Feb. 1, 2008, vol. 8, p. 2.
Barnstable et al., "Production of Monoclonal Antibodies to Group A Erythrocytes, HLA and Other Human Cell Surface Antigens—New tools for Genetic Analysis," Cell, May 1978, vol. 14, pp. 9-20.
Baskin et al., "Copper-free click chemistry for dynamic in vivo imaging," Proceedings of the National Academy of Sciences of the United States of America, Oct. 23, 2007, vol. 104, No. 43, pp. 16793-16797.
Cancer Research Institute, "Peptide Database," retrieved from the Internet on Jul. 3, 2023, <https://www.cancerresearch.org/peptide-database>.

(Continued)

*Primary Examiner* — Amy E Juedes
(74) *Attorney, Agent, or Firm* — Greenberg Traurig, LLP; Melissa Hunter-Ensor; Nathan Hsu

(57) ABSTRACT

This invention relates to peptide-exchange proteins comprising the luminal domain of TAP-binding protein-related (TAPBPR), which functions as a MHC class I peptide-exchange catalyst when presented to mammalian cells either as a soluble extracellular protein or as a membrane bound cell surface protein. This may be useful in modulating immune responses, including for example loading immunogenic peptide onto tumours or other disease cells to induce their recognition by T cells. Peptide-exchange proteins and methods for their use are provided.

4 Claims, 37 Drawing Sheets

Specification includes a Sequence Listing.

(56) References Cited

OTHER PUBLICATIONS

Chen et al., "Analysis of interactions in a tapasin/class I complex provides a mechanism for peptide selection," The EMBO Journal, 2007, vol. 26, pp. 1681-1690.

Dick et al., "Disulfide Bond Isomerization and the Assembly of MHC Class I-Peptide Complexes," Immunity, Jan. 2002, vol. 16, pp. 87-98.

Gure et al., "Cancer-Testis Genes are Coordinately Expressed and Are Markers of Poor Outcome in Non-Small Cell Lung Cancer," Clinical Cancer Research, Nov. 15, 2005, vol. 11, No. 22, pp. 8055-8062.

Hermann et al., "The Binding of TAPBPR and Tapasin to MHC Class I Is Mutually Exclusive," The Journal of Immunology, 2013, vol. 191, pp. 5743-5750.

Hogan et al., "The Peptide Recognized by HLA-A68.2-restricted, Squamous Cell Carcinoma of the Lung-specific Cytotoxic T Lymphocytes Is Derived from a Mutated Elongation Factor 2 Gene," Cancer Research, Nov. 15, 1998, vol. 58, pp. 5144-5150.

Immune Epitope Database and Analysis Resource (IEDB), retrieved from the Internet on Jul. 3, 2023, <https://www.iedb.org/>.

Kawashima et al., "The Multi-epitope Approach for Immunotherapy for Cancer: Identification of Several CTL Epitopes from Various Tumor-Associated Antigens Expressed on Solid Epithelial Tumors," Human Immunology, 1998, vol. 59, pp. 1-14.

Lauss et al., "Mutational and putative neoantigen load predict clinical benefit of adoptive T cell therapy in melanoma," Nature Communications, 2017, vol. 8, Article No. 1738, pp. 1-11.

Li et al., "Cloning and functional characterization of a subunit of the transporter associated with antigen processing," Proceedings of the National Academy of Sciences of the United States of America, Aug. 1997, vol. 94, pp. 8708-8713.

Li et al., "Simple piggyBac transposon-based mammalian cell expression system for inducible protein production," Proceedings of the National Academy of Sciences of the United States of America, Mar. 26, 2013, vol. 110, No. 13, pp. 5004-5009.

Malarkannan et al., "Presentation of Out-of-Frame Peptide/MHC Class I Complexes by a Novel Translation Initiation Mechanism," Immunity, Jun. 1999, vol. 10, pp. 681-690.

Met HiLab, "Tantigen 2.0: Tumor T-cell Antigen Database," retrieved from the Internet on Jul. 3, 2023, <http://projects.met-hilab.org/tadb/index.php>.

Mittal et al., "New insights into cancer immunoediting and its three component phases—elimination, equilibrium and escape," Current Opinion in Immunology, 2014, vol. 27, pp. 16-25.

Murray et al., "Epitope Tagging of the Human Endoplasmic Reticulum HSP70 Protein, BiP, to Facilitate Analysis of BiP-Substrate Interactions," Analytical Biochemistry, 1995, vol. 229, pp. 170-179.

Napoletano et al., "MAGE-A and NY-ESO-1 expression in cervical cancer: Prognostic factors and effects of chemotherapy," American Journal of Obstetrics and Gynecology, Jan. 2008, vol. 198, pp. 99.e1-99.e7.

Neerincx et al., "TAPBPR bridges UDP-glucose:glycoprotein glucosyltransferase 1 onto MHC class I to provide quality control in the antigen presentation pathway," eLife, Apr. 20, 2017, vol. 6, e23049, pp. 1-25.

Nilsson et al., "Short Cytoplasmic Sequences Serve as Retention Signals for Transmembrane Proteins in the Endoplasmic Reticulum," Cell, Aug. 25, 1989, vol. 58, pp. 707-718.

Olsen et al., "Tantigen: a comprehensive database of tumor T cell antigens," Cancer Immunology, Immunotherapy, 2017, vol. 66, pp. 731-735.

Ortmann et al., "A Critical Role for Tapasin in the Assembly and Function of Multimeric MHC Class I-TAP Complexes," Science, Aug. 29, 1997, vol. 277, pp. 1306-1309.

Pardoll, Drew M., "The blockade of immune checkpoints in cancer immunotherapy," Nature Reviews Cancer, Apr. 2012, vol. 12, pp. 252-264.

Parkhurst et al., "Improved induction of melanoma-reactive CTL with peptides from the melanoma antigen gp100 modified at HLA-A*0201-binding residues," The Journal of Immunology, 1996, vol. 157, pp. 2539-2548.

Perosa et al., "β2-Microglobulin-Free HLA Class I Heavy Chain Epitope Mimicry by Monoclonal Antibody HC-10-Specific Peptide," The Journal of Immunology, 2003, vol. 171, pp. 1918-1926.

Rizvi et al., "Mutational landscape determines sensitivity to PD-1 blockade in non-small cell lung cancer," Science, Apr. 3, 2015, vol. 348, No. 6230, pp. 124-128.

Sharma et al., "Primary, Adaptive, and Acquired Resistance to Cancer Immunotherapy," Cell, Feb. 9, 2017, vol. 168, pp. 707-723.

Sim et al., "Defining the expression hierarchy of latent T-cell epitopes in Epstein-Barr virus infection with TCR-like antibodies," Scientific Reports, Nov. 18, 2013, vol. 3, Article No. 3232, pp. 1-7.

Simpson et al., "Cancer/testis antigens, gametogenesis and cancer," Nature Reviews Cancer, Aug. 2005, vol. 5, pp. 615-625.

Snyder et al., "Genetic Basis for Clinical Response to CTLA-4 Blockade in Melanoma," The New England Journal of Medicine, Dec. 4, 2014, vol. 371, No. 23, pp. 2189-2199.

Stammers et al., "Rapid purification and characterisation of HIV-1 reverse transcriptase and RNaseH engineered to incorporate a C-terminal tripeptide α-tubulin epitope," FEBS Letters, Jun. 1991, vol. 283, No. 2, pp. 298-302.

Terpe, K., "Overview of tag protein fusions: from molecular and biochemical fundamentals to commercial systems," Applied Microbiology and Biotechnology, 2003, vol. 60, pp. 523-533.

Theobald et al., "Targeting p53 as a general tumor antigen," Proceedings of the National Academy of Sciences of the United States of America, Dec. 1995, vol. 92, pp. 11993-11997.

Tinguely et al., "MAGE-C1/CT-7 expression in plasma cell myeloma: Sub-cellular localization impacts on clinical outcome," Cancer Science, Apr. 2008, vol. 99, No. 4, pp. 720-725.

Tiwari et al., "Functional equivalents of interferon-mediated signals needed for induction of an mRNA can be generated by double-stranded RNA and growth factors," The EMBO Journal, 1987, vol. 6, No. 11, pp. 3373-3378.

Valmori et al., "Enhanced Generation of Specific Tumor-Reactive CTL In Vitro by Selected Melan-A/MART-1 Immunodominant Peptide Analogues," The Journal of Immunology, 1998, vol. 160, pp. 1750-1758.

Van Allen et al., "Genomic correlates of response to CTLA-4 blockade in metastatic melanoma," Science, Oct. 9, 2015, vol. 350, No. 6257, pp. 207-211.

Velazquez et al., "Expression of the cancer/testis antigen NY-ESO-1 in primary and metastatic malignant melanoma (MM)—correlation with prognostic factors," Cancer Immunity, Jul. 12, 2007, vol. 7, p. 11.

Vita et al., "The immune epitope database (IEDB) 3.0," Nucleic Acids Research, 2015, vol. 43, pp. D405-D412.

Wearsch et al., "Selective loading of high-affinity peptides onto major histocompatibility complex class I molecules by the tapasin-ERp57 heterodimer," Nature Immunology, Aug. 2007, vol. 8, No. 8, pp. 873-881.

Weekes et al., "Quantitative Temporal Viromics: An Approach to Investigate Host-Pathogen Interaction," Cell, Jun. 5, 2014, vol. 157, pp. 1460-1472.

Wills et al., "The Human Cytotoxic T-Lymphocyte (CTL) Response to Cytomegalovirus Is Dominated by Structural Protein pp65: Frequency, Specificity, and T-Cell Receptor Usage of pp65-Specific CTL," Journal of Virology, Nov. 1996, vol. 70, No. 11, pp. 7569-7579.

Zuo et al., "Institute collection and analysis of Nanobodies (iCAN): a comprehensive database and analysis platform for nanobodies," BMC Genomics, 2017, vol. 18, Article No. 797, pp. 1-5.

International Search Report in International Application No. PCT/EP2019/051907 mailed Apr. 15, 2019.

Jiansheng Jiang et al: "Crystal structure of a TAPBPR-MHC I complex reveals the mechanism of peptide editing in antigen presentation", Science, vol. 358, No. 6366, Nov. 24, 2017 (Nov. 24, 2017), pp. 1064-1068.

Jiansheng Jiang et al: "Supplementary Materials.—Crystal structure of a TAPBPR-MHC I complex reveals the mechanism of peptide

(56) References Cited

OTHER PUBLICATIONS editing in antigen presentation", Science, vol. 358, No. 6366, Oct. 12, 2017 (Oct. 12, 2017), pp. 1064-1068.
Database UniParc [Online] Oct. 13, 2017 (Oct. 13, 2017), XP002789643, retrieved from UNIPROT Database accession No. UPI000BEE8220 abstract; sequence.
Database UniParc [Online] Oct. 13, 2017 (Oct. 13, 2017), XP002789644, retrieved from UNIPROT Database accession No. UPI000BEE81F3 sequence.
Christoph Thomas et al: "Structure of the TAPBPR-MHC I complex defines the mechanism of peptide loading and editing", Science, vol. 358, No. 6366, Nov. 24, 2017, pp. 1060-1064.
Database UniProt [Online] Apr. 26, 2005 (Apr. 26, 2005), "RecName: Full=Tapasin-related protein; Short=Tapasin-R; AltName: Full= TAP-binding protein-like; AltName: Full=TAP-binding protein-related protein; Short=TAPBP-R; AltName: Full=Tapasin-like; Flags: Precursor;". XP002789645, retrieved from EBI accession No. UniProt:Q9BX59 Database accession No. Q9BX59 sequence.
Database UniProt [Online] Apr. 26, 2005 (Apr. 26, 2005), "RecName: Full=Tapasin-related protein; Short=Tapasin-R; AltName: Full= TAP-binding protein-like; AltName: Full=TAP-binding protein-related protein; Short=TAPBP-R; AltName: Full=Tapasin-like; Flags: Precursor;". XP002789646, retrieved from EBI accession No. UniProt:Q8VD31 Database accession No. Q8VD31 sequence.
Louise H. Boyle et Al: "Tapasin-related protein TAPBPR is an additional component of the MHC class I presentation pathway", Proceedings of the National Academy of Sciences of the United States of America, vol. 110, No. 9, Feb. 26, 2013 (Feb. 26, 2013), pp. 3465-3470.
Louise H. Boyle et al: "Supporting information.—Tapasin-related protein TAPBPR is an additional component of the MHC class I presentation pathway", Proceedings of the National Academy of Sciences of the United States of America, vol. 110, No. 9, Feb. 11, 2013 (Feb. 11, 2013), pp. 3465-3470.

Clemens Hermann et al: "TAPBPR alters MHC class I peptide presentation by functioning as a peptide exchange catalyst", ELIFE, vol. 4, Oct. 6, 2015 (Oct. 6, 2015).
Giora I. Morozov et al: "Interaction of TAPBPR, a tapasin homolog, with MHC-I molecules promotes peptide editing", Proceedings of the National Academy of Sciences of the United States of America, vol. 113, No. 8, Feb. 23, 2016 (Feb. 23, 2016), pp. E1006-E1015.
F. Tudor Ilca et al: "Utilizing TAPBPR to promote exogenous peptide loading onto cell surface MHC I molecules", Proceedings of the National Academy of Sciences of the United States of America, vol. 115, No. 40, Sep. 13, 2018 (Sep. 13, 2018), pp. E9353-E9361.
F. Tudor Ilca et al: "Supporting information.—Utilizing TAPBPR to promote exogenous peptide loading onto cell surface MHC I molecules", Proceedings of the National Academy of Sciences of the United States of America, vol. 115, No. 40, Sep. 13, 2018, pp. E9353-E9361.
Chen et al., "The modification of Tapasin enhances cytotoxic T lymphocyte activity of intracellularly delivered CTL epitopes via cytoplasmic transduction peptide," Acta Biochimica et Biophysica Sinica, 2013, vol. 45, No. 3, pp. 203-212.
Radcliffe et al., "Identification of Specific Glycoforms of Major Histocompatibility Complex Class I Heavy Chains Suggests That Class I Peptide Loading Is an Adaptation of the Quality Control Pathway Involving Calreticulin and ERp57," The Journal of Biological Chemistry, Nov. 29, 2002, vol. 277, No. 48, pp. 46415-46423.
Teng et al., "A human TAPBP (TAPASIN)-related gene, TAPBP-R," European Journal of Immunology, 2002, vol. 32, pp. 1059-1068.
Office Action dated Jan. 10, 2023 in corresponding Japanese Patent Application No. 2020-560595 (7 pages).
English translation of Office Action dated Jan. 10, 2023 in corresponding Japanese Patent Application No. 2020-560595 (7 pages).
Examination Report dated Jul. 18, 2023 in corresponding European Patent Application No. 19701859.1 (12 pages).

* cited by examiner

```
                         SEQUENCE LISTING

<160> NUMBER OF SEQ ID NOS: 102

<210> SEQ ID NO 1
<211> LENGTH: 1152
<212> TYPE: DNA
<213> ORGANISM: Artificial Sequence
<220> FEATURE:
<223> OTHER INFORMATION: TAPBPR luminal domain (mature sequence without
      21 aa leader sequence)

<400> SEQUENCE: 1
aagccccacc cagcagaggg gcagtggcgg gcagtggacg tggtcctaga ctgtttcctg        60
gtgaaggacg gtgcgcaccg tggagctctc gccagcagtg aggacagggc aagggcctcc       120
cttgtgctga agcaggtgcc agtgctggac gatggctccc tggaggactt caccgatttc       180 caaggggca cactggccca agatgaccca cctattatct tgaggcctc agtggacctg         240 gtccagattc ccaggccga ggccttgctc catgctgact gcagtgggaa ggaggtgacc        300
tgtgagatct cccgctactt tctccagatg acagagacca ctgttaagac agcagcttgg      360
ttcatggcca acgtgcaggt ctctggaggg ggacctagca tctccttggt gatgaagact       420
cccagggtcg ccaagaatga ggtgctctgg cacccaacgc tgaacttgcc actgagcccc       480
caggggactg tgcgaactgc agtggagttc caggtgatga cacagaccca atccctgagc       540
ttcctgctgg gtcctcagc ctccttggac tgtggcttct ccatggcacc gggcttggac       600
ctcatcagtg tggagtggcg actgcagcac aagggcaggg tcagttggt gtacagctgg       660 accgcagggc aggggcaggc tgtgcggaag gcgctaccc tggagcctgc acaactgggc       720
atggccaggg atgcctccct caccctgccc ggcctcacta caggacga ggggacctac        780 atttgccaga tcaccacctc tctgtaccga gctcagcaga tcatccagct caacatccaa       840
gcttccccta agtacgact gagcttggca aacgaagctc tgctgcccac cctcatctgc       900
gacattgctg gctattaccc tctggatgtg gtggtgacgt ggacccgaga ggagctgggt       960
gggtccccag cccaagtctc tggtgcctcc ttctccagcc tcaggcaaag cgtggcaggc     1020
acctacagca tctcctcctc tctcaccgca gaacctggct ctgcaggtgc cacttacacc     1080
tgccaggtca cacacatctc tctggaggag ccccttgggg ccagcaccca ggttgtccca     1140
ccagagcgga ga                                                         1152

<210> SEQ ID NO 2
<211> LENGTH: 384
<212> TYPE: PRT
<213> ORGANISM: Artificial Sequence
<220> FEATURE:
```

<223> OTHER INFORMATION: TAPBPR luminal domain (mature sequence without
      21 aa leader sequence)

<400> SEQUENCE: 2

```
Lys Pro His Pro Ala Glu Gly Gln Trp Arg Ala Val Asp Val Leu
1               5                   10                  15

Asp Cys Phe Leu Val Lys Asp Gly Ala His Arg Gly Ala Leu Ala Ser
                20                  25                  30

Ser Glu Asp Arg Ala Arg Ala Ser Leu Val Leu Lys Gln Val Pro Val
            35                  40                  45

Leu Asp Asp Gly Ser Leu Glu Asp Phe Thr Asp Phe Gln Gly Gly Thr
    50                  55                  60

Leu Ala Gln Asp Asp Pro Pro Ile Ile Phe Glu Ala Ser Val Asp Leu
65                  70                  75                  80

Val Gln Ile Pro Gln Ala Glu Ala Leu Leu His Ala Asp Cys Ser Gly
                85                  90                  95

Lys Glu Val Thr Cys Glu Ile Ser Arg Tyr Phe Leu Gln Met Thr Glu
            100                 105                 110

Thr Thr Val Lys Thr Ala Ala Trp Phe Met Ala Asn Val Gln Val Ser
    115                 120                 125

Gly Gly Gly Pro Ser Ile Ser Leu Val Met Lys Thr Pro Arg Val Ala
130                 135                 140

Lys Asn Glu Val Leu Trp His Pro Thr Leu Asn Leu Pro Leu Ser Pro
145                 150                 155                 160

Gln Gly Thr Val Arg Thr Ala Val Glu Phe Gln Val Met Thr Gln Thr
                165                 170                 175

Gln Ser Leu Ser Phe Leu Leu Gly Ser Ser Ala Ser Leu Asp Cys Gly
            180                 185                 190

Phe Ser Met Ala Pro Gly Leu Asp Leu Ile Ser Val Glu Trp Arg Leu
    195                 200                 205

Gln His Lys Gly Arg Gly Gln Leu Val Tyr Ser Trp Thr Ala Gly Gln
210                 215                 220

Gly Gln Ala Val Arg Lys Gly Ala Thr Leu Glu Pro Ala Gln Leu Gly
225                 230                 235                 240

Met Ala Arg Asp Ala Ser Leu Thr Leu Pro Gly Leu Thr Ile Gln Asp
                245                 250                 255

Glu Gly Thr Tyr Ile Cys Gln Ile Thr Thr Ser Leu Tyr Arg Ala Gln
            260                 265                 270

Gln Ile Ile Gln Leu Asn Ile Gln Ala Ser Pro Lys Val Arg Leu Ser
    275                 280                 285

Leu Ala Asn Glu Ala Leu Leu Pro Thr Leu Ile Cys Asp Ile Ala Gly
290                 295                 300

Tyr Tyr Pro Leu Asp Val Val Thr Trp Thr Arg Glu Glu Leu Gly
305                 310                 315                 320

Gly Ser Pro Ala Gln Val Ser Gly Ala Ser Phe Ser Ser Leu Arg Gln
                325                 330                 335

Ser Val Ala Gly Thr Tyr Ser Ile Ser Ser Ser Leu Thr Ala Glu Pro
            340                 345                 350

Gly Ser Ala Gly Ala Thr Tyr Thr Cys Gln Val Thr His Ile Ser Leu
    355                 360                 365

Glu Glu Pro Leu Gly Ala Ser Thr Gln Val Val Pro Pro Glu Arg Arg
370                 375                 380
```

<210> SEQ ID NO 3

<211> LENGTH: 1968
<212> TYPE: DNA
<213> ORGANISM: Artificial Sequence
<220> FEATURE:
<223> OTHER INFORMATION: TAPBPR-LONG-FcIgG1

<400> SEQUENCE: 3

```
atgggcacac aggagggctg gtgcctgctg ctctgcctgg ctctatctgg agcagcagaa      60
accaagcccc accagcaga ggggcagtgg cgggcagtgg acgtggtcct agactgtttc     120
ctggtgaagg acggtgcgca ccgtggagct ctcgccagca gtgaggacag ggcaagggcc     180
tcccttgtgc tgaagcaggt gccagtgctg acgatggct cccctggagga cttcaccgat     240
ttccaagggg gcacactggc ccaagatgac ccacctatta tctttgaggc ctcagtggac     300
ctggtccaga ttccccaggc cgaggccttg ctccatgctg actgcagtgg aaggaggtg      360
acctgtgaga tctcccgcta ctttctccag atgacagaga ccactgttaa gacagcagct     420
tggttcatgg ccaacgtgca ggtctctgga gggggaccta gcatctcctt ggtgatgaag     480
actcccaggg tcgccaagaa tgaggtgctc tggcacccaa cgctgaactt gccactgagc     540
ccccagggga ctgtgcgaac tgcagtggag ttccaggtga tgacacagac ccaatccctg     600
agcttcctgc tggggtcctc agcctccttg gactgtggct ctccatggc accgggcttg     660
gacctcatca gtgtggagtg gcgactgcag cacaagggca ggggtcagtt ggtgtacagc     720
tggaccgcag gcaggggca ggctgtgcgg aagggcgcta ccctggagcc tgcacaactg     780
ggcatggcca gggatgcctc cctcaccctg cccggcctca ctatacagga cgaggggacc     840
tacatttgcc agatcaccac ctctctgtac cgagctcagc agatcatcca gctcaacatc     900
caagcttccc ctaaagtacg actgagcttg gcaaacgaag ctctgctgcc caccctcatc     960
tgcgacattg ctggctatta ccctctggat gtggtggtga cgtggacccg agaggagctg    1020
ggtgggtccc cagcccaagt ctctggtgcc tccttctcca gcctcaggca aagcgtggca    1080
ggcacctaca gcatctcctc ctctctcacc gcagaacctg gctctgcagg tgccacttac    1140
acctgccagg tcacacacat ctctctggag agcccttg gggccagcac ccaggttgtc    1200
ccaccagagc ggagacacgt gggtggcggt ggctccggtg gcgtggctc cggtggcggt    1260
ggctccacta gtgacaaaac tcacacatgc ccaccgtgcc cagcacctga actcctgggg    1320
ggaccgtcag tcttcctctt ccccccaaaa cccaaggaca cctcatgat ctcccggacc    1380
cctgaggtca catgcgtggt ggtggacgtg agccacgaag accctgaggt caagttcaac    1440
tggtacgtgg acggcgtgga ggtgcataat gccaagacaa agccgcggga ggagcagtac    1500
aacagcacgt accgtgtggt cagcgtcctc accgtcctgc accaggactg gctgaatggc    1560
aaggagtaca agtgcaaggt ctccaacaaa gccctcccag cccccatcga gaaaaccatc    1620
tccaaagcca aagggcagcc ccgagaacca caggtgtaca ccctgccccc atcccgggat    1680
gagctgacca agaaccaggt cagcctgacc tgcctggtca aaggcttcta tcccagcgac    1740
atcgccgtgg agtgggagag caatgggcag ccggagaaca actacaagac cacgcctccc    1800
gtgctggact ccgacggctc cttcttcctc tacagcaagc tcaccgtgga caagagcagg    1860
tggcagcagg ggaacgtctt ctcatgctcc gtgatgcatg aggctctgca caaccactac    1920
acgcagaaga gcctctccct gtctccgggt aaaggcggag gaggatct                 1968
```

<210> SEQ ID NO 4
<211> LENGTH: 656
<212> TYPE: PRT
<213> ORGANISM: Artificial Sequence
<220> FEATURE:
<223> OTHER INFORMATION: TAPBPR-LONG-FcIgG1

<400> SEQUENCE: 4

```
Met Gly Thr Gln Glu Gly Trp Cys Leu Leu Cys Leu Ala Leu Ser
1               5                   10                  15

Gly Ala Ala Glu Thr Lys Pro His Pro Ala Glu Gly Gln Trp Arg Ala
            20                  25                  30

Val Asp Val Val Leu Asp Cys Phe Leu Val Lys Asp Gly Ala His Arg
            35                  40                  45

Gly Ala Leu Ala Ser Ser Glu Asp Arg Ala Arg Ala Ser Leu Val Leu
        50                  55                  60

Lys Gln Val Pro Val Leu Asp Asp Gly Ser Leu Glu Asp Phe Thr Asp
65                  70                  75                  80

Phe Gln Gly Gly Thr Leu Ala Gln Asp Pro Pro Ile Ile Phe Glu
                85                  90                  95

Ala Ser Val Asp Leu Val Gln Ile Pro Gln Ala Glu Ala Leu Leu His
            100                 105                 110

Ala Asp Cys Ser Gly Lys Glu Val Thr Cys Glu Ile Ser Arg Tyr Phe
            115                 120                 125

Leu Gln Met Thr Glu Thr Thr Val Lys Thr Ala Ala Trp Phe Met Ala
        130                 135                 140

Asn Val Gln Val Ser Gly Gly Pro Ser Ile Ser Leu Val Met Lys
145                 150                 155                 160

Thr Pro Arg Val Ala Lys Asn Glu Val Leu Trp His Pro Thr Leu Asn
                165                 170                 175

Leu Pro Leu Ser Pro Gln Gly Thr Val Arg Thr Ala Val Glu Phe Gln
            180                 185                 190

Val Met Thr Gln Thr Gln Ser Leu Ser Phe Leu Leu Gly Ser Ser Ala
            195                 200                 205

Ser Leu Asp Cys Gly Phe Ser Met Ala Pro Gly Leu Asp Leu Ile Ser
        210                 215                 220

Val Glu Trp Arg Leu Gln His Lys Gly Arg Gly Gln Leu Val Tyr Ser
225                 230                 235                 240

Trp Thr Ala Gly Gln Gly Gln Ala Val Arg Lys Gly Ala Thr Leu Glu
                245                 250                 255

Pro Ala Gln Leu Gly Met Ala Arg Asp Ala Ser Leu Thr Leu Pro Gly
            260                 265                 270

Leu Thr Ile Gln Asp Glu Gly Thr Tyr Ile Cys Gln Ile Thr Thr Ser
        275                 280                 285

Leu Tyr Arg Ala Gln Gln Ile Ile Gln Leu Asn Ile Gln Ala Ser Pro
        290                 295                 300

Lys Val Arg Leu Ser Leu Ala Asn Glu Ala Leu Leu Pro Thr Leu Ile
305                 310                 315                 320

Cys Asp Ile Ala Gly Tyr Tyr Pro Leu Asp Val Val Thr Trp Thr
                325                 330                 335

Arg Glu Glu Leu Gly Gly Ser Pro Ala Gln Val Ser Gly Ala Ser Phe
            340                 345                 350

Ser Ser Leu Arg Gln Ser Val Ala Gly Thr Tyr Ser Ile Ser Ser Ser
        355                 360                 365

Leu Thr Ala Glu Pro Gly Ser Ala Gly Ala Thr Tyr Thr Cys Gln Val
        370                 375                 380

Thr His Ile Ser Leu Glu Glu Pro Leu Gly Ala Ser Thr Gln Val Val
385                 390                 395                 400
```

```
Pro Pro Glu Arg Arg His Val Gly Gly Gly Ser Gly Gly Gly
            405                 410                 415
Ser Gly Gly Gly Gly Ser Thr Ser Asp Lys Thr His Thr Cys Pro Pro
            420                 425                 430
Cys Pro Ala Pro Glu Leu Leu Gly Gly Pro Ser Val Phe Leu Phe Pro
            435                 440                 445
Pro Lys Pro Lys Asp Thr Leu Met Ile Ser Arg Thr Pro Glu Val Thr
450                 455                 460
Cys Val Val Val Asp Val Ser His Glu Asp Pro Glu Val Lys Phe Asn
465                 470                 475                 480
Trp Tyr Val Asp Gly Val Glu Val His Asn Ala Lys Thr Lys Pro Arg
                485                 490                 495
Glu Glu Gln Tyr Asn Ser Thr Tyr Arg Val Val Ser Val Leu Thr Val
                500                 505                 510
Leu His Gln Asp Trp Leu Asn Gly Lys Glu Tyr Lys Cys Lys Val Ser
            515                 520                 525
Asn Lys Ala Leu Pro Ala Pro Ile Glu Lys Thr Ile Ser Lys Ala Lys
530                 535                 540
Gly Gln Pro Arg Glu Pro Gln Val Tyr Thr Leu Pro Pro Ser Arg Asp
545                 550                 555                 560
Glu Leu Thr Lys Asn Gln Val Ser Leu Thr Cys Leu Val Lys Gly Phe
                565                 570                 575
Tyr Pro Ser Asp Ile Ala Val Glu Trp Glu Ser Asn Gly Gln Pro Glu
            580                 585                 590
Asn Asn Tyr Lys Thr Thr Pro Pro Val Leu Asp Ser Asp Gly Ser Phe
            595                 600                 605
Phe Leu Tyr Ser Lys Leu Thr Val Asp Lys Ser Arg Trp Gln Gln Gly
610                 615                 620
Asn Val Phe Ser Cys Ser Val Met His Glu Ala Leu His Asn His Tyr
625                 630                 635                 640
Thr Gln Lys Ser Leu Ser Leu Ser Pro Gly Lys Gly Gly Gly Gly Ser
                645                 650                 655

<210> SEQ ID NO 5
<211> LENGTH: 1611
<212> TYPE: DNA
<213> ORGANISM: Artificial Sequence
<220> FEATURE:
<223> OTHER INFORMATION: sTAPBPR-sPD1

<400> SEQUENCE: 5
atgggcacac aggagggctg gtgcctgctg ctctgcctgg ctctatctgg agcagcagaa      60
accaagcccc acccagcaga ggggcagtgg cgggcagtgg acgtggtcct agactgtttc     120
ctggtgaagg acggtgcgca ccgtggagct ctcgccagca gtgaggacag ggcaagggcc     180
tcccttgtgc tgaagcaggt gccagtgctg acgatggct cccctggagga cttcaccgat     240 ttccaagggg gcacactggc ccaagatgac ccacctatta tctttgaggc tcagtggac      300 ctggtccaga ttccccaggc cgaggccttg ctccatgctg actgcagtgg aaggaggtg     360 acctgtgaga tctcccgcta ctttctccag atgacagaga ccactgttaa gacagcagct    420
tggttcatgg ccaacgtgca ggtctctgga gggggaccta gcatctcctt ggtgatgaag    480
actcccaggg tcgccaagaa tgaggtgctc tggcacccaa cgctgaactt gccactgagc    540
ccccagggga ctgtgcgaac tgcagtggag ttccaggtga tgacacagac ccaatccctg    600
```

```
agcttcctgc tgggtcctc agcctccttg gactgtggct tctccatggc accgggcttg    660
gacctcatca gtgtggagtg cgactgcag cacaagggca ggggtcagtt ggtgtacagc    720
tggaccgcag ggcaggggca ggctgtgcgg aagggcgcta ccctggagcc tgcacaactg    780
ggcatggcca gggatgcctc cctcaccctg cccggcctca ctatacagga cgaggggacc    840
tacatttgcc agatcaccac ctctctgtac cgagctcagc agatcatcca gctcaacatc    900
caagcttccc ctaaagtacg actgagcttg caaacgaag ctctgctgcc caccctcatc    960
tgcgacattg ctggctatta ccctctggat gtggtggtga cgtggacccg agaggagctg   1020
ggtgggtccc cagcccaagt ctctggtgcc tccttctcca gcctcaggca aagcgtggca   1080
ggcacctaca gcatctcctc ctctctcacc gcagaacctg gctctgcagg tgccacttac   1140
acctgccagg tcacacacat ctctctggag gagcccttg gggccagcac ccaggttgtc   1200
ccaccagagc ggagacacgt gggtggcggt ggctccggtg gcggtggctc cggtggcggt   1260
ggctccacta gtgactcccc agacaggcc tggaaccccc ccaccttctt cccagccctg   1320
ctcgtggtga ccgaagggga caacgccacc ttcacctgca cttctccaa cacatcggag   1380 agcttccacg tgatctggca ccgcgagagc cccgcggcc agacggacac cctggccgcc   1440
ttccccgagg accgcagcca gccggccag gactgccgct ccgtgtcac acaactgccc   1500 aacgggcgtg acttccacat gagcgtggtc agggcccggc gcaatgacag cggcacctac   1560
gtgtgtgggg tgatctccct ggcccccaag atccagatca agagagcct g              1611
```

<210> SEQ ID NO 6
<211> LENGTH: 537
<212> TYPE: PRT
<213> ORGANISM: Artificial Sequence
<220> FEATURE:
<223> OTHER INFORMATION: sTAPBPR-sPD1

<400> SEQUENCE: 6

```
Met Gly Thr Gln Glu Gly Trp Cys Leu Leu Cys Leu Ala Leu Ser
1               5                   10                  15

Gly Ala Ala Glu Thr Lys Pro His Pro Ala Glu Gly Gln Trp Arg Ala
                20                  25                  30

Val Asp Val Val Leu Asp Cys Phe Leu Val Lys Asp Gly Ala His Arg
            35                  40                  45

Gly Ala Leu Ala Ser Ser Glu Asp Arg Ala Arg Ala Ser Leu Val Leu
        50                  55                  60

Lys Gln Val Pro Val Leu Asp Asp Gly Ser Leu Glu Asp Phe Thr Asp
65                  70                  75                  80

Phe Gln Gly Gly Thr Leu Ala Gln Asp Asp Pro Ile Ile Phe Glu
                85                  90                  95

Ala Ser Val Asp Leu Val Gln Ile Pro Gln Ala Glu Ala Leu Leu His
                100                 105                 110

Ala Asp Cys Ser Gly Lys Glu Val Thr Cys Glu Ile Ser Arg Tyr Phe
            115                 120                 125

Leu Gln Met Thr Glu Thr Thr Val Lys Thr Ala Ala Trp Phe Met Ala
        130                 135                 140

Asn Val Gln Val Ser Gly Gly Pro Ser Ile Ser Leu Val Met Lys
145                 150                 155                 160

Thr Pro Arg Val Ala Lys Asn Glu Val Leu Trp His Pro Thr Leu Asn
                165                 170                 175

Leu Pro Leu Ser Pro Gln Gly Thr Val Arg Thr Ala Val Glu Phe Gln
            180                 185                 190
```

Val Met Thr Gln Thr Gln Ser Leu Ser Phe Leu Leu Gly Ser Ser Ala
            195                 200                 205

Ser Leu Asp Cys Gly Phe Ser Met Ala Pro Gly Leu Asp Leu Ile Ser
    210                 215                 220

Val Glu Trp Arg Leu Gln His Lys Gly Arg Gly Gln Leu Val Tyr Ser
225                 230                 235                 240

Trp Thr Ala Gly Gln Gly Gln Ala Val Arg Lys Gly Ala Thr Leu Glu
                245                 250                 255

Pro Ala Gln Leu Gly Met Ala Arg Asp Ala Ser Leu Thr Leu Pro Gly
            260                 265                 270

Leu Thr Ile Gln Asp Glu Gly Thr Tyr Ile Cys Gln Ile Thr Thr Ser
        275                 280                 285

Leu Tyr Arg Ala Gln Gln Ile Ile Gln Leu Asn Ile Gln Ala Ser Pro
    290                 295                 300

Lys Val Arg Leu Ser Leu Ala Asn Glu Ala Leu Leu Pro Thr Leu Ile
305                 310                 315                 320

Cys Asp Ile Ala Gly Tyr Tyr Pro Leu Asp Val Val Thr Trp Thr
                325                 330                 335

Arg Glu Glu Leu Gly Gly Ser Pro Ala Gln Val Ser Gly Ala Ser Phe
                340                 345                 350

Ser Ser Leu Arg Gln Ser Val Ala Gly Thr Tyr Ser Ile Ser Ser Ser
        355                 360                 365

Leu Thr Ala Glu Pro Gly Ser Ala Gly Ala Thr Tyr Thr Cys Gln Val
    370                 375                 380

Thr His Ile Ser Leu Glu Glu Pro Leu Gly Ala Ser Thr Gln Val Val
385                 390                 395                 400

Pro Pro Glu Arg Arg His Val Gly Gly Gly Ser Gly Gly Gly
                405                 410                 415

Ser Gly Gly Gly Gly Ser Thr Ser Asp Ser Pro Asp Arg Pro Trp Asn
                420                 425                 430

Pro Pro Thr Phe Phe Pro Ala Leu Leu Val Val Thr Glu Gly Asp Asn
            435                 440                 445

Ala Thr Phe Thr Cys Ser Phe Ser Asn Thr Ser Glu Ser Phe His Val
    450                 455                 460

Ile Trp His Arg Glu Ser Pro Ser Gly Gln Thr Asp Thr Leu Ala Ala
465                 470                 475                 480

Phe Pro Glu Asp Arg Ser Gln Pro Gly Gln Asp Cys Arg Phe Arg Val
                485                 490                 495

Thr Gln Leu Pro Asn Gly Arg Asp Phe His Met Ser Val Val Arg Ala
            500                 505                 510

Arg Arg Asn Asp Ser Gly Thr Tyr Val Cys Gly Val Ile Ser Leu Ala
        515                 520                 525

Pro Lys Ile Gln Ile Lys Glu Ser Leu
    530                 535

<210> SEQ ID NO 7
<211> LENGTH: 2088
<212> TYPE: DNA
<213> ORGANISM: Artificial Sequence
<220> FEATURE:
<223> OTHER INFORMATION: TAPBPR-Her2scFv

<400> SEQUENCE: 7
atgggcacac aggagggctg gtgcctgctg ctctgcctgg ctctatctgg agcagcagaa       60

| | |
|---|---|
| accaagcccc acccagcaga ggggcagtgg cgggcagtgg acgtggtcct agactgtttc | 120 |
| ctggtgaagg acggtgcgca ccgtggagct ctcgccagca gtgaggacag gcaagggcc | 180 |
| tcccttgtgc tgaagcaggt gccagtgctg acgatggct ccctggagga cttcaccgat | 240 |
| ttccaagggg gcacactggc ccaagatgac ccacctatta tctttgaggc ctcagtggac | 300 |
| ctggtccaga ttccccaggc cgaggccttg ctccatgctg actgcagtgg aaggaggtg | 360 |
| acctgtgaga tctcccgcta ctttctccag atgacagaga ccactgttaa dacagcagct | 420 |
| tggttcatgg ccaacgtgca ggtctctgga gggggaccta gcatctcctt ggtgatgaag | 480 |
| actcccaggg tcgccaagaa tgaggtgctc tggcacccaa cgctgaactt gccactgagc | 540 |
| ccccagggga ctgtgcgaac tgcagtggag ttccaggtga tgacacagac ccaatccctg | 600 |
| agcttcctgc tggggtcctc agcctccttg gactgtggct ctccatggc accgggcttg | 660 |
| gacctcatca gtgtggagtg cgactgcag cacaagggca gggtcagtt ggtgtacagc | 720 |
| tggaccgcag gcaggggca ggctgtgcg aagggcgcta ccctggagcc tgcacaactg | 780 |
| ggcatggcca gggatgcctc cctcaccctg cccggcctca ctatacagga cgaggggacc | 840 |
| tacatttgcc agatcaccac ctctctgtac cgagctcagc agatcatcca gctcaacatc | 900 |
| caagcttccc ctaaagtacg actgagcttg caaacgaag ctctgctgcc caccctcatc | 960 |
| tgcgacattg ctggctatta ccctctggat gtggtggtga cgtggaccg agaggagctg | 1020 |
| ggtgggtccc cagcccaagt ctctggtgcc tccttctcca gcctcaggca aagcgtggca | 1080 |
| ggcacctaca gcatctcctc ctctctcacc gcagaacctg gctctgcagg tgccacttac | 1140 |
| acctgccagg tcacacacat ctctctggag gagcccttg gggccagcac ccaggttgtc | 1200 |
| ccaccagagc ggagacacgt gggtggcggt ggctccggtg gcggtggctc cggtggcggt | 1260 |
| ggctccacta gtgcggatct ggatcccgg gccatggccc aggtgcagct ggtgcagtct | 1320 |
| ggggcagagg tgaaaaagcc cggggagtct ctgaagatct cctgtaaggg ttctggatac | 1380 |
| agctttacca gctactggat cgcctgggtg cgccagatgc ccgggaaagg cctggagtac | 1440 |
| atggggctca tctatcctgg tgactctgac accaaataca gcccgtcctt ccaaggccag | 1500 |
| gtcaccatct cagtcgacaa gtccgtcagc actgcctact gcaatggag cagtctgaag | 1560 |
| ccctcggaca cgccgtgta ttttgtgcg agacatgacg tgggatattg cagtagttcc | 1620 |
| aactgcgcaa agtggcctga atacttccag cattggggcc agggcaccct ggtcaccgtc | 1680 |
| tcctcaggtg gaggcggttc aggcggaggt ggctctggcg gtggcggatc gcagtctgtg | 1740 |
| ttgacgcagc cgccctcagt gtctgcggcc ccaggacaga aggtcaccat tcctgctct | 1800 |
| ggaagcagct ccaacattgg gaataattat gtatcctggt accagcagct cccaggaaca | 1860 |
| gcccccaaac tcctcatcta tgatcacacc aatcggcccg caggggtccc tgaccgattc | 1920 |
| tctggctcca gtctggcac ctcagcctcc ctggccatca gtgggttccg gtccgaggat | 1980 |
| gaggctgatt attactgtgc ctcctgggac tacaccctct cgggctgggt gttcggcgga | 2040 |
| ggaaccaagc tgaccgtcct aggtgcggcc gccggcggag aggatct | 2088 |

<210> SEQ ID NO 8
<211> LENGTH: 696
<212> TYPE: PRT
<213> ORGANISM: Artificial Sequence
<220> FEATURE:
<223> OTHER INFORMATION: TAPBPR-Her2scFv

<400> SEQUENCE: 8

Met Gly Thr Gln Glu Gly Trp Cys Leu Leu Leu Cys Leu Ala Leu Ser

```
1               5                   10                  15
Gly Ala Ala Glu Thr Lys Pro His Pro Ala Glu Gly Gln Trp Arg Ala
            20                  25                  30

Val Asp Val Val Leu Asp Cys Phe Leu Val Lys Asp Gly Ala His Arg
            35                  40                  45

Gly Ala Leu Ala Ser Ser Glu Asp Arg Ala Arg Ala Ser Leu Val Leu
            50                  55                  60

Lys Gln Val Pro Val Leu Asp Asp Gly Ser Leu Glu Asp Phe Thr Asp
65                  70                  75                  80

Phe Gln Gly Gly Thr Leu Ala Gln Asp Pro Pro Ile Ile Phe Glu
                    85                  90                  95

Ala Ser Val Asp Leu Val Gln Ile Pro Gln Ala Glu Ala Leu Leu His
            100                 105                 110

Ala Asp Cys Ser Gly Lys Glu Val Thr Cys Glu Ile Ser Arg Tyr Phe
            115                 120                 125

Leu Gln Met Thr Glu Thr Thr Val Lys Thr Ala Ala Trp Phe Met Ala
            130                 135                 140

Asn Val Gln Val Ser Gly Gly Pro Ser Ile Ser Leu Val Met Lys
145                 150                 155                 160

Thr Pro Arg Val Ala Lys Asn Glu Val Leu Trp His Pro Thr Leu Asn
                    165                 170                 175

Leu Pro Leu Ser Pro Gln Gly Thr Val Arg Thr Ala Val Glu Phe Gln
            180                 185                 190

Val Met Thr Gln Thr Gln Ser Leu Ser Phe Leu Leu Gly Ser Ser Ala
            195                 200                 205

Ser Leu Asp Cys Gly Phe Ser Met Ala Pro Gly Leu Asp Leu Ile Ser
210                 215                 220

Val Glu Trp Arg Leu Gln His Lys Gly Arg Gly Gln Leu Val Tyr Ser
225                 230                 235                 240

Trp Thr Ala Gly Gln Gly Gln Ala Val Arg Lys Gly Ala Thr Leu Glu
                    245                 250                 255

Pro Ala Gln Leu Gly Met Ala Arg Asp Ala Ser Leu Thr Leu Pro Gly
            260                 265                 270

Leu Thr Ile Gln Asp Glu Gly Thr Tyr Ile Cys Gln Ile Thr Thr Ser
            275                 280                 285

Leu Tyr Arg Ala Gln Gln Ile Ile Gln Leu Asn Ile Gln Ala Ser Pro
            290                 295                 300

Lys Val Arg Leu Ser Leu Ala Asn Glu Ala Leu Leu Pro Thr Leu Ile
305                 310                 315                 320

Cys Asp Ile Ala Gly Tyr Tyr Pro Leu Asp Val Val Thr Trp Thr
                    325                 330                 335

Arg Glu Glu Leu Gly Gly Ser Pro Ala Gln Val Ser Gly Ala Ser Phe
            340                 345                 350

Ser Ser Leu Arg Gln Ser Val Ala Gly Thr Tyr Ser Ile Ser Ser Ser
            355                 360                 365

Leu Thr Ala Glu Pro Gly Ser Ala Gly Ala Thr Tyr Thr Cys Gln Val
            370                 375                 380

Thr His Ile Ser Leu Glu Glu Pro Leu Gly Ala Ser Thr Gln Val Val
385                 390                 395                 400

Pro Pro Glu Arg Arg His Val Gly Gly Gly Ser Gly Gly Gly
                    405                 410                 415

Ser Gly Gly Gly Gly Ser Thr Ser Ala Asp Leu Gly Ser Arg Ala Met
            420                 425                 430
```

Ala Gln Val Gln Leu Val Gln Ser Gly Ala Glu Val Lys Lys Pro Gly
        435                 440                 445

Glu Ser Leu Lys Ile Ser Cys Lys Gly Ser Gly Tyr Ser Phe Thr Ser
        450                 455                 460

Tyr Trp Ile Ala Trp Val Arg Gln Met Pro Lys Gly Leu Glu Tyr
465                 470                 475                 480

Met Gly Leu Ile Tyr Pro Gly Asp Ser Asp Thr Lys Tyr Ser Pro Ser
                    485                 490                 495

Phe Gln Gly Gln Val Thr Ile Ser Val Asp Lys Ser Val Ser Thr Ala
                500                 505                 510

Tyr Leu Gln Trp Ser Ser Leu Lys Pro Ser Asp Ser Ala Val Tyr Phe
        515                 520                 525

Cys Ala Arg His Asp Val Gly Tyr Cys Ser Ser Ser Asn Cys Ala Lys
        530                 535                 540

Trp Pro Glu Tyr Phe Gln His Trp Gly Gln Gly Thr Leu Val Thr Val
545                 550                 555                 560

Ser Ser Gly Gly Gly Gly Ser Gly Gly Gly Gly Ser Gly Gly Gly Gly
                    565                 570                 575

Ser Gln Ser Val Leu Thr Gln Pro Pro Ser Val Ser Ala Ala Pro Gly
                580                 585                 590

Gln Lys Val Thr Ile Ser Cys Ser Gly Ser Ser Ser Asn Ile Gly Asn
        595                 600                 605

Asn Tyr Val Ser Trp Tyr Gln Gln Leu Pro Gly Thr Ala Pro Lys Leu
        610                 615                 620

Leu Ile Tyr Asp His Thr Asn Arg Pro Ala Gly Val Pro Asp Arg Phe
625                 630                 635                 640

Ser Gly Ser Lys Ser Gly Thr Ser Ala Ser Leu Ala Ile Ser Gly Phe
                    645                 650                 655

Arg Ser Glu Asp Glu Ala Asp Tyr Tyr Cys Ala Ser Trp Asp Tyr Thr
                660                 665                 670

Leu Ser Gly Trp Val Phe Gly Gly Gly Thr Lys Leu Thr Val Leu Gly
        675                 680                 685

Ala Ala Ala Gly Gly Gly Gly Ser
        690                 695

<210> SEQ ID NO 9
<211> LENGTH: 1620
<212> TYPE: DNA
<213> ORGANISM: Artificial Sequence
<220> FEATURE:
<223> OTHER INFORMATION: TAPBPR-GFP-NB

<400> SEQUENCE: 9
atgggcacac aggagggctg gtgcctgctg ctctgcctgg ctctatctgg agcagcagaa      60
accaagcccc acccagcaga ggggcagtgg cgggcagtgg acgtggtcct agactgtttc     120
ctggtgaagg acggtgcgca ccgtggagct ctcgccagca gtgaggacag gcaagggcc     180 tcccttgtgc tgaagcaggt gccagtgctg acgatggct ccctggagga cttcaccgat     240
ttccaagggg gcacactggc caagatgac ccacctatta tctttgaggc tcagtggac     300 ctggtccaga ttccccaggc cgaggccttg ctccatgctg actgcagtgg aaggaggtg     360 acctgtgaga tctcccgcta ctttctccag atgacagaga ccactgttaa gacagcagct     420
tggttcatgg ccaacgtgca ggtctctgga ggggaccta gcatctcctt ggtgatgaag     480
actcccaggg tcgccaagaa tgaggtgctc tggcacccaa cgctgaactt gccactgagc     540

```
cccccagggga ctgtgcgaac tgcagtggag ttccaggtga tgacacagac ccaatccctg     600
agcttcctgc tggggtcctc agcctccttg gactgtggct tctccatggc accgggcttg     660
gacctcatca gtgtggagtg gcgactgcag cacaagggca ggggtcagtt ggtgtacagc     720
tggaccgcag ggcaggggca ggctgtgcgg aagggcgcta ccctggagcc tgcacaactg     780
ggcatggcca gggatgcctc cctcaccctg cccggcctca ctatacagga cgagggggacc    840 tacatttgcc agatcaccac ctctctgtac cgagctcagc agatcatcca gctcaacatc     900
caagcttccc ctaaagtacg actgagcttg gcaaacgaag ctctgctgcc cacccttcatc    960 tgcgacattg ctggctatta ccctctggat gtggtggtga cgtggacccg agaggagctg    1020
ggtgggtccc cagcccaagt ctctggtgcc tccttctcca gcctcaggca aagcgtggca    1080
ggcacctaca gcatctcctc ctctctcacc gcagaacctg gctctgcagg tgccacttac    1140
acctgccagg tcacacacat ctctctggag gagccccttg gggccagcac ccaggttgtc    1200
ccaccagagc ggagacacgt gggtggcggt ggctccggtg gcggtggctc cggtggcggt    1260
ggctccacta gtcaggttca gctggttgaa agcggtggtg cactggttca gcctggtggt    1320
agcctgcgtc tgagctgtgc agcaagcggt tttccggtta atcgttatag catgcgttgg    1380
tatcgtcagg caccgggtaa agaacgtgaa tgggttgcag gtatgagcag tgccggtgat    1440
cgtagcagct atgaagatag cgttaaaggt cgttttacca tcagccgtga tgatgcacgt    1500
aataccgttt atctgcaaat gaatagcctg aaaccggaag ataccgcagt gtattattgc    1560
aatgttaacg tgggctttga atattggggt cagggcaccc aggttaccgt tagcagcaaa    1620
```

<210> SEQ ID NO 10
<211> LENGTH: 540
<212> TYPE: PRT
<213> ORGANISM: Artificial Sequence
<220> FEATURE:
<223> OTHER INFORMATION: TAPBPR-GFP-NB

<400> SEQUENCE: 10

```
Met Gly Thr Gln Glu Gly Trp Cys Leu Leu Cys Leu Ala Leu Ser
1               5                   10                  15

Gly Ala Ala Glu Thr Lys Pro His Pro Ala Glu Gly Gln Trp Arg Ala
                20                  25                  30

Val Asp Val Val Leu Asp Cys Phe Leu Val Lys Asp Gly Ala His Arg
            35                  40                  45

Gly Ala Leu Ala Ser Ser Glu Asp Arg Ala Arg Ala Ser Leu Val Leu
        50                  55                  60

Lys Gln Val Pro Val Leu Asp Asp Gly Ser Leu Glu Asp Phe Thr Asp
65                  70                  75                  80

Phe Gln Gly Gly Thr Leu Ala Gln Asp Asp Pro Ile Ile Phe Glu
                85                  90                  95

Ala Ser Val Asp Leu Val Gln Ile Pro Gln Ala Glu Ala Leu Leu His
            100                 105                 110

Ala Asp Cys Ser Gly Lys Glu Val Thr Cys Glu Ile Ser Arg Tyr Phe
        115                 120                 125

Leu Gln Met Thr Glu Thr Thr Val Lys Thr Ala Ala Trp Phe Met Ala
    130                 135                 140

Asn Val Gln Val Ser Gly Gly Pro Ser Ile Ser Leu Val Met Lys
145                 150                 155                 160

Thr Pro Arg Val Ala Lys Asn Glu Val Leu Trp His Pro Thr Leu Asn
                165                 170                 175
```

Leu Pro Leu Ser Pro Gln Gly Thr Val Arg Thr Ala Val Glu Phe Gln
            180                 185                 190

Val Met Thr Gln Thr Gln Ser Leu Ser Phe Leu Leu Gly Ser Ser Ala
            195                 200                 205

Ser Leu Asp Cys Gly Phe Ser Met Ala Pro Gly Leu Asp Leu Ile Ser
            210                 215                 220

Val Glu Trp Arg Leu Gln His Lys Gly Arg Gly Gln Leu Val Tyr Ser
225                 230                 235                 240

Trp Thr Ala Gly Gln Gly Gln Ala Val Arg Lys Gly Ala Thr Leu Glu
            245                 250                 255

Pro Ala Gln Leu Gly Met Ala Arg Asp Ala Ser Leu Thr Leu Pro Gly
            260                 265                 270

Leu Thr Ile Gln Asp Glu Gly Thr Tyr Ile Cys Gln Ile Thr Thr Ser
            275                 280                 285

Leu Tyr Arg Ala Gln Gln Ile Ile Gln Leu Asn Ile Gln Ala Ser Pro
            290                 295                 300

Lys Val Arg Leu Ser Leu Ala Asn Glu Ala Leu Leu Pro Thr Leu Ile
305                 310                 315                 320

Cys Asp Ile Ala Gly Tyr Tyr Pro Leu Asp Val Val Thr Trp Thr
            325                 330                 335

Arg Glu Glu Leu Gly Gly Ser Pro Ala Gln Val Ser Gly Ala Ser Phe
            340                 345                 350

Ser Ser Leu Arg Gln Ser Val Ala Gly Thr Tyr Ser Ile Ser Ser Ser
            355                 360                 365

Leu Thr Ala Glu Pro Gly Ser Ala Gly Ala Thr Tyr Thr Cys Gln Val
            370                 375                 380

Thr His Ile Ser Leu Glu Glu Pro Leu Gly Ala Ser Thr Gln Val Val
385                 390                 395                 400

Pro Pro Glu Arg Arg His Val Gly Gly Gly Ser Gly Gly Gly
            405                 410                 415

Ser Gly Gly Gly Gly Ser Thr Ser Gln Val Gln Leu Val Glu Ser Gly
            420                 425                 430

Gly Ala Leu Val Gln Pro Gly Gly Ser Leu Arg Leu Ser Cys Ala Ala
            435                 440                 445

Ser Gly Phe Pro Val Asn Arg Tyr Ser Met Arg Trp Tyr Arg Gln Ala
450                 455                 460

Pro Gly Lys Glu Arg Glu Trp Val Ala Gly Met Ser Ser Ala Gly Asp
465                 470                 475                 480

Arg Ser Ser Tyr Glu Asp Ser Val Lys Gly Arg Phe Thr Ile Ser Arg
            485                 490                 495

Asp Asp Ala Arg Asn Thr Val Tyr Leu Gln Met Asn Ser Leu Lys Pro
            500                 505                 510

Glu Asp Thr Ala Val Tyr Tyr Cys Asn Val Asn Val Gly Phe Glu Tyr
            515                 520                 525

Trp Gly Gln Gly Thr Gln Val Thr Val Ser Ser Lys
            530                 535                 540

<210> SEQ ID NO 11
<211> LENGTH: 1665
<212> TYPE: DNA
<213> ORGANISM: Artificial Sequence
<220> FEATURE:
<223> OTHER INFORMATION: sTAPBPR-LONG-PD-L1-NB1

<400> SEQUENCE: 11

```
atgggcacac aggagggctg gtgcctgctg ctctgcctgg ctctatctgg agcagcagaa      60
accaagcccc acccagcaga ggggcagtgg cgggcagtgg acgtggtcct agactgtttc    120
ctggtgaagg acgtgcgca ccgtggagct ctcgccagca gtgaggacag ggcaagggcc    180
tcccttgtgc tgaagcaggt gccagtgctg acgatggct ccctggagga cttcaccgat    240
ttccaagggg gcacactggc ccagatgac ccacctatta tctttgaggc ctcagtggac    300
ctggtccaga ttccccaggc cgaggccttg ctccatgctg actgcagtgg aaggaggtg    360
acctgtgaga tctcccgcta ctttctccag atgacagaga ccactgttaa gacagcagct    420
tggttcatgg ccaacgtgca ggtctctgga gggggaccta gcatctcctt ggtgatgaag    480
actcccaggg tcgccaagaa tgaggtgctc tggcacccaa cgctgaactt gccactgagc    540
ccccagggga ctgtgcgaac tgcagtggag ttccaggtga tgacacagac ccaatccctg    600
agcttcctgc tggggtcctc agcctccttg gactgtggct tctccatggc accgggcttg    660
gacctcatca gtgtggagtg gcgactgcag cacaagggca ggggtcagtt ggtgtacagc    720
tggaccgcag ggcaggggca ggctgtgcgg aagggcgcta ccctggagcc tgcacaactg    780
ggcatggcca gggatgcctc cctcaccctg cccggcctca ctatacagga cgaggggacc    840
tacatttgcc agatcaccac ctctctgtac cgagctcagc agatcatcca gctcaacatc    900
caagcttccc ctaaagtacg actgagcttg caaacgaag ctctgctgcc acccctcatc    960
tgcgacattg ctggctatta ccctctggat gtggtggtga cgtggaccg agaggagctg   1020
ggtgggtccc cagcccaagt ctctggtgcc tccttctcca gcctcaggca aagcgtggca   1080
ggcacctaca gcatctcctc ctctctcacc gcagaacctg gctctgcagg tgccacttac   1140
acctgccagg tcacacacat ctctctggag gagccccttg ggccagcac ccaggttgtc   1200
ccaccagagc ggagacacgt gggtggcggt ggctccggtg gcgttggctc cggtggcggt   1260
ggctccacta gtgaggtgca gctggtggag agcggcggcg gcctggtgca gcccggcggc   1320
agcctgagac tgagctgcgc cgccagcggc ttcaccctgg actactacgc catcggctgg   1380
ttcagacagg cccccggcaa ggagagagag tgggccagca gcatcagcag cagcgacggc   1440
agcacctact acgccgacag cgtgaagggc agattcacca tcagcagaga caacgccaag   1500
aacaccgtgt tcctgcagat gaacagcctg aagcccgagg acaccgccgt gtacagctgc   1560
gccgccagcc aggccccat caccatcgcc accatgatga gcccttcta cgactactgg   1620
ggccagggca cccaggtgac cgtgagcagc ggcggaggag gatct                    1665
```

<210> SEQ ID NO 12
<211> LENGTH: 555
<212> TYPE: PRT
<213> ORGANISM: Artificial Sequence
<220> FEATURE:
<223> OTHER INFORMATION: sTAPBPR-LONG-PD-L1-NB1

<400> SEQUENCE: 12

Met Gly Thr Gln Glu Gly Trp Cys Leu Leu Cys Leu Ala Leu Ser
1               5                   10                  15

Gly Ala Ala Glu Thr Lys Pro His Pro Ala Glu Gly Gln Trp Arg Ala
            20                  25                  30

Val Asp Val Val Leu Asp Cys Phe Leu Val Lys Asp Gly Ala His Arg
        35                  40                  45

Gly Ala Leu Ala Ser Ser Glu Asp Arg Ala Arg Ala Ser Leu Val Leu
    50                  55                  60

-continued

Lys Gln Val Pro Val Leu Asp Asp Gly Ser Leu Glu Asp Phe Thr Asp
 65                  70                  75                  80

Phe Gln Gly Gly Thr Leu Ala Gln Asp Pro Pro Ile Ile Phe Glu
                 85                  90                  95

Ala Ser Val Asp Leu Val Gln Ile Pro Gln Ala Glu Ala Leu Leu His
                100                 105                 110

Ala Asp Cys Ser Gly Lys Glu Val Thr Cys Glu Ile Ser Arg Tyr Phe
            115                 120                 125

Leu Gln Met Thr Glu Thr Thr Val Lys Thr Ala Ala Trp Phe Met Ala
        130                 135                 140

Asn Val Gln Val Ser Gly Gly Pro Ser Ile Ser Leu Val Met Lys
145                 150                 155                 160

Thr Pro Arg Val Ala Lys Asn Glu Val Leu Trp His Pro Thr Leu Asn
                165                 170                 175

Leu Pro Leu Ser Pro Gln Gly Thr Val Arg Thr Ala Val Glu Phe Gln
                180                 185                 190

Val Met Thr Gln Thr Gln Ser Leu Ser Phe Leu Leu Gly Ser Ser Ala
            195                 200                 205

Ser Leu Asp Cys Gly Phe Ser Met Ala Pro Gly Leu Asp Leu Ile Ser
        210                 215                 220

Val Glu Trp Arg Leu Gln His Lys Gly Arg Gly Gln Leu Val Tyr Ser
225                 230                 235                 240

Trp Thr Ala Gly Gln Gly Ala Val Arg Lys Gly Ala Thr Leu Glu
                245                 250                 255

Pro Ala Gln Leu Gly Met Ala Arg Asp Ala Ser Leu Thr Leu Pro Gly
                260                 265                 270

Leu Thr Ile Gln Asp Glu Gly Thr Tyr Ile Cys Gln Ile Thr Thr Ser
            275                 280                 285

Leu Tyr Arg Ala Gln Gln Ile Ile Gln Leu Asn Ile Gln Ala Ser Pro
        290                 295                 300

Lys Val Arg Leu Ser Leu Ala Asn Glu Ala Leu Leu Pro Thr Leu Ile
305                 310                 315                 320

Cys Asp Ile Ala Gly Tyr Tyr Pro Leu Asp Val Val Thr Trp Thr
                325                 330                 335

Arg Glu Glu Leu Gly Gly Ser Pro Ala Gln Val Ser Gly Ala Ser Phe
                340                 345                 350

Ser Ser Leu Arg Gln Ser Val Ala Gly Thr Tyr Ser Ile Ser Ser Ser
            355                 360                 365

Leu Thr Ala Glu Pro Gly Ser Ala Gly Ala Thr Tyr Thr Cys Gln Val
        370                 375                 380

Thr His Ile Ser Leu Glu Glu Pro Leu Gly Ala Ser Thr Gln Val Val
385                 390                 395                 400

Pro Pro Glu Arg Arg His Val Gly Gly Gly Ser Gly Gly Gly
                405                 410                 415

Ser Gly Gly Gly Gly Ser Thr Ser Glu Val Gln Leu Val Glu Ser Gly
            420                 425                 430

Gly Gly Leu Val Gln Pro Gly Gly Ser Leu Arg Leu Ser Cys Ala Ala
        435                 440                 445

Ser Gly Phe Thr Leu Asp Tyr Tyr Ala Ile Gly Trp Phe Arg Gln Ala
        450                 455                 460

Pro Gly Lys Glu Arg Glu Trp Ala Ser Ser Ile Ser Ser Ser Asp Gly
465                 470                 475                 480

Ser Thr Tyr Tyr Ala Asp Ser Val Lys Gly Arg Phe Thr Ile Ser Arg

```
                    485                 490                 495
Asp Asn Ala Lys Asn Thr Val Phe Leu Gln Met Asn Ser Leu Lys Pro
                500                 505                 510

Glu Asp Thr Ala Val Tyr Ser Cys Ala Ala Ser Gln Ala Pro Ile Thr
            515                 520                 525

Ile Ala Thr Met Met Lys Pro Phe Tyr Asp Tyr Trp Gly Gln Gly Thr
        530                 535                 540

Gln Val Thr Val Ser Ser Gly Gly Gly Ser
545                 550                 555

<210> SEQ ID NO 13
<211> LENGTH: 1656
<212> TYPE: DNA
<213> ORGANISM: Artificial Sequence
<220> FEATURE:
<223> OTHER INFORMATION: sTAPBPR-LONG-PD-L1-NB2

<400> SEQUENCE: 13
atgggcacac aggagggctg gtgcctgctg ctctgcctgg ctctatctgg agcagcagaa      60
accaagcccc acccagcaga ggggcagtgg cgggcagtgg acgtggtcct agactgtttc     120
ctggtgaagg acggtgcgca ccgtggagct ctcgccagca gtgaggacag gcaagggcc     180 tcccttgtgc tgaagcaggt gccagtgctg gacgatggct ccctggagga cttcaccgat     240
ttccaagggg gcacactggc ccaagatgac ccacctatta tctttgaggc ctcagtggac     300
ctggtccaga ttccccaggc cgaggccttg ctccatgctg actgcagtgg aaggaggtg     360 acctgtgaga tctcccgcta ctttctccag atgacagaga ccactgttaa cacagcagct     420
tggttcatgg ccaacgtgca ggtctctgga gggggaccta gcatctcctt ggtgatgaag     480
actcccaggg tcgccaagaa tgaggtgctc tggcacccaa cgctgaactt gccactgagc     540
ccccagggga ctgtgcgaac tgcagtggag ttccaggtga tgacacagac ccaatccctg     600
agcttcctgc tggggtcctc agcctccttg gactgtggct ctccatggc accgggcttg     660 gacctcatca gtgtggagtg gcgactgcag cacaagggca ggggtcagtt ggtgtacagc     720
tggaccgcag gcaggggca ggctgtgcgg aagggcgcta ccctggagcc tgcacaactg     780
ggcatggcca gggatgcctc cctcacccttg cccggcctca ctatacagga cgaggggacc     840
tacatttgcc agatcaccac ctctctgtac cgagctcagc agatcatcca gctcaacatc     900
caagcttccc ctaaagtacg actgagcttg gcaaacgaag ctctgctgcc caccctcatc     960
tgcgacattg ctggctatta ccctctggat gtggtggtga cgtggaccg agaggagctg    1020 ggtgggtccc cagcccaagt ctctggtgcc tccttctcca gcctcaggca aagcgtggca    1080
ggcacctaca gcatctcctc ctctctcacc gcagaacctg gctctgcagg tgccacttac    1140
acctgccagg tcacacacat ctctctggag gagccccttg ggccagcac ccaggttgtc    1200 ccaccagagc ggagacacgt gggtggcggt ggctccggtg gcgtggctc cggtggcggt    1260 ggctccacta gtgaggtgca gctggtggag agcggcggcg gctggtgca gcccggcggc    1320 agcctgagac tgagctgcgc cgccagcggc ttcacccctgg actactacgc caagtgctgg    1380
ttcagacagg cccccggcaa ggagagagag tgggtgagct gcatcagcag cagcgacggc    1440
agcacctact acgccgacag cgtgaagggc agattcacca tcagcagaga caacgccaag    1500
aacaccgtgt acctgcagat gaacagcctg aagcccgagg acaccgccgt gtacttctgc    1560
gccgccagac acgcggcccc cctgaccgtg gagtacttct tcgactactg gggccagggc    1620
acccaggtga ccgtgagcag cggcggagga ggatct                              1656
```

<210> SEQ ID NO 14
<211> LENGTH: 552
<212> TYPE: PRT
<213> ORGANISM: Artificial Sequence
<220> FEATURE:
<223> OTHER INFORMATION: sTAPBPR-LONG-PD-L1-NB2

<400> SEQUENCE: 14

| | | | | | | | | | | | | | | |
|---|---|---|---|---|---|---|---|---|---|---|---|---|---|---|
| Met | Gly | Thr | Gln | Glu | Gly | Trp | Cys | Leu | Leu | Cys | Leu | Ala | Leu | Ser |
| 1 | | | | 5 | | | | | 10 | | | | | 15 |
| Gly | Ala | Ala | Glu | Thr | Lys | Pro | His | Pro | Ala | Glu | Gly | Gln | Trp | Arg | Ala |
| | | | 20 | | | | | 25 | | | | | 30 | | |
| Val | Asp | Val | Val | Leu | Asp | Cys | Phe | Leu | Val | Lys | Asp | Gly | Ala | His | Arg |
| | | 35 | | | | | 40 | | | | | 45 | | | |
| Gly | Ala | Leu | Ala | Ser | Ser | Glu | Asp | Arg | Ala | Arg | Ala | Ser | Leu | Val | Leu |
| | 50 | | | | | 55 | | | | | 60 | | | | |
| Lys | Gln | Val | Pro | Val | Leu | Asp | Asp | Gly | Ser | Leu | Glu | Asp | Phe | Thr | Asp |
| 65 | | | | | 70 | | | | | 75 | | | | | 80 |
| Phe | Gln | Gly | Gly | Thr | Leu | Ala | Gln | Asp | Asp | Pro | Pro | Ile | Ile | Phe | Glu |
| | | | | 85 | | | | | 90 | | | | | 95 | |
| Ala | Ser | Val | Asp | Leu | Val | Gln | Ile | Pro | Gln | Ala | Glu | Ala | Leu | Leu | His |
| | | | 100 | | | | | 105 | | | | | 110 | | |
| Ala | Asp | Cys | Ser | Gly | Lys | Glu | Val | Thr | Cys | Glu | Ile | Ser | Arg | Tyr | Phe |
| | | 115 | | | | | 120 | | | | | 125 | | | |
| Leu | Gln | Met | Thr | Glu | Thr | Thr | Val | Lys | Thr | Ala | Ala | Trp | Phe | Met | Ala |
| | 130 | | | | | 135 | | | | | 140 | | | | |
| Asn | Val | Gln | Val | Ser | Gly | Gly | Pro | Ser | Ile | Ser | Leu | Val | Met | Lys |
| 145 | | | | | 150 | | | | | 155 | | | | | 160 |
| Thr | Pro | Arg | Val | Ala | Lys | Asn | Glu | Val | Leu | Trp | His | Pro | Thr | Leu | Asn |
| | | | | 165 | | | | | 170 | | | | | 175 | |
| Leu | Pro | Leu | Ser | Pro | Gln | Gly | Thr | Val | Arg | Thr | Ala | Val | Glu | Phe | Gln |
| | | | 180 | | | | | 185 | | | | | 190 | | |
| Val | Met | Thr | Gln | Thr | Gln | Ser | Leu | Ser | Phe | Leu | Leu | Gly | Ser | Ser | Ala |
| | | 195 | | | | | 200 | | | | | 205 | | | |
| Ser | Leu | Asp | Cys | Gly | Phe | Ser | Met | Ala | Pro | Gly | Leu | Asp | Leu | Ile | Ser |
| | 210 | | | | | 215 | | | | | 220 | | | | |
| Val | Glu | Trp | Arg | Leu | Gln | His | Lys | Gly | Arg | Gly | Gln | Leu | Val | Tyr | Ser |
| 225 | | | | | 230 | | | | | 235 | | | | | 240 |
| Trp | Thr | Ala | Gly | Gln | Gly | Gln | Ala | Val | Arg | Lys | Gly | Ala | Thr | Leu | Glu |
| | | | | 245 | | | | | 250 | | | | | 255 | |
| Pro | Ala | Gln | Leu | Gly | Met | Ala | Arg | Asp | Ala | Ser | Leu | Thr | Leu | Pro | Gly |
| | | | 260 | | | | | 265 | | | | | 270 | | |
| Leu | Thr | Ile | Gln | Asp | Glu | Gly | Thr | Tyr | Ile | Cys | Gln | Ile | Thr | Thr | Ser |
| | | 275 | | | | | 280 | | | | | 285 | | | |
| Leu | Tyr | Arg | Ala | Gln | Gln | Ile | Ile | Gln | Leu | Asn | Ile | Gln | Ala | Ser | Pro |
| | 290 | | | | | 295 | | | | | 300 | | | | |
| Lys | Val | Arg | Leu | Ser | Leu | Ala | Asn | Glu | Ala | Leu | Leu | Pro | Thr | Leu | Ile |
| 305 | | | | | 310 | | | | | 315 | | | | | 320 |
| Cys | Asp | Ile | Ala | Gly | Tyr | Tyr | Pro | Leu | Asp | Val | Val | Val | Thr | Trp | Thr |
| | | | | 325 | | | | | 330 | | | | | 335 | |
| Arg | Glu | Glu | Leu | Gly | Gly | Ser | Pro | Ala | Gln | Val | Ser | Gly | Ala | Ser | Phe |
| | | | 340 | | | | | 345 | | | | | 350 | | |
| Ser | Ser | Leu | Arg | Gln | Ser | Val | Ala | Gly | Thr | Tyr | Ser | Ile | Ser | Ser | Ser |
| | | 355 | | | | | 360 | | | | | 365 | | | |

```
Leu Thr Ala Glu Pro Gly Ser Ala Gly Ala Thr Tyr Thr Cys Gln Val
    370                 375                 380

Thr His Ile Ser Leu Glu Glu Pro Leu Gly Ala Ser Thr Gln Val Val
385                 390                 395                 400

Pro Pro Glu Arg Arg His Val Gly Gly Gly Ser Gly Gly Gly Gly
                405                 410                 415

Ser Gly Gly Gly Ser Thr Ser Glu Val Gln Leu Val Glu Ser Gly
            420                 425                 430

Gly Gly Leu Val Gln Pro Gly Gly Ser Leu Arg Leu Ser Cys Ala Ala
        435                 440                 445

Ser Gly Phe Thr Leu Asp Tyr Tyr Ala Lys Cys Trp Phe Arg Gln Ala
    450                 455                 460

Pro Gly Lys Glu Arg Glu Trp Val Ser Cys Ile Ser Ser Ser Asp Gly
465                 470                 475                 480

Ser Thr Tyr Tyr Ala Asp Ser Val Lys Gly Arg Phe Thr Ile Ser Arg
                485                 490                 495

Asp Asn Ala Lys Asn Thr Val Tyr Leu Gln Met Asn Ser Leu Lys Pro
            500                 505                 510

Glu Asp Thr Ala Val Tyr Phe Cys Ala Ala Arg His Gly Gly Pro Leu
        515                 520                 525

Thr Val Glu Tyr Phe Phe Asp Tyr Trp Gly Gln Gly Thr Gln Val Thr
    530                 535                 540

Val Ser Ser Gly Gly Gly Gly Ser
545                 550

<210> SEQ ID NO 15
<211> LENGTH: 1632
<212> TYPE: DNA
<213> ORGANISM: Artificial Sequence
<220> FEATURE:
<223> OTHER INFORMATION: sTAPBPR-LONG-PD-L1-NB4

<400> SEQUENCE: 15
atgggcacac aggagggctg gtgcctgctg ctctgcctgg ctctatctgg agcagcagaa     60
accaagcccc acccagcaga ggggcagtgg cgggcagtgg acgtggtcct agactgtttc    120
ctggtgaagg acgtgcgcca ccgtggagct ctcgccagca gtgaggacag gcaagggcc    180 tcccttgtgc tgaagcaggt gccagtgctg acgatggct ccctggagga cttcaccgat    240
ttccaagggg gcacactggc ccaagatgac ccacctatta tctttgaggc ctcagtggac    300
ctggtccaga ttccccaggc cgaggccttg ctccatgctg actgcagtgg aaggaggtg    360 acctgtgaga tctcccgcta ctttctccag atgacagaga ccactgttaa gacagcagct    420
tggttcatgg ccaacgtgca ggtctctgga ggggaccta gcatctcctt ggtgatgaag    480
actcccaggg tcgccaagaa tgaggtgctc tggcacccaa cgctgaactt gccactgagc    540
ccccagggga ctgtgcgaac tgcagtggag ttccaggtga tgacacagac ccaatccctg    600
agcttcctgc tggggtcctc agcctccttg gactgtggct ctccatggc accgggcttg    660 gacctcatca gtgtggagtg cgactgcag cacaagggca gggtcagtt ggtgtacagc    720 tggaccgcag gcagggca ggctgtgcgg aaggcgcta ccctggagcc tgcacaactg    780
ggcatggcca gggatgcctc cctcacccctg cccggcctca ctatacagga cgagggacc    840 tacatttgcc agatcaccac ctctctgtac cgagctcagc agatcatcca gctcaacatc    900
caagcttccc ctaaagtacg actgagcttg gcaaacgaag ctctgctgcc cacccctcatc    960
```

```
tgcgacattg ctggctatta ccctctggat gtggtggtga cgtggacccg agaggagctg    1020
ggtgggtccc cagcccaagt ctctggtgcc tccttctcca gcctcaggca aagcgtggca    1080
ggcacctaca gcatctcctc ctctctcacc gcagaacctg gctctgcagg tgccacttac    1140
acctgccagg tcacacacat ctctctggag gagccccttg gggccagcac ccaggttgtc    1200
ccaccagagc ggagacacgt gggtggcggt ggctccggtg gcggtggctc cggtggcggt    1260
ggctccacta gtgaggtgca gctggtggag agcggcggcg gcctggtgca ggccggcggc    1320
agcctgagac tgagctgcgc cgccagcggc agcaccttca gccagtacga cgtgggctgg    1380
tacagacagg cccccggcaa gcagagagag ctggtggcct tcagcagcag cggcggcaga    1440
accatctacc ccgacagcgt gaagggcaga ttcaccttca gcagagacaa caccaagaac    1500
accgtgtacc tgcagatgac cagcctgaag cccgaggaca ccgccgtgta ctactgcaag    1560
atcgactggt acctgaacag ctactggggc cagggcaccc aggtgaccgt gagcagcggc    1620
ggaggaggat ct                                                        1632
```

<210> SEQ ID NO 16  
<211> LENGTH: 544  
<212> TYPE: PRT  
<213> ORGANISM: Artificial Sequence  
<220> FEATURE:  
<223> OTHER INFORMATION: sTAPBPR-LONG-PD-L1-NB4

<400> SEQUENCE: 16

```
Met Gly Thr Gln Glu Gly Trp Cys Leu Leu Cys Leu Ala Leu Ser
1               5                   10                  15

Gly Ala Ala Glu Thr Lys Pro His Pro Ala Glu Gly Gln Trp Arg Ala
            20                  25                  30

Val Asp Val Leu Asp Cys Phe Leu Val Lys Asp Gly Ala His Arg
        35                  40                  45

Gly Ala Leu Ala Ser Ser Glu Asp Arg Ala Arg Ala Ser Leu Val Leu
    50                  55                  60

Lys Gln Val Pro Val Leu Asp Asp Gly Ser Leu Glu Asp Phe Thr Asp
65                  70                  75                  80

Phe Gln Gly Gly Thr Leu Ala Gln Asp Asp Pro Pro Ile Ile Phe Glu
                85                  90                  95

Ala Ser Val Asp Leu Val Gln Ile Pro Gln Ala Glu Ala Leu Leu His
                100                 105                 110

Ala Asp Cys Ser Gly Lys Glu Val Thr Cys Glu Ile Ser Arg Tyr Phe
            115                 120                 125

Leu Gln Met Thr Glu Thr Thr Val Lys Thr Ala Ala Trp Phe Met Ala
    130                 135                 140

Asn Val Gln Val Ser Gly Gly Pro Ser Ile Ser Leu Val Met Lys
145                 150                 155                 160

Thr Pro Arg Val Ala Lys Asn Glu Val Leu Trp His Pro Thr Leu Asn
                165                 170                 175

Leu Pro Leu Ser Pro Gln Gly Thr Val Arg Thr Ala Val Glu Phe Gln
                180                 185                 190

Val Met Thr Gln Thr Gln Ser Leu Ser Phe Leu Leu Gly Ser Ser Ala
            195                 200                 205

Ser Leu Asp Cys Gly Phe Ser Met Ala Pro Gly Leu Asp Leu Ile Ser
    210                 215                 220

Val Glu Trp Arg Leu Gln His Lys Gly Arg Gly Gln Leu Val Tyr Ser
225                 230                 235                 240
```

Trp Thr Ala Gly Gln Gly Gln Ala Val Arg Lys Gly Ala Thr Leu Glu
                245                 250                 255

Pro Ala Gln Leu Gly Met Ala Arg Asp Ala Ser Leu Thr Leu Pro Gly
            260                 265                 270

Leu Thr Ile Gln Asp Glu Gly Thr Tyr Ile Cys Gln Ile Thr Thr Ser
        275                 280                 285

Leu Tyr Arg Ala Gln Gln Ile Ile Gln Leu Asn Ile Gln Ala Ser Pro
    290                 295                 300

Lys Val Arg Leu Ser Leu Ala Asn Glu Ala Leu Leu Pro Thr Leu Ile
305                 310                 315                 320

Cys Asp Ile Ala Gly Tyr Tyr Pro Leu Asp Val Val Val Thr Trp Thr
                325                 330                 335

Arg Glu Glu Leu Gly Gly Ser Pro Ala Gln Val Ser Gly Ala Ser Phe
            340                 345                 350

Ser Ser Leu Arg Gln Ser Val Ala Gly Thr Tyr Ser Ile Ser Ser Ser
        355                 360                 365

Leu Thr Ala Glu Pro Gly Ser Ala Gly Ala Thr Tyr Thr Cys Gln Val
    370                 375                 380

Thr His Ile Ser Leu Glu Glu Pro Leu Gly Ala Ser Thr Gln Val Val
385                 390                 395                 400

Pro Pro Glu Arg Arg His Val Gly Gly Gly Ser Gly Gly Gly Gly Gly
                405                 410                 415

Ser Gly Gly Gly Gly Ser Thr Ser Glu Val Gln Leu Val Glu Ser Gly
            420                 425                 430

Gly Gly Leu Val Gln Ala Gly Gly Ser Leu Arg Leu Ser Cys Ala Ala
        435                 440                 445

Ser Gly Ser Thr Phe Ser Gln Tyr Asp Val Gly Trp Tyr Arg Gln Ala
    450                 455                 460

Pro Gly Lys Gln Arg Glu Leu Val Ala Phe Ser Ser Gly Gly Arg
465                 470                 475                 480

Thr Ile Tyr Pro Asp Ser Val Lys Gly Arg Phe Thr Phe Ser Arg Asp
                485                 490                 495

Asn Thr Lys Asn Thr Val Tyr Leu Gln Met Thr Ser Leu Lys Pro Glu
            500                 505                 510

Asp Thr Ala Val Tyr Tyr Cys Lys Ile Asp Trp Tyr Leu Asn Ser Tyr
        515                 520                 525

Trp Gly Gln Gly Thr Gln Val Thr Val Ser Ser Gly Gly Gly Gly Ser
    530                 535                 540

<210> SEQ ID NO 17
<211> LENGTH: 1407
<212> TYPE: DNA
<213> ORGANISM: Artificial Sequence
<220> FEATURE:
<223> OTHER INFORMATION: hTAPBPR full length (with TMD and cytoplasmic
      tail) (V41_G151_V169 polymorphisms as used in our studies)

<400> SEQUENCE: 17
atgggcacac aggagggctg gtgcctgctg ctctgcctgg ctctatctgg agcagcagaa      60
accaagcccc acccagcaga ggggcagtgg cgggcagtgg acgtggtcct agactgtttc     120
ctggtgaagg acggtgcgca ccgtggagct ctcgccagca gtgaggacag ggcaagggcc     180
tcccttgtgc tgaagcaggt gccagtgctg acgatggct ccctggagga cttcaccgat     240
ttccaagggg gcacactggc ccaagatgac ccacctatta tctttgaggc ctcagtggac     300
ctggtccaga ttccccaggc cgaggccttg ctccatgctg actgcagtgg gaaggaggtg     360

```
acctgtgaga tctcccgcta ctttctccag atgacagaga ccactgttaa gacagcagct    420
tggttcatgg ccaacgtgca ggtctctgga gggggaccta gcatctcctt ggtgatgaag    480
actcccaggg tcgccaagaa tgaggtgctc tggcacccaa cgctgaactt gccactgagc    540
ccccagggga ctgtgcgaac tgcagtggag ttccaggtga tgacacagac ccaatccctg    600
agcttcctgc tggggtcctc agcctccttg gactgtggct ctccatggc accgggcttg     660 gacctcatca gtgtggagtg cgactgcag cacaagggca ggggtcagtt ggtgtacagc     720
tggaccgcag gcagggggca ggctgtgcgg aagggcgcta ccctggagcc tgcacaactg    780
ggcatggcca gggatgcctc cctcaccctg cccggcctca ctatacagga cgaggggacc    840
tacatttgcc agatcaccac ctctctgtac cgagctcagc agatcatcca gctcaacatc    900
caagcttccc ctaaagtacg actgagcttg caaacgaag ctctgctgcc caccctcatc     960
tgcgacattg ctggctatta ccctctggat gtggtggtga cgtggacccg agaggagctg   1020
ggtgggtccc cagcccaagt ctctggtgcc tccttctcca gcctcaggca aagcgtggca   1080
ggcacctaca gcatctcctc ctctctcacc gcagaacctg gctctgcagg tgccacttac   1140
acctgccagg tcacacacat ctctctggag gagccccttg gggccagcac ccaggttgtc   1200
ccaccagagc ggagaacagc cttgggagtc atctttgcca gcagtctctt ccttcttgca   1260
ctgatgttcc tggggcttca gagacggcaa gcacctacag gacttgggct gcttcaggct   1320
gaacgctggg agaccacttc ctgtgctgac acacagagct cccatctcca tgaagaccgc   1380
acagcgcgtg taagccagcc cagctga                                       1407
```

<210> SEQ ID NO 18
<211> LENGTH: 468
<212> TYPE: PRT
<213> ORGANISM: Artificial Sequence
<220> FEATURE:
<223> OTHER INFORMATION: hTAPBPR full length (with TMD and cytoplasmic tail) (V41_G151_V169 polymorphisms as used herein)

<400> SEQUENCE: 18

```
Met Gly Thr Gln Glu Gly Trp Cys Leu Leu Cys Leu Ala Leu Ser
1               5                   10                  15

Gly Ala Ala Glu Thr Lys Pro His Pro Ala Glu Gly Gln Trp Arg Ala
            20                  25                  30

Val Asp Val Val Leu Asp Cys Phe Leu Val Lys Asp Gly Ala His Arg
        35                  40                  45

Gly Ala Leu Ala Ser Ser Glu Asp Arg Ala Arg Ala Ser Leu Val Leu
    50                  55                  60

Lys Gln Val Pro Val Leu Asp Asp Gly Ser Leu Glu Asp Phe Thr Asp
65                  70                  75                  80

Phe Gln Gly Gly Thr Leu Ala Gln Asp Asp Pro Ile Ile Phe Glu
                85                  90                  95

Ala Ser Val Asp Leu Val Gln Ile Pro Gln Ala Glu Ala Leu Leu His
            100                 105                 110

Ala Asp Cys Ser Gly Lys Glu Val Thr Cys Glu Ile Ser Arg Tyr Phe
        115                 120                 125

Leu Gln Met Thr Glu Thr Thr Val Lys Thr Ala Ala Trp Phe Met Ala
    130                 135                 140

Asn Val Gln Val Ser Gly Gly Gly Pro Ser Ile Ser Leu Val Met Lys
145                 150                 155                 160

Thr Pro Arg Val Ala Lys Asn Glu Val Leu Trp His Pro Thr Leu Asn
```

```
                    165                 170                 175
Leu Pro Leu Ser Pro Gln Gly Thr Val Arg Thr Ala Val Glu Phe Gln
            180                 185                 190

Val Met Thr Gln Thr Gln Ser Leu Ser Phe Leu Leu Gly Ser Ser Ala
        195                 200                 205

Ser Leu Asp Cys Gly Phe Ser Met Ala Pro Gly Leu Asp Leu Ile Ser
    210                 215                 220

Val Glu Trp Arg Leu Gln His Lys Gly Arg Gly Gln Leu Val Tyr Ser
225                 230                 235                 240

Trp Thr Ala Gly Gln Gly Gln Ala Val Arg Lys Gly Ala Thr Leu Glu
                245                 250                 255

Pro Ala Gln Leu Gly Met Ala Arg Asp Ala Ser Leu Thr Leu Pro Gly
            260                 265                 270

Leu Thr Ile Gln Asp Glu Gly Thr Tyr Ile Cys Gln Ile Thr Thr Ser
        275                 280                 285

Leu Tyr Arg Ala Gln Gln Ile Ile Gln Leu Asn Ile Gln Ala Ser Pro
    290                 295                 300

Lys Val Arg Leu Ser Leu Ala Asn Glu Ala Leu Leu Pro Thr Leu Ile
305                 310                 315                 320

Cys Asp Ile Ala Gly Tyr Tyr Pro Leu Asp Val Val Thr Trp Thr
                325                 330                 335

Arg Glu Glu Leu Gly Gly Ser Pro Ala Gln Val Ser Gly Ala Ser Phe
            340                 345                 350

Ser Ser Leu Arg Gln Ser Val Ala Gly Thr Tyr Ser Ile Ser Ser Ser
        355                 360                 365

Leu Thr Ala Glu Pro Gly Ser Ala Gly Ala Thr Tyr Thr Cys Gln Val
    370                 375                 380

Thr His Ile Ser Leu Glu Glu Pro Leu Gly Ala Ser Thr Gln Val Val
385                 390                 395                 400

Pro Pro Glu Arg Arg Thr Ala Leu Gly Val Ile Phe Ala Ser Ser Leu
                405                 410                 415

Phe Leu Leu Ala Leu Met Phe Leu Gly Leu Gln Arg Arg Gln Ala Pro
            420                 425                 430

Thr Gly Leu Gly Leu Leu Gln Ala Glu Arg Trp Glu Thr Thr Ser Cys
        435                 440                 445

Ala Asp Thr Gln Ser Ser His Leu His Glu Asp Arg Thr Ala Arg Val
    450                 455                 460

Ser Gln Pro Ser
465

<210> SEQ ID NO 19
<211> LENGTH: 1356
<212> TYPE: DNA
<213> ORGANISM: Artificial Sequence
<220> FEATURE:
<223> OTHER INFORMATION: mouse TAPBPR full length

<400> SEQUENCE: 19
atgggcttgg agcccagctg gtatctgctg ctctgtttgg ctgtctctgg ggcagcaggg      60
actgaccctc ccacagcgcc caccacagca gaaagacagc ggcagcccac ggacatcatc     120
ttagactgct tcttggtgac agaagacagg caccgcgggg cttttgccag cagtggggac     180
agggagaggg ccttgcttgt gctgaagcag gtaccagtgc tggatgatgg ctccctggaa     240
ggcatcacag atttccaggg gagcactgag accaaacagg attcacctgt tatctttgag     300
```

```
gcctcagtgg acttggtaca gattccccag gcagaggcgt tgctccatgc tgactgcagc    360
gggaaggcag tgacctgcga gatctccaag tatttcctcc aggccagaca agaggccact    420
tttgagaaag cacattggtt catcagcaac atgcaggttt ctagaggtgg ccccagtgtc    480
tccatggtga tgaagactct aagagatgct gaagttggag ctgtccggca ccctacactg    540
aacctacctc tgagtgccca gggcacagtg aagactcaag tggagttcca ggtgacatca    600
gagacccaaa ccctgaacca cctgctgggg tcctctgtct ccctgcactg cagtttctcc    660
atggcaccag acctggacct cactggcgtg gagtggcggc tgcagcataa aggcagcggc    720
cagctggtgt acagctggaa gacagggcag gggcaggcca gcgcaagggc gctacactg    780 gagcctgagg agctactcag ggctggaaac gcctctctca ccttacccaa cctcactcta    840
aaggatgagg ggacctacat ctgccagatc tccacctctc tgtatcaagc tcaacagatc    900
atgccactta acatcctggc tccccccaaa gtacaactgc acttggcaaa caaggaccct    960
ctgccttccc tcgtctgcag cattgccggc tactatcctc tggatgtggg agtgacgtgg   1020
attcgagagg agctgggtgg aattccagcc caagtctctg gtgcctcctt ctccagcctc   1080
aggcagagca cgatgggaac ctacagcatt tcttccacgg tgatggctga cccaggcccc   1140
acaggtgcca cttatacctg ccaagtcgcc cacgtctccc tggaggagcc ccttacaacc   1200
agcatgaggg ttttgccaaa tccagagcag agaggaacct gggagtcat ctttgccagc   1260 atcatcttcc tttctgcgct gttgttgttt ctgggacttc acagacagca agcttcttcg   1320
tcaaggtcca ccaggcctat gaggcattct gggtga                             1356
```

<210> SEQ ID NO 20
<211> LENGTH: 451
<212> TYPE: PRT
<213> ORGANISM: Artificial Sequence
<220> FEATURE:
<223> OTHER INFORMATION: mouse TAPBPR full length

<400> SEQUENCE: 20

```
Met Gly Leu Glu Pro Ser Trp Tyr Leu Leu Cys Leu Ala Val Ser
1               5                   10                  15

Gly Ala Ala Gly Thr Asp Pro Pro Thr Ala Pro Thr Thr Ala Glu Arg
            20                  25                  30

Gln Arg Gln Pro Thr Asp Ile Ile Leu Asp Cys Phe Leu Val Thr Glu
        35                  40                  45

Asp Arg His Arg Gly Ala Phe Ala Ser Ser Gly Asp Arg Glu Arg Ala
    50                  55                  60

Leu Leu Val Leu Lys Gln Val Pro Val Leu Asp Gly Ser Leu Glu
65                  70                  75                  80

Gly Ile Thr Asp Phe Gln Gly Ser Thr Glu Thr Lys Gln Asp Ser Pro
                85                  90                  95

Val Ile Phe Glu Ala Ser Val Asp Leu Val Gln Ile Pro Gln Ala Glu
            100                 105                 110

Ala Leu Leu His Ala Asp Cys Ser Gly Lys Ala Val Thr Cys Glu Ile
        115                 120                 125

Ser Lys Tyr Phe Leu Gln Ala Arg Gln Glu Ala Thr Phe Glu Lys Ala
    130                 135                 140

His Trp Phe Ile Ser Asn Met Gln Val Ser Arg Gly Gly Pro Ser Val
145                 150                 155                 160

Ser Met Val Met Lys Thr Leu Arg Asp Ala Glu Val Gly Ala Val Arg
                165                 170                 175
```

His Pro Thr Leu Asn Leu Pro Leu Ser Ala Gln Gly Thr Val Lys Thr
            180                 185                 190

Gln Val Glu Phe Gln Val Thr Ser Glu Thr Gln Thr Leu Asn His Leu
        195                 200                 205

Leu Gly Ser Ser Val Ser Leu His Cys Ser Phe Ser Met Ala Pro Asp
    210                 215                 220

Leu Asp Leu Thr Gly Val Glu Trp Arg Leu Gln His Lys Gly Ser Gly
225                 230                 235                 240

Gln Leu Val Tyr Ser Trp Lys Thr Gly Gln Gly Ala Lys Arg Lys
                245                 250                 255

Gly Ala Thr Leu Glu Pro Glu Glu Leu Leu Arg Ala Gly Asn Ala Ser
            260                 265                 270

Leu Thr Leu Pro Asn Leu Thr Leu Lys Asp Glu Gly Thr Tyr Ile Cys
        275                 280                 285

Gln Ile Ser Thr Ser Leu Tyr Gln Ala Gln Gln Ile Met Pro Leu Asn
    290                 295                 300

Ile Leu Ala Pro Pro Lys Val Gln Leu His Leu Ala Asn Lys Asp Pro
305                 310                 315                 320

Leu Pro Ser Leu Val Cys Ser Ile Ala Gly Tyr Tyr Pro Leu Asp Val
                325                 330                 335

Gly Val Thr Trp Ile Arg Glu Glu Leu Gly Gly Ile Pro Ala Gln Val
            340                 345                 350

Ser Gly Ala Ser Phe Ser Ser Leu Arg Gln Ser Thr Met Gly Thr Tyr
        355                 360                 365

Ser Ile Ser Ser Thr Val Met Ala Asp Pro Gly Pro Thr Gly Ala Thr
    370                 375                 380

Tyr Thr Cys Gln Val Ala His Val Ser Leu Glu Glu Pro Leu Thr Thr
385                 390                 395                 400

Ser Met Arg Val Leu Pro Asn Pro Glu Gln Arg Gly Thr Leu Gly Val
                405                 410                 415

Ile Phe Ala Ser Ile Ile Phe Leu Ser Ala Leu Leu Leu Phe Leu Gly
            420                 425                 430

Leu His Arg Gln Gln Ala Ser Ser Ser Arg Ser Thr Arg Pro Met Arg
        435                 440                 445

His Ser Gly
    450

<210> SEQ ID NO 21
<211> LENGTH: 1176
<212> TYPE: DNA
<213> ORGANISM: Artificial Sequence
<220> FEATURE:
<223> OTHER INFORMATION: luminal domains of mouse TAPBPR

<400> SEQUENCE: 21
gaccctccca cagcgcccac cacagcagaa agacagcggc agcccacgga catcatctta      60
gactgcttct tggtgacaga agacaggcac cgcggggctt tgccagcag tggggacagg     120 gagagggcct tgcttgtgct gaagcaggta ccagtgctgg atgatggctc cctggaaggc     180
atcacagatt ccaggggag cactgagacc aaacaggatt cacctgttat ctttgaggcc     240
tcagtggact tggtacagat cccccaggca gaggcgttgc tccatgctga ctgcagcggg     300
aaggcagtga cctgcgagat ctccaagtat ttcctccagg ccagacaaga ggccactttt     360
gagaaagcac attggttcat cagcaacatg caggtttcta gaggtggccc cagtgtctcc     420
atggtgatga agactctaag agatgctgaa gttggagctg tccggcaccc tacactgaac     480

```
ctacctctga gtgcccaggg cacagtgaag actcaagtgg agttccaggt gacatcagag      540
acccaaaccc tgaaccacct gctgggtcc tctgtctccc tgcactgcag tttctccatg       600
gcaccagacc tggacctcac tggcgtggag tggcggctgc agcataaagg cagcggccag      660
ctggtgtaca gctggaagac agggcagggg caggccaagc gcaagggcgc tacactggag      720
cctgaggagc tactcagggc tggaaacgcc tctctcacct tacccaacct cactctaaag      780
gatgagggga cctacatctg ccagatctcc acctctctgt atcaagctca acagatcatg      840
ccacttaaca tcctggctcc ccccaaagta caactgcact ggcaaacaa ggaccctctg       900 ccttccctcg tctgcagcat tgccggctac tatcctctgg atgtgggagt gacgtggatt      960
cgagaggagc tgggtggaat tccagcccaa gtctctggtg cctccttctc cagcctcagg    1020
cagagcacga tgggaaccta cagcatttct tccacggtga tggctgaccc aggccccaca    1080
ggtgccactt ataccctgcca agtcgcccac gtctccctgg aggagcccct tacaaccagc   1140
atgagggttt tgccaaatcc agagcagaga ggaacc                              1176
```

<210> SEQ ID NO 22
<211> LENGTH: 392
<212> TYPE: PRT
<213> ORGANISM: Artificial Sequence
<220> FEATURE:
<223> OTHER INFORMATION: luminal domains of mouse TAPBPR

<400> SEQUENCE: 22

```
Asp Pro Pro Thr Ala Pro Thr Thr Ala Glu Arg Gln Arg Gln Pro Thr
1               5                   10                  15

Asp Ile Ile Leu Asp Cys Phe Leu Val Thr Glu Asp Arg His Arg Gly
                20                  25                  30

Ala Phe Ala Ser Ser Gly Asp Arg Glu Arg Ala Leu Leu Val Leu Lys
            35                  40                  45

Gln Val Pro Val Leu Asp Asp Gly Ser Leu Glu Gly Ile Thr Asp Phe
        50                  55                  60

Gln Gly Ser Thr Glu Thr Lys Gln Asp Ser Pro Val Ile Phe Glu Ala
65                  70                  75                  80

Ser Val Asp Leu Val Gln Ile Pro Gln Ala Glu Ala Leu Leu His Ala
                85                  90                  95

Asp Cys Ser Gly Lys Ala Val Thr Cys Glu Ile Ser Lys Tyr Phe Leu
            100                 105                 110

Gln Ala Arg Gln Glu Ala Thr Phe Glu Lys Ala His Trp Phe Ile Ser
        115                 120                 125

Asn Met Gln Val Ser Arg Gly Gly Pro Ser Val Ser Met Val Met Lys
130                 135                 140

Thr Leu Arg Asp Ala Glu Val Gly Ala Val Arg His Pro Thr Leu Asn
145                 150                 155                 160

Leu Pro Leu Ser Ala Gln Gly Thr Val Lys Thr Gln Val Glu Phe Gln
                165                 170                 175

Val Thr Ser Glu Thr Gln Thr Leu Asn His Leu Leu Gly Ser Ser Val
            180                 185                 190

Ser Leu His Cys Ser Phe Ser Met Ala Pro Asp Leu Asp Leu Thr Gly
        195                 200                 205

Val Glu Trp Arg Leu Gln His Lys Gly Ser Gly Gln Leu Val Tyr Ser
        210                 215                 220

Trp Lys Thr Gly Gln Gly Gln Ala Lys Arg Lys Gly Ala Thr Leu Glu
225                 230                 235                 240
```

```
Pro Glu Glu Leu Leu Arg Ala Gly Asn Ala Ser Leu Thr Leu Pro Asn
                245                 250                 255

Leu Thr Leu Lys Asp Glu Gly Thr Tyr Ile Cys Gln Ile Ser Thr Ser
            260                 265                 270

Leu Tyr Gln Ala Gln Gln Ile Met Pro Leu Asn Ile Leu Ala Pro Pro
        275                 280                 285

Lys Val Gln Leu His Leu Ala Asn Lys Asp Pro Leu Pro Ser Leu Val
    290                 295                 300

Cys Ser Ile Ala Gly Tyr Tyr Pro Leu Asp Val Gly Val Thr Trp Ile
305                 310                 315                 320

Arg Glu Glu Leu Gly Gly Ile Pro Ala Gln Val Ser Gly Ala Ser Phe
                325                 330                 335

Ser Ser Leu Arg Gln Ser Thr Met Gly Thr Tyr Ser Ile Ser Ser Thr
            340                 345                 350

Val Met Ala Asp Pro Gly Pro Thr Gly Ala Thr Tyr Thr Cys Gln Val
        355                 360                 365

Ala His Val Ser Leu Glu Glu Pro Leu Thr Thr Ser Met Arg Val Leu
    370                 375                 380

Pro Asn Pro Glu Gln Arg Gly Thr
385                 390

<210> SEQ ID NO 23
<211> LENGTH: 267
<212> TYPE: PRT
<213> ORGANISM: Artificial Sequence
<220> FEATURE:
<223> OTHER INFORMATION: 23 Anti-HER2 svFc

<400> SEQUENCE: 23

Ala Asp Leu Gly Ser Arg Ala Met Ala Gln Val Gln Leu Val Gln Ser
1               5                   10                  15

Gly Ala Glu Val Lys Lys Pro Gly Glu Ser Leu Lys Ile Ser Cys Lys
                20                  25                  30

Gly Ser Gly Tyr Ser Phe Thr Ser Tyr Trp Ile Ala Trp Val Arg Gln
            35                  40                  45

Met Pro Gly Lys Gly Leu Glu Tyr Met Gly Leu Ile Tyr Pro Gly Asp
        50                  55                  60

Ser Asp Thr Lys Tyr Ser Pro Ser Phe Gln Gly Gln Val Thr Ile Ser
65                  70                  75                  80

Val Asp Lys Ser Val Ser Thr Ala Tyr Leu Gln Trp Ser Ser Leu Lys
                85                  90                  95

Pro Ser Asp Ser Ala Val Tyr Phe Cys Ala Arg His Asp Val Gly Tyr
            100                 105                 110

Cys Ser Ser Ser Asn Cys Ala Lys Trp Pro Glu Tyr Phe Gln His Trp
        115                 120                 125

Gly Gln Gly Thr Leu Val Thr Val Ser Ser Gly Gly Gly Ser Gly
    130                 135                 140

Gly Gly Gly Ser Gly Gly Gly Ser Gln Ser Val Leu Thr Gln Pro
145                 150                 155                 160

Pro Ser Val Ser Ala Ala Pro Gly Gln Lys Val Thr Ile Ser Cys Ser
            165                 170                 175

Gly Ser Ser Ser Asn Ile Gly Asn Asn Tyr Val Ser Trp Tyr Gln Gln
        180                 185                 190

Leu Pro Gly Thr Ala Pro Lys Leu Leu Ile Tyr Asp His Thr Asn Arg
    195                 200                 205
```

```
Pro Ala Gly Val Pro Asp Arg Phe Ser Gly Ser Lys Ser Gly Thr Ser
        210                 215                 220

Ala Ser Leu Ala Ile Ser Gly Phe Arg Ser Glu Asp Glu Ala Asp Tyr
225                 230                 235                 240

Tyr Cys Ala Ser Trp Asp Tyr Thr Leu Ser Gly Trp Val Phe Gly Gly
                245                 250                 255

Gly Thr Lys Leu Thr Val Leu Gly Ala Ala Ala
        260                 265

<210> SEQ ID NO 24
<211> LENGTH: 214
<212> TYPE: PRT
<213> ORGANISM: Artificial Sequence
<220> FEATURE:
<223> OTHER INFORMATION: 24 Anti-HER2 (trastuzumab) Light chain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 451
<212> TYPE: PRT
<213> ORGANISM: Artificial Sequence
<220> FEATURE:
<223> OTHER INFORMATION: Anti-HER2 (trastuzumab) Heavy chain

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

-continued

```
            20                  25                  30
Tyr Ile His Trp Val Arg Gln Ala Pro Gly Lys Gly Leu Glu Trp Val
            35                  40                  45
Ala Arg Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Pro Lys Ser Cys
                210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
```

```
Pro Gly Lys
    450

<210> SEQ ID NO 26
<211> LENGTH: 126
<212> TYPE: PRT
<213> ORGANISM: Artificial Sequence
<220> FEATURE:
<223> OTHER INFORMATION: Anti-PDL1 nanobody

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Trp Ala
        35                  40                  45

Ser Ser Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Phe
65                  70                  75                  80

Leu Gln Met Asn Ser Leu Lys Pro Glu Asp Thr Ala Val Tyr Ser Cys
                85                  90                  95

Ala Ala Ser Gln Ala Pro Ile Thr Ile Ala Thr Met Met Lys Pro Phe
            100                 105                 110

Tyr Asp Tyr Trp Gly Gln Gly Thr Gln Val Thr Val Ser Ser
        115                 120                 125

<210> SEQ ID NO 27
<211> LENGTH: 123
<212> TYPE: PRT
<213> ORGANISM: Artificial Sequence
<220> FEATURE:
<223> OTHER INFORMATION: Anti-PDL1 nanobody

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Lys Cys Trp Phe Arg Gln Ala Pro Gly Lys Glu Arg Glu Trp Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Phe Cys
                85                  90                  95

Ala Ala Arg His Gly Pro Leu Thr Val Glu Tyr Phe Phe Asp Tyr
            100                 105                 110

Trp Gly Gln Gly Thr Gln Val Thr Val Ser Ser
        115                 120

<210> SEQ ID NO 28
<211> LENGTH: 124
<212> TYPE: PRT
<213> ORGANISM: Artificial Sequence
<220> FEATURE:
<223> OTHER INFORMATION: Anti-PDL1 nanobody
```

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Tyr
            20                  25                  30

Ala Ile Gly Trp Phe Arg Gln Ala Pro Gly Lys Ala Arg Glu Gly Val
        35                  40                  45

Ser Cys Ile Ser Gly Gly Asp Asn Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Gly Gly Trp Lys Tyr Cys Ser Gly Tyr Asp Pro Glu Tyr Ile
            100                 105                 110

Tyr Trp Gly Gln Gly Thr Gln Val Thr Val Ser Ser
            115                 120

<210> SEQ ID NO 29
<211> LENGTH: 115
<212> TYPE: PRT
<213> ORGANISM: Artificial Sequence
<220> FEATURE:
<223> OTHER INFORMATION: Anti-PDL1 nanobody

<400> SEQUENCE: 29

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Gln Tyr
            20                  25                  30

Asp Val Gly Trp Tyr Arg Gln Ala Pro Gly Lys Gln Arg Glu Leu Val
        35                  40                  45

Ala Phe Ser Ser Ser Gly Gly Arg Thr Ile Tyr Pro Asp Ser Val Lys
    50                  55                  60

Gly Arg Phe Thr Phe Ser Arg Asp Asn Thr Lys Asn Thr Val Tyr Leu
65                  70                  75                  80

Gln Met Thr Ser Leu Lys Pro Glu Asp Thr Ala Val Tyr Tyr Cys Lys
                85                  90                  95

Ile Asp Trp Tyr Leu Asn Ser Tyr Trp Gly Gln Gly Thr Gln Val Thr
            100                 105                 110

Val Ser Ser
115

<210> SEQ ID NO 30
<211> LENGTH: 114
<212> TYPE: PRT
<213> ORGANISM: Artificial Sequence
<220> FEATURE:
<223> OTHER INFORMATION: Anti-PDL1 nanobody

<400> SEQUENCE: 30

Glu Val Gln Leu Val Glu Ser Gly Gly Gly Leu Val Gln Ala Gly Gly
1               5                   10                  15

Ser Leu Arg Leu Ser Cys Ala Ala Ser Gly Val Asp Ala Ser Asn Ser
            20                  25                  30

Ala Met Gly Trp Tyr Arg Gln Ala Pro Gly Lys Gln Arg Glu Trp Val
        35                  40                  45

Ala Arg Ile Thr Gly Gly Gly Leu Ile Ala Tyr Thr Asp Ser Val Lys
            50                  55                  60

Gly Arg Phe Thr Ile Ser Arg Asp Asn Ala Lys Ser Thr Val Tyr Leu
 65                  70                  75                  80

Gln Met Trp Ser Leu Glu Pro Glu Asp Thr Ala Val Tyr Tyr Cys Asn
                85                  90                  95

Thr Ile Asn Ser Arg Asp Gly Trp Gly Gln Gly Thr Gln Val Thr Val
            100                 105                 110

Ser Ser

<210> SEQ ID NO 31
<211> LENGTH: 111
<212> TYPE: PRT
<213> ORGANISM: Artificial Sequence
<220> FEATURE:
<223> OTHER INFORMATION: Anti-PDL1 nanobody

<400> SEQUENCE: 31

Glu Val Gln Leu Val Glu Ser Gly Gly Gly Leu Val Gln Ala Gly Gly
 1               5                  10                  15

Ser Leu Thr Ile Ser Cys Ala Ala Ser Gly Ile Thr Phe Ser Asp Ser
            20                  25                  30

Ile Val Ser Trp Tyr Arg Arg Ala Arg Gly Lys Gln Arg Glu Trp Val
        35                  40                  45

Ala Gly Ile Ser Asn Gly Gly Thr Thr Lys Tyr Ala Glu Ser Val Leu
    50                  55                  60

Gly Arg Phe Thr Ile Ser Arg Asp Asn Ala Lys Asn Met Val Tyr Leu
 65                  70                  75                  80

Gln Met Trp Gly Leu Asn Pro Glu Asp Thr Ala Val Tyr Leu Cys Lys
                85                  90                  95

Val Arg Gln Tyr Trp Gly Gln Gly Thr Gln Val Thr Val Ser Ser
            100                 105                 110

<210> SEQ ID NO 32
<211> LENGTH: 21
<212> TYPE: PRT
<213> ORGANISM: Artificial Sequence
<220> FEATURE:
<223> OTHER INFORMATION: Human TAPBPR TMD

<400> SEQUENCE: 32

Thr Ala Leu Gly Val Ile Phe Ala Ser Ser Leu Phe Leu Leu Ala Leu
 1               5                  10                  15

Met Phe Leu Gly Leu
            20

<210> SEQ ID NO 33
<211> LENGTH: 1362
<212> TYPE: DNA
<213> ORGANISM: Artificial Sequence
<220> FEATURE:
<223> OTHER INFORMATION: hTAPBPR-CD8 cytoplasmic tail

<400> SEQUENCE: 33
atgggcacac aggagggctg gtgcctgctg ctctgcctgg ctctatctgg agcagcagaa      60
accaagcccc acccagcaga ggggcagtgg cgggcagtgg acgtggtcct agactgtttc    120
ctggtgaagg acggtgcgca ccgtggagct ctcgccagca gtgaggacag gcaagggcc     180 tcccttgtgc tgaagcaggt gccagtgctg acgatggct cctggagga cttcaccgat     240

-continued

```
ttccaagggg gcacactggc ccaagatgac ccacctatta tctttgaggc ctcagtggac       300
ctggtccaga ttcccaggc cgaggccttg ctccatgctg actgcagtgg aaggaggtg        360
acctgtgaga tctcccgcta ctttctccag atgacagaga ccactgttaa gacagcagct      420
tggttcatgg ccaacgtgca ggtctctgga gggggaccta gcatctcctt ggtgatgaag      480
actcccaggg tcgccaagaa tgaggtgctc tggcacccaa cgctgaactt gccactgagc      540
ccccagggga ctgtgcgaac tgcagtggag ttccaggtga tgacacagac caatccctg       600
agcttcctgc tggggtcctc agcctccttg gactgtggct ctccatggc accgggcttg      660
gacctcatca gtgtggagtg cgactgcag acaagggca ggggtcagtt ggtgtacagc       720
tggaccgcag gcagggca ggctgtgcgg aagggcgcta ccctggagcc tgcacaactg       780
ggcatggcca gggatgcctc cctcaccctg cccggcctca ctatacagga cgaggggacc      840
tacatttgcc agatcaccac ctctctgtac cgagctcagc agatcatcca gctcaacatc     900
caagcttccc ctaaagtacg actgagcttg caaacgaag ctctgctgcc caccctcatc      960
tgcgacattg ctggctatta ccctctggat gtggtggtga cgtggaccg agaggagctg     1020
ggtgggtccc cagcccaagt ctctggtgcc tccttctcca gcctcaggca aagcgtggca    1080
ggcacctaca gcatctcctc ctctctcacc gcagaacctg gctctgcagg tgccacttac     1140
acctgccagg tcacacacat ctctctggag gagcccttg gggccagcac ccaggttgtc     1200
ccaccagagc ggagaacagc cttgggagtc atctttgcca gcagtctctt ccttcttgca    1260
ctgatgttcc tggggcttca gagacgaaga cgtgtttgca aatgtccccg gcctgtggtc    1320
aaatcgggag acaagcccag cctttcggcg agatacgtct aa                       1362
```

<210> SEQ ID NO 34
<211> LENGTH: 453
<212> TYPE: PRT
<213> ORGANISM: Artificial Sequence
<220> FEATURE:
<223> OTHER INFORMATION: TAPBPR-CD8 cytoplasmic tail

<400> SEQUENCE: 34

```
Met Gly Thr Gln Glu Gly Trp Cys Leu Leu Cys Leu Ala Leu Ser
1               5                   10                  15

Gly Ala Ala Glu Thr Lys Pro His Pro Ala Glu Gly Gln Trp Arg Ala
            20                  25                  30

Val Asp Val Val Leu Asp Cys Phe Leu Val Lys Asp Gly Ala His Arg
        35                  40                  45

Gly Ala Leu Ala Ser Ser Glu Asp Arg Ala Arg Ala Ser Leu Val Leu
    50                  55                  60

Lys Gln Val Pro Val Leu Asp Asp Gly Ser Leu Glu Asp Phe Thr Asp
65                  70                  75                  80

Phe Gln Gly Gly Thr Leu Ala Gln Asp Asp Pro Pro Ile Ile Phe Glu
                85                  90                  95

Ala Ser Val Asp Leu Val Gln Ile Pro Gln Ala Glu Ala Leu Leu His
            100                 105                 110

Ala Asp Cys Ser Gly Lys Glu Val Thr Cys Glu Ile Ser Arg Tyr Phe
        115                 120                 125

Leu Gln Met Thr Glu Thr Thr Val Lys Thr Ala Ala Trp Phe Met Ala
    130                 135                 140

Asn Val Gln Val Ser Gly Gly Gly Pro Ser Ile Ser Leu Val Met Lys
145                 150                 155                 160
```

-continued

```
Thr Pro Arg Val Ala Lys Asn Glu Val Leu Trp His Pro Thr Leu Asn
                165                 170                 175
Leu Pro Leu Ser Pro Gln Gly Thr Val Arg Thr Ala Val Glu Phe Gln
            180                 185                 190
Val Met Thr Gln Thr Gln Ser Leu Ser Phe Leu Leu Gly Ser Ser Ala
        195                 200                 205
Ser Leu Asp Cys Gly Phe Ser Met Ala Pro Gly Leu Asp Leu Ile Ser
    210                 215                 220
Val Glu Trp Arg Leu Gln His Lys Gly Arg Gly Gln Leu Val Tyr Ser
225                 230                 235                 240
Trp Thr Ala Gly Gln Gly Gln Ala Val Arg Lys Gly Ala Thr Leu Glu
                245                 250                 255
Pro Ala Gln Leu Gly Met Ala Arg Asp Ala Ser Leu Thr Leu Pro Gly
            260                 265                 270
Leu Thr Ile Gln Asp Glu Gly Thr Tyr Ile Cys Gln Ile Thr Thr Ser
        275                 280                 285
Leu Tyr Arg Ala Gln Gln Ile Ile Gln Leu Asn Ile Gln Ala Ser Pro
    290                 295                 300
Lys Val Arg Leu Ser Leu Ala Asn Glu Ala Leu Leu Pro Thr Leu Ile
305                 310                 315                 320
Cys Asp Ile Ala Gly Tyr Tyr Pro Leu Asp Val Val Thr Trp Thr
                325                 330                 335
Arg Glu Glu Leu Gly Gly Ser Pro Ala Gln Val Ser Gly Ala Ser Phe
                340                 345                 350
Ser Ser Leu Arg Gln Ser Val Ala Gly Thr Tyr Ser Ile Ser Ser Ser
            355                 360                 365
Leu Thr Ala Glu Pro Gly Ser Ala Gly Ala Thr Tyr Thr Cys Gln Val
    370                 375                 380
Thr His Ile Ser Leu Glu Glu Pro Leu Gly Ala Ser Thr Gln Val Val
385                 390                 395                 400
Pro Pro Glu Arg Arg Thr Ala Leu Gly Val Ile Phe Ala Ser Ser Leu
                405                 410                 415
Phe Leu Leu Ala Leu Met Phe Leu Gly Leu Gln Arg Arg Arg Arg Val
            420                 425                 430
Cys Lys Cys Pro Arg Pro Val Val Lys Ser Gly Asp Lys Pro Ser Leu
        435                 440                 445
Ser Ala Arg Tyr Val
    450

<210> SEQ ID NO 35
<211> LENGTH: 9
<212> TYPE: PRT
<213> ORGANISM: Artificial Sequence
<220> FEATURE:
<223> OTHER INFORMATION: HLA binding peptide
<220> FEATURE:
<221> NAME/KEY: misc_feature
<222> LOCATION: (5)..(5)
<223> OTHER INFORMATION: K = lysine labelled with TAMRA

<400> SEQUENCE: 35

Glu Thr Val Ser Lys Gln Ser Asn Val
1               5

<210> SEQ ID NO 36
<211> LENGTH: 9
<212> TYPE: PRT
<213> ORGANISM: Artificial Sequence
```

```
<220> FEATURE:
<223> OTHER INFORMATION: HLA nonbinding peptide
<220> FEATURE:
<221> NAME/KEY: misc_feature
<222> LOCATION: (5)..(5)
<223> OTHER INFORMATION: K = lysine labelled with TAMRA

<400> SEQUENCE: 36

Glu Gly Val Ser Lys Gln Ser Asn Gly
1               5

<210> SEQ ID NO 37
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: misc_feature
<222> LOCATION: (8)..(8)
<223> OTHER INFORMATION: K = lysine labelled with TAMRA

<400> SEQUENCE: 37

Tyr Val Val Pro Phe Val Ala Lys Val
1               5

<210> SEQ ID NO 38
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: misc_feature
<222> LOCATION: (8)..(8)
<223> OTHER INFORMATION: K = lysine labelled with TAMRA

<400> SEQUENCE: 38

Tyr Val Val Pro Lys Val Ala Lys Val
1               5

<210> SEQ ID NO 39
<211> LENGTH: 9
<212> TYPE: PRT
<213> ORGANISM: Artificial Sequence
<220> FEATURE:
<223> OTHER INFORMATION: MHC binding peptide

<400> SEQUENCE: 39

Tyr Val Val Pro Phe Val Ala Lys Val
1               5

<210> SEQ ID NO 40
<211> LENGTH: 9
<212> TYPE: PRT
<213> ORGANISM: Artificial Sequence
<220> FEATURE:
<223> OTHER INFORMATION: MHC binding peptide

<400> SEQUENCE: 40

Glu Thr Val Ser Glu Gln Ser Asn Val
1               5

<210> SEQ ID NO 41
<211> LENGTH: 9
<212> TYPE: PRT
<213> ORGANISM: Artificial Sequence
<220> FEATURE:
<223> OTHER INFORMATION: MHC binding peptide
```

```
<400> SEQUENCE: 41

Glu Thr Val Ser Glu Gln Ser Asn Gly
1               5

<210> SEQ ID NO 42
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: misc_feature
<222> LOCATION: (5)..(5)
<223> OTHER INFORMATION: K = lysine labelled with TAMRA

<400> SEQUENCE: 42

Asn Leu Val Pro Lys Val Ala Thr Val
1               5

<210> SEQ ID NO 43
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: misc_feature
<222> LOCATION: (5)..(5)
<223> OTHER INFORMATION: K = lysine labelled with TAMRA

<400> SEQUENCE: 43

Cys Leu Gly Gly Lys Leu Thr Met Val
1               5

<210> SEQ ID NO 44
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: misc_feature
<222> LOCATION: (5)..(5)
<223> OTHER INFORMATION: K = lysine labelled with TAMRA

<400> SEQUENCE: 44

Tyr Leu Leu Glu Lys Leu Trp Arg Leu
1               5

<210> SEQ ID NO 45
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: misc_feature
<222> LOCATION: (5)..(5)
<223> OTHER INFORMATION: K = lysine labelled with TAMRA

<400> SEQUENCE: 45

Ser Arg Tyr Trp Lys Ile Arg Thr Arg
1               5

<210> SEQ ID NO 46
<211> LENGTH: 9
<212> TYPE: PRT
<213> ORGANISM: Artificial Sequence
```

```
<220> FEATURE:
<223> OTHER INFORMATION: MHC binding peptide

<400> SEQUENCE: 46

Tyr Leu Leu Glu Met Leu Trp Arg Leu
1               5

<210> SEQ ID NO 47
<211> LENGTH: 9
<212> TYPE: PRT
<213> ORGANISM: Artificial Sequence
<220> FEATURE:
<223> OTHER INFORMATION: MHC binding peptide

<400> SEQUENCE: 47

Cys Leu Gly Gly Leu Leu Thr Met Val
1               5

<210> SEQ ID NO 48
<211> LENGTH: 9
<212> TYPE: PRT
<213> ORGANISM: Artificial Sequence
<220> FEATURE:
<223> OTHER INFORMATION: MHC binding peptide

<400> SEQUENCE: 48

Asn Leu Val Pro Met Val Ala Thr Val
1               5

<210> SEQ ID NO 49
<211> LENGTH: 9
<212> TYPE: PRT
<213> ORGANISM: Artificial Sequence
<220> FEATURE:
<223> OTHER INFORMATION: Antigenic peptide
<220> FEATURE:
<221> NAME/KEY: misc_feature
<222> LOCATION: (5)..(5)
<223> OTHER INFORMATION: K = lysine labelled with TAMRA

<400> SEQUENCE: 49

Ile Met Asp Gln Lys Pro Phe Ser Val
1               5

<210> SEQ ID NO 50
<211> LENGTH: 10
<212> TYPE: PRT
<213> ORGANISM: Artificial Sequence
<220> FEATURE:
<223> OTHER INFORMATION: Antigenic peptide
<220> FEATURE:
<221> NAME/KEY: misc_feature
<222> LOCATION: (5)..(5)
<223> OTHER INFORMATION: K = lysine labelled with TAMRA

<400> SEQUENCE: 50

Glu Leu Ala Gly Lys Gly Ile Leu Thr Val
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Antigenic peptide
<220> FEATURE:
<221> NAME/KEY: misc_feature
<222> LOCATION: (5)..(5)
<223> OTHER INFORMATION: k = lysine labelled with TAMRA
```

<400> SEQUENCE: 51

Leu Leu Gly Arg Lys Ser Phe Glu Val
1               5

<210> SEQ ID NO 52
<211> LENGTH: 9
<212> TYPE: PRT
<213> ORGANISM: Artificial Sequence
<220> FEATURE:
<223> OTHER INFORMATION: Antigenic peptide
<220> FEATURE:
<221> NAME/KEY: misc_feature
<222> LOCATION: (5)..(5)
<223> OTHER INFORMATION: k = lysine labelled with TAMRA

<400> SEQUENCE: 52

Arg Leu Leu Gln Lys Thr Glu Leu Val
1               5

<210> SEQ ID NO 53
<211> LENGTH: 8
<212> TYPE: PRT
<213> ORGANISM: Artificial Sequence
<220> FEATURE:
<223> OTHER INFORMATION: Binding peptide
<220> FEATURE:
<221> NAME/KEY: misc_feature
<222> LOCATION: (7)..(7)
<223> OTHER INFORMATION: K = lysine labelled with TAMRA

<400> SEQUENCE: 53

Ser Ile Ile Asn Phe Glu Lys Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Binding peptide

<400> SEQUENCE: 54

Ser Ile Ile Asn Phe Glu Lys Leu
1               5

<210> SEQ ID NO 55
<211> LENGTH: 5
<212> TYPE: PRT
<213> ORGANISM: Artificial Sequence
<220> FEATURE:
<223> OTHER INFORMATION: linker sequence

<400> SEQUENCE: 55

Gly Gly Gly Gly Ser
1               5

<210> SEQ ID NO 56
<211> LENGTH: 15
<212> TYPE: PRT
<213> ORGANISM: Artificial Sequence
<220> FEATURE:
<223> OTHER INFORMATION: Linker sequence

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 22
<212> TYPE: PRT
<213> ORGANISM: Artificial Sequence
<220> FEATURE:
<223> OTHER INFORMATION: Linker sequence

<400> SEQUENCE: 57

Gly Ser Thr Val Ala Ala Pro Ser Thr Val Ala Ala Pro Ser Thr Val
1               5                   10                  15

Ala Ala Pro Ser Gly Ser
            20

<210> SEQ ID NO 58
<211> LENGTH: 19
<212> TYPE: PRT
<213> ORGANISM: Artificial Sequence
<220> FEATURE:
<223> OTHER INFORMATION: Linker sequence

<400> SEQUENCE: 58

His Val Gly Gly Gly Gly Ser Gly Gly Gly Ser Gly Gly Gly Gly
1               5                   10                  15

Ser Thr Ser

<210> SEQ ID NO 59
<211> LENGTH: 10
<212> TYPE: PRT
<213> ORGANISM: Artificial Sequence
<220> FEATURE:
<223> OTHER INFORMATION: Affinity tag

<400> SEQUENCE: 59

Met Arg Gly Ser His His His His His His
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Affinity tag

<400> SEQUENCE: 60

Asp Tyr Lys Asp Asp Asp Asp Lys
1               5

<210> SEQ ID NO 61
<211> LENGTH: 15
<212> TYPE: PRT
<213> ORGANISM: Artificial Sequence
<220> FEATURE:
<223> OTHER INFORMATION: Affinity tag

<400> SEQUENCE: 61

Lys Glu Thr Ala Ala Ala Lys Phe Glu Arg Gln His Met Asp Ser
1               5                   10                  15

<210> SEQ ID NO 62
<211> LENGTH: 8
<212> TYPE: PRT
<213> ORGANISM: Artificial Sequence
<220> FEATURE:
<223> OTHER INFORMATION: Affinity tag

<400> SEQUENCE: 62

```
Trp Ser His Pro Gln Phe Glu Lys
1               5

<210> SEQ ID NO 63
<211> LENGTH: 10
<212> TYPE: PRT
<213> ORGANISM: Artificial Sequence
<220> FEATURE:
<223> OTHER INFORMATION: Affinity tag

<400> SEQUENCE: 63

Glu Gln Lys Leu Ile Ser Glu Glu Asp Leu
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Affinity tag

<400> SEQUENCE: 64

Met Lys Ala Glu Phe Arg Arg Gln Glu Ser Asp Arg
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Affinity tag

<400> SEQUENCE: 65

Met Arg Asp Ala Leu Asp Arg Leu Asp Arg Leu Ala
1               5                   10

<210> SEQ ID NO 66
<211> LENGTH: 9
<212> TYPE: PRT
<213> ORGANISM: Artificial Sequence
<220> FEATURE:
<223> OTHER INFORMATION: tumour antigen

<400> SEQUENCE: 66

Arg Leu Leu Gln Glu Thr Glu Leu Val
1               5

<210> SEQ ID NO 67
<211> LENGTH: 9
<212> TYPE: PRT
<213> ORGANISM: Artificial Sequence
<220> FEATURE:
<223> OTHER INFORMATION: tumour antigen

<400> SEQUENCE: 67

Ile Met Asp Gln Val Pro Phe Ser Val
1               5

<210> SEQ ID NO 68
<211> LENGTH: 9
<212> TYPE: PRT
<213> ORGANISM: Artificial Sequence
<220> FEATURE:
<223> OTHER INFORMATION: tumour antigen

<400> SEQUENCE: 68
```

-continued

Tyr Leu Glu Pro Gly Pro Val Thr Ala
1               5

<210> SEQ ID NO 69
<211> LENGTH: 9
<212> TYPE: PRT
<213> ORGANISM: Artificial Sequence
<220> FEATURE:
<223> OTHER INFORMATION: tumour antigen

<400> SEQUENCE: 69

Ser Leu Leu Met Trp Ile Thr Gln Cys
1               5

<210> SEQ ID NO 70
<211> LENGTH: 9
<212> TYPE: PRT
<213> ORGANISM: Artificial Sequence
<220> FEATURE:
<223> OTHER INFORMATION: tumour antigen

<400> SEQUENCE: 70

Leu Leu Gly Arg Asn Ser Phe Glu Val
1               5

<210> SEQ ID NO 71
<211> LENGTH: 10
<212> TYPE: PRT
<213> ORGANISM: Artificial Sequence
<220> FEATURE:
<223> OTHER INFORMATION: tumour antigen

<400> SEQUENCE: 71

Glu Leu Ala Gly Ile Gly Ile Leu Thr Val
1               5                   10

<210> SEQ ID NO 72
<211> LENGTH: 9
<212> TYPE: PRT
<213> ORGANISM: Artificial Sequence
<220> FEATURE:
<223> OTHER INFORMATION: tumour antigen

<400> SEQUENCE: 72

Gly Leu Tyr Asp Gly Met Glu His Leu
1               5

<210> SEQ ID NO 73
<211> LENGTH: 9
<212> TYPE: PRT
<213> ORGANISM: Artificial Sequence
<220> FEATURE:
<223> OTHER INFORMATION: tumour antigen

<400> SEQUENCE: 73

Phe Met Asn Lys Phe Ile Tyr Glu Ile
1               5

<210> SEQ ID NO 74
<211> LENGTH: 9
<212> TYPE: PRT
<213> ORGANISM: Artificial Sequence
<220> FEATURE:
<223> OTHER INFORMATION: tumour antigen

<400> SEQUENCE: 74

Ser Leu Leu Phe Leu Leu Phe Ser Leu

```
1               5

<210> SEQ ID NO 75
<211> LENGTH: 10
<212> TYPE: PRT
<213> ORGANISM: Artificial Sequence
<220> FEATURE:
<223> OTHER INFORMATION: tumour antigen

<400> SEQUENCE: 75

Gly Val Tyr Asp Gly Arg Glu His Thr Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: tumour antigen

<400> SEQUENCE: 76

Glu Ala Ala Gly Ile Gly Ile Leu Thr Val
1               5                   10

<210> SEQ ID NO 77
<211> LENGTH: 9
<212> TYPE: PRT
<213> ORGANISM: Artificial Sequence
<220> FEATURE:
<223> OTHER INFORMATION: tumour antigen

<400> SEQUENCE: 77

Phe Leu Thr Gly Asn Gln Leu Ala Val
1               5

<210> SEQ ID NO 78
<211> LENGTH: 9
<212> TYPE: PRT
<213> ORGANISM: Artificial Sequence
<220> FEATURE:
<223> OTHER INFORMATION: tumour antigen

<400> SEQUENCE: 78

Arg Leu Ala Arg Leu Ala Leu Val Leu
1               5

<210> SEQ ID NO 79
<211> LENGTH: 9
<212> TYPE: PRT
<213> ORGANISM: Artificial Sequence
<220> FEATURE:
<223> OTHER INFORMATION: influenza epitope

<400> SEQUENCE: 79

Gly Ile Leu Gly Phe Val Phe Thr Leu
1               5

<210> SEQ ID NO 80
<211> LENGTH: 9
<212> TYPE: PRT
<213> ORGANISM: Artificial Sequence
<220> FEATURE:
<223> OTHER INFORMATION: influenza epitope

<400> SEQUENCE: 80

Ala Ile Met Asp Lys Asn Ile Ile Leu
1               5
```

```
<210> SEQ ID NO 81
<211> LENGTH: 9
<212> TYPE: PRT
<213> ORGANISM: Artificial Sequence
<220> FEATURE:
<223> OTHER INFORMATION: HIV epitope

<400> SEQUENCE: 81

Ile Leu Lys Glu Pro Val His Gly Val
1               5

<210> SEQ ID NO 82
<211> LENGTH: 9
<212> TYPE: PRT
<213> ORGANISM: Artificial Sequence
<220> FEATURE:
<223> OTHER INFORMATION: HIV epitope

<400> SEQUENCE: 82

Ser Leu Tyr Asn Thr Val Ala Thr Leu
1               5

<210> SEQ ID NO 83
<211> LENGTH: 9
<212> TYPE: PRT
<213> ORGANISM: Artificial Sequence
<220> FEATURE:
<223> OTHER INFORMATION: HIV epitope

<400> SEQUENCE: 83

Lys Leu Thr Pro Leu Cys Val Thr Leu
1               5

<210> SEQ ID NO 84
<211> LENGTH: 10
<212> TYPE: PRT
<213> ORGANISM: Artificial Sequence
<220> FEATURE:
<223> OTHER INFORMATION: Hepatitis B epitope

<400> SEQUENCE: 84

Phe Leu Pro Ser Asp Phe Phe Pro Ser Val
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Hepatitis B epitope

<400> SEQUENCE: 85

Trp Leu Ser Leu Leu Val Pro Phe Val
1               5

<210> SEQ ID NO 86
<211> LENGTH: 9
<212> TYPE: PRT
<213> ORGANISM: Artificial Sequence
<220> FEATURE:
<223> OTHER INFORMATION: Human cytomegalovirus epitopes

<400> SEQUENCE: 86

Val Leu Glu Glu Thr Ser Val Met Leu
1               5
```

```
<210> SEQ ID NO 87
<211> LENGTH: 9
<212> TYPE: PRT
<213> ORGANISM: Artificial Sequence
<220> FEATURE:
<223> OTHER INFORMATION: Varicella zoster virus epitope

<400> SEQUENCE: 87

Ile Leu Ile Glu Gly Ile Phe Phe Val
1               5

<210> SEQ ID NO 88
<211> LENGTH: 10
<212> TYPE: PRT
<213> ORGANISM: Artificial Sequence
<220> FEATURE:
<223> OTHER INFORMATION: Measeles epitope

<400> SEQUENCE: 88

Ile Leu Pro Gly Gln Asp Leu Gln Tyr Val
1               5                   10

<210> SEQ ID NO 89
<211> LENGTH: 10
<212> TYPE: PRT
<213> ORGANISM: Artificial Sequence
<220> FEATURE:
<223> OTHER INFORMATION: ZIKA epitope

<400> SEQUENCE: 89

Phe Leu Val Glu Asp His Gly Phe Gly Val
1               5                   10

<210> SEQ ID NO 90
<211> LENGTH: 9
<212> TYPE: PRT
<213> ORGANISM: Artificial Sequence
<220> FEATURE:
<223> OTHER INFORMATION: ZIKA epitope

<400> SEQUENCE: 90

Lys Ser Tyr Phe Val Arg Ala Ala Lys
1               5

<210> SEQ ID NO 91
<211> LENGTH: 9
<212> TYPE: PRT
<213> ORGANISM: Artificial Sequence
<220> FEATURE:
<223> OTHER INFORMATION: exogenous peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X = V or L

<400> SEQUENCE: 91

Xaa Leu Xaa Xaa Xaa Xaa Xaa Xaa Xaa
1               5

<210> SEQ ID NO 92
```

```
<211> LENGTH: 9
<212> TYPE: PRT
<213> ORGANISM: Artificial Sequence
<220> FEATURE:
<223> OTHER INFORMATION: exogenous peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: X = L or I or V
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X = K or R

<400> SEQUENCE: 92

Xaa Xaa Xaa Xaa Xaa Xaa Xaa Xaa Xaa
1               5

<210> SEQ ID NO 93
<211> LENGTH: 9
<212> TYPE: PRT
<213> ORGANISM: Artificial Sequence
<220> FEATURE:
<223> OTHER INFORMATION: exogenous peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: X = T or V
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X = L or V

<400> SEQUENCE: 93

Xaa Xaa Xaa Xaa Xaa Xaa Xaa Xaa Xaa
1               5

<210> SEQ ID NO 94
<211> LENGTH: 9
<212> TYPE: PRT
<213> ORGANISM: Artificial Sequence
<220> FEATURE:
<223> OTHER INFORMATION: exogenous peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(9)
<223> OTHER INFORMATION: Xaa can be any naturally occurring amino acid

<400> SEQUENCE: 94

Xaa Arg Xaa Xaa Xaa Xaa Xaa Xaa Xaa
1               5

<210> SEQ ID NO 95
```

```
<211> LENGTH: 9
<212> TYPE: PRT
<213> ORGANISM: Artificial Sequence
<220> FEATURE:
<223> OTHER INFORMATION: exogenous peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X = I or V

<400> SEQUENCE: 95

Xaa Pro Xaa Xaa Xaa Xaa Xaa Xaa Xaa
1               5

<210> SEQ ID NO 96
<211> LENGTH: 10
<212> TYPE: PRT
<213> ORGANISM: Artificial Sequence
<220> FEATURE:
<223> OTHER INFORMATION: exogenous peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: X = Q or K
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X = F or Y

<400> SEQUENCE: 96

Xaa Xaa Xaa Xaa Xaa Xaa Xaa Xaa Xaa Leu
1               5                   10

<210> SEQ ID NO 97
<211> LENGTH: 6
<212> TYPE: PRT
<213> ORGANISM: Artificial Sequence
<220> FEATURE:
<223> OTHER INFORMATION: HLA motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 97

Pro Xaa Xaa Trp Asp Arg
1               5

<210> SEQ ID NO 98
<211> LENGTH: 9
<212> TYPE: PRT
<213> ORGANISM: Artificial Sequence
<220> FEATURE:
<223> OTHER INFORMATION: MHC binding peptide

<400> SEQUENCE: 98
```

```
Glu Gly Val Ser Glu Gln Ser Asn Gly
1               5

<210> SEQ ID NO 99
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: MISC_FEATURE
<222> LOCATION: (5)..(5)
<223> OTHER INFORMATION: K = lysine labelled with TAMRA

<400> SEQUENCE: 99

Phe Met Val Phe Lys Gln Thr His Ile
1               5

<210> SEQ ID NO 100
<211> LENGTH: 9
<212> TYPE: PRT
<213> ORGANISM: Artificial Sequence
<220> FEATURE:
<223> OTHER INFORMATION: MHC binding peptide

<400> SEQUENCE: 100

Ser Arg Tyr Trp Ala Ile Arg Thr Arg
1               5

<210> SEQ ID NO 101
<211> LENGTH: 9
<212> TYPE: PRT
<213> ORGANISM: Artificial Sequence
<220> FEATURE:
<223> OTHER INFORMATION: MHC binding peptide
<220> FEATURE:
<221> NAME/KEY: MISC_FEATURE
<222> LOCATION: (5)..(5)
<223> OTHER INFORMATION: K = lysine labelled with TAMRA

<400> SEQUENCE: 101

Glu Gly Val Ala Lys Gln Ser Asn Gly
1               5

<210> SEQ ID NO 102
<211> LENGTH: 9
<212> TYPE: PRT
<213> ORGANISM: Artificial Sequence
<220> FEATURE:
<223> OTHER INFORMATION: MHC binding peptide

<400> SEQUENCE: 102

Glu Gly Val Ser Glu Gln Ser Asn Gln
1               5
```

PEPTIDE EXCHANGE PROTEIN

CROSS REFERENCE TO RELATED APPLICATIONS

This application is a U.S. National Phase application under 35 U.S.C. 371 of International Application No. PCT/EP2019/051907, filed Jan. 25, 2019, which claims priority to and the benefit of GB Application No. 1801323.5 filed Jan. 26, 2018 and GB Application No. 1813737.2 filed Aug. 23, 2018, the entire disclosure of each of which is incorporated herein by reference.

FIELD

The present invention relates to peptide exchange catalysts and their use in modulating the peptide repertoire displayed by MHC class I molecules on the surface of mammalian cells.

BACKGROUND

Although cancer immunotherapy has finally come of age, new therapies are in desperate need for patients with tumours resistant to current treatments[1]. With the use of immune checkpoint inhibitors such as anti-PD1 and anti-CTLA4, there is now potential to harness the function of T lymphocytes to recognise and destroy tumours[1,2]. However, such therapies are currently only beneficial for some patients particularly those with tumours of high mutational load[3-6]. Tumours can escape either natural or immunotherapy-induced immune control by a number of mechanisms including when the process of immunoediting selects for tumours with low immunogenicity[7]. Therefore, the ability to increase the immunogenicity of tumours may provide therapeutic benefit to a wider cohort of patients, including those with a lower mutational load.

As cytotoxic T lymphocytes recognise immunogenic peptides presented on MHC class I molecules, the ability to directly manipulate the antigens displayed on these molecules would be a fundamental step forward in our ability to boost both antitumour and antiviral immune responses. Over the past few years, we have been exploring the function TAPBPR, an IFN-γ-inducible MHC class I dedicated chaperone in the antigen processing and presentation pathway[7]. TAPBPR functions as a peptide editor on MHC class I molecules[8,9] and influences the final peptide repertoire expressed on the surface of cells[8]. Within the ER/cis-Golgi TAPBPR bridges UDP-glucose:glycoprotein glucosyltransferase 1 (UGT1), an resident enzyme which monitors glycoprotein folding, onto MHC class I to provide a quality control checkpoint[10]. Although TAPBPR resides intracellularly when expressed at natural levels, we have previously observed that over-expression of TAPBPR results in some of the TAPBPR protein being mislocalised to the cell surface[11].

SUMMARY

The present inventors have unexpectedly discovered that the luminal domain of TAPBPR retains its ability to function as a MHC class I peptide-exchange catalyst when presented to mammalian cells either as a soluble extracellular protein or as a membrane bound cell surface protein. Soluble or cell surface peptide exchange catalysts may be useful in a range of therapeutic applications in the modulation of immune responses, including for example loading immunogenic peptide onto tumours or other disease cells to induce their recognition by T cells.

A first aspect of the invention provides a peptide-exchange protein comprising a fragment of TAP-binding protein-related (TAPBPR), said fragment consisting of the TAPBPR luminal domain.

A peptide-exchange protein of the first aspect may be soluble or surface-bound. A surface-bound peptide-exchange protein of the first aspect may further comprise a heterologous transmembrane domain.

A second aspect of the invention provides a peptide-exchange protein comprising a TAPBPR fragment consisting of the TAPBPR luminal domain and TAPBPR transmembrane domain.

A surface-bound peptide-exchange protein of the first aspect or a peptide-exchange protein of the second aspect may further comprise a heterologous cell surface targeting sequence.

A third aspect of the invention provides a peptide-exchange protein comprising a TAPBPR fragment and a targeting domain, wherein the TAPBPR fragment comprises the TAPBPR luminal domain.

A peptide-exchange protein of third aspect may be soluble. The TAPBPR fragment may consist of the luminal domain.

A fourth aspect of the invention provides a nucleic acid encoding a peptide-exchange protein of the first, second, or third aspects.

A fifth aspect of the invention provides a vector comprising a nucleic acid of the fourth aspect.

A sixth aspect of the invention provides a mammalian cell comprising a peptide-exchange protein of the second aspect at its surface.

A seventh aspect provides an in vitro, ex vivo, or in vivo method of increasing the immunogenicity of mammalian cells comprising;
providing a population of mammalian cells having surface MHC class I molecules, and
contacting the population of mammalian cells with an immunogenic peptide and a peptide exchange protein of the first, second or third aspect,
such that the peptide exchange protein loads the immunogenic peptide onto MHC class I molecules on the surface of the cells in the population,
thereby increasing the immunogenicity of the mammalian cells.

The mammalian cells may be disease cells, such as cancer cells or cells infected with a pathogen.

An eighth aspect provides a method of increasing the immunogenicity of target cells in an individual comprising;
administering a peptide exchange protein of the third aspect to the individual, wherein the targeting domain of the peptide exchange protein binds to target cells in the individual, and
administering an immunogenic peptide to the individual, such that the peptide exchange protein loads the immunogenic peptide onto MHC class I molecules on the surface of the target cells,
thereby increasing the immunogenicity of said target cells.

The target cells may be disease cells, such as cancer cells or cells infected with a pathogen.

A ninth aspect provides a method of stimulating or promoting an immune response in an individual comprising;
administering a peptide exchange protein of the third aspect to the individual, wherein the targeting domain of the peptide exchange protein binds to antigen presenting cells in the individual, and administering an immunogenic peptide to the individual, such that the peptide exchange protein loads the immunogenic peptide onto surface MHC class I molecules of the antigen presenting cells and the antigen presenting cells stimulate or promote an immune response in the individual.

A tenth aspect provides a method of producing antigen presenting cells for activating T cells comprising;

providing a population of antigen presenting cells previously obtained from an individual, and contacting the antigen presenting cells with an immunogenic peptide and a peptide exchange protein of the first, second, or third aspect, such that the peptide exchange protein loads the immunogenic peptide onto MHC class I molecules on the surface of the antigen presenting cells.

A method of the tenth aspect may be an in vitro or ex vivo method.

In some embodiments, the loaded antigen presenting cells may be administered to an individual to stimulate a T cell immune response in the individual against the immunogenic peptide.

In other embodiments, the antigen presenting cells may be contacted with a population of T cells to activate the T cells against the immunogenic peptide. The activated T cells may be administered to an individual to stimulate a T cell immune response in the individual against the immunogenic peptide.

An eleventh aspect provides a method of reducing an immune response in an individual comprising;

administering a peptide exchange protein of the third aspect to the individual, wherein the targeting domain of the peptide exchange protein binds to target cells in the individual, and administering a non-immunogenic peptide to the individual, such that the peptide exchange protein loads MHC class I molecules on the surface of target cells with the non-immunogenic peptide, such that the immunogenicity of the target cells is reduced in the individual.

Suitable target cells include antigen presenting cells or cells associated with tissues or organs that elicit an immune response, such as an autoimmune response, in the individual. This may be useful for example in the treatment of autoimmune disease, immune-mediated inflammatory disease, or organ rejection in the individual.

A twelfth aspect of the invention provides an in vitro method of producing a MHC class I molecule displaying a target peptide comprising;

contacting an MHC class I molecule with a peptide exchange protein of the first or second aspect and an target peptide, such that the peptide exchange protein loads the target peptide onto the MHC class I molecule, thereby producing an MHC class I molecule displaying the target peptide.

The MHC class I molecule may display an initial peptide that is replaced by the target peptide following contact with the peptide exchange protein.

In some embodiments, the MHC class I molecule displaying the target peptide may be contacted with a population of T cells to identify and/or isolate T cells that specifically bind to it.

Other aspects and embodiments of the invention are described in more detail below.

BRIEF DESCRIPTION OF THE FIGURES

In FIGS. 6a, 6b, & 6e IFNγ treated cells were used. Equivalent experiments of 6b-e were performed using HeLaM-HLA-ABC$^{KO}$ expressing HLA-A*02:01 and can be found in FIG. 16. *P≤0.05, *P≤0.001, **P≤0.0001 using unpaired two-tailed t-test.

DETAILED DESCRIPTION

Figure 1:
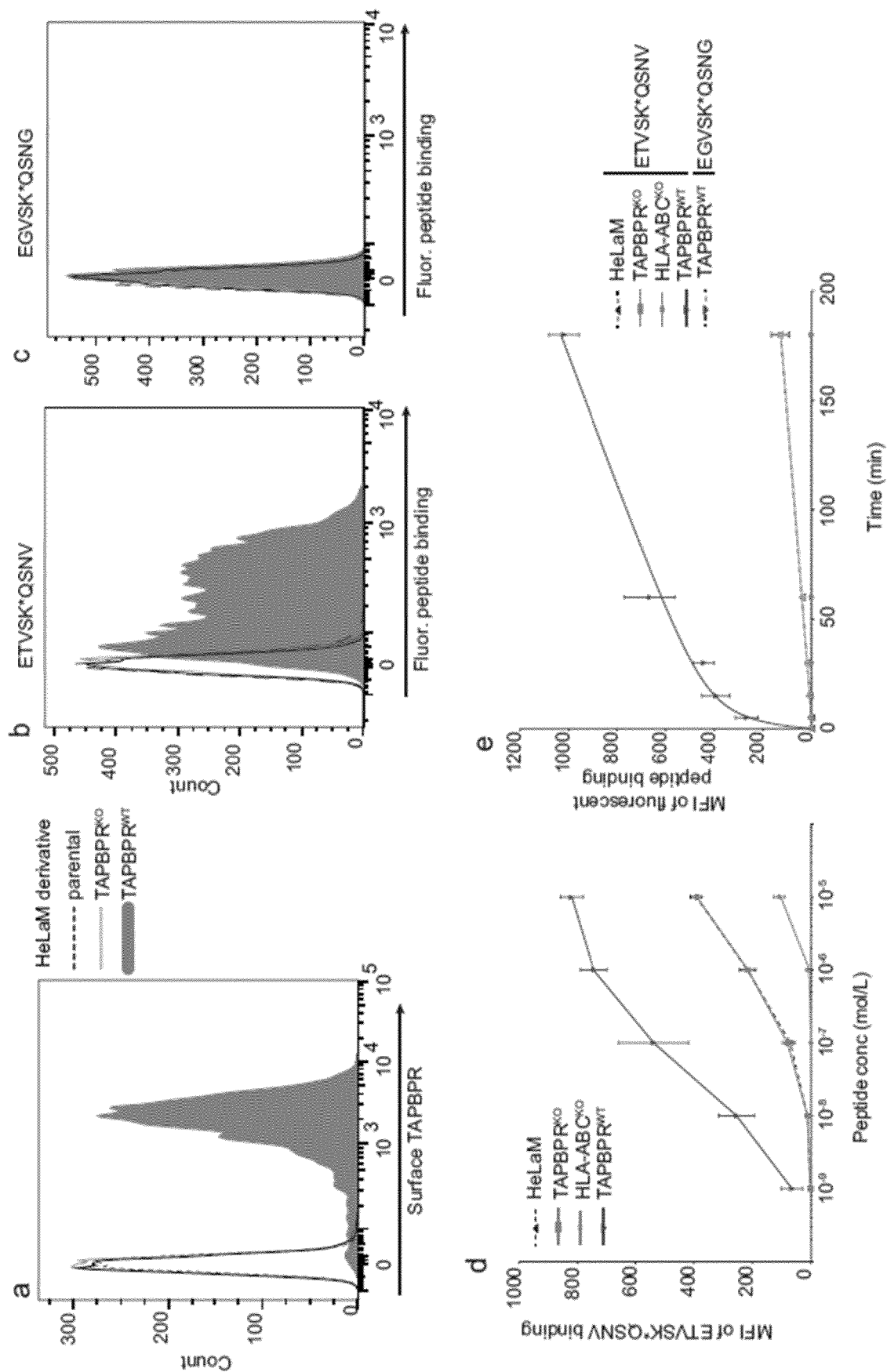
FIG. 1 shows that peptide-receptive MHC class I is present on cells expressing surface TAPBPR. (a) Overexpression of TAPBPR results in its expression at the cell surface. IFN-γ treated HeLaM cells and HeLaM-TAPBPR$^{KO}$-/+ transduction with TAPBPR$^{WT}$ were stained using the TAPBPR-specific mAb PeTe-4. (b-e) Cells over-expressing TAPBPR$^{WT}$ show increased binding to exogenous peptide compared to control cells. IFN-γ treated cells were incubated with a HLA-A*68:02 specific fluorescent peptide ETVSK*QSNV or its nonbinding variant EGVSK*QSNG (in which the anchor residues are mutated) then analysed using flow cytometry. (b,c) Histograms of the typical peptide binding observed when cells were incubated with 10 nM (b) ETVSK*QSNV or (c) EGVSK*QSNG for 15 min at 37° C. (d) Dose response curves and (e) time course showing the increased binding of exogenous peptide to cells over-expressing TAPBPR$^{WT}$ compared to HeLaM, TAPBPR deficient (TAPBPR$^{KO}$), or HLA-A, -B, -C deficient (HLA-ABC$^{KO}$) variants when cells were treated with (d) increasing concentration of ETVSK*QSNV for 15 min or (e) 10 nM ETVSK*QSNV from 0-180 min at 37° C. In (e) the binding observed with 10 nM of EGVSK*QSNG is included as a control. Line graphs show mean fluorescent intensity (MFI)-/+s.e.m from three independent experiments.

This invention relates to a recombinant peptide-exchange protein that comprises a fragment of TAP-binding protein-related (TAPBPR). The luminal domain of TAPBPR is shown herein to function as a peptide editor and a peptide-exchange protein comprising this domain acts as an extracellular or cell surface MHC class I peptide-exchange catalyst that is capable of loading exogenous peptide onto MHC class I molecules on the surface of a cell.

The peptide-exchange protein may comprise a fragment of TAP-binding protein-related (TAPBPR). A fragment is a truncated TAPBPR protein that lacks one or more amino acids of the full-length protein but retains peptide exchange activity. For example, a fragment may lack a contiguous sequence of 10 or more, 20 or more, 50 or more of 100 or more amino acids, relative to the full-length TABPR protein. In some embodiments, a TAPBPR fragment may lack the ectodomain and/or transmembrane domain of the full-length TAPBPR protein. A suitable TAPBPR fragment may comprise or consist of the luminal domain of the full-length TAPBPR protein.

TAPBPR may be mammalian TAPBPR, for example mouse or human TAPBPR, preferably human TAPBPR.

Human TAPBPR (Gene ID: 55080) is an intracellular peptide exchange catalyst that localises predominately to the endoplasmic reticulum (ER). Human TAPBPR may have the reference amino acid sequence of NCBI database entry NP_060479.3, XP_005253757.1 or SEQ ID NO: 18 and may be encoded by the reference nucleotide sequence of NM_018009.4 or SEQ ID NO: 17. 31 alleles of TAPBPR have been identified within the human population which result in changes to this protein. 6 are major isoforms which the individual variants being found at a frequency of 15-30% within different populations. Mouse TAPBPR (Gene ID: 213233) may have the reference amino acid sequence of NCBI database entry NP_663366.2 or SEQ ID NO: 20 and may be encoded by the reference nucleotide sequence of NM_145391.2 or SEQ ID NO: 19.

The TAPBPR fragment may comprise the luminal domain of TAPBPR. The luminal domain of TAPBPR is located at residues 22-405 of the full length human TAPBPR (including leader: for example SEQ ID NO: 18) and comprises an N-terminal unique domain, an IgV domain and an IgC domain. In some embodiments, the luminal domain may comprise residue I261 (TN5 patch), residues E205, R207, Q209, Q272 (TN6 patch), H210, K211 & R213 (TN7 patch), and residues 335-339, which are all involved in binding to MHC class I (Hermann et al (2013) J Immunology 191: 5743-5750). The luminal domain may further comprise residues 22-35, which form a loop which interacts with the peptide-binding groove of MHC class I. A suitable TAPBPR luminal domain may comprise the amino acid sequence of SEQ ID NO: 2 or SEQ ID NO: 22 or a variant of one of these sequences. A TAPBPR luminal domain may be encoded by a nucleotide sequence of SEQ ID NO: 1 or SEQ ID NO: 21 or a variant of one of these sequences.

A peptide-exchange protein as described herein may be soluble and not bound to a membrane either at the surface or within a mammalian cell. In particular, the peptide-exchange protein may lack transmembrane domains, membrane anchors or other features that might covalently attach it to an intracellular membrane or the cell membrane during or after expression.

In a soluble peptide-exchange protein as described herein, the TAPBPR fragment may consist of the luminal domain of TAPBPR. A soluble peptide-exchange protein may lack sequence from TAPBPR outside the luminal domain i.e. the TAPBPR fragment may be the only TAPBPR sequence in the peptide-exchange protein. For example, the peptide-exchange protein may lack the TAPBPR transmembrane domain, ectodomain or other non-luminal domains.

In other embodiments, a peptide-exchange protein as described herein may be bound to the plasma membrane at the surface of a mammalian cell. For example, the peptide-exchange protein may comprise a transmembrane domain (TMD) that attaches the protein to the plasma membrane. The TMD may be a TAPBPR TMD or a heterologous TMD. In some embodiments, the TMD may be sufficient to localise the peptide-exchange protein to the plasma membrane after expression. In other embodiments, the surface bound peptide-exchange protein may further comprise a cell surface targeting sequence that localises the peptide-exchange protein to the plasma membrane after expression.

In a surface bound peptide-exchange protein comprising a heterologous transmembrane domain, the TAPBPR fragment may comprise the luminal domain of TAPBPR. In other surface bound peptide-exchange proteins, the TAPBPR fragment may comprise both the luminal domain and TMD of TAPBPR. The TMD of TAPBPR is located at residues 407-426 of the full length human TAPBPR sequence (including leader) and may comprise the amino acid sequence of SEQ ID NO: 32 or a variant thereof. A suitable TAPBPR fragment may lack the cytoplasmic tail located at residues 427-468 of the full length human TAPBPR of the full length human TAPBPR sequence (as shown in SEQ ID NO: 18).

The TAPBPR fragment of the peptide-exchange protein displays peptide-exchange activity and is capable of loading cell-surface MHC class I molecules with an exogenous peptide.

A cell displaying MHC class I molecules may be exposed to (i) a soluble extracellular peptide-exchange protein as described herein (ii) a cell having a surface bound peptide-exchange protein as described herein or (iii) a chimeric peptide-exchange protein as described herein that binds to the surface of the cells displaying the MHC class I molecules.

The loading of cell-surface MHC class I molecules as described herein may increase the number of MHC class I molecules on the surface of a cell which present the exogenous peptide relative to cells not treated with the peptide-exchange protein. For example, the number of MHC class I molecules on the surface of a cell which present the exogenous peptide may be increased by 30 fold or more, 40 fold or more, 50 fold or more, 60 fold or more, 70 fold or more, 80 fold or more, 90 fold or more, 100 fold or more, 150 fold or more or 200 fold or more exogenous peptide in the presence relative to the absence of TAPBPR. Cells may present none or substantially none of the exogenous peptide in the absence of treatment with the peptide-exchange protein.

In some embodiments, the endogenous peptides presented by the cell displaying MHC class I molecules may not have the same amino acid sequence as the exogenous peptide. In other embodiments, the cell may present low levels of endogenous peptide with the same amino acid sequence as the exogenous peptide. The peptide-exchange protein may increase the amount of peptide having the amino acid sequence that is presented by loading MHC class I molecules on the cell surface with exogenous peptide.

Sufficient exogenous peptide may be loaded onto cell-surface MHC class I molecules to stimulate a T cell response to the peptide in an individual.

In some embodiments, the peptide-exchange protein may consist of the TAPBPR fragment. This may be useful for example in altering the immunogenicity of mammalian cells in vitro or ex vivo. In a soluble peptide-exchange protein, the TAPBPR fragment may comprise the TAPBPR luminal domain. For example, the TAPBPR fragment may lack the TAPBPR TMD and the TAPBPR cytoplasmic tail and may for example consist of the luminal domain. In a surface bound peptide-exchange protein, the TAPBPR fragment may comprise the TAPBPR luminal domain and TMD. The TAPBPR fragment may lack the TAPBPR cytoplasmic tail and may for example consist of the TAPBPR luminal domain and TMD.

In other embodiments, the peptide-exchange protein may further comprise one or more domains in addition to the TAPBPR fragment. The one or more additional domains may be heterologous domains (i.e. amino acid sequences not derived from TAPBPR). For example, a surface-bound peptide-exchange protein may comprise a heterologous TMD and/or cell surface targeting sequence. In some embodiments, the peptide-exchange protein may be a fusion protein comprising the TAPBPR fragment and one or more heterologous domains.

The absence of the TAPBPR cytoplasmic tail may be sufficient to localise a peptide-exchange protein comprising a TAPBPR or heterologous TMD to the cell membrane. Suitable heterologous TMDs may include the platelet derived growth factor receptor (PDGFR) TMD, the influenza hemagglutinin TMD and the influenza neuraminidase TMD. In other embodiments, the peptide-exchange protein may further comprise a heterologous cell surface targeting sequence. A cell surface targeting sequence is an amino acid sequence that directs a protein expressed in a cell to the plasma membrane. Suitable cell surface targeting sequences may include the cytoplasmic domains of CD8, MHC class I molecules, Transferrin receptor, CD147, VSVG, NCAM, CD44 or E-cadherin. Examples of suitable peptide exchange proteins may include the TAPBPR-CD8 construct of SEQ ID NO: 34 or a variant thereof.

The term "heterologous" refers to a polypeptide or nucleic acid that is foreign to a particular biological system, such as a host cell, and is not naturally occurring in that system. A heterologous polypeptide or nucleic acid may be introduced to a biological system by artificial means, for example using recombinant techniques. For example, heterologous nucleic acid encoding a polypeptide may be inserted into a suitable expression construct which is in turn used to transform a host cell to produce the polypeptide. A heterologous polypeptide or nucleic acid may be synthetic or artificial or may exist in a different biological system, such as a different species or cell type. A recombinant polypeptide may be expressed from heterologous nucleic acid that has been introduced into a cell by artificial means, for example using recombinant techniques. A recombinant polypeptide may be identical to a polypeptide that is naturally present in the cell or may be different from the polypeptides that are naturally present in that cell.

The term "endogenous" refers to a peptide, polypeptide or nucleic acid or other factor that is generated by natural processes in a biological system, such as a host cell. The term "exogenous" refers to a peptide, polypeptide or nucleic acid that is not generated by natural processes in a biological system and is produced and/or introduced to the system by artificial means, for example by administration or recombinant expression. An exogenous factor may be synthesised using conventional techniques, such as solid-phase synthesis. An exogenous factor may be identical to a factor that is naturally present in a biological system (i.e. an endogenous factor) or may be different from the factors that are naturally present in that biological system.

Preferably, the peptide-exchange protein further comprises a targeting domain. The peptide-exchange protein described herein may be a chimeric protein or fusion protein comprising a targeting domain and a TAPBPR fragment comprising or consisting of the TAPBPR luminal domain. Chimeric peptide-exchange proteins as described herein are preferably soluble and may be useful for example in altering the immunogenicity of mammalian cells in vivo, as well as for in vitro and ex vivo applications.

In some embodiments, the TAPBPR fragment may be at the N terminal of the peptide exchange protein and the targeting domain may be at the C terminal of the peptide exchange protein. In other embodiments, the TAPBPR fragment may be at the C terminal of the peptide exchange protein and the targeting domain may be at the N terminal of the peptide exchange protein.

The targeting domain may be directly connected to the TAPBPR fragment or may be connected via a linker.

Suitable linkers are well-known in the art and include chemical and peptidyl linkers. For example, a peptidyl linker may comprise a sequence of amino acid residues, for example, 5 to 30 or 5 to 22 amino acid residues, preferably 10 to 20 amino acid residues, more preferably about 12 amino acid residues.

Any linker sequence may be employed. Preferably, the linker sequence is a heterologous sequence. Suitable linker amino acid sequences are well known in the art and may include the amino acid sequences GGGGS, (GGGGS)$_3$ or GSTVAAPSTVAAPSTVAAPSGS, HVGGGGSGGGGSGGGGSTS or variants thereof.

The targeting domain allows the chimeric peptide exchange protein to selectively target a specific population of target cells in an individual. The targeting domain of the chimeric peptide exchange protein binds specifically to the target cells. Preferably, the targeting domain of the chimeric peptide exchange protein binds selectively to target cells relative to non-target cells i.e. it shows increased binding to target cells relative to non-target cells. Binding of the targeting domain to the target cells allows the TAPBPR fragment of the chimeric protein to act selectively at the surface of the target cells relative to non-target cells (i.e. cells to which the targeting domain does not bind), for example to load MHC class I molecules on the surface of the target cell with exogenous peptide.

Target cells may comprise MHC class I molecules on the cell surface. MHC class I molecules are heterodimers comprising an α chain and β2-microglobulin. MHC class I molecules are expressed on all nucleated human cells. An individual inherits a set of HLA-A, -B and -C genes from each parent. These genes are co-dominantly expressed and nucleated cells in mammals express up to 6 different classical MHC class I molecules. MHC class I molecules are highly polymorphic within the α chain and there is huge variation within the population. MHC class I molecules may include HLA-A molecules, HLA-B molecules, such as HLA-B51, HLA-B15, HLA-B38, and HLA-B57 and HLA-C molecules, such as HLA-Cw1. Preferred MHC class I molecules include HLA-A.

In some embodiments, the target cells may be disease cells, such as cancer cells, cells infected with a pathogen, or other cells that cause disease. Increasing the immunogenicity of disease cells in an individual using a chimeric peptide exchange protein may generate or increase the strength of immune responses against the disease cells in the individual. This may lead to a reduction or eradication of disease cells in the individual and may exert a therapeutic effect.

In other embodiments, the target cells may be antigen presenting cells. Loading the surface MHC I molecules of antigen presenting cells with an exogenous immunogenic peptide useful in increasing or eliciting immune responses, for example T cell immune responses, against disease cells in vivo, thereby exerting a therapeutic effect.

In other embodiments, the target cells may be host cells that elicit an immune reaction, such as an autoimmune or auto inflammatory response. Loading the surface MHC I molecules of the host cells with an exogenous non-immunogenic peptide may be useful in reducing or preventing autoimmune or immune mediated inflammatory responses against the cells in vivo, thereby exerting a therapeutic effect.

The targeting domain may specifically bind to a marker, such a receptor or antigen that is present on the surface of a target cell of the individual. The binding affinity of the targeting domain for its target cell marker may be higher than the binding affinity of TAPBPR for MHC class I molecules.

Suitable targeting domains include any molecule that are capable of specific binding to a cell marker. For example, the targeting domain may be a ligand for a receptor on the surface of the target cell or an antibody molecule that specifically binds to an antigen on the surface of the target cell.

In some preferred embodiments, a chimeric peptide-exchange protein comprising a targeting domain may show no binding or substantially no binding to MHC class I molecules on the surface of a cell if the target cell marker that is bound by the targeting domain is not present on the surface of the cell.

An antibody molecule is a polypeptide or protein comprising an antibody antigen-binding site. The term encompasses any immunoglobulin whether natural or partly or wholly synthetically produced. Antibody molecules may have been isolated or obtained by purification from natural sources, or else obtained by genetic recombination, or by chemical synthesis, and that they may contain unnatural amino acids.

Suitable antibody molecules may include whole antibodies and fragments thereof. Fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) single-domain antibodies (sdAb) (also called nanobodies (Nb)) (Ward et al. (1989) Nature 341, 544-546; McCafferty et al., (1990) Nature, 348, 552-554; Holt et al. (2003) Trends in Biotechnology 21, 484-490), which consist of either a monomeric VH domain or a monomeric VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger et al. (1993a), Proc. Natl. Acad. Sci. USA 90 6444-6448).

Fv, scFv, diabody, sdAb and other antibody molecules may be stabilized by the incorporation of disulphide bridges, for example linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

In some preferred embodiments, the targeting domain may specifically bind to a target molecule, such as a tumour antigen, on a cancer cell. For example, the targeting domain may be an antibody molecule that binds to a tumour antigen.

The expression of one or more antigens (i.e. tumour antigens) may distinguish cancer cells from normal somatic cells in an individual. Normal somatic cells in an individual may not express the one or more antigens or may express them in a different manner, for example at lower levels, in different tissue and/or at a different developmental stage. Tumour antigens may therefore be used to target chimeric peptide exchange proteins specifically to cancer cells.

Tumour antigens expressed by cancer cells may include, for example, cancer-testis (CT) antigens encoded by cancer-germ line genes, such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2(HOM-MEL-40), SSX-3, SSX-4, SSX-5, SCP-I and XAGE and immunogenic fragments thereof (Simpson et al. Nature Rev (2005) 5, 615-625, Gure et al., Clin Cancer Res (2005) 11, 8055-8062; Velazquez et al., Cancer Immun (2007) 7, 11; Andrade et al., Cancer Immun (2008) 8, 2; Tinguely et al., Cancer Science (2008); Napoletano et al., Am J of Obstet Gyn (2008) 198, 99 e91-97).

Other tumour antigens include, for example, overexpressed, upregulated or mutated proteins and differentiation antigens particularly melanocyte differentiation antigens such as p53, ras, CEA, MUC1, PMSA, PSA, tyrosinase, Melan-A, MART-1, gp100, gp75, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, ErbB2/her2, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, PDL1, CD20, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, TPS, tyrosinase related proteins such as TRP-1, TRP-2 and ABC transporters expressed on the surface of tumours that are the mediators of drug resistance, such as. P-gp, BCRP and MRP1, Other tumour antigens include out-of-frame peptide-MHC complexes generated by the non-AUG translation initiation mechanisms employed by "stressed" cancer cells (Malarkannan et al. Immunity (1999) 10(6):681-90).

Other tumour antigens are well-known in the art (see for example WO00/20581; Cancer Vaccines and Immunotherapy (2000) Eds Stern, Beverley and Carroll, Cambridge University Press, Cambridge) The sequences of these tumour antigens are readily available from public databases but are also found in WO1992/020356 A1, WO1994/005304 A1, WO1994/023031 A1, WO1995/020974 A1, WO1995/023874 A1 and WO1996/026214 A1.

Suitable targeting domains, such as antibody molecules that specifically bind to tumour antigens, are well known in the art and may be generated using conventional techniques. For example, a suitable targeting domain that specifically binds to ErbB2 (Her2) may comprise the VH and VL domains of SEQ ID NOs: 24 and 25 (trastuzumab) or the set of CDRs therein or the scFv of SEQ ID NO:23; a suitable targeting domain that specifically binds to PD-L1 may comprise PD-1, the antibody antigen-binding domain of atezolizumab or durvalumab or a nanobody sequence of any of SEQ ID NOs 25 to 31; and a suitable targeting domain that specifically binds to CD20 may comprise the antibody antigen-binding domain of rituximab. Other suitable targeting domains, for example nanobody targeting domains, are publically available (see for example Zuo et al. iCAN: Institute Collection and Analysis of Nanobodies).

In other embodiments, the targeting domain may specifically bind to a marker, such as a receptor, on an antigen presenting cell, such as a dendritic cell. For example, the targeting domain may be an Fc region that binds to an Fc receptor on the antigen presenting cell. Suitable Fc regions are well known in the art.

The targeting domain may be an antibody molecule that binds to a surface marker on the antigen presenting cell or a ligand or binding protein of the surface marker. Antigen presenting cells may include dendritic cells of any sub-type. XCR1+ dendritic cells mediate the cross-presentation of antigen for the activation of effector CD8+ T cells. Surface markers on XCR1+ dendritic cells may include XCR1, DNGR1 (CLEC9A) and BDCA3 (also known as CD141). CD172α+ dendritic cells induce T helper 2 (TH2) or TH17 cells, and promote of humoral immune responses. Surface markers on CD172α+ dendritic cells include CD172α and BDCA1 (also known as CD1c). Plasmacytoid DCs produce of type I interferon (IFN) during viral infections. Surface markers on plasmacytoid DCs include BDCA2 and BDCA4. Monocyte-derived DCs promote local T cell responses and enhance inflammation and chemokine production. Surface markers on monocyte-derived DCs include FcεRI and FcγRI expression is upregulated on activation. Macrophages eliminate pathogens and promote tissue homeostasis. Surface markers on macrophages include CD68. Expression of FcγRI is also upregulated on activation. Other suitable markers for dendritic cells include CD19, CD20, CD38, CD14 and/or Langerin/CD207.

In other preferred embodiments, the targeting domain may specifically bind to an antigen on a pathogen-infected cell. For example, the targeting domain may bind to a pathogen protein or a host cell protein whose surface expression is up-regulated by pathogen infection. For an HIV infected cell, the targeting domain may specifically bind to a marker on the cell surface, such as gp120 or gp41. Suitable targeting domains include antibody molecules or CD4, which specifically binds to surface gp120. For a CMV infected cell, the targeting domain may specifically bind to a viral protein such as UL11, UL142, UL9, UL1, UL5, UL16, UL55 (gB), UL74 (gO), UL75 (gH), UL155 (gL), which are all found on the surface of infected cells (Weekes et al (2014) Cell 157:1460-1472). Host proteins whose expression is upregulated or induced on the surface of infected cells include inhibitory NK receptor KLRG-1, which may be specifically bound using an E-cadherin (CDH1) targeting domain (Weekes et al (2014) Cell 157: 1460-1472).

Examples of suitable chimeric peptide exchange proteins may include the TAPBPR-LONG-FcIgG1 construct of SEQ ID NO: 4, the sTAPBPR-sPD1 construct of SEQ ID NO: 6, the TAPBPR-Her2scFv construct of SEQ ID NO: 8, and the sTAPBPR-GFP sdAb construct of SEQ ID NO: 10; the sTAPBPR-LONG-PD-L1-NB1 construct of SEQ ID NO: 12; the sTAPBPR-LONG-PD-L1-NB2 construct of SEQ ID NO: 14; the sTAPBPR-LONG-PD-L1-NB4 construct of SEQ ID NO: 16; and variants of any of these reference sequences.

A protein described herein that is a variant of a reference sequence, such as a peptide exchange protein sequence described above, may have 1 or more amino acid residues altered relative to the reference sequence. For example, 50 or fewer amino acid residues may be altered relative to the reference sequence, preferably 45 or fewer, 40 or fewer, 30 or fewer, 20 or fewer, 15 or fewer, 10 or fewer, 5 or fewer or 3 or fewer, 2 or 1. For example, a variant described herein may comprise the sequence of a reference sequence with 50 or fewer, 45 or fewer, 40 or fewer, 30 or fewer, 20 or fewer, 15 or fewer, 10 or fewer, 5 or fewer, 3 or fewer, 2 or 1 amino acid residues mutated. For example, a chimeric protein described herein may comprise an amino acid sequence with 50 or fewer, 45 or fewer, 40 or fewer, 30 or fewer, 20 or fewer, 15 or fewer, 10 or fewer, 5 or fewer, 3 or fewer, 2 or 1 amino acid residue altered relative to any one of SEQ ID NOs: 2, 4, 6, 8, 10, 12, 14, 16, 18, 20, 22 and 34.

An amino acid residue in the reference sequence may be altered or mutated by insertion, deletion or substitution, preferably substitution for a different amino acid residue. Such alterations may be caused by one or more of addition, insertion, deletion or substitution of one or more nucleotides in the encoding nucleic acid.

A protein as described herein that is a variant of a reference sequence, such as a peptide exchange protein sequence described above, may share at least 50% sequence identity with the reference amino acid sequence, at least 55%, at least 60%, at least 65%, at least 70%, at least about 80%, at least 90%, at least 95%, at least 98% or at least 99% sequence identity. For example, a variant of a protein described herein may comprise an amino acid sequence that has at least 50% sequence identity with the reference amino acid sequence, at least 55%, at least 60%, at least 65%, at least 70%, at least about 80%, at least 90%, at least 95%, at least 98% or at least 99% sequence identity with the reference amino acid sequence, for example one or more of SEQ ID NOS: 2, 4, 6, 8, 10, 12, 14, 16, 18, 20, and 22.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm may be used (Nucl. Acids Res. (1997) 25 3389-3402). Sequence identity and similarity may also be determined using Genomequest™ software (Gene-IT, Worcester MA USA).

Sequence comparisons are preferably made over the full-length of the relevant sequence described herein.

A peptide exchange protein described herein may further comprise one or more heterologous amino acid sequences additional to the TAPBPR fragment and optional targeting domain and/or linker. For example, the peptide exchange protein may further comprise one or more additional domains which improve stability, pharmacokinetics, targeting, affinity, purification and/or production properties.

In some embodiments, the peptide exchange protein described herein may further comprise a protease recognition site located between the targeting domain and the TAPBPR fragment. This may be useful for example, in clearing TAPBPR from the target cell, if required. Suitable proteases may include trypsin, chymotrypsin, factor Xa, tobacco etch virus (TEV) protease, thrombin and papain. Other suitable site specific proteases are well-known in the art and any site-specific endoprotease may be used.

In some embodiments, the peptide exchange protein may further comprise a reactive moiety to permit the use of "click chemistry" for conjugation with the targeting domain or other domain. Click-chemistry may for example involve the Cu(I)-catalysed coupling between two components, one containing an azido group and the other a terminal acetylene group, to form a triazole ring. Since azido and alkyne groups are inert to the conditions of other coupling procedures and other functional groups found in proteins are inert to click chemistry conditions, click-chemistry allows the controlled attachment of almost any linker or chemical group to the peptide exchange protein under mild conditions and in particular allows the chemical conjugation of a targeting domain to a TAPBPR fragment. For example, cysteine residues of the peptide exchange protein may be reacted with a bifunctional reagent containing a thiol-specific reactive group at one end (e.g. iodoacetamide, maleimide or phenylthiosulfonate) and an azide or acetylene at the other end. Label groups may be attached to the terminal azide or acetylene using click-chemistry. For example, a second linker with either an acetylene or azide group on one end of a linker and a chelate (for metal isotopes) or leaving group (for halogen labelling) on the other end (Baskin, J. (2007) *PNAS* 104(43)16793-97) may be employed.

Peptide exchange proteins as described herein may be provided using synthetic or recombinant techniques which are standard in the art.

In some embodiments, the peptide exchange protein described herein may be produced with an affinity tag, which may, for example, be useful for purification. An affinity tag is a heterologous peptide sequence which forms one member of a specific binding pair. Polypeptides containing the tag may be purified by the binding of the other member of the specific binding pair to the polypeptide, for example in an affinity column. For example, the tag sequence may form an epitope which is bound by an antibody molecule. Suitable affinity tags include for example, glutathione-S-transferase, (GST), maltose binding domain (MBD), MRGS(H)$_6$, DYKDDDDK (FLAG™), T7-, S-(KETAAAKFER-QHMDS), poly-Arg ($R_{5-6}$), poly-His ($H_{2-10}$), poly-Cys ($C_4$) poly-Phe ($F_{11}$) poly-Asp ($D_{5-16}$), SUMO tag (Invitrogen Champion pET SUMO expression system), Strept-tag II (WSHPQFEK), c-myc (EQKLISEEDL), Influenza-HA tag (Murray, P. J. et al (1995) *Anal Biochem* 229, 170-9), Glu-Glu-Phe tag (Stammers, D. K. et al (1991) *FEBS Lett* 283, 298-302), Tag. 100 (Qiagen; 12 aa tag derived from mammalian MAP kinase 2), Cruz tag 09™ (MKAEFRRQESDR, Santa Cruz Biotechnology Inc.) and Cruz tag 22™ (MRDALDRLDRLA, Santa Cruz Biotechnology Inc.). Known tag sequences are reviewed in Terpe (2003) Appl. Microbiol. Biotechnol. 60 523-533. In preferred embodiments, a poly-His tag such as $(H)_6$, His-SUMO tag (Invitrogen Champion pET SUMO expression system), or MRGS$(H)_6$ may be used.

The affinity tag sequence may be separated from the peptide exchange protein described herein after purification, for example, using a site-specific protease.

In some embodiments, the peptide exchange protein described herein may be coupled to a leader peptide to direct secretion of the peptide exchange protein from cell into the culture medium as a precursor protein.

A range of suitable leader peptides are known in the art. The leader peptide may be heterologous to the TAPBPR fragment described herein i.e. it may be a non-TAPBPR leader sequence. For example, an α-factor secretion signal or BiP leader sequence may be employed. The leader peptide is located at the N terminus of the precursor protein. After expression of the precursor, the leader peptide is then removed by post-translational processing after expression of the precursor to generate the mature peptide exchange protein.

Peptide exchange proteins as described herein may be isolated, in the sense of being free from contaminants, such as other polypeptides and/or cellular components.

Peptide exchange proteins load MHC class I molecules on the surface of the cells with exogenous peptide. An exogenous peptide is a peptide that is not generated naturally by the cells with the MHC class I molecules. For example, it may have been administered to the individual. Exogenous peptide may have the same amino acid sequence as an endogenous peptide that is generated naturally by the cells or a different amino acid sequence.

In some embodiments, the immunogenicity of the exogenous peptide may be different to the immunogenicity of endogenous peptides displayed in the MHC class I molecules (i.e. it may be higher or lower). For example, an exogenous peptide as described herein may be immunogenic or non-immunogenic, depending on the application. In other embodiments, the immunogenicity of the exogenous peptide may be the same as the immunogenicity of one or more endogenous peptides displayed in the MHC class I molecules. For example, the exogenous peptide may have the same amino acid sequence as one or more endogenous peptides. Loading of MHC class I molecules with the exogenous peptide as described here may increase the total amount of peptide with the amino acid sequence that is displayed on the cells and may thereby increase or reduce the immunogenicity of the cells.

Peptides that are displayed by MHC class I molecules are well-known in the art (see for example the on-line Immune Epitope Database and Analysis Resource (IEDB); Vita et al Nucl Acid Res 2014 Oct. 9 piii:gku938) and further peptides may be identified using immunopeptidomic techniques. Direct binding of peptides to MHC class I molecules may be confirmed by testing the binding of labelled peptides in cellular assays or using MHC beads. Binding of non-labelled peptide to MHC class I molecules may be determined by staining treated cells with TCR-tetramers specific for the peptide.

An immunogenic peptide is an exogenous peptide that is capable of generating an immune response in an individual when loaded onto an MHC class I molecule. For example, the immunogenic peptide/MHC class I complex may be recognised by T cells. The presence of MHC class I molecules loaded with immunogenic peptide on the surface of target cells may induce or increase immune responses against the target cells.

Suitable immunogenic peptides are known in the art and may for example be candidates in vaccines for cancer or infection. In some embodiments, immunogenic peptides for loading onto MHC class I may be antigens naturally expressed on a patient's own tumour; neoantigens or other peptides derived from tumours; or peptides derived from pathogens, such as viruses.

In some embodiments, the immunogenic peptide may comprise an antigen or an epitope that is characteristic of a disease cell. For example, the immunogenic peptide may comprise an antigen or an epitope that is characteristic of a cancer cell or a pathogen-infected cell.

Epitopes that are characteristic of cancer cells are well known in the art and include epitopes from tumour antigens. Suitable antigens and epitopes are described elsewhere herein. Preferred tumour antigens from which immunogenic peptides may be derived include neoantigens, tumour-specific, differentiation and overexpressed proteins, such as ErbB2/Her2 (e.g. RLLQETELV), gp100 (e.g. IMDQVPFSV and YLEPGPVTA), NY-Eso-1 (e.g. SLLMWITQC), p53 (e.g. LLGRNSFEV), MART1 (e.g. ELAGIGILTV), MAGE-10 (e.g. GLYDGMEHL), human AFP (e.g. FMNKFIYEI), Mesothelin (e.g. SLLFLLFSL), MAGE-A4 (e.g. GVYDGREHTV), MART-1 (e.g EAAGIGILTV, ELAGIGILTV) and 5T4 (e.g. FLTGNQLAV, RLARLALVL).

Other tumour antigens and epitopes are well known in the art (see for example the Cancer Research Institute NY on-line peptide database; Tumor T cell antigen database, Olsen et al (2017) Cancer Immunol Immunother. doi: 10.1007/s00262-017-1978-y; Immune Epitope and Analysis Resource, Vita et al Nucleic Acids Res. 2014 Oct. 9. pii: gku938).

Epitopes that are characteristic of pathogen-infected cells are well known in the art and include epitopes from viral proteins. Suitable epitopes are described elsewhere herein and may include influenza epitopes (e.g. GILGFVFTL, AIMDKNIIL), HIV epitopes (e.g. ILKEPVHGV, SLYNTVATL, KLTPLCVTL), hepatitis B epitopes (e.g. FLPSDFFPSV, WLSLLVPFV), Human cytomegalovirus (CMV) epitopes (e.g. NLVPMVATV, VLEETSVML), Epstein Barr virus (EBV) epitopes (e.g. YLLEMLWRL, CLGGLLTMV), Varicella-zoster virus epitopes (e.g. ILIEGIFFV), Measles epitopes (e.g. ILPGQDLQYV), ZIKA (e.g. FLVEDHGFGV, KSYFVRAAK), and Ebola virus epitopes. Other viral epitopes are well known in the art (see for example Immune Epitope and Analysis Resource, Vita et al Nucleic Acids Res. 2014 Oct. 9. pii: gku938).

In some embodiments, MHC class I molecules on cancer cells may be loaded with immunogenic peptides comprising one or more viral epitopes. This may be useful in eliciting anti-viral immune responses against the cancer cells.

In other embodiments, the immunogenic peptide may comprise an antigen or an epitope that is not characteristic of a disease cell but is still capable of eliciting an immune response against cells displaying it at the cell surface. For example, the immunogenic peptide may comprise a synthetic epitope. Suitable synthetic epitopes are well known in the art. A synthetic epitope may be generated for example by replacing an amino acid exposed to the TCR in a peptide displayed on MHC class I molecules with an artificial amino acid, such as 3-cyclohexylalanine (CHA).

A non-immunogenic peptide is an exogenous peptide that does not generate an immune response in an individual when loaded onto an MHC class I molecule. The presence of MHC class I molecules loaded with non-immunogenic peptide on the surface of target cells may prevent or reduce immune responses against the target cells.

Suitable exogenous peptides may be 8-15mers, for example 8-11mers, preferably 9mers. The exogenous peptide may be compatible with some or all of the MHC class I molecules present on the surface of the target cells. For example, the sequence of the exogenous peptide may include suitable anchor residues required for association with some or all of the MHC class I molecules on the surface of the target cells.

The MHC class I molecules on the surface of the target cells may include HLA-A molecules, such as HLA-A68 and HLA-A2. MHC class I molecules may be identified using conventional techniques, such as tissue typing or flow cytometry.

Suitable sequences for display by the MHC class I molecules on the surface of the target cells may be determined using standard techniques. For example, when HLA-A2 molecules are present on the surface of the target cells, the exogenous peptide may have the sequence xLxxxxxxV/L, where X is independently any amino acid; when HLA-A*03:01 molecules are present on the surface of the target cells, the exogenous peptide may have the sequence xL/I/VxxxxxxK/R, where X is independently any amino acid; when HLA-A*68:02 molecules are present on the surface of the target cells, the exogenous peptide may have the sequence xT/VxxxxxxL/V, where X is independently any amino acid; when HLA-B*27:05 molecules are present on the surface of the target cells, the exogenous peptide may have the sequence xRxxxxxxx, where X is independently any amino acid; when HLA-B*51:01 molecules are present on the surface of the target cells, the exogenous peptide may have the sequence xPxxxxxxI/V, where X is independently any amino acid; and when HLA-B*15:03 molecules are present on the surface of the target cells, the exogenous peptide may have the sequence xQ/KxxxxxXF/YL, where X is independently any amino acid.

Other aspects of the invention provide a nucleic acid encoding a peptide exchange protein described herein as described above and a vector comprising such a nucleic acid.

Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication, promoter regions and selectable markers, which allow for its selection, expression and replication in bacterial hosts such as *E. coli*. Vectors may be plasmids, viral e.g. phage, or phagemid, as appropriate. For further details see, for example, Molecular Cloning: a Laboratory Manual: 3rd edition, Russell et al., 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, are described in detail in Current Protocols in Molecular Biology, Ausubel et al. eds. John Wiley & Sons, 1992.

A nucleic acid or vector as described herein may be introduced into a host cell. Another aspect of the invention provides a recombinant cell comprising a nucleic acid or vector that expresses a peptide exchange protein as described above. A range of host cells suitable for the production of recombinant peptide exchange protein are known in the art. Suitable host cells may include prokaryotic cells, in particular bacteria such as *Escherichia coli* and *Lactococcus lactis* and eukaryotic cells, including mammalian cells such as CHO and CHO-derived cell lines (Lec cells), HeLa, COS, HEK293 and HEK-EBNA cells, amphibian cells such as Xenopus oocytes, insect cells such as *Trichoplusia ni*, Sf9 and Sf21 and yeast cells, such as *Pichia pastoris*.

Techniques for the introduction of nucleic acid into cells are well established in the art and any suitable technique may be employed, in accordance with the particular circumstances. For eukaryotic cells, suitable techniques may include calcium phosphate transfection, DEAE-Dextran, electroporation, liposome-mediated transfection and transduction using retrovirus or other virus, e.g. adenovirus, AAV, lentivirus or vaccinia. For bacterial cells, suitable techniques may include calcium chloride transformation, electroporation and transfection using bacteriophage. Marker genes such as antibiotic resistance or sensitivity genes may be used in identifying clones containing nucleic acid of interest, as is well-known in the art.

The introduction may be followed by expression of the nucleic acid to produce the encoded peptide exchange protein. In some embodiments, host cells (which may include cells actually transformed although more likely the cells will be descendants of the transformed cells) may be cultured in vitro under conditions for expression of the nucleic acid, so that the encoded serpin polypeptide is produced. When an inducible promoter is used, expression may require the activation of the inducible promoter.

The expressed polypeptide comprising or consisting of the peptide exchange protein may be isolated and/or purified, after production. This may be achieved using any convenient method known in the art. Techniques for the purification of recombinant polypeptides are well known in the art and include, for example HPLC, FPLC or affinity chromatography. In some embodiments, purification may be performed using an affinity tag on the polypeptide as described above.

Another aspect of the invention provides a method of producing a peptide exchange protein described herein comprising expressing a heterologous nucleic acid encoding the peptide exchange protein in a host cell and optionally isolating and/or purifying the peptide exchange protein thus produced. After production, the peptide exchange protein may be investigated further, for example the pharmacological properties and/or activity may be determined. Methods and means of protein analysis are well-known in the art.

A peptide exchange protein described herein as described herein may be useful in therapy. For example, the peptide exchange protein may be administered to an individual to modulate the immunogenicity of target cells or the peptide exchange protein may be used to modulate the immunogenicity of cells in vitro or ex vivo, which are then administered to an individual. A peptide exchange protein for administration to an individual is preferably a chimeric peptide exchange protein comprising a targeting domain. This allows the immunogenicity of target cells in the individual to be modulated.

Whilst the peptide exchange protein may be administered alone, it will usually be administered in the form of a pharmaceutical composition, which may comprise at least one component in addition to the chimeric peptide exchange protein. Thus pharmaceutical compositions may comprise, in addition to the peptide exchange protein itself, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by bolus, infusion, injection or any other suitable route, as discussed below.

The peptide exchange protein may be administered in combination with an exogenous peptide, preferably an immunogenic peptide. In some embodiments, the peptide exchange protein and the exogenous peptide may be formulated in the same pharmaceutical composition. In other embodiments, the peptide exchange protein and the exogenous peptide may be formulated in separate pharmaceutical compositions.

In some embodiments, the peptide exchange protein and/or exogenous peptide may be provided in a lyophilised form for reconstitution prior to administration. For example, a lyophilised peptide exchange protein and/or exogenous peptide may be re-constituted in sterile water and mixed with saline prior to administration to an individual.

For parenteral, for example sub-cutaneous, intra-tumoural, intra-muscular or intra-venous administration, e.g. by injection, the pharmaceutical composition comprising the peptide exchange protein and/or exogenous peptide described herein, nucleic acid or cell may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringers Injection, and Lactated Ringers Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/ or non-ionic surfactants, such as TWEEN™, PLURONICS™ or polyethylene glycol (PEG). Suitable carriers, excipients, etc. can be found in standard pharmaceutical texts, for example, Remington's Pharmaceutical Sciences, 18th edition, Mack Publishing Company, Easton, Pa., 1990.

Pharmaceutical compositions and formulations may conveniently be presented in unit dosage form and may be prepared by any methods well known in the art of pharmacy. Such methods include the step of bringing into association the chimeric protein described herein with the carrier which constitutes one or more accessory ingredients. In general, the compositions are prepared by uniformly and intimately bringing into association the active compound with liquid carriers or finely divided solid carriers or both, and then if necessary shaping the product.

A pharmaceutical composition comprising a peptide exchange protein and/or exogenous peptide as described herein may be administered alone or in combination with other treatments, either simultaneously or sequentially dependent upon the condition to be treated.

Peptide exchange proteins described herein may be useful in modulating the immunogenicity of mammalian cells in vivo, in vitro or ex vivo. For example a method may comprise;

providing a population of mammalian cells having surface MHC class I molecules, contacting the population of mammalian cells with an exogenous peptide and a peptide exchange protein comprising a TAPBPR fragment consisting of the luminal domain of TAPBPR, such that the peptide exchange protein loads the exogenous peptide onto the surface MHC class I molecules of the cells in the population, thereby modulating the immunogenicity of the mammalian cells.

Surface MHC class I molecules that have been loaded with immunogenic exogenous peptides are accessible to T cell receptors. The loading of the surface MHC class I molecules with immunogenic peptides may induce or increase T cell recognition of the cells of the mammalian cells and may increase the immunogenicity of the mammalian cells.

In some embodiments, the mammalian cells may be antigen presenting cells (APCs), such as dendritic cells. The loading of the surface MHC class I molecules with immunogenic exogenous peptides may increase the ability of the APCs to induce immune responses, for example immune responses against the antigenic epitopes contained in the immunogenic peptide. APCs loaded with immunogenic peptide as described above may be used to stimulate T cells in vitro or ex vivo or administered to an individual to stimulate T cells in vivo.

A method of producing antigen presenting cells for generating or increasing an immune response in an individual may comprise;

providing a population of antigen presenting cells previously obtained from the individual, and contacting the antigen presenting cells with a peptide exchange protein and an immunogenic peptide, such that the peptide exchange protein loads the immunogenic peptide onto surface MHC class I molecules of the antigen presenting cells, the antigen presenting cells being capable of stimulating T cells to generate an immune response The method may an in vitro or an ex vivo method.

The immunogenic peptide may comprise one or more antigenic epitopes. The antigen presenting cells may activate T cells against the antigenic epitopes of the immunogenic peptide. For example, the antigenic epitopes of the immunogenic peptide may be present on disease cells in the individual. The antigen presenting cells may activate T cells capable of generating an immune response against the disease cells in the individual.

In some embodiments, following production, the antigen presenting cells may be administered to an individual to activate T cells and generate or increase a T cell immune response in the individual.

In other embodiments, following production, the antigen presenting cells may be contacted with a population of T cells to activate the T cells against the one or more antigenic epitopes of the immunogenic peptide in vivo or ex vivo. The activated T cells may be administered to an individual to generate a T cell immune response in the individual. The individual may be the individual from which the population of T cells was obtained (autologous) or a different individual (allogeneic).

Suitable antigen presenting cells include any cell that expresses the MHC class I molecules against which the immune response is to be directed. In some embodiments, dendritic cells may be preferred.

Peptide exchange proteins described herein may be useful in modulating the immunogenicity of mammalian cells in vivo. This may be useful in immunotherapeutic applications, for example in which the generation or enhancement of an immune response might have a therapeutic effect. Suitable applications might include the treatment of conditions associated with the presence of populations of disease cells in an individual. These conditions might include cancer and infection with an intracellular pathogen. Other suitable applications might include the treatment of autoimmune or auto inflammatory conditions in which the reduction in immunogenicity of a cell or tissue might have a therapeutic effect. The targeting domain of a peptide exchange protein as described above may preferentially or selectively direct the protein to target cells within the individual relative to non-target cells.

A peptide exchange protein described herein may be used in a method of treatment of the human or animal body, including therapeutic and prophylactic or preventative treatment (e.g. treatment before the onset of a condition in an individual to reduce the risk of the condition occurring in the individual; delay its onset; or reduce its severity after onset). Prophylactic or preventative treatment may include vaccination. The method of treatment may comprise administering a peptide exchange protein described herein and an immunogenic peptide to an individual in need thereof.

A method of increasing the immunogenicity of target cells in an individual may comprise;
 administering a peptide exchange protein as described above to the individual, wherein peptide exchange protein comprises a targeting domain which binds to target cells in the individual, and
 administering an immunogenic peptide to the individual, such that the peptide exchange protein loads the immunogenic peptide onto surface MHC class I molecules of the target cells,
 thereby increasing the immunogenicity of the target cells.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In some preferred embodiments, the individual is a human. In other preferred embodiments, non-human mammals, especially mammals that are conventionally used as models for demonstrating therapeutic efficacy in humans (e.g. murine, primate, porcine, canine, or rabbit animals) may be employed.

Suitable target cells may include disease cells i.e. cells that are associated with a disease condition in the individual, such as cells infected with virus or other intracellular pathogen, or cancer or tumour cells.

In some preferred embodiments, the target cells are cancer cells. A method of treatment of cancer in an individual may comprise;
 administering a peptide exchange protein described above to the individual, wherein peptide exchange protein comprises a targeting domain which binds to cancer cells in the individual, and
 administering an immunogenic peptide to the individual, such that the peptide exchange protein loads the immunogenic peptide onto surface MHC class I molecules of the cancer cells of the individual,
 thereby eliciting or increasing an immune response in the individual against the cancer cells.

Cancer may be characterised by the abnormal proliferation of malignant cancer cells and may include leukaemias, such as AML, CML, ALL and CLL, lymphomas, such as Hodgkin lymphoma, non-Hodgkin lymphoma and multiple myeloma, and solid cancers such as sarcomas, skin cancer, melanoma, bladder cancer, brain cancer, breast cancer, uterus cancer, ovary cancer, prostate cancer, lung cancer, colorectal cancer, cervical cancer, liver cancer, head and neck cancer, oesophageal cancer, pancreas cancer, renal cancer, adrenal cancer, stomach cancer, testicular cancer, cancer of the gall bladder and biliary tracts, thyroid cancer, thymus cancer, cancer of bone, and cerebral cancer, as well as cancer of unknown primary (CUP).

In some embodiments, cancer cells within an individual may be immunologically distinct from normal somatic cells in the individual (i.e. the cancerous tumour may be immunogenic). For example, the cancer cells may be capable of eliciting a systemic immune response in the individual against one or more antigens expressed by the cancer cells. The tumour antigens that elicit the immune response may be specific to cancer cells or may be shared by one or more normal cells in the individual. In other embodiments, cancer cells within an individual may not be immunologically distinct from normal somatic cells in the individual until MHC class I molecules on the surface of the cancer cells are loaded with exogenous immunogenic peptide using a peptide exchange protein as described herein.

In some embodiments, the individual may have minimal residual disease (MRD) after an initial cancer treatment.

An individual with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in an individual may include identification of a particular cell type (e.g. a cancer cell) in a sample of a body fluid or tissue obtained from the individual.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of T cells, and a decrease in levels of tumour-specific antigens. Administration of T cells modified as described herein may improve the capacity of the individual to resist cancer growth, in particular growth of a cancer already present the subject and/or decrease the propensity for cancer growth in the individual.

In other preferred embodiments, the target cells are pathogen-infected cells.

A method of treatment of pathogen infection in an individual may comprise;
administering a peptide exchange protein described above to the individual, wherein peptide exchange protein comprises a targeting domain which binds to pathogen-infected cells in the individual, and
administering an immunogenic peptide to the individual, such that the peptide exchange protein loads the immunogenic peptide onto surface MHC class I molecules of the pathogen-infected cells of the individual,
thereby eliciting or increasing an immune response in the individual against the pathogen-infected cells.

Pathogen infection may include viral infection, for example HIV, EBV, CMV or hepatitis infection.

In other preferred embodiments, the target cells are antigen presenting cells, such as dendritic cells. Antigen presenting cells present antigenic epitopes to T cells to activate a T cell response against the antigen. A method of treatment of a condition associated with disease cells in an individual may comprise;
administering a peptide exchange protein described herein to the individual, wherein the peptide exchange protein comprises a targeting domain that binds to antigen presenting cells in the individual, and
administering an immunogenic peptide to the individual, such that the peptide exchange protein loads the immunogenic peptide onto surface MHC class I molecules of the antigen presenting cells,
such that said antigen presenting cells generate or increase an immune response in the individual against the disease cells.

Disease cells may include cancer cells or pathogen-infected cells. For example, this may be useful in treating pathogen infections in which a peptide vaccine is currently used to induce CD8+ T cells responses, such as infections of HIV, EBV, CMV, hepatitis viruses, influenza, polio, human papilloma virus, measles, mumps, rubella, chicken pox, ebola, or zika; or cancer, for example by boosting the number of T cells capable of recognising a particular antigen.

In other embodiments, methods described herein may be useful in reducing immunogenicity. A method of reducing an immune response in an individual may comprise;
administering a chimeric peptide exchange protein to the individual, wherein the targeting domain of the chimeric peptide exchange protein binds to target cells in the individual,
administering a non-immunogenic peptide to the individual, such that the peptide exchange protein replaces immunogenic peptides in surface MHC class I molecules with non-immunogenic peptides and the immunogenicity of the target cells is reduced in the individual.

The chimeric peptide exchange protein may for example, reduce the immunogenicity of the donor organ and/or antigen presentation cells removing recognition of self/donor-peptides (e.g. alloantigens/minor histocompatibility antigens) which are the target of the immune recognition.

In some preferred embodiments, the individual may have an autoimmune disease or immune-mediated inflammatory disease. A method of treatment of autoimmune or immune-mediated inflammatory disease in an individual may comprise;
administering a peptide exchange protein described above to the individual,
wherein peptide exchange protein comprises a targeting domain which binds to cells in the individual having surface MHC class I molecules displaying an immunogenic peptide, and
administering an non-immunogenic peptide to the individual, such that the peptide exchange protein replaces the immunogenic peptide in the surface MHC class I molecules with the non-immunogenic peptide,
thereby preventing or reducing an immune response in the individual against the cells.

In other preferred embodiments, methods described herein may be useful in organ or tissue transplantation. A method of treating diseases associated with MHC class I molecules in an individual may comprise;
administering a chimeric peptide exchange protein described herein to the individual, wherein the targeting domain of the chimeric peptide exchange protein binds to target cells in the individual which have disease associated MHC class I molecules on their surface,
administering an exogenous peptide to the individual, such that the peptide exchange protein loads the surface MHC class I molecules with the exogenous peptide,
such that the MHC class I molecules are stabilised by the exogenous peptide.

In other embodiments, methods described herein may be useful in treating diseases associated with MHC class I molecules. A method of treating diseases associated with MHC class I molecules in an individual may comprise;
administering a chimeric peptide exchange protein described herein to the individual, wherein the targeting domain of the chimeric peptide exchange protein binds to target cells in the individual which have disease associated MHC class I molecules on their surface, and
administering an exogenous peptide to the individual, such that the peptide exchange protein loads the surface MHC class I molecules with the exogenous peptide,
such that the MHC class I molecules are stabilised by the exogenous peptide.

MHC class I associated diseases may include the spondyloarthropathies (associated with HLA-B27), Behcet's disease (associated with HLA-B51), Birdshot Chorioretinopathy (associated with HLA-A29) psoriasis and psoriatic arthritis (associated with HLA-Cw6).

Administration is normally in a "therapeutically effective amount" or "prophylactically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners.

A composition may be administered alone or in combination with other treatments, either simultaneously or sequentially dependent upon the circumstances of the individual to be treated. For example, a composition may be administered in combination with vaccination, immune checkpoint inhibition, other immunotherapies and potentially chemotherapy and radiotherapy.

Prescription of treatment, e.g. decisions on dosage etc, is within the responsibility of general practitioners and other medical doctors and may depend on the severity of the symptoms and/or progression of a disease being treated. Appropriate doses of therapeutic polypeptides are well known in the art (Ledermann J. A. et al. (1991) Int. J. Cancer 47: 659-664; Bagshawe K. D. et al. (1991) Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of a chimeric protein described herein may be determined by comparing its in vitro activity and in vivo activity in an animal model. Methods for extrapolation of effective dosages in mice and other test animals to humans are known. The precise dose will depend upon a number of factors, including whether the chimeric protein described herein is for prevention or for treatment, the size and location of the area to be treated, the precise nature of the chimeric protein described herein and the nature of any detectable label or other molecule attached to the chimeric protein described herein.

A typical dose of a peptide exchange protein will be in the range of 0.1 mg/kg to 100 mg/kg. For example, a dose in the range 100 µg to 1 g may be used for systemic applications. An initial higher loading dose, followed by one or more lower doses, may be administered. This is a dose for a single treatment of an adult patient, which may be proportionally adjusted for children and infants. Treatments may be repeated at daily, twice-weekly, weekly or monthly intervals, at the discretion of the physician.

In some embodiments, pre-vaccination and/or re-vaccination with tumour or viral antigens may be required before administration of the TAPBPR/peptide combination intended to be delivered to the tumour/infection site. The vaccination strategy may employ TAPBPR to load peptides or may involve standard vaccination regimens.

The treatment schedule for an individual may be dependent on the pharmocokinetic and pharmacodynamic properties of the peptide exchange protein described herein composition, the route of administration and the nature of the condition being treated.

Treatment may be periodic, and the period between administrations may be about 12 hours or more, 24 hours or more, 36 hours or more, 48 hours or more, 96 hours or more, or one week or more. Suitable formulations and routes of administration are described above.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment may also be prophylactic (i.e. prophylaxis). For example, an individual susceptible to or at risk of the occurrence or re-occurrence of disease may be treated as described herein. Such treatment may prevent or delay the occurrence or re-occurrence of the disease in the individual.

Other aspects of the invention relate to kits for use in increasing immunogenicity or stimulating immune responses as described herein. A kit may comprise a peptide exchange protein and an immunogenic peptide as described above.

A kit may further comprise an additional therapeutic agent, such as a vaccine or immune checkpoint inhibitor.

Other aspects of the invention relate to methods and reagents for identifying, characterising or isolating T cells in vitro or ex vivo using MHC class I molecules that display a target peptide.

A method of producing a MHC class I molecule displaying a target peptide may comprise;
    contacting an MHC class I molecule with a peptide exchange protein described above and an target peptide, such that the peptide exchange protein loads the target peptide onto the MHC class I molecule,
    thereby producing an MHC class I molecule displaying the target peptide.

Preferably, the MHC class I molecule is contacted with a soluble peptide exchange protein. Soluble peptide exchange proteins are described in detail above.

The target peptide may be a peptide which is capable of specific binding to a T cell when displayed by a MHC class I molecule. For example, the target peptide may comprise a viral, bacterial, cancer or autoimmune antigenic epitope. MHC class I molecules displaying the target peptide may be useful in identifying, quantifying, characterising or isolating T cells within a population of T cells that specifically bind to the MHC class I molecule/target peptide complex.

The MHC class I molecule may display an initial peptide that is replaced by the target peptide following contact with the peptide exchange protein. The sequence of the initial peptide is independent of the target peptide being employed, and any convenient peptide that can be displayed by MHC class I molecules may be employed.

In some embodiments, the MHC class I molecule may be immobilised on a solid support, such as a bead. The MHC class I molecule may be a member of a population of MHC class I molecules immobilised on the solid support. For example, the peptide exchange protein may be contacted with a population of MHC class I molecules immobilised on the solid support may load target peptide onto the MHC class I molecules in the immobilised population.

MHC class I molecules may be immobilised on the solid support by any convenient technique. For example, the MHC class I molecules may be biotinylated and may be bound to the support through a biotin/streptavidin interaction.

In other embodiments, the MHC class I molecule may be in solution, for example as a sub-unit of a multimer. The peptide exchange protein may be contacted in solution with a multimer that comprises multiple MHC class I molecules. Preferred multimers include tetramers of biotinylated MHC class I molecules linked by streptavidin. The streptavidin may be labelled, for example with a fluorophore such as phycoerythrin. Tetramers of biotinylated MHC class I molecules are well known in the art (Altman et al Science 1996, 274: 94-96).

In some embodiments, the MHC class I molecules displaying the target peptide may be contacted with a population of T cells, for example a population of T cells previously obtained from an individual. The binding of the MHC class I molecules to T cells in the population may be determined. Binding may be determined by any convenient technique, such as flow cytometry.

The frequency or number of T cells within the population that bind to the MHC class I molecules displaying the target molecule may be determined. This may be useful in research or for diagnostic or prognostic applications.

T cells that bind to the MHC class I molecules displaying the target molecule may be isolated and/or expanded in vitro, for example for use in therapeutic applications.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

EXPERIMENTAL

1. Materials and Methods 1.1 Constructs

The production of full-length $TAPBPR^{WT}$ and $TAPBPR^{TN5}$ was performed using the lentiviral vector pHRSIN-C56W-UbEM, which produces TAPBPR under the control of the spleen focus-forming virus (SFFV) promoter and the GFP derivative emerald under the control of an ubiquitin promoter, as previously described[11,15]. The cloning of the chimeric constructs $TAPBPR^{PM}$ and $tapasin^{PM}$ was performed in the same lentiviral vector, by a twostep PCR procedure, where the ectodomain and transmembrane domain of either TAPBPR or tapasin were amplified and then fused to the cytoplasmic tail of CD8. $TAPBPR^{ER}$ was created using a similar procedure, in which the ectodomain of TAPBPR was fused to the transmembrane and cytoplasmic domains of tapasin. To produce secreted versions of $TAPBPR^{WT}$ or $TAPBPR^{TN5}$, the luminal domains of both were cloned into a piggyback transposon-based mammalian cell expression system as described in Li et al[22].

1.2 Cell Culture

HeLaM cells, a variant HeLa cell line that is more responsive to IFN[23], their modified variants, HEK-293T cells and MCF7 cells were maintained in Dulbecco's Modified Eagle's medium (DMEM; Sigma-Aldrich, UK) supplemented with 10% fetal bovine serum (FBS) (Gibco, Thermo Fisher Scientific), 100 U/ml penicillin and 100 µg/ml streptomycin (Gibco, Thermo Fisher Scientific) at 37° C. with 5% CO2. To induce expression of endogenously expressed TAPBPR and up-regulate other components of the MHC class I antigen processing and presentation pathway, HeLaM and MCF7 cells were treated with 200 U/ml IFN-γ (Peprotech, UK) for 48-72 h where indicated.

1.3 Antibodies

The following TAPBPR-specific antibodies were used: PeTe4, a mouse monoclonal antibody (mAb) specific for the native conformation of TAPBPR, raised against amino acids 22-406 of human TAPBPR 11 that does not cross-react with tapasin 15, and ab57411, a mouse mAb raised against amino acids 23-122 of TAPBPR that is reactive to denatured TAPBPR (Abcam, UK). The following MHC class I-specific antibodies were used: W6/32, a pan-MHC class I mAb that recognises a conformation-specific epitope on the MHC class I α2 domain, independently of the presence of β2m and peptide 24; HC10, a MHC class I-specific mAb that recognises HLA-A, -B, and -C molecules containing a PxxWDR motif at amino acids 57-62 in the α1 domain 25,26; biotinylated anti-HLA-A68-reactive mAb, specific for HLA-A2 and -A68 heavy chain/β2m heterodimers (One Lambda, Thermo Fisher Scientific, Canoga Park, CA); BB7.2, an antibody specific for HLA-A2 heavy chain/62m heterodimer. Other antibodies used include: Pasta-1, the tapasin-specific mAb (Dick et al., 2002); rabbit anti-calnexin (Enzo Life Sciences, UK); rabbit mAb to UGT1 (ab124879, Abcam); IgG2a isotype control as a negative control (Sigma-Aldrich).

1.4 Lentiviral Transduction and Transfections

Lentivirus was produced by transfecting HEK-293T cells with lentiviral vectors along with the packaging vector pCMVΔR8.91 and the envelope vector pMD.G using Fugene (Promega, UK). Viral supernatant was collected at 48 h and used to transduce a previously described TAPBPR-knockout HeLaM cell line) (HeLaM-$TAPBPR^{KO}$) (Neerincx et al., 2017). $TAPBPR^{WT}$, $TAPBPR^{TN5}$, $TAPBPR^{PM}$, $TAPBPR^{ER}$, $tapasin^{WT}$ and $tapasin^{PM}$ were reconstituted in the HeLaM-$TAPBPR^{KO}$ cell line.

1.5 MHC Class I-Binding Peptides

The following MHC-class I specific peptides were used: HLA-A*68:02-binding peptide ETVSEQSNV, its derivative EGVSEQSNG, obtained by replacing its anchor residues (amino acids on positions 2 and 9) with glycine, as well as their fluorescently-labelled versions ETVSK$^{TAMRA}$QSNV and respectively EGVSK$^{TAMRA}$QSNG, obtained by replacing the glutamate on position 5 with a lysine, labelled with 5-carboxytetramethylrhodamine [TAMRA] (from Peptide Synthetics, UK); HLA-A*02:01 binding peptides NLVPMVATV, YLLEMLWRL, CLGGLLTMV and YVVPFVAKV, together with their fluorescently-labelled variants NLVPK$^{TAMRA}$VATV, FMVFK$^{TAMRA}$QTHI, CLGGK$^{TAMRA}$LTMV, YLLEK$^{TAMRA}$LWRL and respectively YVVPFVAK$^{TAMRA}$V (from Peptide Synthetics, UK); HLA-B*27:05 specific peptide SRYWAIRTR and its fluorescently-labelled variant SRYWK$^{TAMRA}$IRTR (from Peptide Synthetics, UK).

1.6 Flow Cytometry

Following trypsinisation, cells were washed in 1% bovine serum albumin (BSA), dissolved in 1×PBS at 4° C. and then stained for 30 min at 4° C. in 1% BSA containing one of the following antibodies: W6/32, pete4, pasta-1, anti-HLA-A68-reactive mAb, BB7.2 or with an isotype control antibody. After washing the cells to remove excess unbound antibody, the primary antibodies bound to the cells were detected by incubation at 4° C. for 25 min with either goat anti-mouse Alexa-Fluor 647 IgG (Invitrogen Molecular Probes, Thermo Fisher Scientific) or with Alexa-Fluor 647-conjugated streptavidin (Invitrogen Molecular Probes, Thermo Fisher Scientific) for the biotinylated anti-HLA-A68 mAb. After subsequent three rounds of washing, the fluorescence levels were detected using a BD FACScan analyser with Cytek modifications and analysed using FlowJo (FlowJo, LLC, Ashland, OR).

1.7 Immunoprecipitation, Gel Electrophoresis and Western Blotting

Cells were harvested then washed in phosphate-buffered saline (PBS). For surface TAPBPR immunoprecipitation experiments, cells were incubated with 2 μg Pete4 antibody in 1% BSA in 1×PBS for 1 h with rotation at 4° C. Excess antibody was removed by washing the cells 5 times in 1×PBS at 4° C. Cells were then lysed and the intracellular TAPBPR immunoprecipitation was further performed similarly to the TAPBPR immunoprecipitation from the whole cell lysates.

For TAPBPR immunoprecipitation experiments from whole cell lysates, cells were lysed in 1% triton X-100 (VWR, Radnor, PN), Tris-buffered saline (TBS) (20 mM Tris-HCl, 150 mM NaCl, 2.5 mM CaCl2)) supplemented with 10 mM NEM, 1 mM phenylmethylsulfonyl fluoride (PMSF) (Sigma-Aldrich), and protease inhibitor cocktail (Roche, UK) for 30 min at 4° C. Nuclei and cell debris were pelleted by centrifugation at 13,000×g for 15 min and supernatants were collected. Immunoprecipitation was performed with Pete4 antibody coupled to protein A sepharose (GE Healthcare) for 2 h at 4° C. with rotation. Following immunoprecipitation, beads were washed thoroughly in 0.1% detergent-TBS to remove unbound protein. For separation by gel electrophoresis, the samples were heated at 94° C. for 10 min in sample buffer (125 mM Tris-HCl pH 6.8, 4% SDS, 20% glycerol, 0.04% bromophenol blue), supplemented with 100 mM β-mercaptoethanol. In order to analyse the samples by western blotting, proteins were transferred onto an Immobilon transfer membrane (Merck Millipore). Membranes were blocked using 5% (w/v) dried milk and 0.1% (v/v) Tween 20 in PBS for 30 min and subsequently incubated with the indicated primary antibody for 1-16 h. After washing, membranes were incubated with species-specific HRP-conjugated secondary antibodies, washed and detected by enhanced chemiluminescence using Western Lightning (Perkin Elmer, UK) and Super RX film (Fujifilm, UK). Films were scanned on a CanoScan8800F using MX Navigator Software (Canon, UK).

1.8 Expression and Purification of TAPBPR Protein

Secreted forms of either TAPBPR$^{WT}$ or TAPBPR$^{TN5}$ were expressed in 293T cells, using the PiggyBac expression system as described in 22. For that, the C-terminally His-tagged ectodomain of either protein was cloned into a modified version of the PB-T-PAF vector, lacking the protein A using NheI and NotI (Thermo Fisher Scientific). In brief, 2×10$^5$ 293 T cells were transfected with 100 ng PB-RN plasmid, 100 ng PBase plasmid and 800 ng PB-T-TAPBPR or PB-T-TAPASIN. 48 h after transfection, cells were selected for stable integration using Dulbecco's Modified Eagle's medium (DMEM; Sigma-Aldrich, UK) supplemented with 10% fetal bovine serum (FBS) (Gibco, Thermo Fisher Scientific), 1×P/S, 3 μg/ml Puromycin (Invivogen) and 700 μg G418 (Gibco, Thermo Scientific) for 7 days. For protein production, 6×10$^7$ cells were induced with 2 μg/ml Doxycycline for 5 to 7 days in 200 ml DMEM supplemented with 5% FCS and 100 U/ml penicillin. After 7 days, the media was collected and TAPBPR was purified using NiSepharose™ excel beads (GE Lifesciences). Proteins were eluted with 250 mM imidazole in PBS (Sigma) and subsequently dialysed against PBS (Sigma) for 48 h. For purity assessment, elution fractions were analysed by SDSPAGE, followed by Coomassie staining.

1.9 Peptide Binding

Target cell lines were seeded at 25,000-30,000 cells/well in 12-well plates and stimulated with IFN-γ. Following the stimulation period, the cells were washed 3 times with 1×PBS and incubated with 300 μL pre-warmed opti-MEM (Thermo Fisher Scientific, UK). In case the peptide binding was done in the presence of recombinant TAPBPR, the cells were then treated with or without recombinant TAPBPR (100 nM for HLA-A*68:02 or 1 μM for HLA-A*02:01). After 15 min, the desired TAMRA-labelled peptide was added to the cells and incubated at 37° C. (15 min for HLA-A*68:02 or 60 min for HLA-A*02:01). In case the peptide binding was facilitated by over-expressed TAPBPR, the labelled peptide was directly added to the cells, without using recombinant TAPBPR. Following the peptide treatment, the cells were washed three times in 1×PBS and harvested. The level of bound peptide/cell was determined by flow cytometry, using the YelFL1 channel (Cytek).

1.10 Peptide Exchange

Cells were seeded at 25,000 cells/well and stimulated with IFN-γ for 48 hours, then washed and treated with 10 nM TAMRA-labelled peptide of interest diluted in opti-MEM for 15 min at 37° C., as described above. Following the binding step, the peptide-containing media was removed, the cells were washed and then treated with media alone or with different concentrations of non-labelled peptide for another 15 min at 37° C. The cells were then washed and harvested and the level of bound peptide per cell was determined by flow cytometry, using the YelFL1 channel (Cytek).

1.11 TCR-Like mAb Staining

TCR-like mAb specific for peptides derived from then Epstein-Barr Virus (EBV) latent gene products Latent Membrane Protein 2A (LMP2A$_{426-434}$: CLGGLLTMV) and Latent Membrane Protein 1 (LMP1$_{125-133}$: YLLEMLWRL) in association with HLA-A*02:01 (Sim et al., 2013) were used to stain target cells, following treatment with 10 nM of the corresponding peptide, in the presence of recombinant TAPBPR. After washing, the level of bound TCR-like mAb bound was detected using the goat anti-mouse Alexa-Fluor 647 IgG and subsequently measured by flow cytometry.

1.12 FluoroSpot T Cell Assay

Target cells (MCF-7 cells or HeLaM cells deficient of HLA heavy chain A, B and C and reconstituted with HLA-A*02:01 heavy chain) were seeded at 80,000 cells/well of a 6-well plate and stimulated with 200 units of IFN-γ (Peprotech, UK) for 72 hours. Cells were then washed 3 times with 1×PBS (Sigma-Aldrich, UK) and incubated with 600 μL pre-warmed opti-MEM, containing either recombinant WT TAPBPR, TN5 TAPBPR mutant, or without TAPBPR. After 15 min, 100 pM NLVPMVATV peptide was added to the desired samples and incubated for another 60 min. Following the peptide treatment, cells were washed 3 times in 1×PBS and harvested. Each sample was then washed again twice in 1×PBS and resuspended in X-VIVO 15 medium at 1 mil cells/mL. Target cells were first irradiated and then added to a 96-well plate, pre-blocked overnight, at 50,000 cells/well together with 8,000 T cells/well. The plate was incubated overnight at 37° C. and developed the following day.

2. Results

2.1 Peptide-Receptive MHC Class I is Present on Cells Expressing Surface TAPBPR To explore whether surface TAPBPR was potentially capable of functioning as a peptide editor on surface MHC class I molecules, we first asked whether the fluorescent peptide ETVSK*QSNV, a variant of the neoantigen ETVSEQSNV that binds to HLA-A*68:02 with high affinity, exhibited increased binding to cells expressing surface TAPBPR compared to cells lacking surface TAPBPR. While IFN-γ treated HeLaM-TAPBPR$^{KO}$ (HeLaM$^{KO}$) and HeLaM cells do not express any TAPBPR at their cell surface, over-expression of TAPBPR$^{WT}$ in HeLaM-TAPBPR$^{KO}$ resulted in a significant amount of surface expressed TAPBPR (FIG. 1a). When cells expressing surface TAPBPR were incubated with 10 nM exogenous peptide for 15 min at 37° C., we observed a significant enhancement in fluorescence indicative of peptide binding to these cells (FIG. 1b). In contrast, we did not observe any binding of ETVSK*QSNV to the cell lines lacking surface TAPBPR under identical conditions (FIG. 1b). To ensure cellular fluorescence observed was a direct consequence of peptide binding to MHC class I, we also incubated cells with a variant fluorescent peptide (EGVSK*QSNG) in which the anchor residues permitting binding to HLA-A*68:02 were mutated. This did not bind to any of the cell lines (FIG. 1c). The enhancement in peptide binding to IFN-γ treated HeLa-$^{KO}$TAPBPR$^{WT}$ compared to HeLaM or HeLaM$^{KO}$ cells was observed over a wide range of peptide concentrations (FIG. 1d). At higher peptide concentrations, exogenous peptide binding to cells lacking surface TAPBPR was observed (FIG. 1d). However, this TAPBPR-independent peptide binding to cells was ~120 times less efficient as ~1.2 μM peptide was required to obtain a similar fluorescence as observed with 10 nM peptide in a TAPBPR-promoted manner required (FIG. 1d). Peptide binding to cells was dependent on MHC class I given HLA-A,B,C deficient HeLaM cells were unable to bind exogenous peptide until concentrations of 10 μM were used. When we explored the kinetics of TAPBPR-promoted peptide binding over time, we observed a striking increase in the ability of cells to load exogenous peptide onto surface MHC class I compared to TAPBPR-independent conditions upon incubation with 10 nM peptide (FIG. 1e). For examples, after 60 min we observed a 21-fold increase in the level of fluorescent peptide bound to HeLaKO-TAPBPR$^{WT}$ compared to the HeLaM and HeLaM$^{KO}$ controls (FIG. 1e). These findings are supportive of a role of surface TAPBPR in loading antigenic peptides onto surface MHC class I molecules. Furthermore, we also observed high levels of exogenous peptide loading on HeLaM$^{KO}$TAPBPR$^{WT}$ cells at 4° C., which inhibits membrane trafficking, further suggesting peptide loading was occurring directly at the cell surface, rather than in endocytic vesicles.

Figure 2:
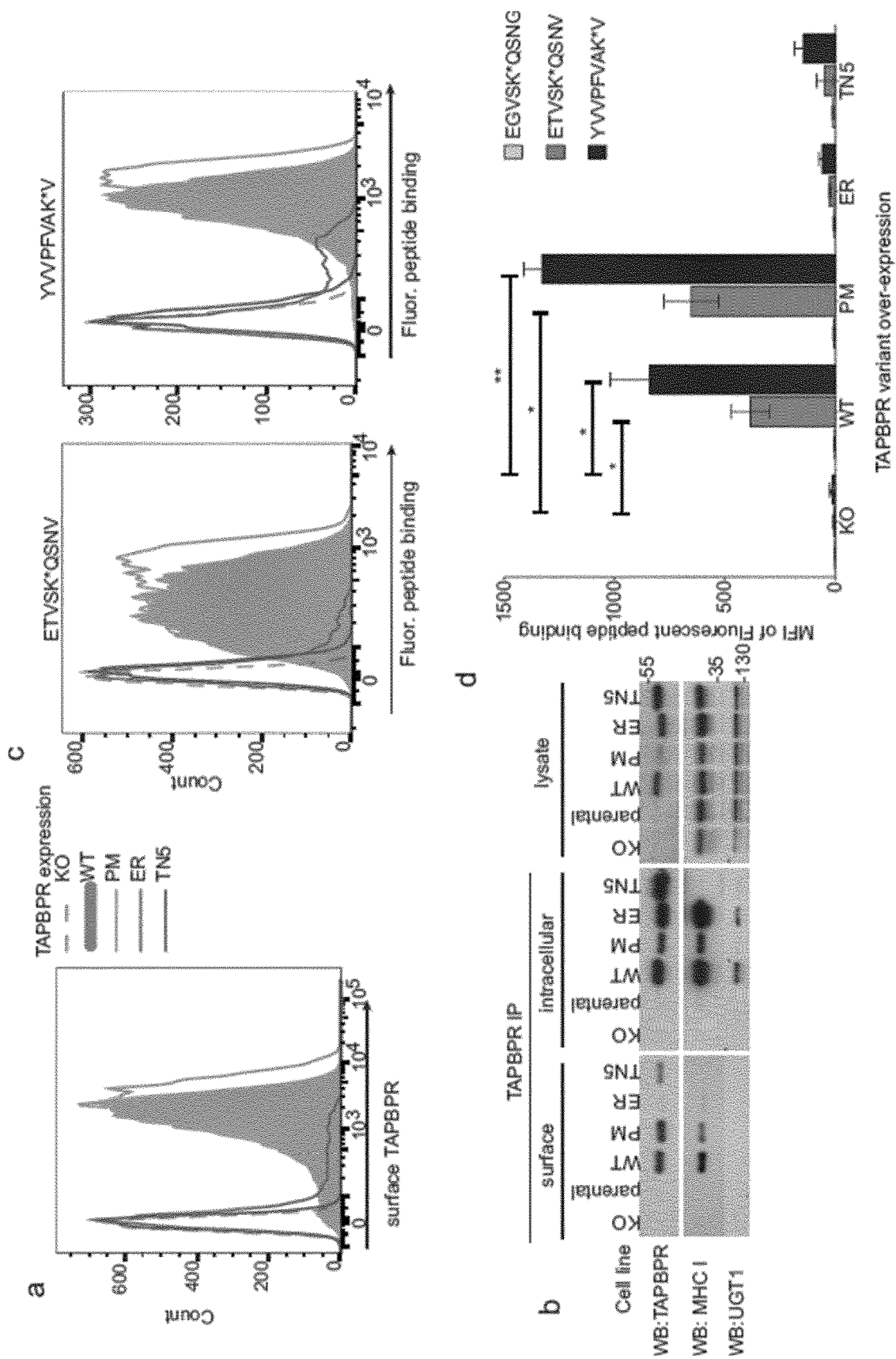
FIG. 2 shows that surface expressed TAPBPR enhances exogenous peptide association onto MHC class I molecules. (a,b) TAPBPR targeted to the plasma membrane (PM), but not the endoplasmic reticulum (ER), is detectable on the surface of cells and associates with MHC class I there. (a) Cell surface detection of TAPBPR using PeTe-4 on IFN-γ treated HeLaM-TAPBPR$^{KO}$ cells -/+ transduction with TAPBPR$^{WT}$, TAPBPR$^{PM}$, TAPBPR$^{ER}$ or TAPBPR$^{TN5}$. Note: As Transduction of TAPBPR$^{PM}$ into HeLaM$^{KO}$ cells resulted in extremely high surface expression of TAPBPR cells with a low transduction level were subsequently used to produce a cell line with similar TAPBPR surface expression as TAPBPR$^{WT}$ expressing cells. (b) Immunoprecipitation of the cell surface pool of TAPBPR, by staining intact cells with PeTe-4 before lysis and addition of Protein-A sepharose, and the remaining intracellular TAPBPR pool, followed by Western blotting for TAPBPR, MHC class I (using HC10) and UGT1 on immunoprecipitates and lysates as indicated. (c, d) Cells expressing TAPBPR on their surface show a substantial enhancement in exogenous peptide association on MHC class I compared to cell with intracellular TAPBPR. IFN-γ treated cells were incubated with 10 nM ETVSK*QSNV, YVVPFVAK*V or EGVSK*QSNG for 15 min at 37° C. and analysed using flow cytometry. (e,f,g) Cells expressing tapasin target to the PM show a slight enhancement in exogenous peptide association compared to cells with intracellular tapasin. IFN-γ treated HeLaMTAPBPR$^{KO}$-/+ transduction with tapasin$^{WT}$ or tapasin$^{PM}$ were either (e) stained with Pasta1 or (f,g) incubated with 10 nM ETVSK*QSNV, YVVPFVAK*V or EGVSK*QSNG for 15 min at 37° C., followed by flow cytometric analysis. (c,f) Histograms of the typical fluorescent peptide binding observed. (d,g) Bar charts show MFI-/+s.e.m of fluorescent peptide binding from three independent experiments.*P≤0.05, **P≤0.01, n/s not significant, using unpaired two-tailed t-test.
Figure 2:
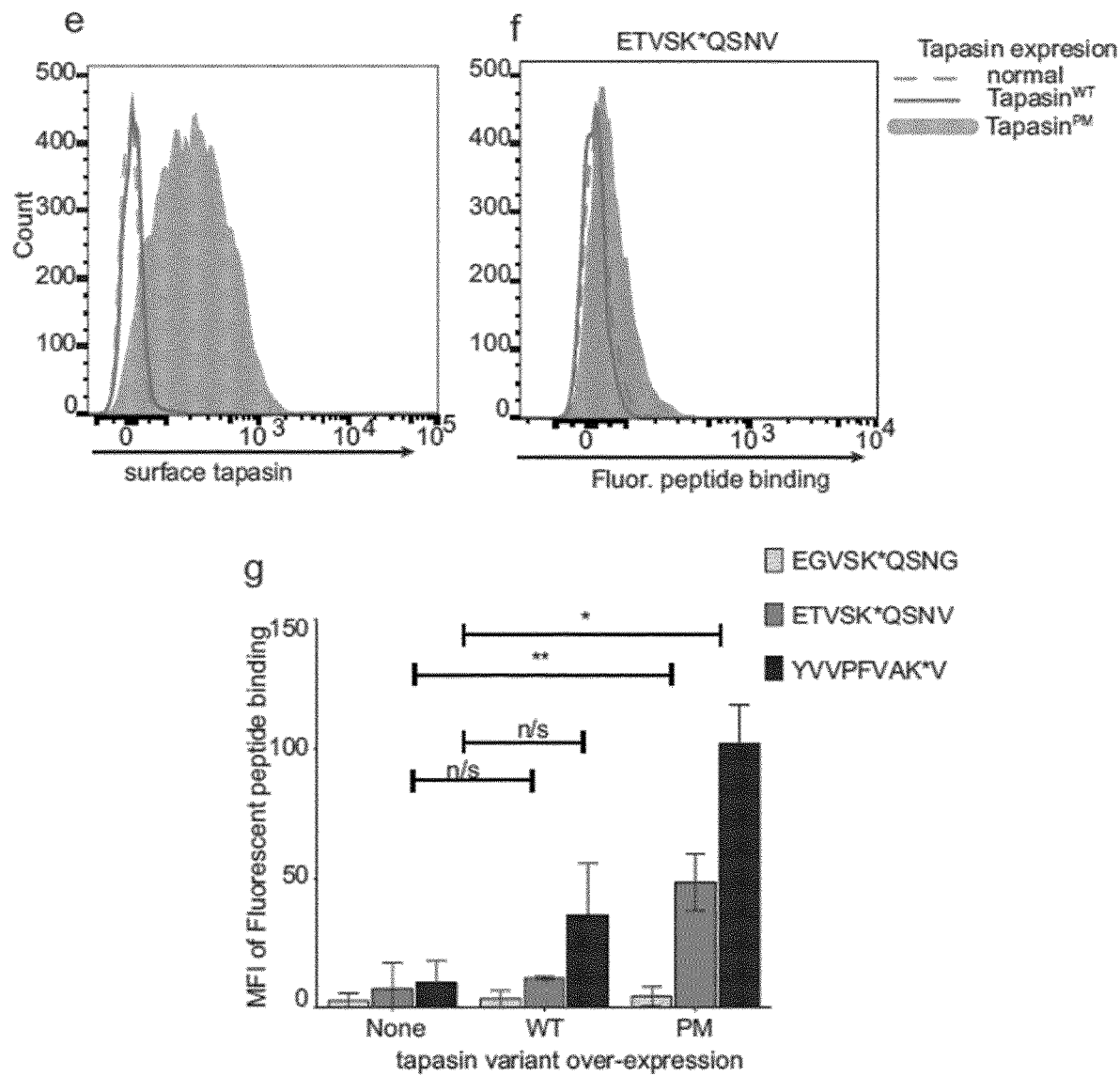

2.2 Surface Expressed TAPBPR Enhances Exogenous Peptide Association onto MHC Class Molecules To provide definitive proof that the surface pool of TAPBPR, rather than over-expression of the protein, was responsible for loading exogenous peptide onto MHC class I, we produced two chimeric TAPBPR constructs to target TAPBPR to different subcellular sites. Plasma membrane (PM) targeting of the lumen portion of TAPBPR was achieved by replacing cytoplasmic tail of TAPBPR with that of CD8 (TAPBPR$^{PM}$)[12] while TAPBPR was retained in the endoplasmic reticulum (ER) by replacing its transmembrane domain and cytoplasmic tail with those of tapasin (TAPBPR$^{ER}$)[13,14]. In contrast to TAPBPR$^{PM}$, which was expressed at very high levels on the cell surface, TAPBPR$^{ER}$ was not detectable on the plasma membrane (FIG. 2a). Immunoprecipitation of the surface pool of TAPBPR indicated that MHC class I was associated with surface expressed TAPBPR on TAPBPR$^{WT}$ and TAPBPR$^{PM}$ transduced cells but not from those transduced with TAPBPR$^{TN5}$, a mutated TAPBPR variant which does not bind to MHC class I[15] (FIG. 2b). As the amount of surface TAPBPR isolated (FIG. 2b) closely correlated with surface TAPBPR expression observed using flow cytometry (FIG. 2a) with barely detectable quantities isolated from cells expressing TAPBPR$^{ER}$, and UGT1 was not detectable in the surface pull-downs (FIG. 2b) we appeared to have isolated only the surface pool of TAPBPR, and not the intracellular pool. Isolation of the intracellular TAPBPR pool, from cells post-surface TAPBPR preclear, confirmed all TAPBPR variants were expressed and that TAPBPR$^{WT}$, TAPBPR$^{PM}$ and TAPBPR$^{ER}$ molecules exhibited strong associations with MHC class I (FIG. 2b). In contrast to TAPBPR$^{PM}$, a significant association of UGT1 with both TAPBPR$^{WT}$ and TAPBPR$^{ER}$ was observed, supportive of the predicted subcellular localisation of the chimeric proteins (FIG. 2b). When the ability of the cell lines to bind to two exogenous HLA-A*68:02 specific fluorescent peptides, ETVSK*QSNV and YVVPFVAK*V, was tested, only cells expressing surface TAPBPR exhibited significant peptide association in the presence of 10 nM exogenous peptide for 15 min at 37° C. (FIGS. 2c & d). No fluorescent peptide binding was observed on cells expressing TAPBPR$^{ER}$ (FIGS. 2c & d). These results provide indication that surface TAPBPR, rather than its over-expression, is responsible for the loading of exogenous peptide onto MHC class I.

2.3 Surface Expressed Tapasin Also Enhances Exogenous Peptide Association onto MHC Class I Molecules, but to a Lesser Extent than TAPBPR As tapasin is also an MHC class I peptide editor, we asked whether this molecule could similarly load exogenous peptide onto MHC class I when expressed at the cell surface. In contrast to the overexpression of TAPBPR$^{WT}$, the overexpression of tapasin$^{WT}$ does not result in this protein being expressed at the cell surface (FIG. 2e), most likely due to the ER retention motif found in its cytoplasmic tail[13,14]. Therefore, we replaced the cytoplasmic tail of tapasin with that of CD8 (tapasin$^{PM}$) which resulted in its expression at the cell surface (FIG. 2e). When the ability of tapasin overexpressing cells to bind to ETVSK*QSNV and YVVPFVAK*V was tested, a slight but significant increase in exogenous fluorescent peptide binding to HLA-A*68:02 was observed with cells expressing tapasin at the cell surface (FIGS. 2f & g). These results provide indication that surface tapasin is also capable of enhancing exogenous peptide association onto MHC class I. However, exogenous peptide binding observed with tapasin$^{PM}$ was ~10 times less than that observed with TAPBPR$^{PM}$.

2.4 Surface TAPBPR Functions as Peptide Exchange Catalyst on Surface MHC Class I Molecules There are two conceivable mechanisms by which surface expressed TAPBPR could promote the loading of exogenous peptide onto MHC class I; it may drag peptide-receptive MHC class I molecules with it through the secretory pathway to the cell surface and/or it may retain its ability to function as a peptide exchange catalyst in this atypical location. To explore this further, we developed an assay to determine whether surface expressed TAPBPR was capable of promoting peptide exchange on MHC class I molecules.

Figure 3:
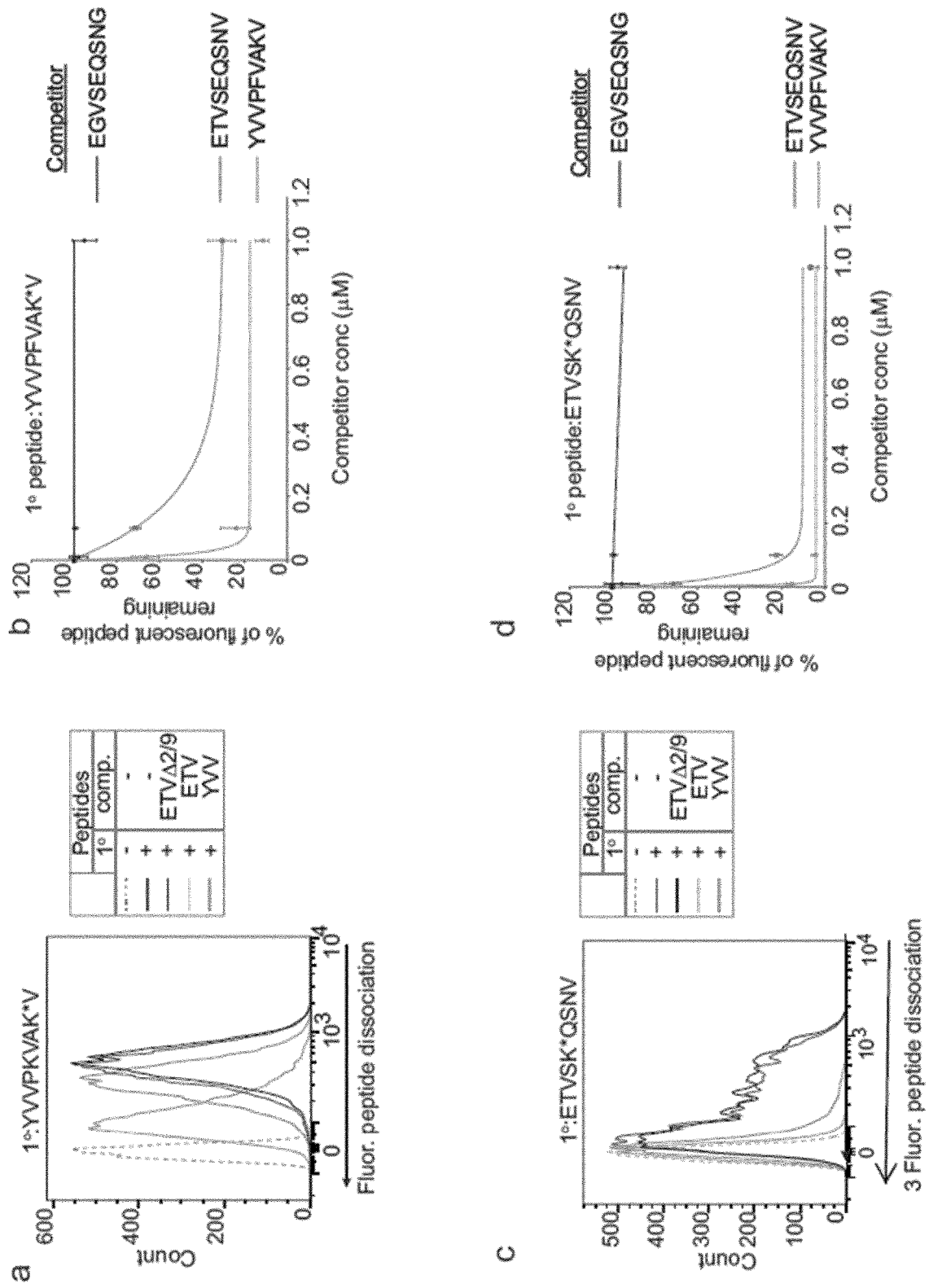
FIG. 3 shows that surface TAPBPR functions as a MHC class I peptide exchange catalyst. Dissociation of the fluorescent peptide (a, b) YVVPKVAK*V (YVV*) or (c, d) ETVSK*QSNV (ETV*) from IFN-γ treated HeLa$^{KO}$TAPB-PR$^{WT}$ cells in the absence or presence of unlabeled competitor peptides YVVPFVAKV (YVV), ETVSEQSNV (ETV) or ETVSEQSNG (ETVΔ2/9). Cells were incubated with 10 nM fluorescent peptide for 15 min at 37° C., washed, then subsequently incubated with increasing concentrations of unlabeled competitor peptide for 15 min at 37° C. (a,c) Histograms show the typical dissociation of fluorescent peptide observed following incubation with 100 nM competitor peptide. (b,d) Line graphs show the percentage of fluorescent peptide remaining −/+s.e.m following treatment with increasing concentrations of unlabeled peptide from (b) four and (d) three independent experiments.

First, cells were incubated with 10 nM fluorescently-labelled peptide for 15 min at 37° C. to allow surface MHC class I molecules to bind to labelled peptides. The, after extensive washing to remove any unbound fluorescent peptide, the ability of the cells to exchange the labelled peptide was assessed by incubating the cell with various unlabeled competitor peptides for 15 min at 37° C. Using this method we observed dissociation of both YVVPKVAK*V (FIGS. 3a & b) and ETVSK*QSNV (FIGS. 3c & d) in the presence of high affinity unlabeled competitor peptide either (ETVSEQSNV or YVVPFVAKV). No dissociation of the fluorescent peptide from HLA-A*68:02 was observed on HeLa$^{KO}$-TAPBPR$^{WT}$ cells in the presence of EGVAK*QSNG, which cannot bind to HLA-A*68:02 (FIG. 3). Our results provide indication surface TAPBPR can promote peptide exchange on surface MHC class I molecules in a peptide affinity (YVVPFVAKV>ETVSEQSNV>EGVSEQSNQ) and peptide-concentration dependent manner (FIGS. 3b & d). These findings demonstrate TAPBPR still retains its ability to function as a peptide exchange catalyst when expressed on the cell surface and that it is capable of peptide exchange on surface MHC class I molecules.

2.5 Exogenous Soluble TAPBPR Binds to Surface MHC Class I Molecules

Figure 4:
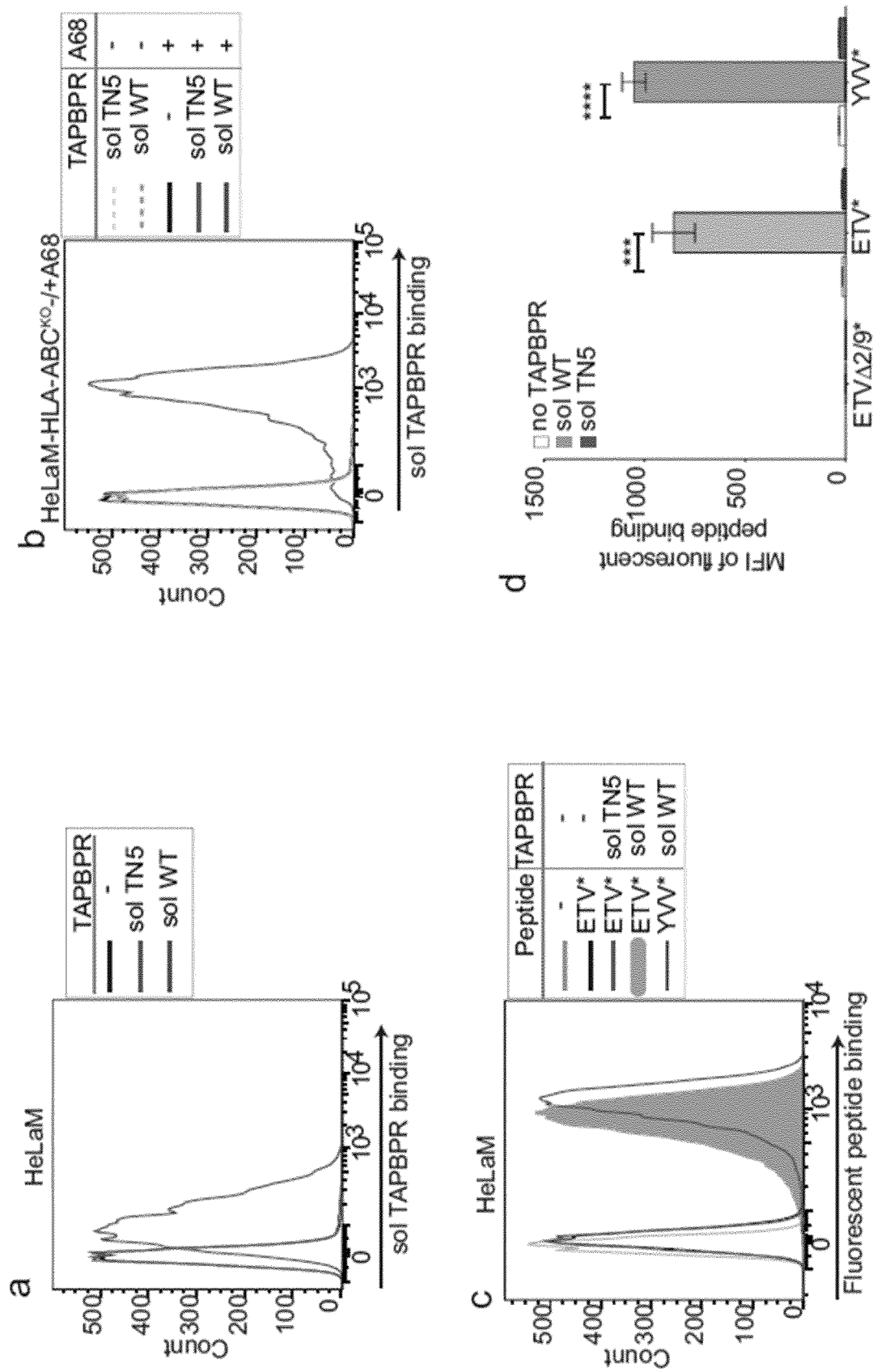
FIG. 4 shows that exogenous soluble TAPBPR enhances exogenous peptide association onto surface MHC class I. (a,b) Exogenous soluble TAPBPR binds to surface MHC class I molecules and (c-f) enhances the binding of exogenous peptide in an affinity based manner. IFN-γ treated (a,c) HeLaM and (b,e) HeLaM HLA-ABC$^{KO}$ cells −/+HLA-A*68:02 reconstitution were incubated in the absence or presence of 100 nM soluble TAPBPR$^{WT}$ (sol WT) or TAPB-PR$^{TN5}$ (sol TN5) for 15 min at 37° C., followed by (a,b) detection of surface bound TAPBPR using PeTe-4 or (c-f) incubated with and without 10 nM ETVSK*QSNV (ETV*), YVVPFVAK*V (YVV*) or EGVSK*QSNG (ETVΔ2/9) for 15 min at 37° C. and analysed using flow cytometry. (c,e) Histograms of the typical fluorescent peptide binding observed (d, f) Bar graphs show the MFI of fluorescent peptide binding −/+s.e.m from three independent experiments. (g) Dose response curves of IFN-γ treated HeLaM and HeLaM-HLA-ABC$^{KO}$ cells treated −/+100 nM TAPBPR with increasing concentrations of ETVSK*QSNV for 15 min at 37° C. Line graphs show MFI−/+s.e.m from three independent experiments. (h & i) IFN-γ treated HeLaM-HLA-ABC$^{KO}$ cells reconstituted with HLA-A*02:01 were incubated in the absence or presence of 1 μM soluble TAPBPRWT for 15 min at 37° C. followed by incubation with and without 10 nM of the HLA-A2 binding peptide NLVPK*VATV (NLV*), CLGGK*LTMV (CLG*), YLLEK*LWRL (YLL*), and YVVPFVAK*V (YVV*), or as non-HLA-A2 binding controls ETVSK*QSNV (ETV*) (specific for HLA-A*68:02) and SRYWK*IRTR (SRY*) (specific for HLA-B*27) for 15 min at 37° C. (h) Histograms of the typical fluorescent peptide binding observed using flow cytometry. (i) Bar graphs showing the MFI of fluorescent peptide binding to HeLaM HLA-ABC$^{KO}$+A2−/+s.e.m from two independent experiments with duplicates. *P≤0.001, **P≤0.0001, n/s not significant, using unpaired two-tailed t-test.
Figure 4:
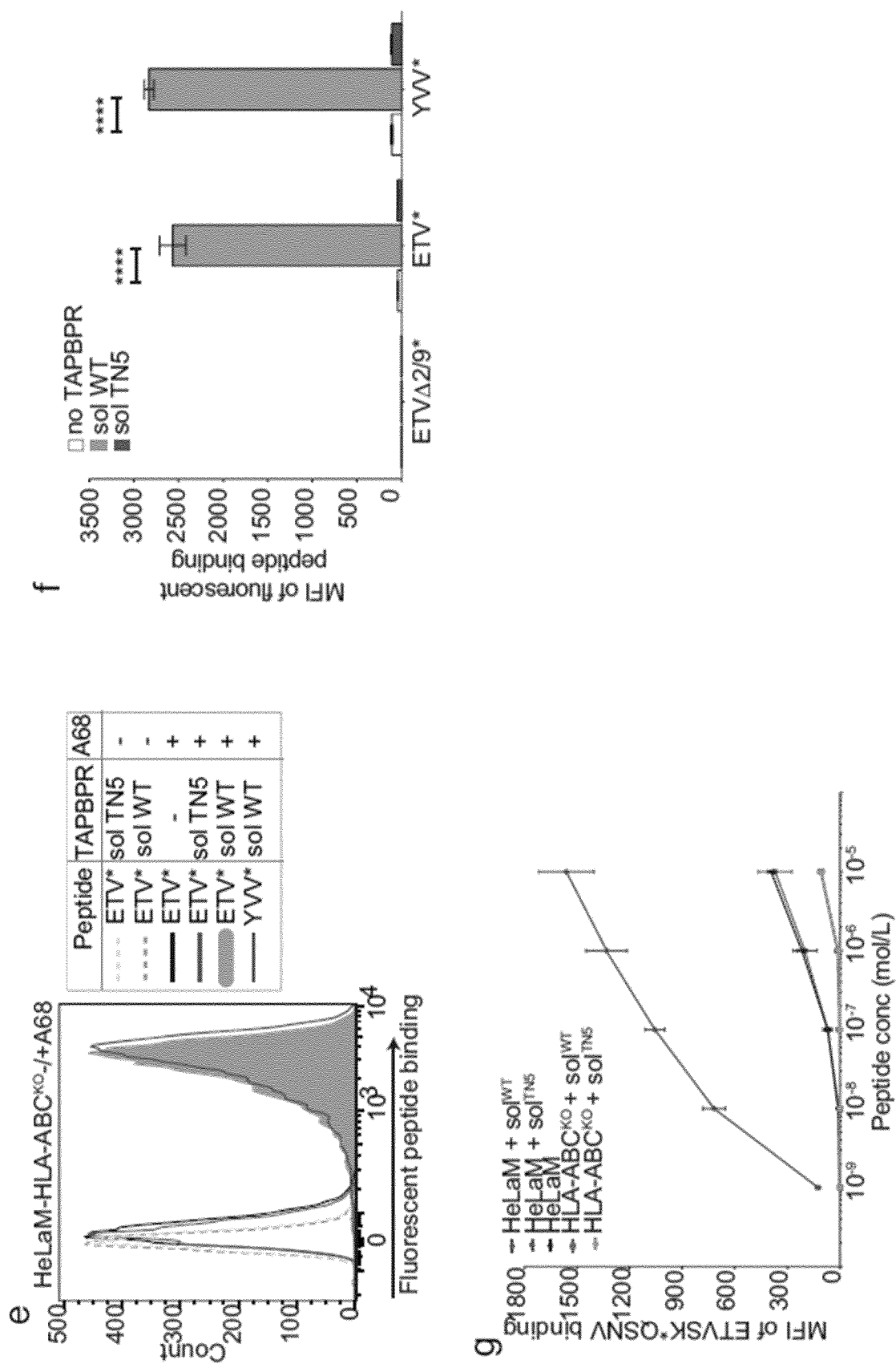
Figure 4:
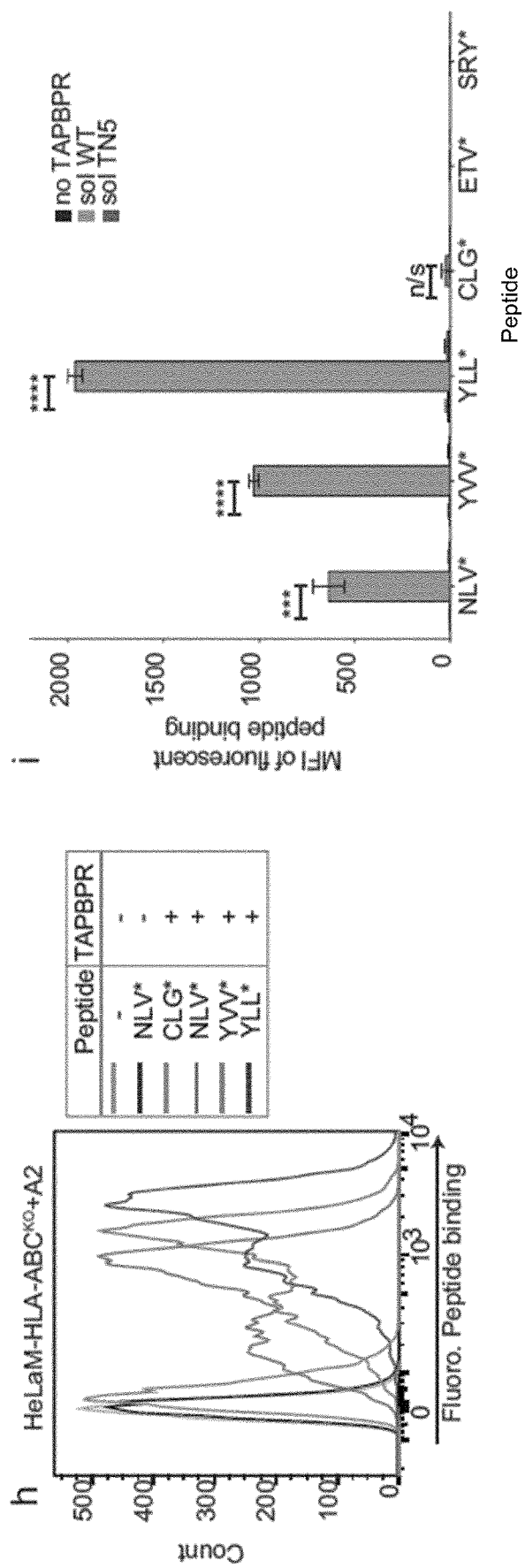

As plasma-membrane bound TAPBPR functions as a peptide exchange catalyst on HLA-A*68:02, we were curious whether exogenous soluble TAPBPR added to cells was also capable of the same catalytic function, or whether it needed its membrane anchor for proper orientation. First, we tested whether exogenous TAPBPR, which consists of its N-terminally IgV and IgC domains, but lacking the transmembrane and cytoplasmic tail, could bind to surface MHC class I molecules. When HeLaM cells were incubated with 100 nM of exogenous TAPBPR$^{WT}$ for 15 min at 37° C., TAPBPR was clearly detectable on the cell surface using the TAPBPR-specific mAb PeTe-4 (FIG. 4a). The binding of TAPBPR to cells appeared to be entirely dependent on it association with MHC class I since: 1) Exogenous TAPBPR$^{TN5}$ (a mutant that cannot bind to MHC class I[15]) did not bind to cells (FIG. 4a), 2) Exogenous TAPBPR$^{WT}$ could no longer bind HeLaM lacking classical MHC class I expression (HeLaM-HLA-ABC$^{KO}$) (FIG. 4b) and 3) The binding of exogenous TAPBPR$^{WT}$ to HeLaMHLA-ABC$^{KO}$ cells was restored when HLA-A*A68:02 expression was reconstituted (FIG. 4b). These results demonstrate that exogenous soluble TAPBPR can bind to HLA-A*68:02 expressed on the cell surface.

2.6 Exogenous Soluble TAPBPR Enhances Peptide Association onto Surface MHC Class I We next asked whether the exogenous TAPBPR bound to surface MHC class I molecules was capable of peptide exchange similarly to the membrane anchored version. Following incubation of cells for 15 min at 37° C. in the presence or absence of 100 nM exogenous TAPBPR, cells were treated with or without 10 nM fluorescent peptide for an additional 15 mins. In contrast to the extremely low levels of exogenous peptide binding observed on HeLaM cells in the absence of TAPBPR$^{WT}$ or when treated with TAPBPR$^{TN5}$, a significant enhancement in the binding of exogenous fluorescent peptides ETVSK*QSNV and YVVPKVAK*V to HeLaM was observed when cells were treated with exogenous TAPBPR$^{WT}$ (FIG. 4c &d). No association of EGVAK*QSNG was observed in any of the conditions tested (FIGS. 4c & d). The binding of exogenous peptide to cells via TAPBPR was shown to be mediate via HLA-A*68:02 since no binding of ETVSK*QSNV (FIGS. 4e & f) or YVVPKVAK*V was observed to cell lacking MHC class I expression and peptide association was restored when HLA-A*68:02 expression was reconstituted (FIGS. 4e & f). Soluble TAPBPR$^{WT}$ enhanced exogenous peptide binding to cells over a wide range of peptide concentrations (FIG. 4g). These results clearly demonstrate that exogenous TAPBPR can load peptides on HLA-A*68:02 and that the luminal domain of TAPBPR is sufficient for the position of TAPBPR onto MHC class I molecules.

To ensure the results observed were not an anomaly of HLA-A*68:02, we extended our analysis to test the ability of TAPBPR to load a range of exogenous peptides onto another human MHC class I molecule, HLA-A*02:01. Exogenous TAPBPR$^{WT}$ significantly promoted the binding of fluorescent variants of NLVPMVATV (an immunogenic peptide derived from the CMV protein pp65[16]), YVVPFVAKV (derived from human CCR4-NOT transcription complex subunit 1[8]) and YLLEMLWRL (an immunogenic peptide derived from the EBV protein Latent membrane protein 1 (LMP1)[17] (FIGS. 4h & i). The TAPBPR promoted loading of these exogenous peptides was dependent on HLA-A2 as no fluorescent peptide binding was observed on HLA-A2 negative cells. Exogenous TAPBPR$^{WT}$ also appeared to slightly promote the binding of a fluorescent variant of CLGGLLTMV (an immunogenic peptide derived from the EBV protein Latent membrane protein 1) although not to significant levels (FIGS. 4h & i) but did not promote the binding of peptides specific for other MHC class I molecules onto HLA-A2 (FIG. 4i). Exogenous TAPBPR$^{TN5}$, which cannot bind to MHC class I, did not promote the binding of any peptides to HLA-A2 (FIG. 4i). Together, our data strongly suggests exogenous TAPBPR can promote the loading exogenous peptide onto surface MHC class I in an affinity-based manner.

Figure 22:
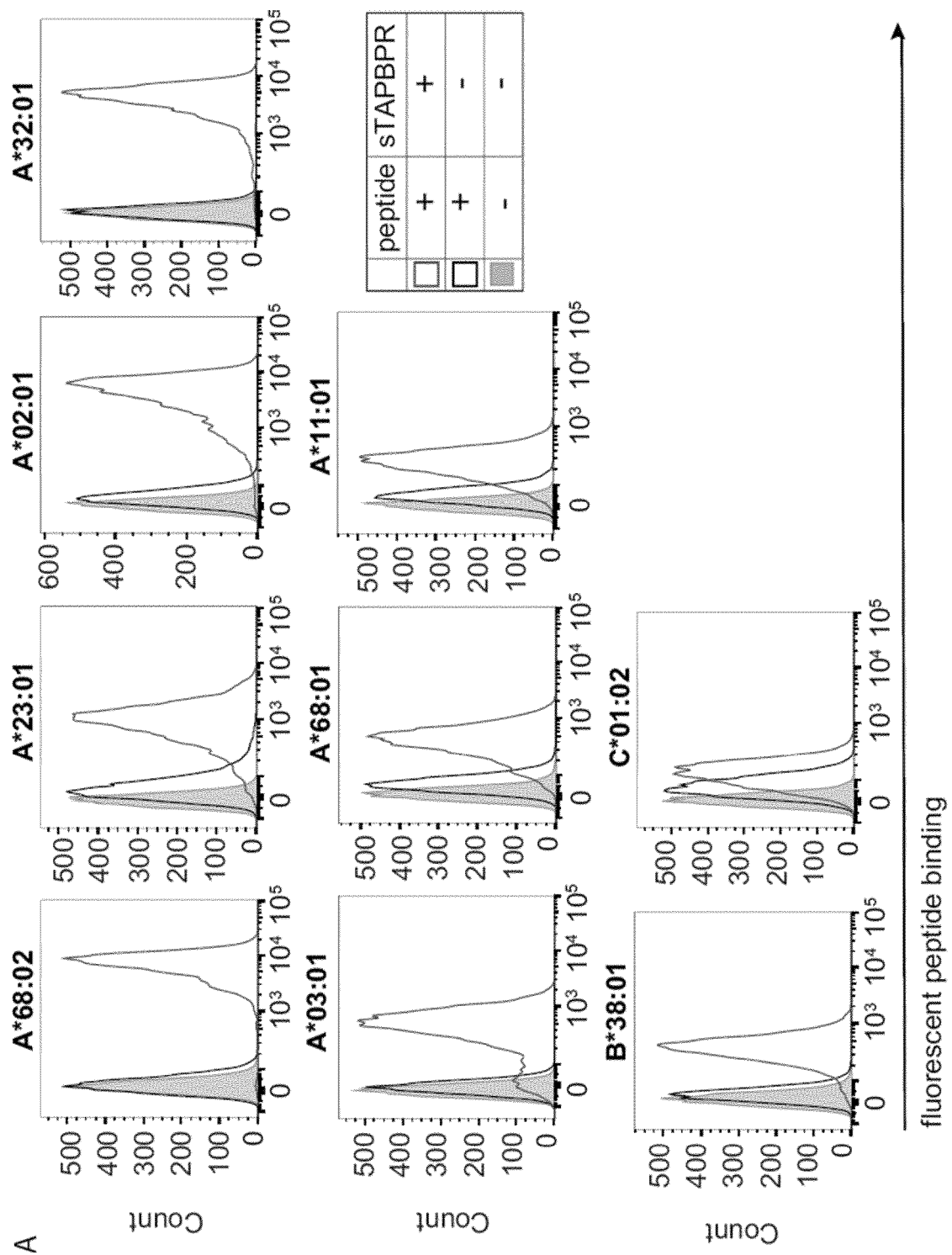
FIG. 22 shows that TAPBPR can mediate peptide exchange on a wide range of HLA molecules, particularly HLA-A molecules. HeLa-HLA-ABC$^{KO}$ cells expressing individual HLA I allomorphs were incubated with 1 μM TAPBPR for 15 min at 37° C., after which fluorescently-labelled peptide, specific for each corresponding HLA I allomorph, was added for an allele-dependent time period (15 min for A*68:02 and A*23:01 and 60 min for the others) and at an allele-dependent concentration (10 nM for A*68:02, A*02:01, A*23:01, A*32:01 and 100 nM for the others). Histograms shows the level of bound fluorescent peptide to each HLA I-expressing cell line when cells were incubated with peptide alone (black line) or with peptide and TAPBPR (blue line). A sample not treated with peptide was included as a negative control (solid grey line). TAPBPR was found to promote peptide exchange on all these HLA molecules.

TAPBPR was found to promote peptide exchange on a wide range of different HLA molecules, particularly HLA-A molecules (FIG. 22), including A*68:02, A*23:01, A*02:01, A*32:01, A*03:01, A*68:01, and A*11:01.

Figure 17:
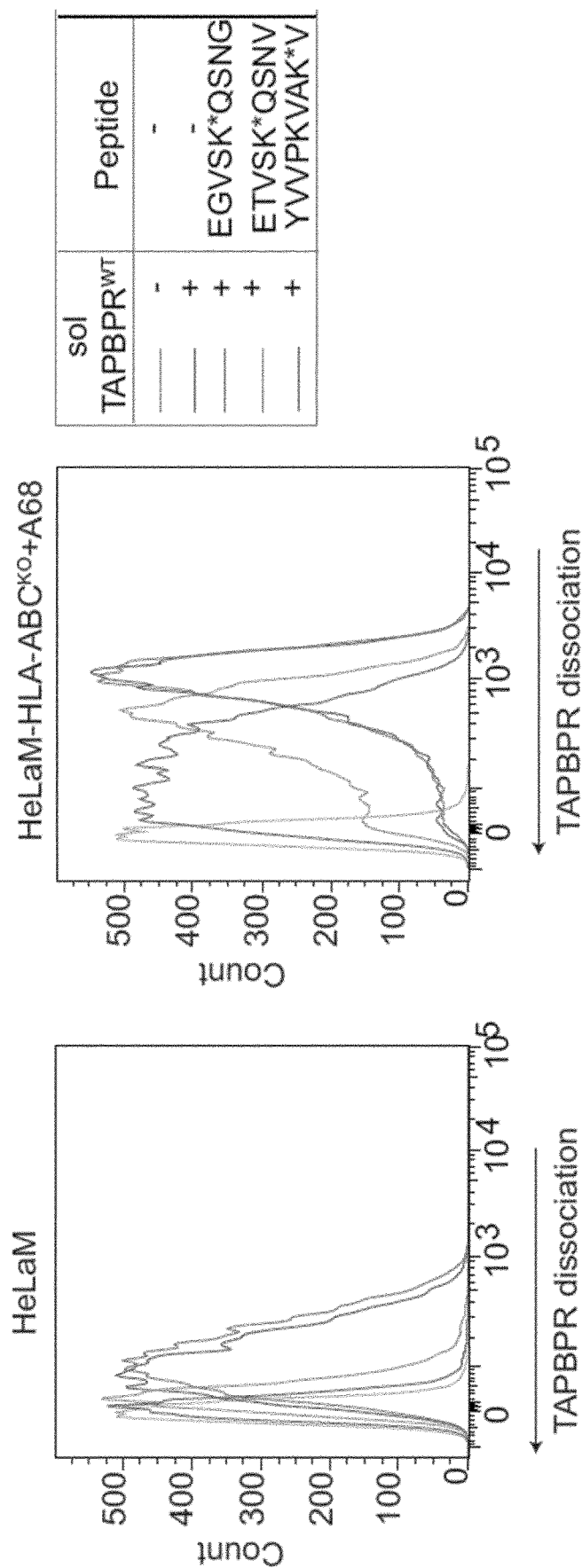
FIG. 17 shows that soluble TAPBPR dissociates from cells upon high affinity peptide binding. IFN-γ treated HeLaM cell and HeLa-HLA-ABC$^{KO}$ reconstituted with HLA-A*68:02 were incubated −/+100 nM soluble TAPBPR$^{WT}$ for 15 min at 37° C., followed by incubation with −/+10 nM EGVSK*QSNG (a non-HLA binding peptide), ETVSK*QSNV (a HLA binding peptide) or YVVPFVAK*V (a HLA binding peptide with high affinity) for 15 min at 37° C. Subsequently, the amount of TAPBPR remaining on the cell surface was detected by staining with the TAPBPR specific mAb PeTe4.

2.7 Antigenic Peptides Loaded onto MHC Class I Via TAPBPR are Available to the T Cell Receptor We subsequently determined whether the peptides loaded via TAPBPR were available for T cell receptor (TCR) detection. Encouragingly, soluble TAPBPR was found to dissociate from cells upon high affinity peptide binding onto surface MHC I molecules (FIG. 17), raising the possibility that TAPBPR-loaded peptide:MHC complexes might be fully accessible for T cell receptors (TCR) detection.

Figure 5:
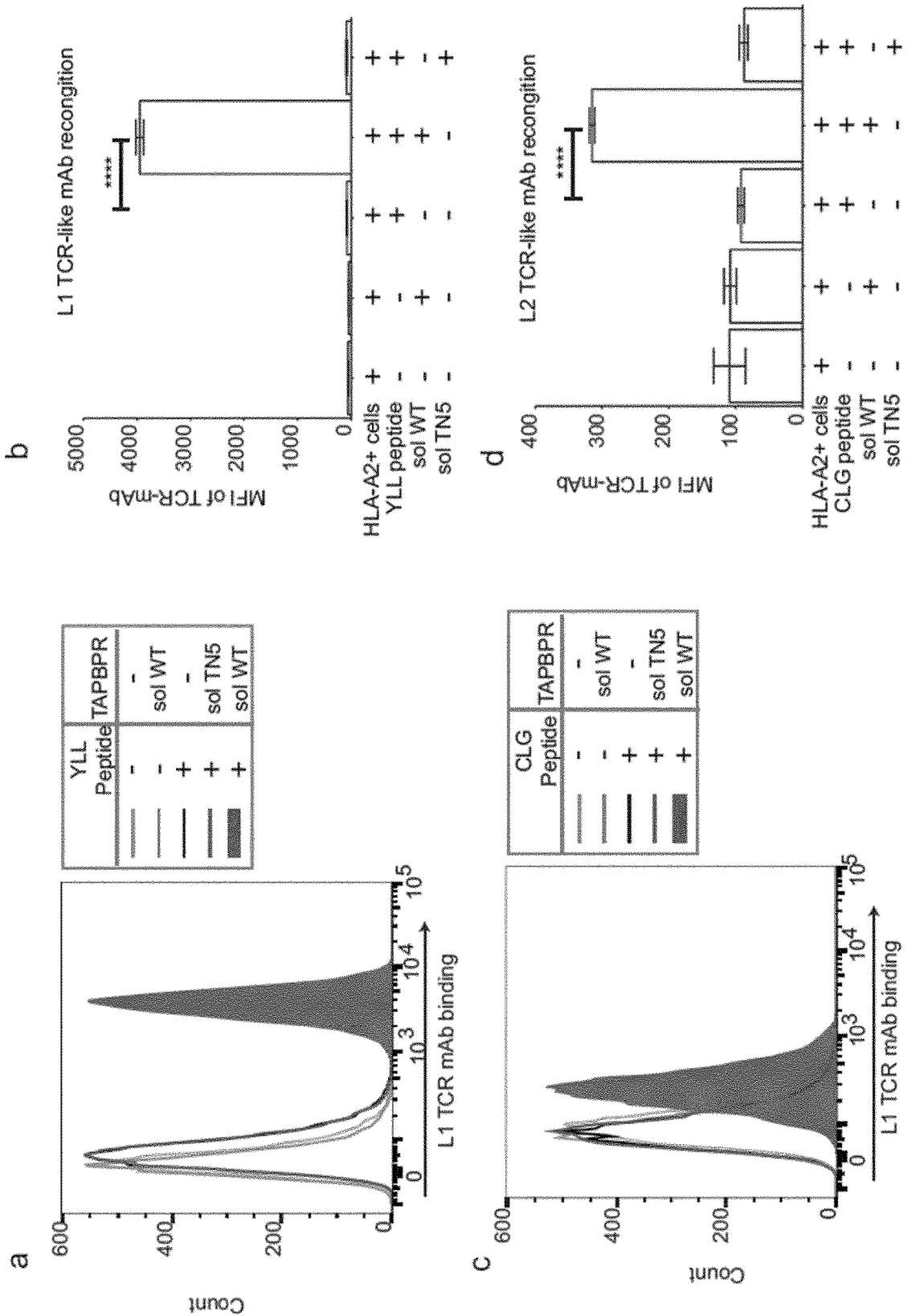
FIG. 5 shows antigenic peptides loaded onto MHC class I via TAPBPR are available to the T cell receptor. IFN-γ treated HeLaM HLA-ABC$^{KO}$ cells reconstituted with HLA-A*02:01 were incubated in the absence or presence of 1 μM soluble TAPBPR$^{WT}$ (sol WT) or TAPBPR$^{TN5}$ (sol TN5) for 15 min at 37° C. followed by 15 min treatment with or without 10 nM unlabeled HLA-A2 binding peptide (a,b) YLLEMLWRL, (c,d) CLGGLLTMV or (e) NLVPMVATV. After washing, cells were either stained with the TCR-like mAb (a,b) L1 which recognises YLLEMLWRL/HLA-A2 complexes, (c,d) L2 which recognises CLGGLLTMV/HLA-A2 complexes or (e) irradiated followed by incubation with a HLA-A2 restricted NLVPMVATV specific CD8+ T cell line. Bar graphs (b, d) show the MFI of TCR-like mAb binding −/+s.e.m from three independent experiments or (e) T cell activity measured by detecting IFN-γ secretion in fluorospot assays from triplicate wells representative of two independent experiments. *P≤0.001, **P≤0.0001 using unpaired two-tailed t-test.
Figure 5:
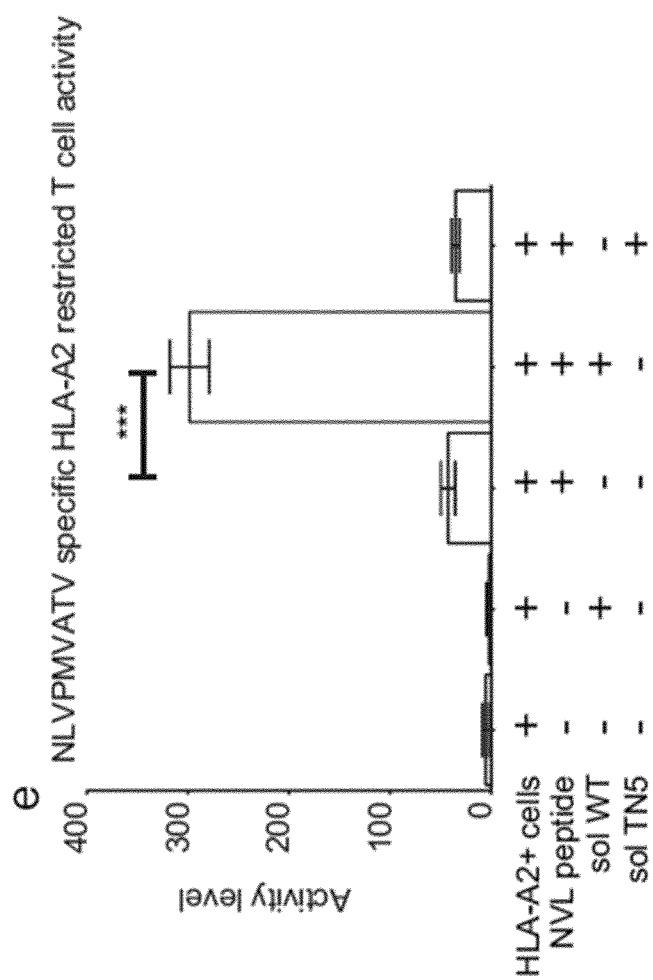

To explore this, we first asked if two anti-EBV TCR-like mAbs L1 and L2, specific for LMP1$_{125-133}$ and LMP2$_{426-434}$ derived peptides presented on HLA-A*02:01 respectively[17], could recognise YLLEMLWRL and CLGGLLTMV loaded onto surface HLA-A2 by exogenous TAPBPR. A significant increase in TCR detection of their respective peptide observed on HeLa-HLA-ABC$^{KO}$ A2+ cells in the presence of exogenous TAPBPR$^{WT}$, compared to cells treated with peptide alone or incubated with peptide following treatment with exogenous TAPBPR$^{TN5}$ (FIG. 5a-d). The ability of the TCR-like mAb to recognise peptide loaded onto HLA-A2 via TAPBPR strongly reflects the level of peptide binding (FIG. 4h&i), with the largest increase in recognition observed with L1-TCR recognition of YLLEMLWRL (FIG. 5a&b). Next, we tested the ability of TAPBPR loaded peptide to stimulate T cells by using FluoroSpot assays to measure IFN-γ production from a HLA-A2 restricted CD8+ T cell line specific for the immunogenic peptide NLVPMVATV derived from the cytomegalovirus (CMV) protein pp65[16]( ). We observed a significant increase in the stimulation of the T cells incubated with NLVPMVATV after treatment with exogenous TAPBPR$^{WT}$, compared to cells incubated with peptide alone or to cells incubated with peptide following treatment with exogenous TAPBPR$^{TN5}$ (FIG. 5e). These results not only demonstrate that peptide loaded onto MHC class I via TAPBPR is present on the cell surface, but that it is also accessible for recognition by CD8+ T cells.

2.8 TAPBPR can Load Antigenic Peptide onto Tumour Cells and Induce their Recognition by T Cells As the ability to load immunogenic peptide onto tumour cells would prove very useful for cancer immunotherapy, we tested the ability of TAPBPR to load tumour or viral peptides onto the breast cancer cell line MCF-7.

We found that soluble TAPBPR$^{WT}$ significantly enhanced the loading of fluorescent derivatives of the tumour antigens IMDQVPFSV (derived from gp100)[28], ELAGIGILTV (from Melan-A/MART-1)[29], LLGRNSFEV (derived from p53)[30] and RLLQETELV (from HER-2/neu)[31] (FIG. 6a) onto HLA-A*02:01 naturally expressed on MCF-7, a breast cancer cell line. Exogenous soluble TAPBPR$^{WT}$ also enhanced the association of both YLLEK*LWRL (from EBV LMP1) and NLVPK*VATV (from CMV) onto HLA-A2 molecules expressed on the MCF-7 cells compared to those treated with peptide alone or incubated with peptide following treatment with exogenous TAPBPR$^{TN5}$ (FIG. 6b).

Figure 6:
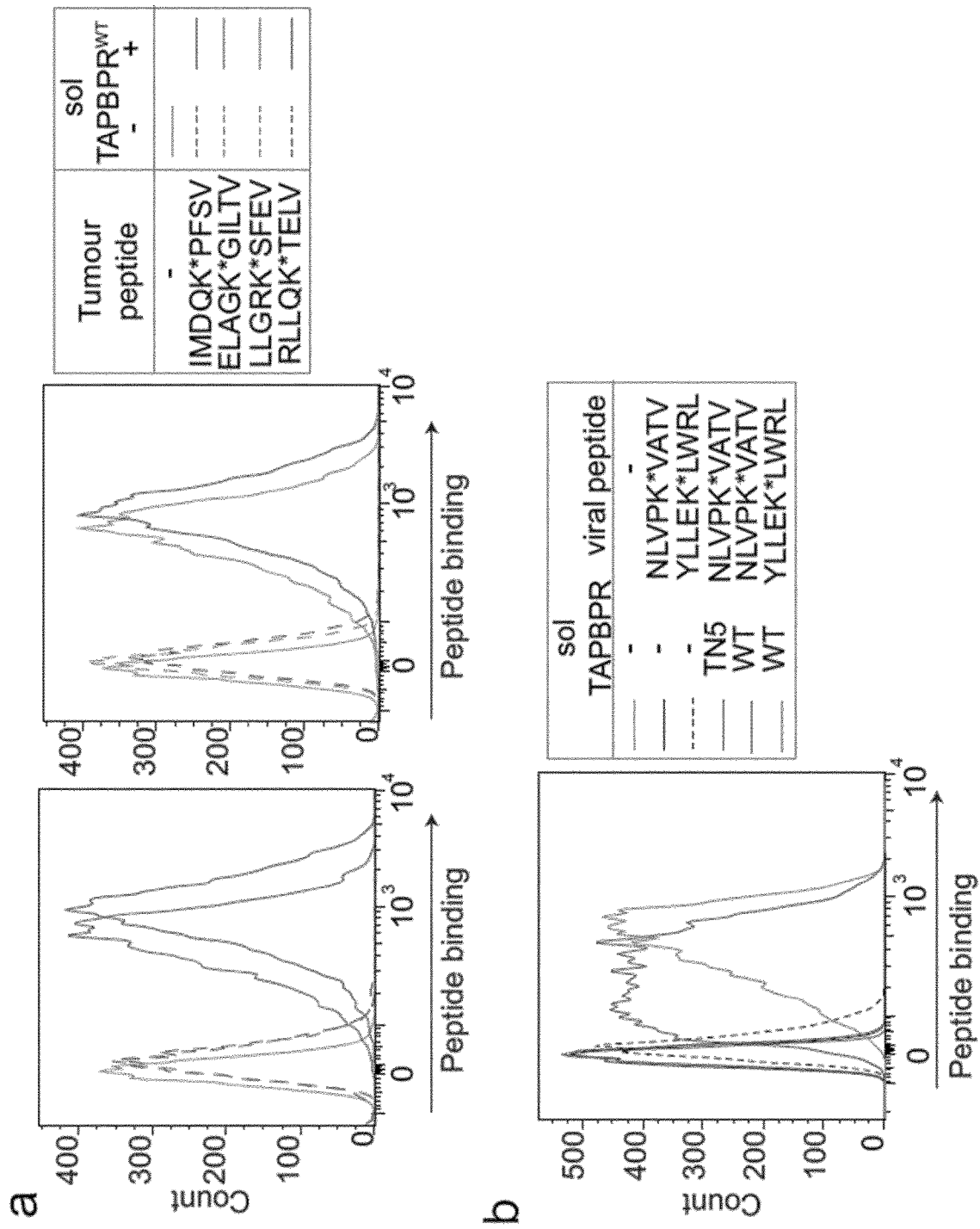
FIG. 6 shows TAPBPR can load antigenic peptide onto tumour cells and induce their recognition by T cells. MCF-7 cells were treated −/+1 μM soluble TAPBPR$^{WT}$ or TAPB-PR$^{TN5}$ for 15 min at 37° C. followed by 60 min incubation −/+10 nM (6a) IMDQK*PFSV, ELAGK*GILTV, LLGRK*SFEV, or RLLQK*TELV, (6b) NLVPK*VATV or YLLEK*LWRL or (6c & d) YLLEMLWRL (YLL) followed by staining with the TCR-like mAb L1 specific for YLLEMLWRL/HLA-A2 complexes. (6d) The MFI of L1 binding to MCF-7 cells −/+SD from three independent experiments. (6e) Bar graphs show T cell activity measured by IFN-γ secretion in fluorospot assays of a HLA-A2 restricted NLVPMVATV specific CD8+ T cell line when incubated with MCF-7 target cells as treated in FIG. 6b with the exception that non-fluorescent NLVPMVATV peptide at 100 pM was used. Results are from triplicate wells representative of two independent experiments. Error bars−/+SD. Note.
Figure 6:
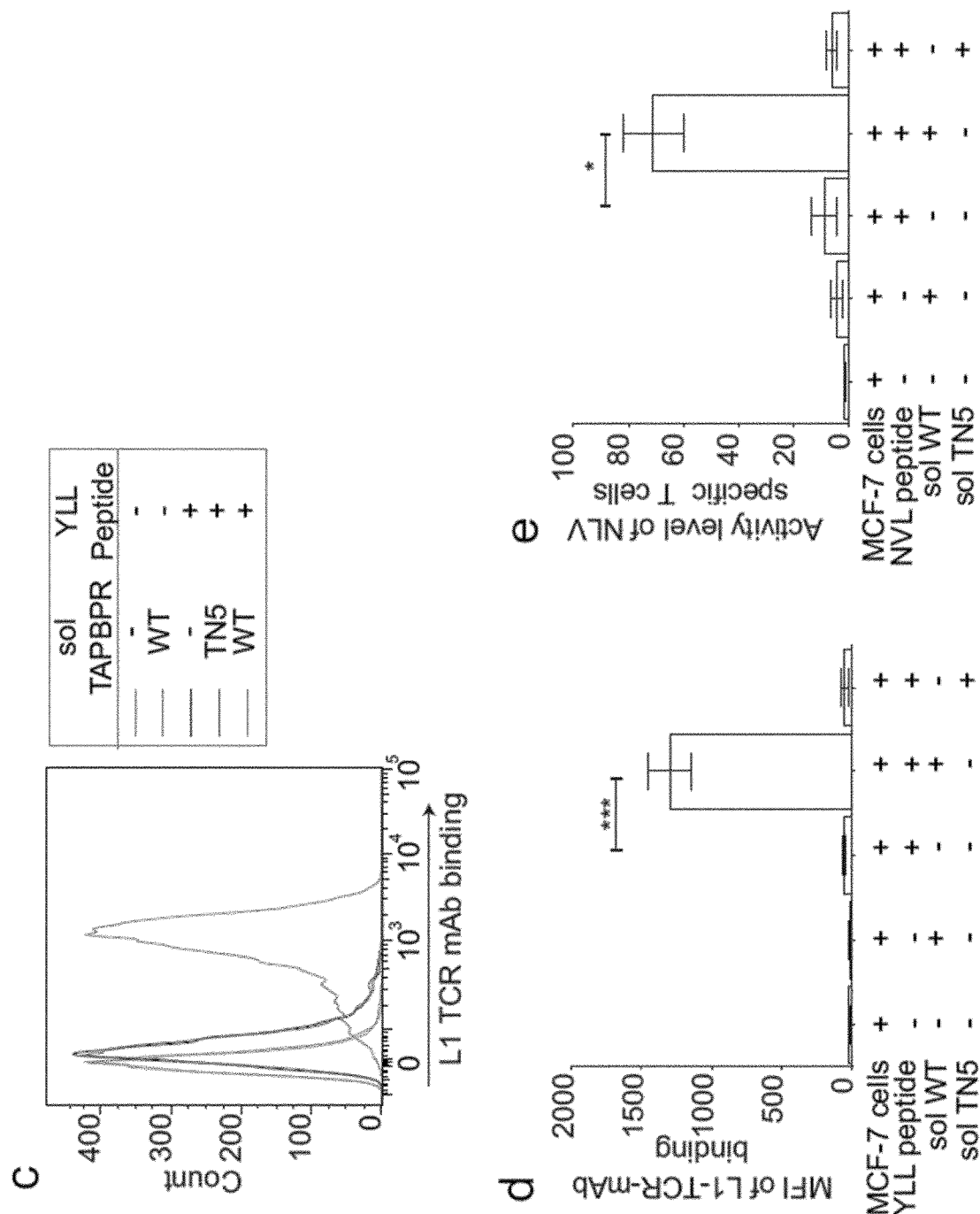
Figure 18:
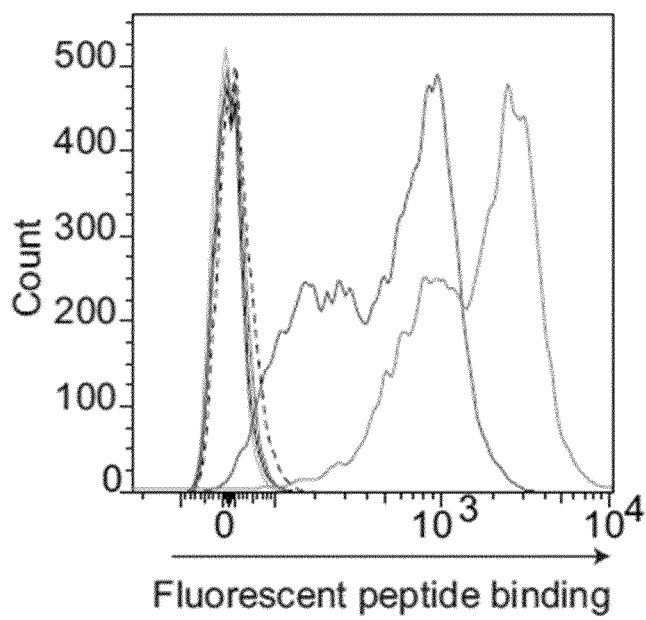
FIG. 18 shows peptide loading and TCR recognition of HLA-A2 molecules expressed on HeLaM cells. HeLaM-HLA-ABC$^{KO}$ cells reconstituted with HLA-A*02:01 were incubated −/+10 μM soluble TAPBPR$^{WT}$ or TAPBPR$^{TN5}$ for 15 min at 37° C. followed by 60 min treatment−/+10 nM (16a) NLVPK*VATV or YLLEK*LWRL or (16b) YLLEMLWRL (YLL) followed by staining with the TCR-like mAb L1 specific for YLLEMLWRL/HLA-A2 complexes. (16c) The MFI of L1 binding to HeLaM-HLA-ABC$^{KO}$ cells −/+SD from three independent experiments. (16d) Bar graphs show T cell activity measured by IFN-γ secretion in fluorospot assays of a HLA-A2 restricted NLVPMVATV specific CD8+ T cell line when incubated with HeLaM-HLA-ABC$^{KO}$ target cells as treated in a with the exception that non-fluorescent NLVPMVATV peptide at 100 pM was used. Results are from triplicate wells representative of two independent experiments. Error bars−/+SD. Note: In 18a & 18d IFNγ treated cells were used. *$P \leq 0.001$, **$P \leq 0.0001$ using unpaired two-tailed t-test.
Figure 18:
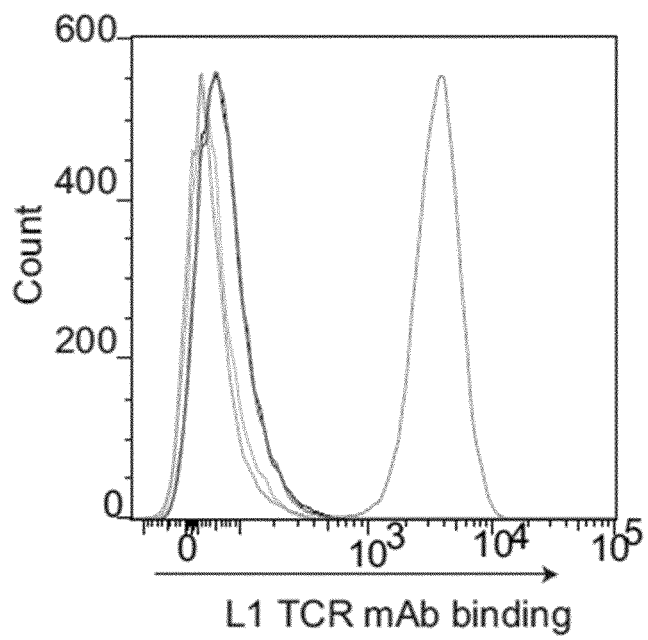
Figure 18:
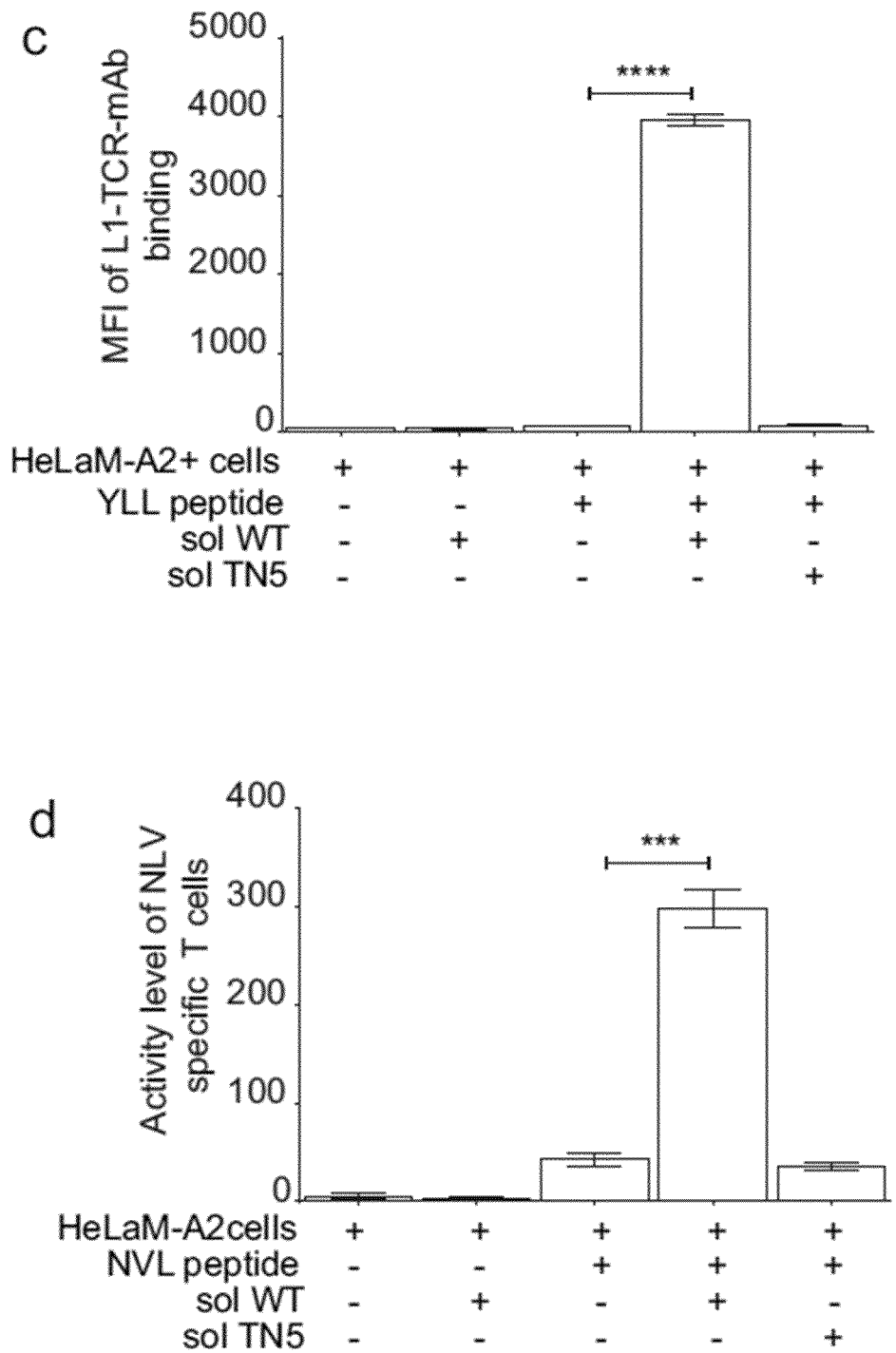

We found that YLLEMLWRL loaded onto MCF-7 cells by TAPBPR was strongly detected by the anti-EBV TCR-like mAb L1, specific for LMP1$_{125-133}$ presented on HLA-A*02:01 (17) (FIGS. 6c & 6d). Furthermore, NLVPMVATV loaded onto MCF-7 cells by soluble TAPBPR significantly increased the stimulation, measured by IFNγ secretion, of human CD8+ T cells specific for pp65$_{495-503}$ presented on HLA-A2 (16) when incubated with unlabeled peptide, compared to MCF-7 cells incubated with peptide alone or peptide with exogenous TAPBPR$^{TN5}$ (FIG. 6e). We have further verified these findings using HeLaM-HLA-ABC$^{KO}$-A2+ (FIG. 18). These results demonstrate that soluble TAPBPR can efficiently load antigenic peptides onto tumour cell lines for recognition by CD8+ T cells and could be used to enhance T cell responses to tumours.

2.9 Chimeric TAPBPR

Figure 7:
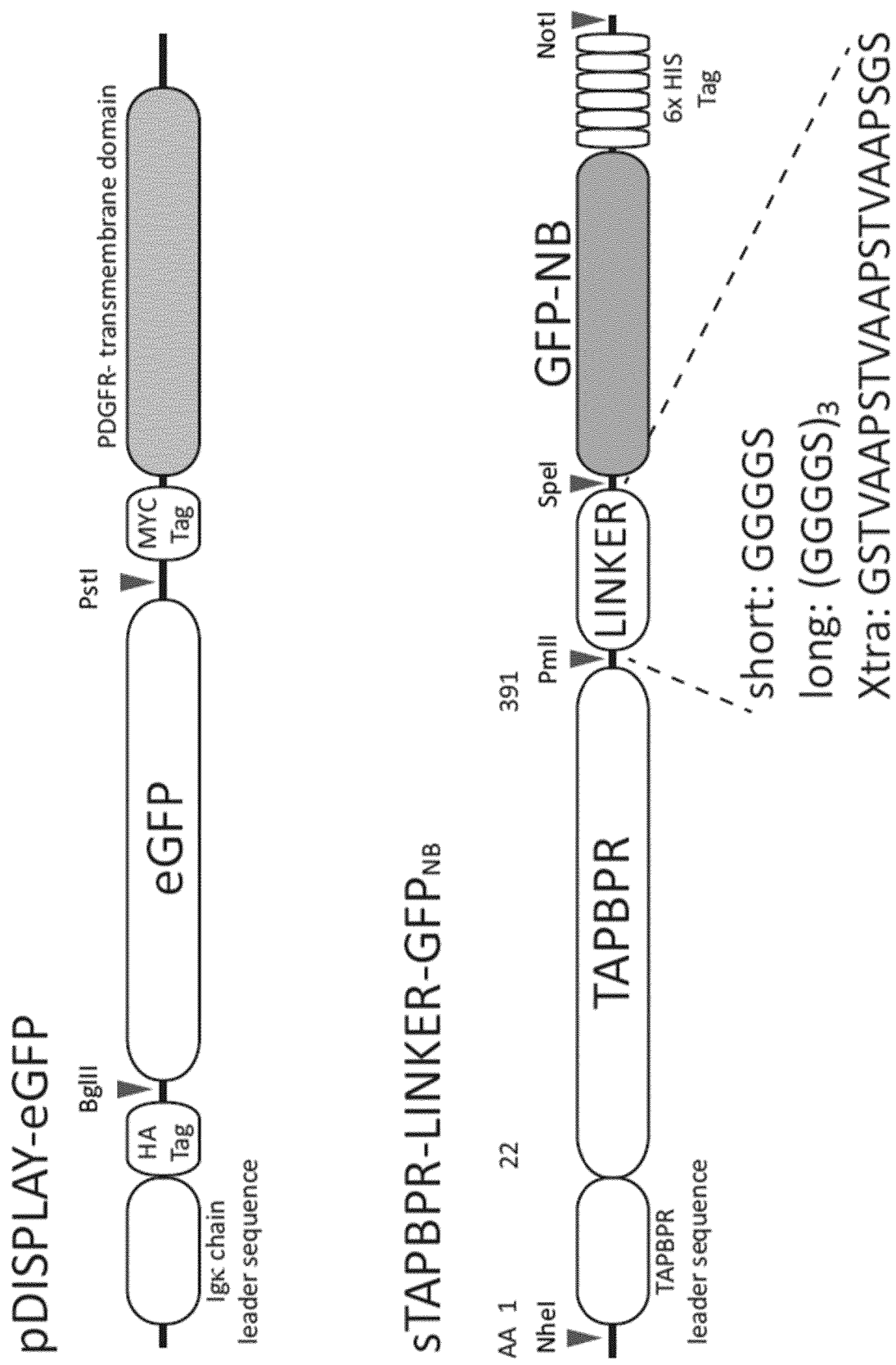
FIG. 7 shows constructs used for proof-of-concept of the chimeric peptide exchange approach. (Top) pDisplay-eGFP vector transduced into target cells to expressed GFP on the plasma membrane. (Bottom) sTAPBPR-linker-GFPNB. This construct makes soluble TAPBPR linked to a GFP nanobody. Three different variants have been made with varying linker regions to provide a flexible region between the antibody target and MHC class I. This insert is in the piggyBac vector and protein is produced in 293T cells. Yield=~5 mg/L (from adherent cell line) Note: TAPBPR in a non-glycosylated protein.
Figure 21:
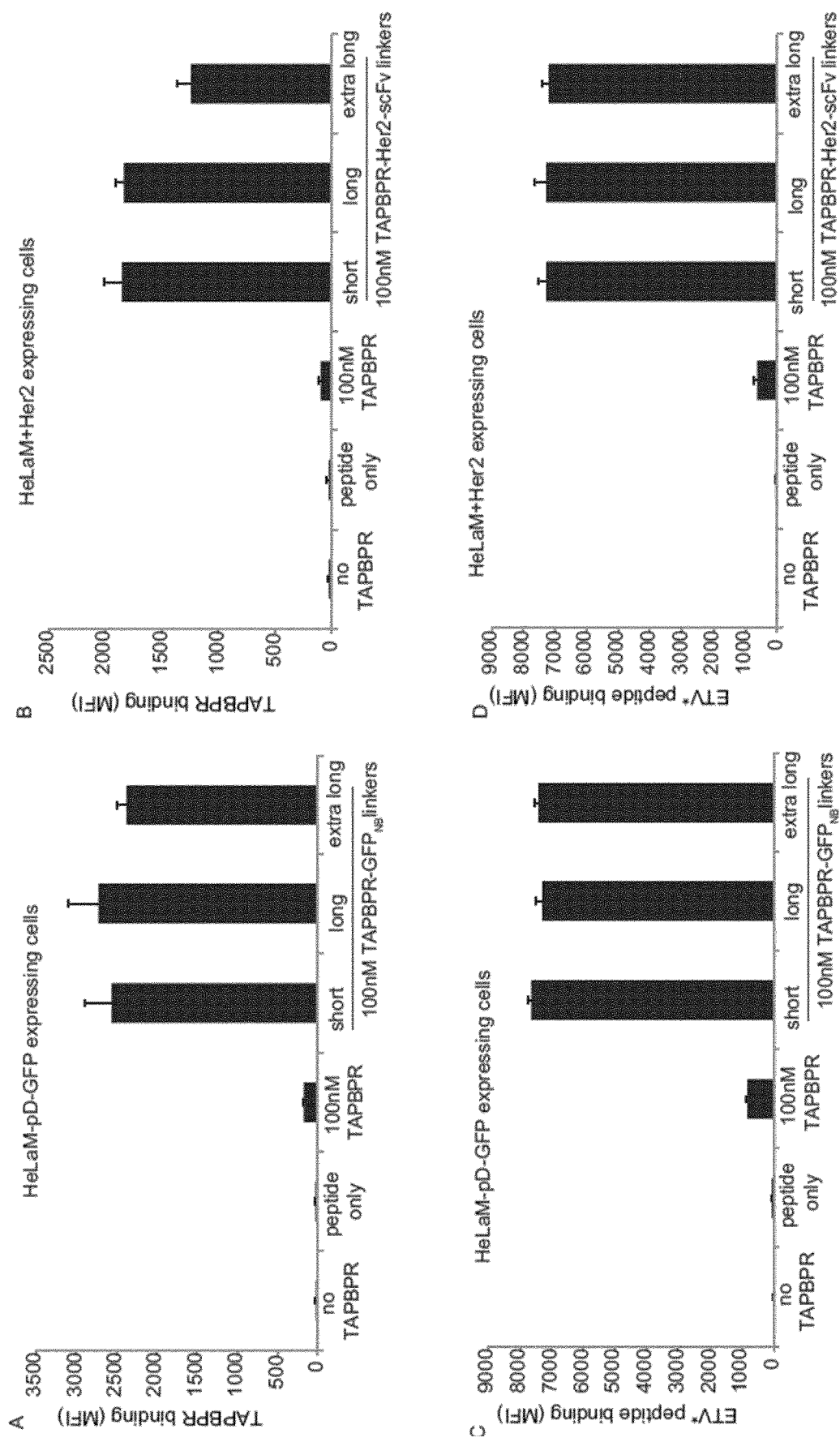
FIG. 21 shows that TAPBPR fusion proteins with various lengths of linkers between the TAPBPR and antibody fragment all work efficiently. Three different linker sequences (see FIG. 7 for sequence) were inserted between the TAPBPR and antibody fragment for both the (A&C) TAPBPR-GFP$_{NB}$ fusion and (B&D) the TAPBPR-Her2-scFv fusion. (A & B) show the ability of TAPBPR-fusion to bind to cells expressing the antibody fragment ligand is similar regardless whether the short, long or extra-long linker is used. (C&D) shown that the ability of the TAPBPR-fusion to mediate peptide loading onto HLA molecules expressed on HeLaM cells is similar regardless of whether the short, long or extra-long linker is used. Note in this application, the long linker was selected for TAPBPR-antibody fusions unless indicated otherwise.

TAPBPR-linker-GFP nanobody fusion products (with a range of linkers) were generated (FIG. 7). These products were used to demonstrate that TAPBPR-Ab fusion products retain full functionality. TAPBPR fusion proteins with various lengths of linkers between the TAPBPR and the antibody fragment were shown to work efficiently (FIG. 21).

2.10 Peptide Loading on Cervical Cancer Cells

Figure 8:
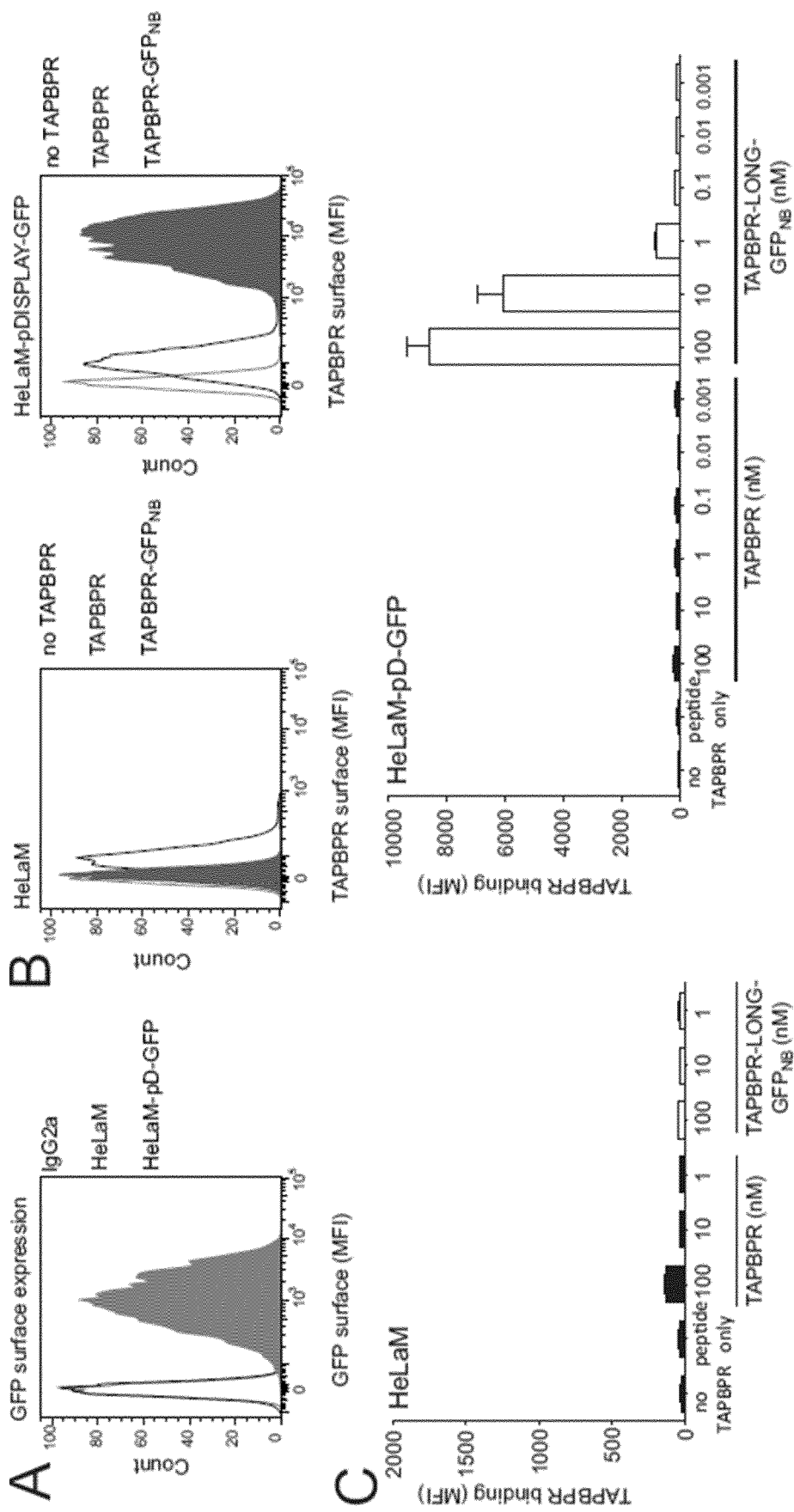
FIG. 8 shows TAPBR binding and peptide exchange mediated by TAPBPR-fused to a nanobody specific for GFP on HeLa cells. (A) shows the surface expression of GFP on HeLaM and HeLaM transfected with the pDisplay-eGFP construct (pD-GFP) using an anti-GFP antibody. (B) Histograms and (C) Bar graphs compare the binding of recombinant soluble TAPBPR (TAPBPR) with recombinant TAPBPR-fused to a nanobody specific for GFP (TAPBPR-GFP$_{NB}$) to HeLaM cells (left) and HeLaM-pD-GFP cells (right). Histograms show the level of TAPBPR when the two cell lines were incubated with 100 nM protein while bar graphs summarise results using a range of concentrations of protein (0.001-100 nM). (D & E) shows the binding of a fluorescent variant of an exogenous neoantigen peptide ETVSK*QSNV (ETV*) to HLA-A68 (MHC class I) expressed on HeLa when cells treated as in B & C where incubated with 10 nM peptide for 15 min after incubation with the indicated recombinant TAPBPR protein. Each bar represents mean and standard deviation of three independent experiments.
Figure 8:
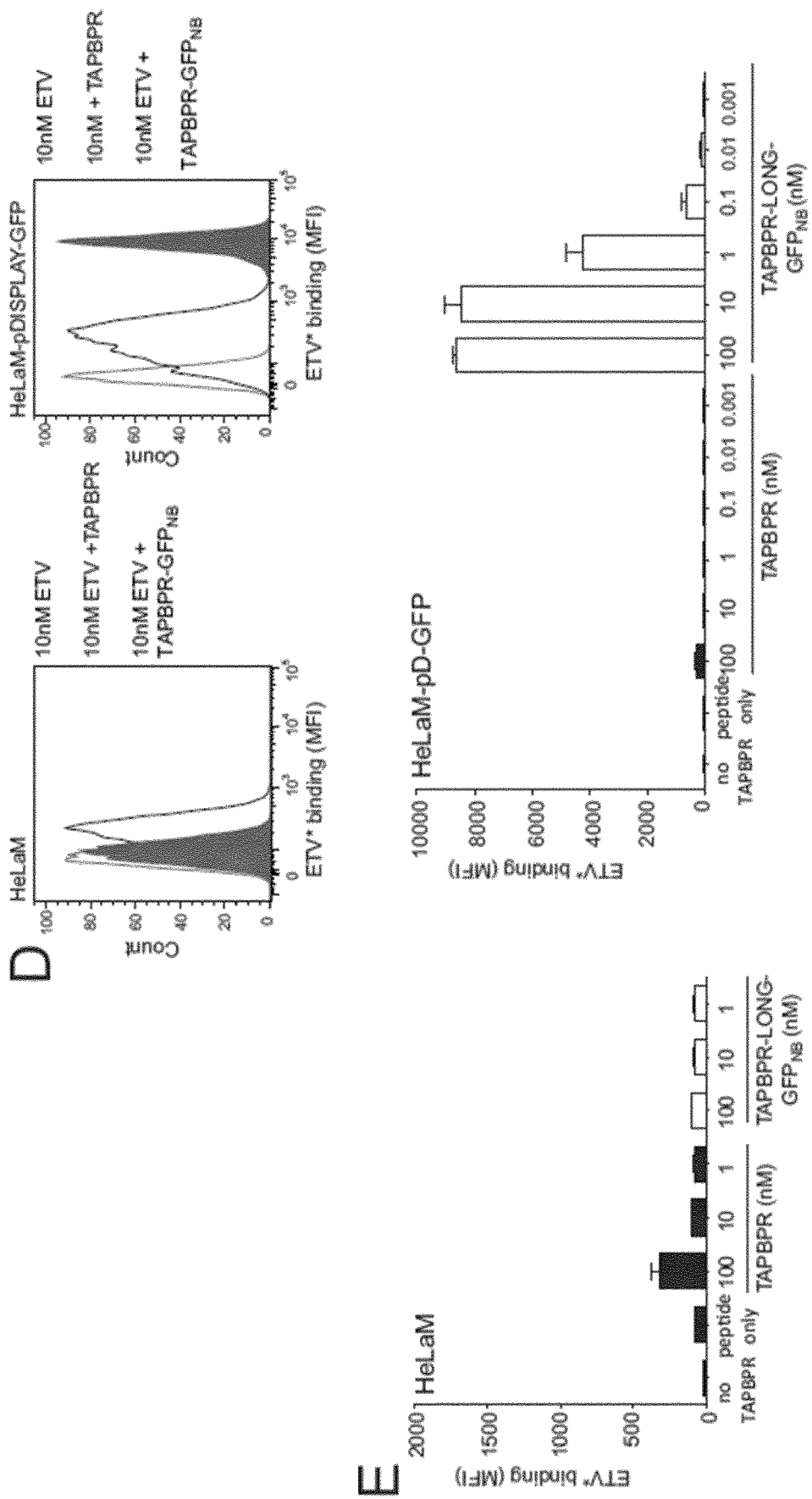

We found TAPBPR fused to the GFP-specific nanobody bound to HeLaM cells expressing GFP on their cell surface but was unable to bind or load peptides onto HeLaM cells without surface GFP i.e. bystander cells (FIG. 8). At 100 nM recombinant protein, while soluble TAPBPR alone bound at low levels to HeLaM cells due to its interaction with HLA-A*68:02, the TAPBPR-GFP$_{NB}$ fusion protein exhibited extremely high levels of binding to HeLaM cells expression surface GFP (FIGS. 8B & 8C). However, at 100 nM the TAPBPR-GFP$_{NB}$ fusion protein exhibited no binding to HeLaM cells lacking GFP (FIGS. 8B and 8C). At 10 nM recombinant protein, while soluble TAPBPR alone did not exhibit any binding to either of the HeLaM cell lines (FIG. 8C), we found that the TAPBPR-GFP$_{NB}$ fusion protein exhibited high levels of binding, specifically to cells expressing GFP (FIG. 8C). This demonstrates the majority of this TAPBPR fusion protein binding comes from the antibody tag.

Figure 9:
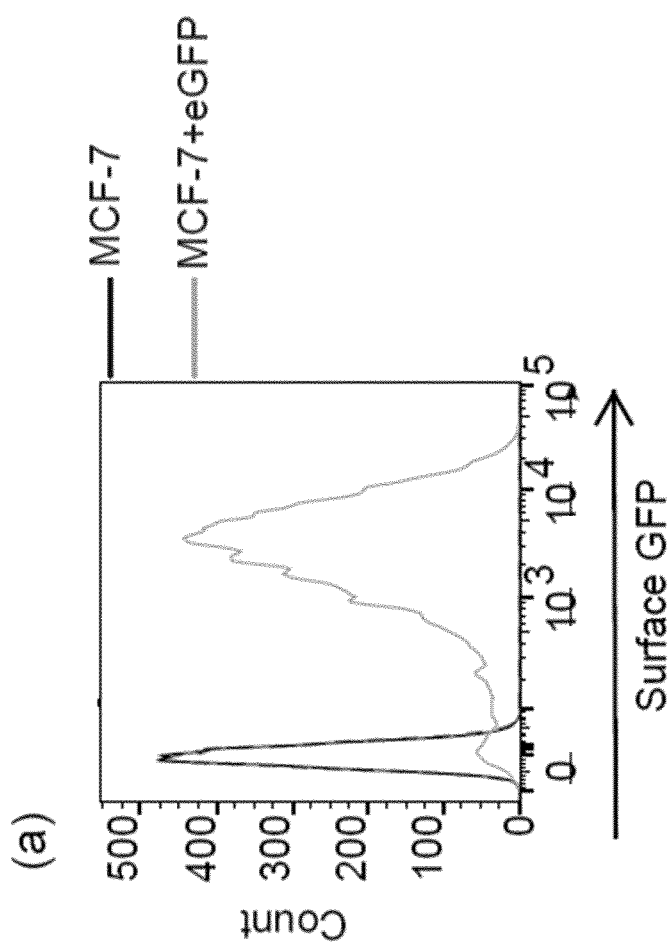
FIG. 9 shows peptide exchange mediated by TAPBPR-fused to a nanobody specific for GFP on MCF-7 cells. (a) shows the expression of GFP on the surface of MCF-7 cells −/+ transfection with the pDisplay-eGFP construct. (b) shows the binding of TAPBPR to the MCF-7 cells −/+ surface GFP when incubated with 10 nM recombinant protein. (c) shows the binding of a fluorescent exogenous viral peptide NLVPK*VATV (derivative of NLVPMVATV from CMV) to HLA-A2 (MHC class I) expressed on MCF-7 cells.
Figure 9:
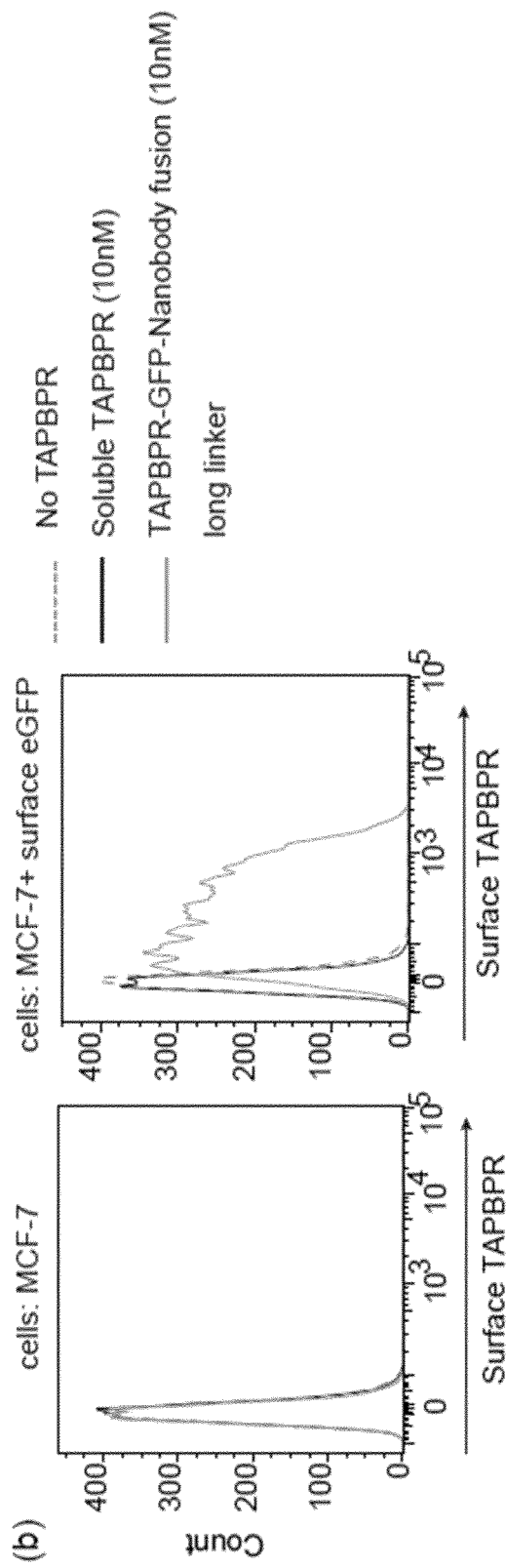
Figure 9:
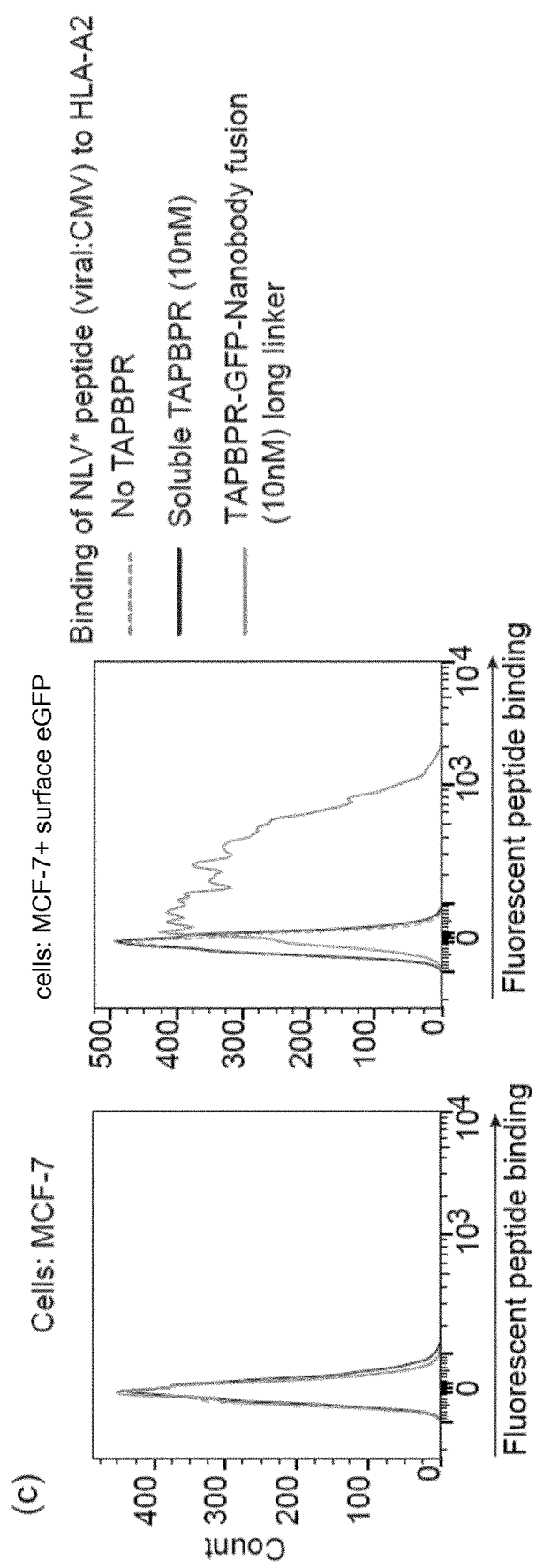

While the TAPBPR-GFP nanobody fusion was unable to load exogenous peptide efficiently onto HeLaM cells in the absence of surface GFP, it was extremely efficient at loading peptides onto surface GFP positive cells (FIGS. 8D &8E). Even at 1 nM the TAPBPR-GFP$_{NB}$ fusion was capable of loading exogenous peptides onto antibody-target expressing cells (FIG. 8E). Soluble TAPBPR exhibited no peptide loading at using similar concentrations of protein (FIG. 8E). Data shown is for TAPBPR fusion product with the long linker, but similar results were found for all three different linkers (short, long and extra-long). Together, these results suggest that the MHC I binding site on TAPBPR is masked by the antibody fragment in the non-surface bound state. However, upon the antibody fragment binding to its target, the MHC class I binding site on TAPBPR is exposed, allowing the TAPBPR to function as a peptide exchange catalyst on cell surface expressed MHC class I molecules. This provides essential proof-of-concept data that TAPBPR functionality can be directed to desired cell types expressing a specific marker 2.11 Peptide Loading on Breast Cancer Cells The effect of TAPBPR fused to the GFP nanobody on the breast cancer cell line MCF-7 was determined. MCF-7 expresses HLA-A2, a very common MHC class I molecule. The cells were made to express GFP on their cell surface (FIG. 9a) and the ability of the TAPBPR-GFP nanobody fusion to bind to the cells was tested (FIG. 9b). Again, this revealed the TAPBPR-GFP-nanobody fusion would bind to cells expressing GFP on their cell surface, but did not bind to GFP-negative cells (FIG. 9b), demonstrating the ability to target TAPBPR to a specific cell population which expresses a particular cell surface marker. TAPBPR-GFP-nanobody fusion was subsequently tested for its ability to load an immunogenic viral peptide (NLVPMVATV peptide derived from CMV) to MCF-7 cells (FIG. 9c). This demonstrated that the TAPBPR fusion product was capable of loading viral peptides on this breast cancer cell line in a targeted manner (dependent on the specificity of the attached antibody).

2.12 Chimeric Proteins with Tumour Specificity

Figure 10:
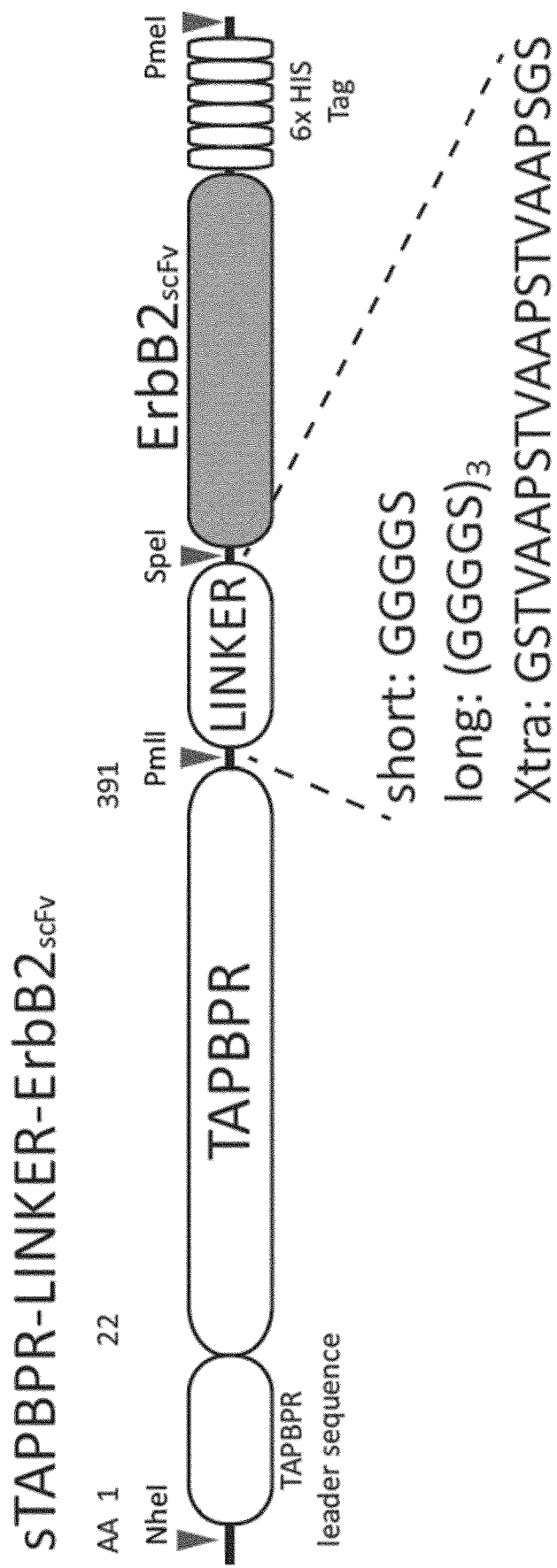
FIG. 10 shows chimeric proteins comprising soluble TAPBPR linked to a Her2-specific-scFv. Three different variants were made with varying linker regions to provide a flexible region between the antibody target and MHC class I. The insert was in the piggyBac vector and protein was produced in 293T cells. Similar Yield as the GFP NB were obtained=~5 mg/L (from adherent cell line).

While the data above with the TAPBPR-GFP-nanobody provide proof-of-concept data regarding the ability to selectively target TAPBPR, we next designed a TAPBPR-antibody conjugated which would permit TAPBPR to be targeted to a marker found naturally on tumour cell lines. We therefore produced TAPBPR linked to a scFv with specificity for the tumour cell marker ErbB2 (Her2) (FIG. 10).

Figure 11:
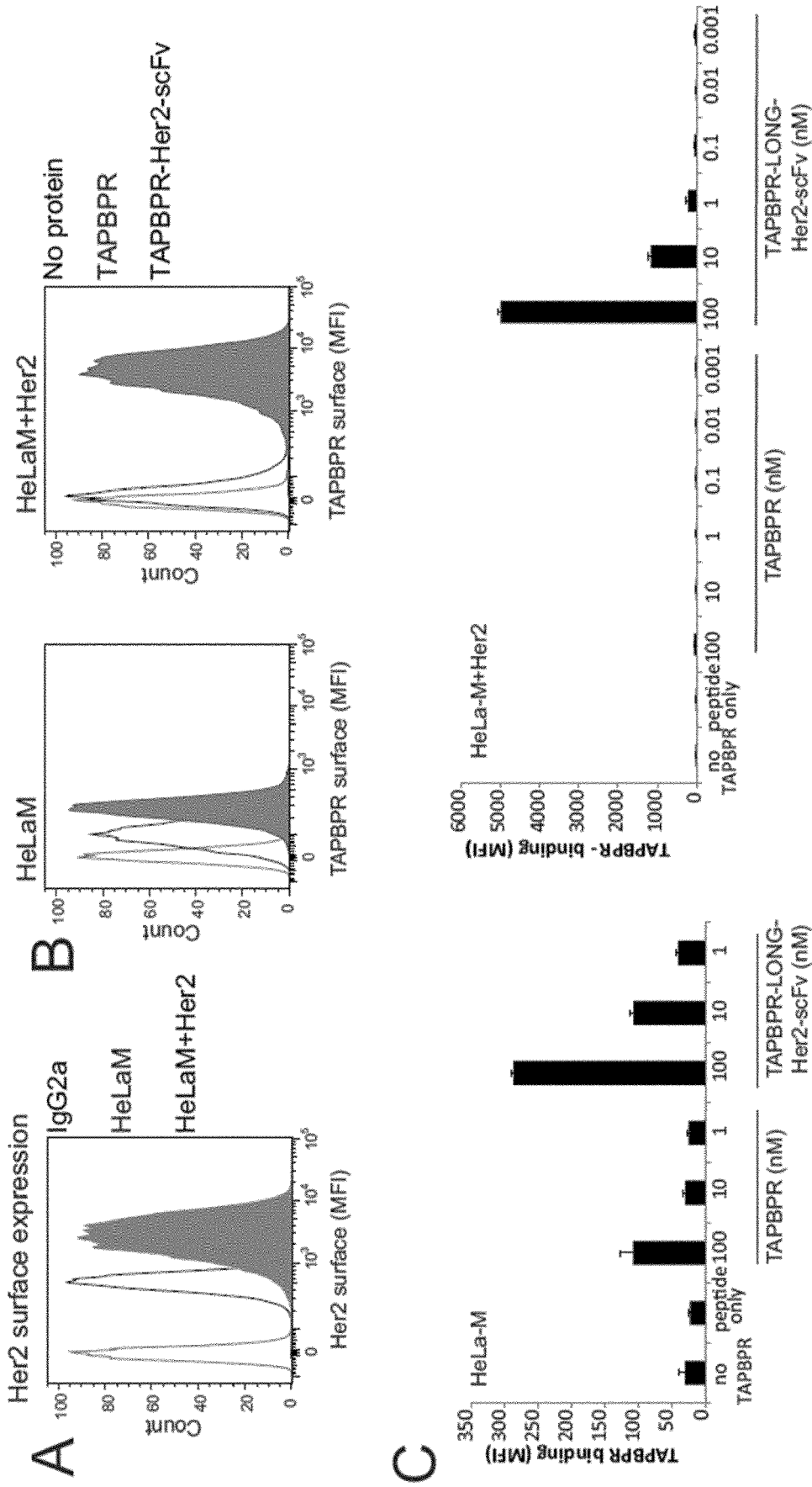
FIG. 11 shows that soluble TAPBPR linked an anti-Her2 scFv targets TAPBPR binding to a tumour cell line in a Her2 dependent manner and functions to load immunogenic peptides onto the cell line. (A) shows the surface expression of Her on HeLaM and HeLaM over-expressing Her2 (+Her2) using an anti-Her2 antibody. Note, there is endogenous Her2 on HeLa. (B) Histograms and (C) Bar graphs compare the binding of recombinant soluble TAPBPR (TAPBPR) with recombinant TAPBPR-fused to a scFv specific for Her2 (TAPBPR-Her2-scFv) to HeLaM cells (left) and HeLaM+Her2 (right). Histograms show the level of TAPBPR when the two cell lines were incubated with 100 nM protein while bar graphs summarise results using a range of concentrations of protein (0.001-100 nM). (D & E) shows the binding of a fluorescent variant of an exogenous neoantigen peptide ETVSK*QSNV (ETV*) to HLA-A68 (MHC class I) expressed on HeLa when cells treated as in B & C were incubated with 10 nM peptide for 15 min after incubation with the indicated recombinant TAPBPR protein. Each bar represents mean and standard deviation of three independent experiments.
Figure 11:
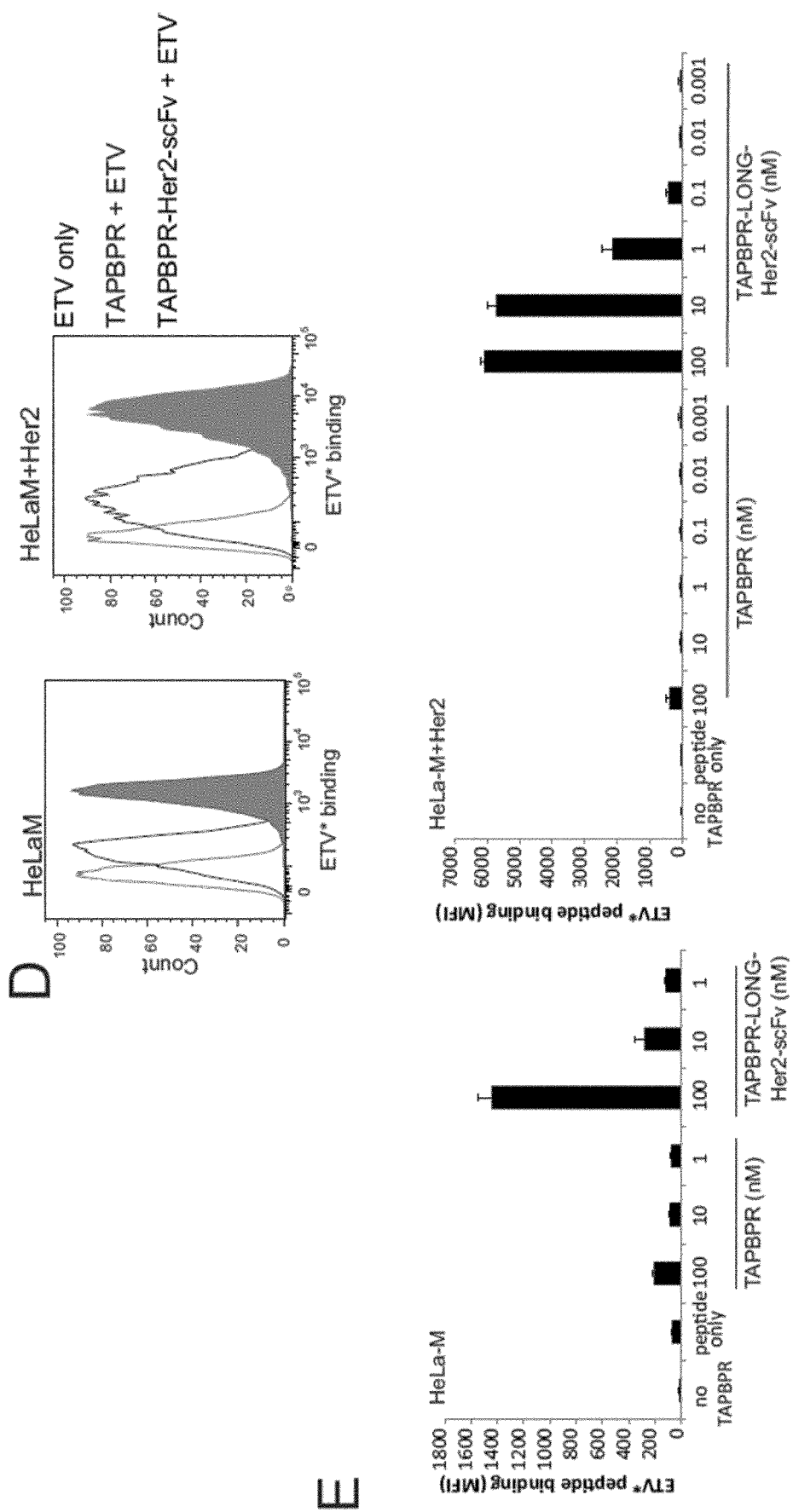
Figure 12:
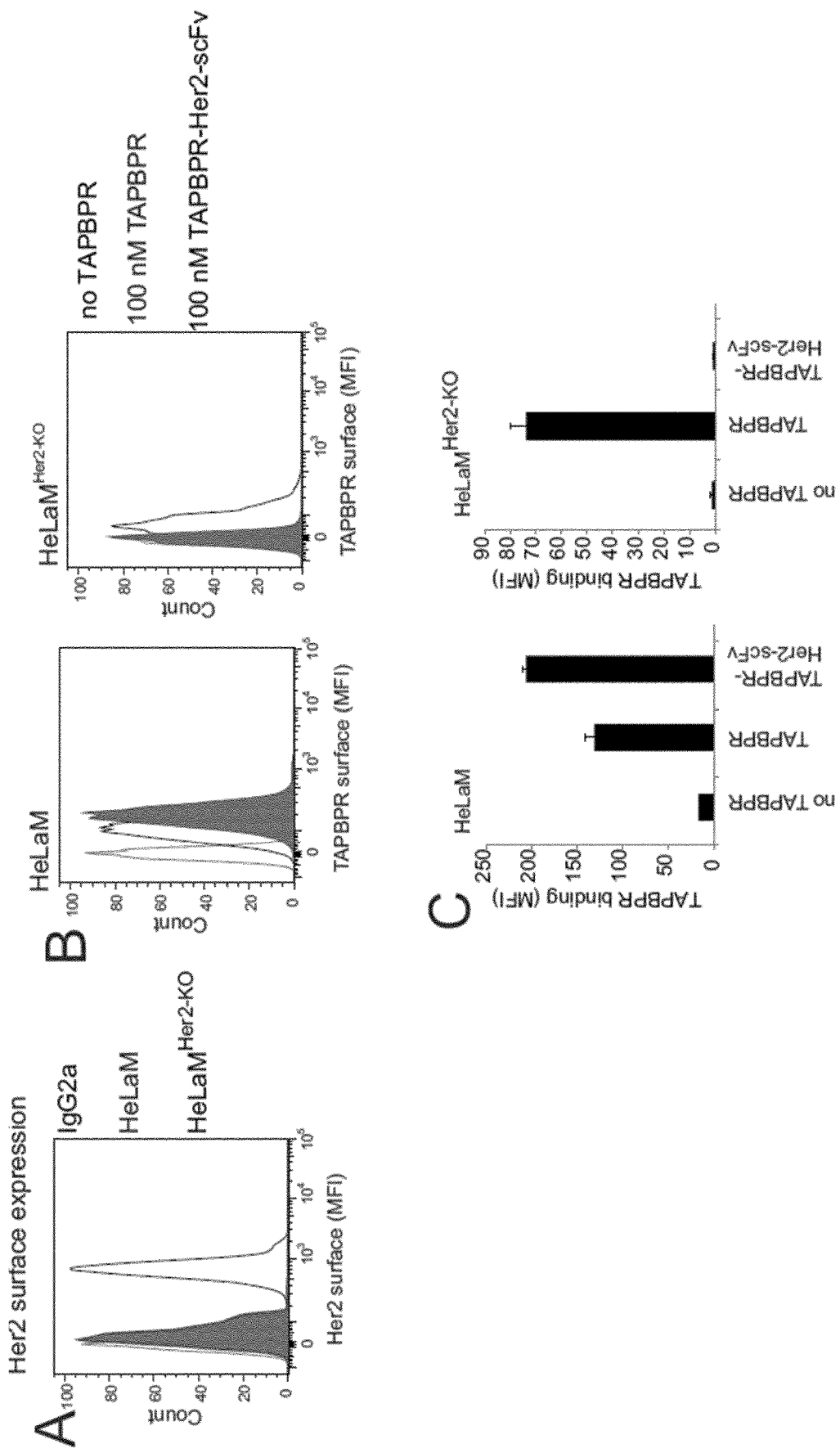
FIG. 12 shows that soluble TAPBPR linked to an anti-Her2 scFv targets TAPBPR binding to a tumour cell line in a Her2 dependent manner. (A) shows the surface expression of Her2 on HeLaM and HeLaM in which Her2 has been knocked out (HeLaM-$^{Her2-KO}$). (B) Histograms and (C) Bar graphs compare the binding of 100 nM recombinant soluble TAPBPR (TAPBPR) with 100 nM recombinant TAPBPR-fused to a scFv specific for Her2 (TAPBPR-Her2-scFv) to HeLaM cells (left) and HeLaM$^{Her2KO}$ cells (right). (D & E) shows the binding of a fluorescent variant of an exogenous neoantigen peptide ETVSK*QSNV (ETV*) to HLA-A68 (MHC class I) expressed on HeLaM when cells treated as in B & C where incubated with 10 nM peptide for 15 min after incubation with the indicated recombinant TAPBPR protein. Each bar represents mean and standard deviation of three independent experiments.
Figure 12:
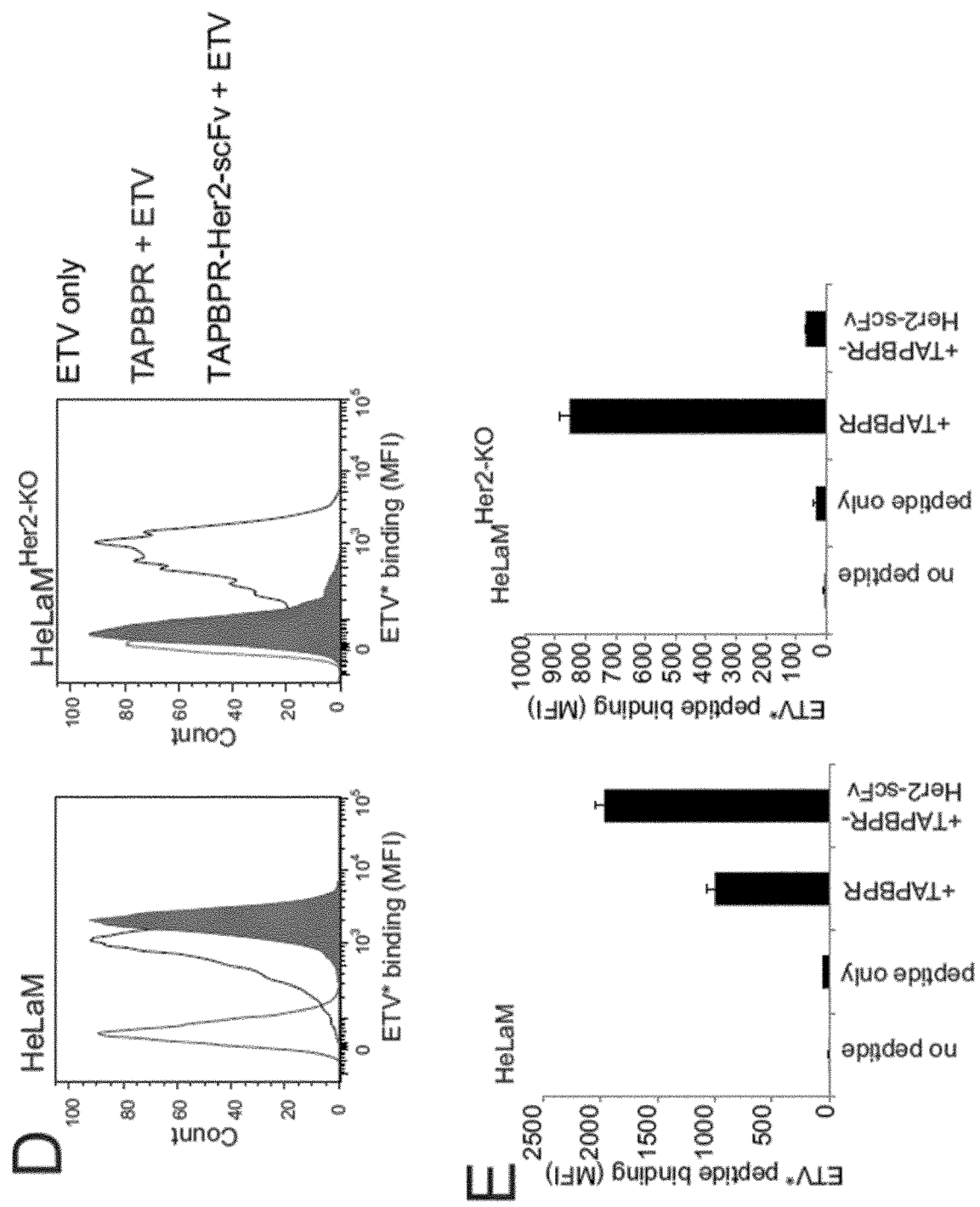

Soluble TAPBPR linked to the anti-Her2 scFv was shown to bind to tumour cell lines in a Her2 dependent manner and functioned to load immunogenic peptides onto the cell lines (FIGS. 11 & 12). Very strong binding of TAPBPR-Her2-scFv was observed to cells over-expressing Her2 (FIGS. 11B & 11C). Furthermore, we observed increased binding of the TAPBPR-Her2-scFv to HeLaM cells which naturally express Her2 (see FIG. 11A for endogenous Her2 level on HeLaM) compared to soluble TAPBPR alone (FIGS. 11B and 11C). Data shown is for TAPBPR fusion product with the long linker, but similar results were found this the short and extra-long linker variants.

To confirm the binding of the TAPBPR-Her2-scFv to HeLaM cells was dominantly via the scFv binding to Her2, as opposed to TAPBPR binding to MHC I, we produced a HeLaM cell line in which Her2 was knocked out (FIG. 12A). Upon treatment with the recombinant TAPBPR proteins, we observed no binding at all of the TAPBPR-Her2-scFv protein to the Her2-deficient HeLaM cell (FIGS. 12B and 12C). In contrast, soluble TAPBPR alone was still capable of binding to the HeLaM cells lacking Her2 (FIGS. 12B & 12C). Together, these results demonstrate that the TAPBPR-Her2-scFv fusion binds to cells in a Her2-dependent manner and that this fusion protein is incapable of binding to cells that lack surface Her2 expression i.e bystander cells which are MHC class I positive. Therefore, the TAPBPR-Her2-scFv shows specificity for Her2, which may be useful therapeutically to target TAPBPR to Her2 positive tumour cell lines, while leaving healthy cells alone.

Figure 13:
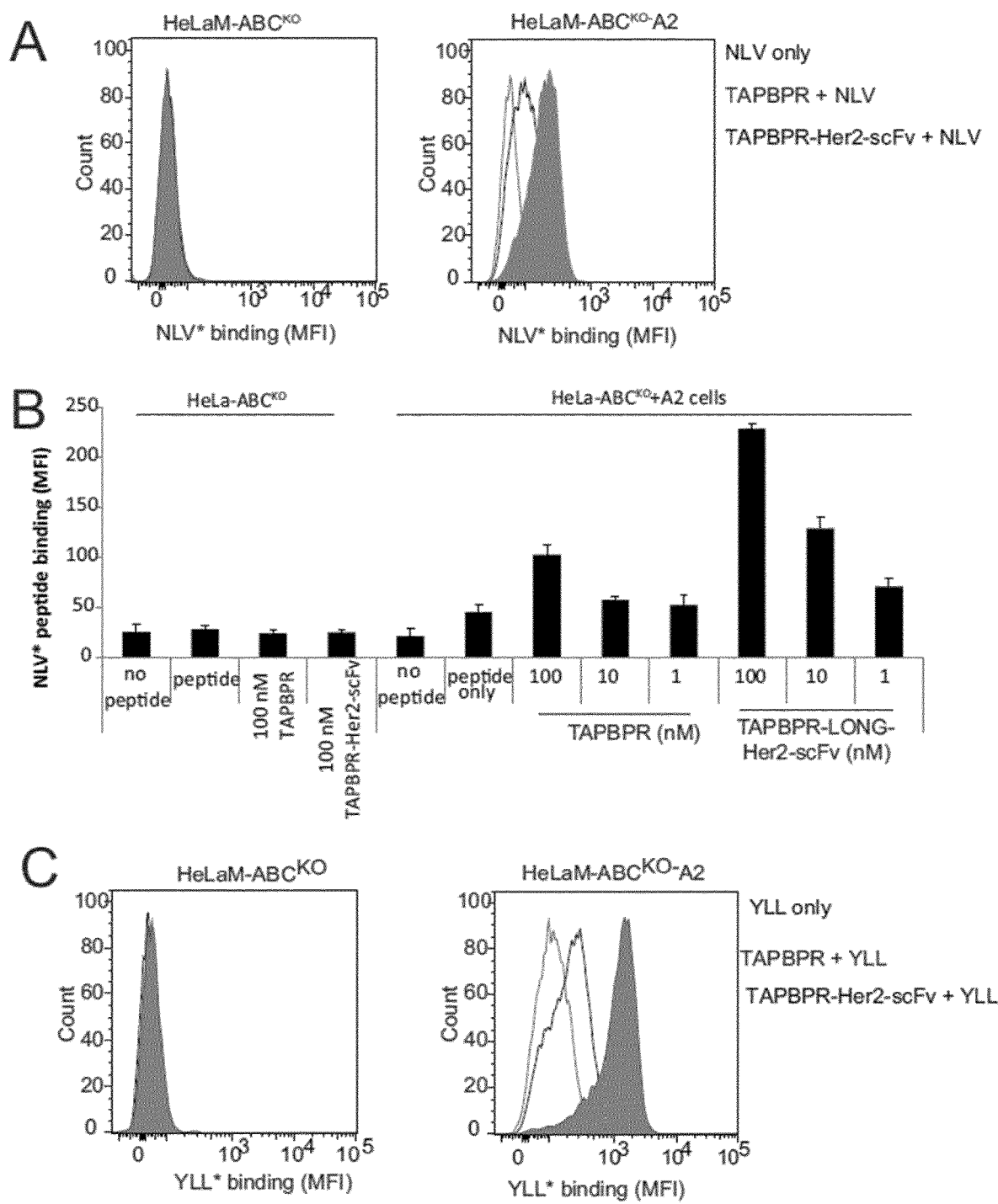
FIG. 13 shows that TAPBPR-Her2scFv can load immunogenic viral peptides which are recognised by viral specific T cell receptors. (A-D) shows the binding of a fluorescent variant of the viral peptides (A&B) NLVPK*VATV (NLV*) derived from pp65 protein from CMV or (C&D) YLLEK*LWRL (YLL*) derived from EBV onto HeLaM cells lacking expression of HLA-ABC (HeLaM-ABC$^{KO}$)-/+ HLA-A2 transduction, following incubation with 10 nM peptide for 15 min after incubation with the indicated recombinant TAPBPR protein. For the histograms in A & C 100 nM of the indicated recombinant TAPBPR protein was used. (E) shows staining with the T cell receptor-like mAb LMP-1 on cells treated with TAPBPR as above incubated with non-fluorescent YLLEMLWRL peptide from EBV. The TCR is specific for YLLEMLWRL peptide presented on HLA-A2 molecules. Each bar represents mean and standard deviation of three independent experiments
Figure 13:
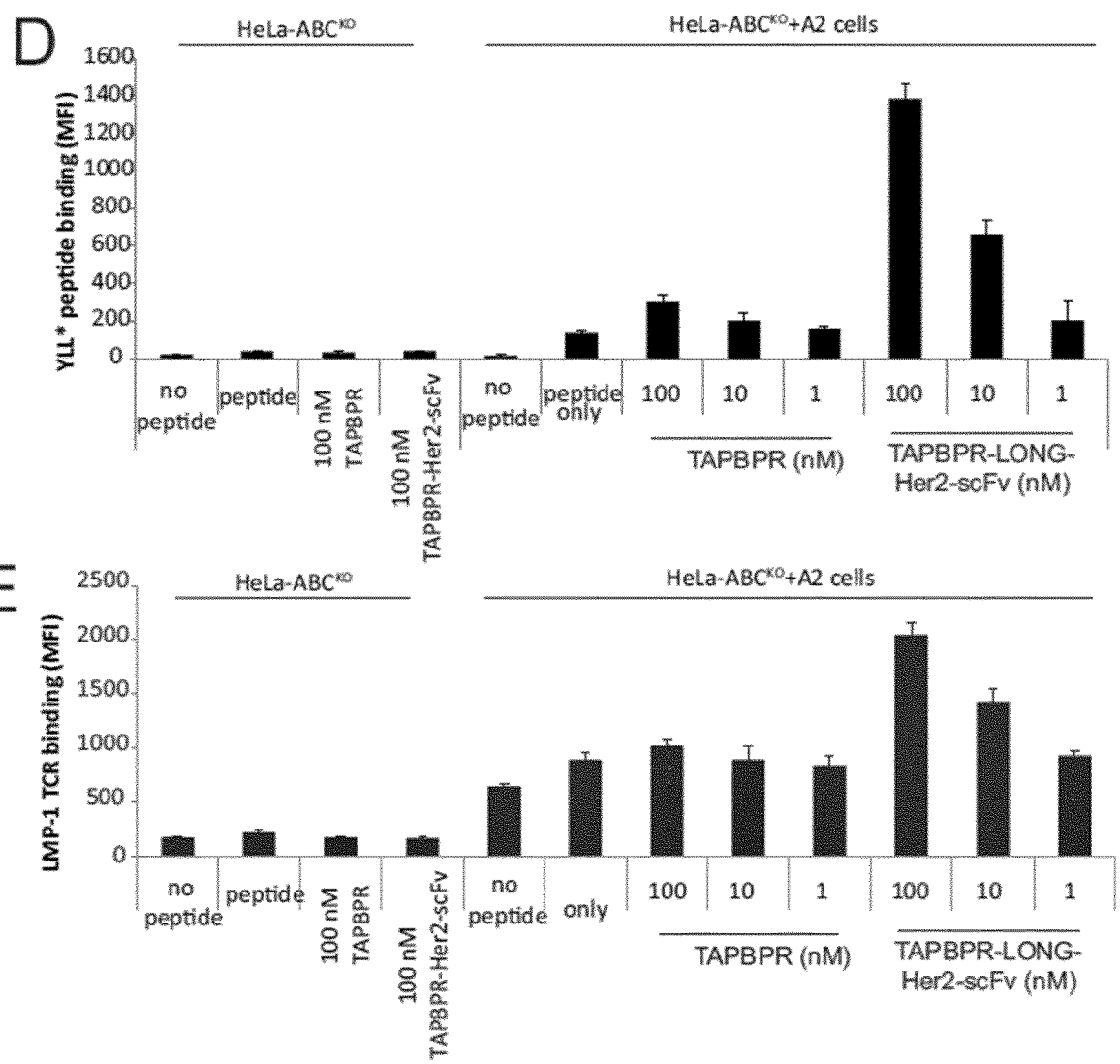

Next, we tested whether the TAPBPR-Her2-scFv was capable of promoting the loading of exogenous peptides onto cells in a Her2-dependent manner. Our results show that the TAPBPR-Her2-scFv fusion protein is very efficient at loading exogenous peptide onto the surface of HeLaM cells in a Her2-dependent manner (FIGS. 11D, 11E, 12D &12E). We found it efficiently loaded a fluorescent variant of the neo-antigen ETVSEQSNV (ETV*) onto surface expressed HLA-A*68:02 molecules in a Her2 dependent manner (FIGS. 11D, 11E, 12D &12E). Furthermore, we tested if the TAPBPR-Her2-scFv was capable of loading viral peptides onto another MHC class I molecule, HLA-A2. We found that the TAPBPR-Her2-scFV could load fluorescent variants of both the CMV-derived peptide NLVPMVATV (NLV) (FIGS. 13A & 13B) and the EBV derived peptide YLLEMLWRL (YLL) (FIGS. 13C &13D) onto surface expressed HLA-A2 molecules. This peptide loading was dependent expression of HLA-A2 as no peptide loading was observed on cells lacking HLA-A, -B and -C expression (FIG. 13). Furthermore, the TAPBPR-Her2-scFv was more efficient at loading these peptides than soluble TAPBPR alone (FIG. 13A-D).

In contrast to soluble TAPBPR, which dissociates from the cells following loading peptide onto MHC class I, it was likely that TAPBPR-antibody fusion proteins would remain bound to the surface of cells via the antibody:target interaction. Therefore, we next tested whether the T cell receptor would have access to peptide:MHC I complexes on cells treated with TAPBPR-Her2-scFv fusion protein. This revealed that the TCR-like mAb LMP-1 could recognise YLLEMLWRL/HLA-A2 complexes on cells treated with the TAPBPR-Her2-scFv (FIG. 13E). In fact, the TCR-like mAb LMP-1 bound better to cells treated with the TAPBPR-Her2-scFv fusion+peptide, that to those treated with soluble TAPBPR+peptide (FIG. 13E). This likely reflect the fact that the TAPBPR-Her2-scFv is more efficient than soluble TAPBPR at loading YLL peptide onto these cells (FIG. 13D).

Figure 14:
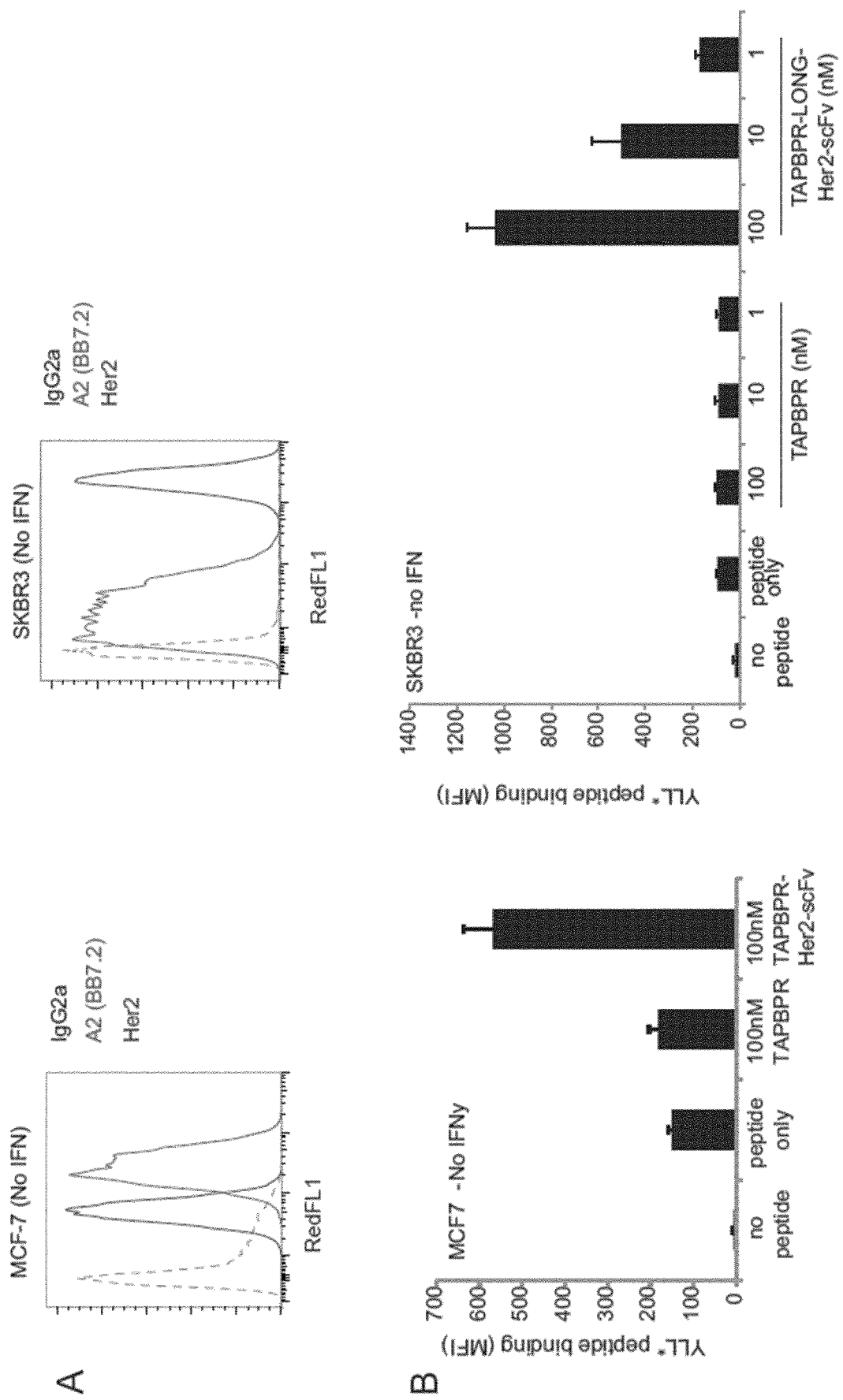
FIG. 14 shows TAPBPR-Her2-scFv fusion proteins work on human breast cell lines expressing Her2 including cells with low MHC class I. (A) Flow cytometric analysis of MHC class I (HLA-A2) and Her2 expression on the human breast cancer cell lines MCF-7 & SKBR3. Bar graphs show (B) the binding YLL* peptide and (C) the binding of TCR-like mAb reagent LMP-1 which recognises the EBV specific peptide YLL in the context of HLA-A2, when SKBR3 and MCF-7 cells were incubated with no peptide, peptide alone, or peptide in the presence of 100 nM soluble TAPBPR or 100 nM TAPBPR-Her2 antibody fusion protein. These results clearly demonstrate that the TAPBPR-her 2 antibody fusion protein works extremely efficiently on both these breast cancer cell lines, despite expressing either low levels of MHC class I (SKBR3) or low levels of Her2 (MCF-7) and that the fusion protein is superior to the soluble TAPBPR protein alone.
Figure 14:
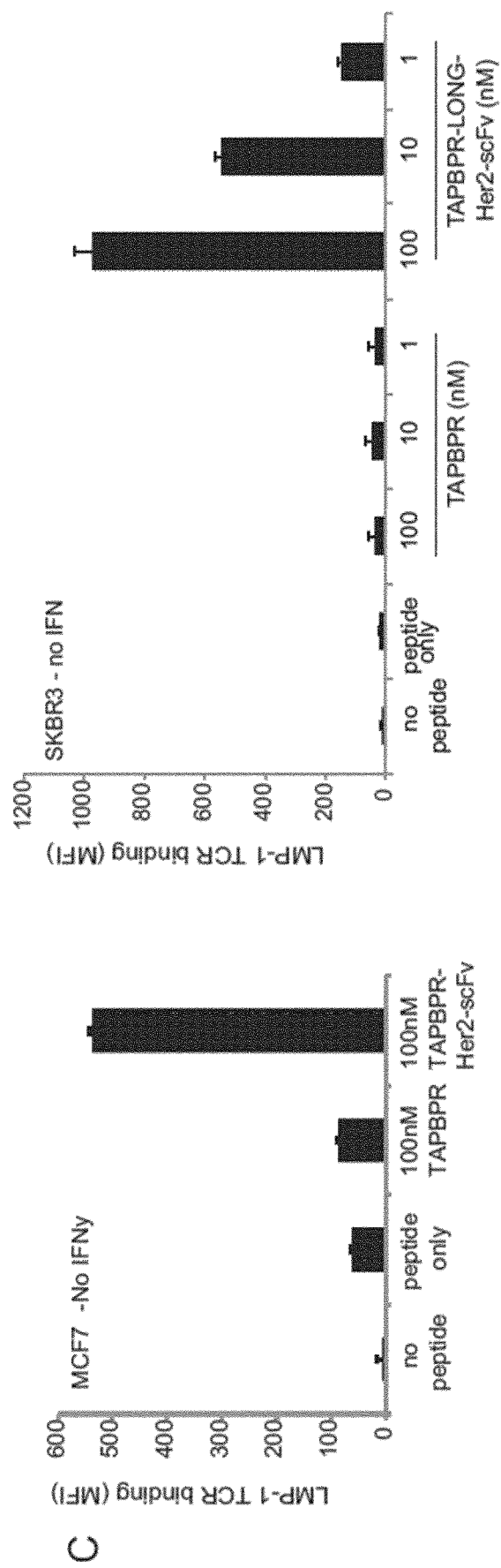

Having shown that the TAPBPR-Her2-scFv exhibits exclusive specificity to cell expressing Her2, we explored whether the TAPBPR-Her2-scFv may be useful therapeutically to target Her2 positive tumour cell lines (FIG. 14). We tested the ability of the TAPBPR-Her2-scFv to load immunogenic peptides onto two breast cancer cell lines; MCF-7 cells (which express low levels of Her2 but high MHC class I) and SKBR3 (which express high levels of Her2 but low levels of MHC class I) (FIG. 14). Our results demonstrate that the TAPBPR-Her2-scFv efficiently loads antigenic peptides onto both of these breast cancer cell lines, that it is more efficient that soluble TAPBPR, and that the level of peptide loading observed is proportional to the expression of Her2 on the cell lines (FIG. 14B).

Given that many tumours down-regulate MHC I expression, it is extremely promising to observe efficient peptide loading using the TAPBPR-Her2-scFV protein on the SKBR3 cell line which is known to have low MHC I expression. This implies that low level MHC class I expression may not be a barrier to being able to use TAPBPR-antibody fusion proteins therapeutically. Finally, we tested the ability of the TCR to detect peptide:MHC I complexes loaded by TAPBPR. This revealed the TCR-like specific mAb LMP-1 bound extremely well to cells treated with the TAPBPR-Her2-scFV and peptide (FIG. 14C). In fact, significantly more YLL/HLA-A2 complexes were accessible for TCR binding when cells were treated with the TAPBPR-Her2-scFv+peptide, than those treated with soluble TAPBPR+ peptide or peptide alone (FIG. 14C). Together this data demonstrates that the TAPBPR-Her2-scFV fusion protein is extremely efficient at loading exogenous, immunogenic peptides onto the surface of Her-2 positive tumour cell lines and that the resultant peptide:MHC I complexes are accessible to TCR binding. This data support the concept that a TAPBPR-Her2-scFv protein may have the translational potential to selectively increase the immunogenicity of Her2 positive tumours and induce the recognition of such tumours by viral specific T cells, even on tumours with low MHC class I expression.

Figure 20:
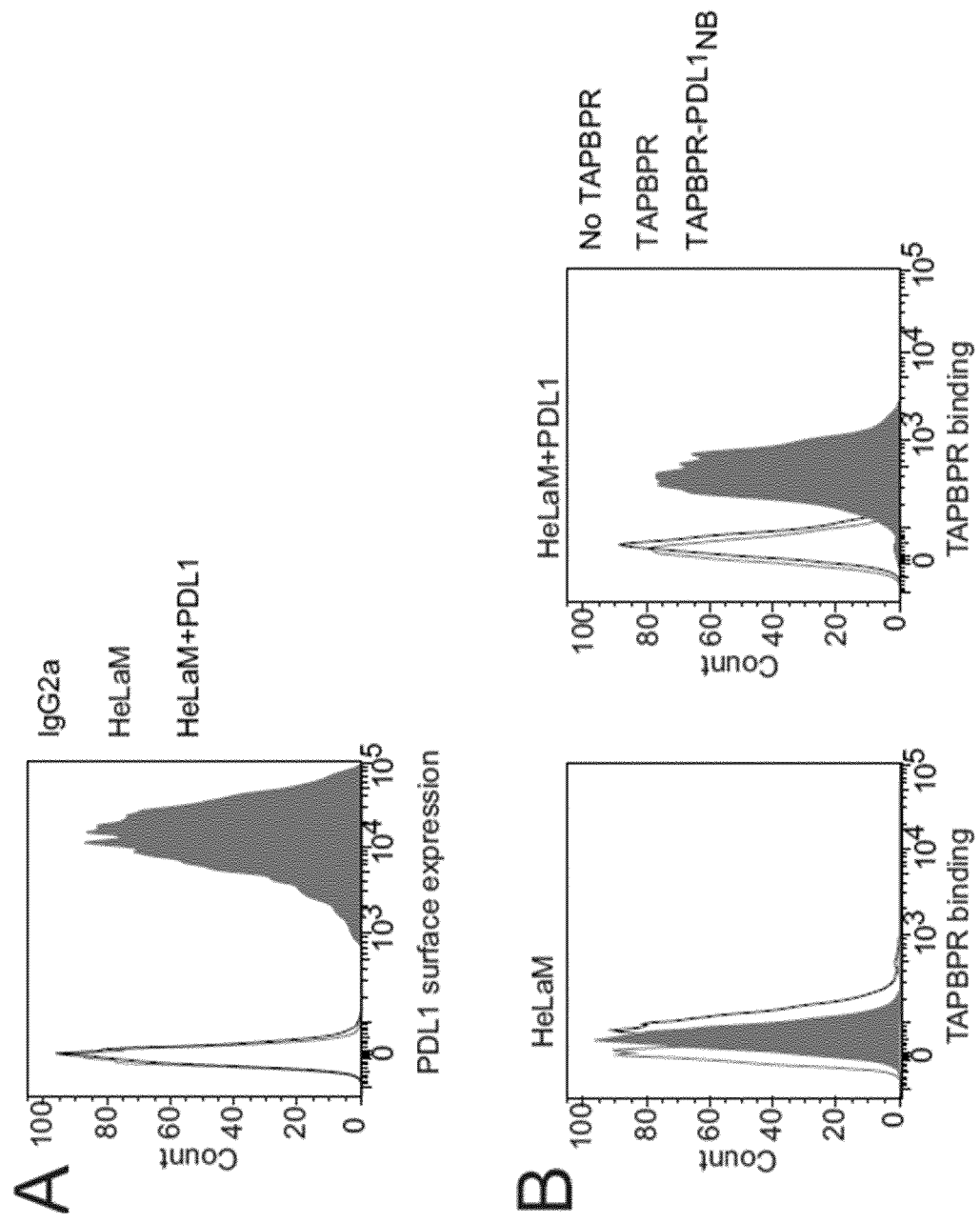
FIG. 20 shows that soluble TAPBPR linked to a PD-L1 specific nanobody targets TAPBPR binding to tumours in a PD-L1 dependent manner and functions to load immunogenic peptides onto a tumour cell line. (A) shows the surface expression of PD-L1 on HeLaM and HeLaM over-expressing PD-L1 (+PDL1). (B) Histograms and (C) Bar graphs compare the binding of recombinant soluble TAPBPR (TAPBPR) with recombinant TAPBPR-fused to a nanobody specific for PD-L1 (TAPBPR−PD-L1$_{NB}$) to HeLaM cells (left) and HeLaM+PDL1 (right). Histograms show the level of TAPBPR when the two cell lines were incubated with 100 nM protein while bar graphs summarise results using a range of concentrations of protein (0.001-100 nM). (D & E) shows the binding of a fluorescent variant of an exogenous neoantigen peptide ETVSK*QSNV (ETV*) to HLA-A68 (MHC class I) expressed on HeLa when cells treated as in B & C where incubated with 10 nM peptide for 15 min after incubation with the indicated recombinant TAPBPR protein. Each bar represents mean and standard deviation of three independent experiments.
Figure 20:
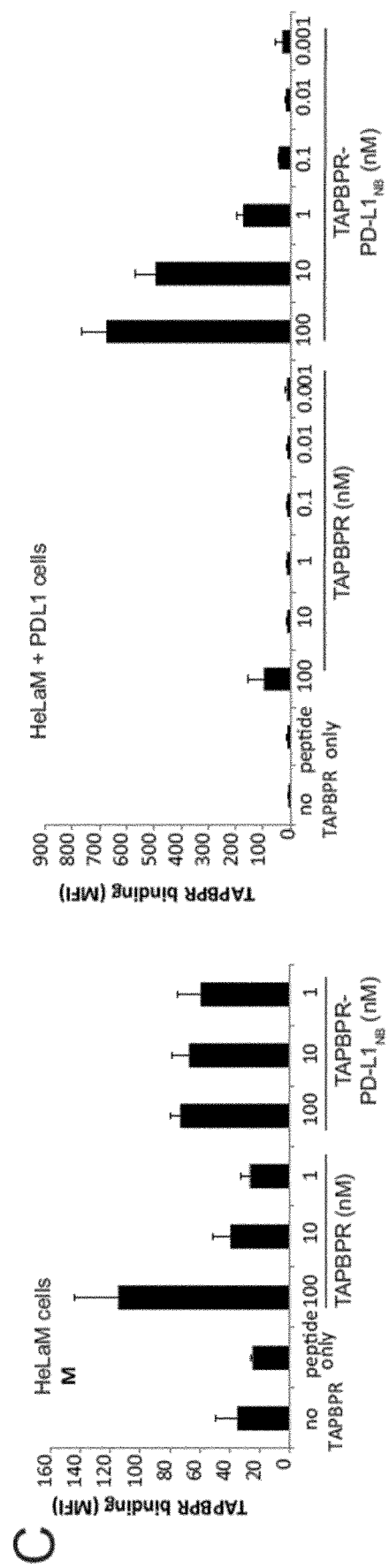
Figure 20:
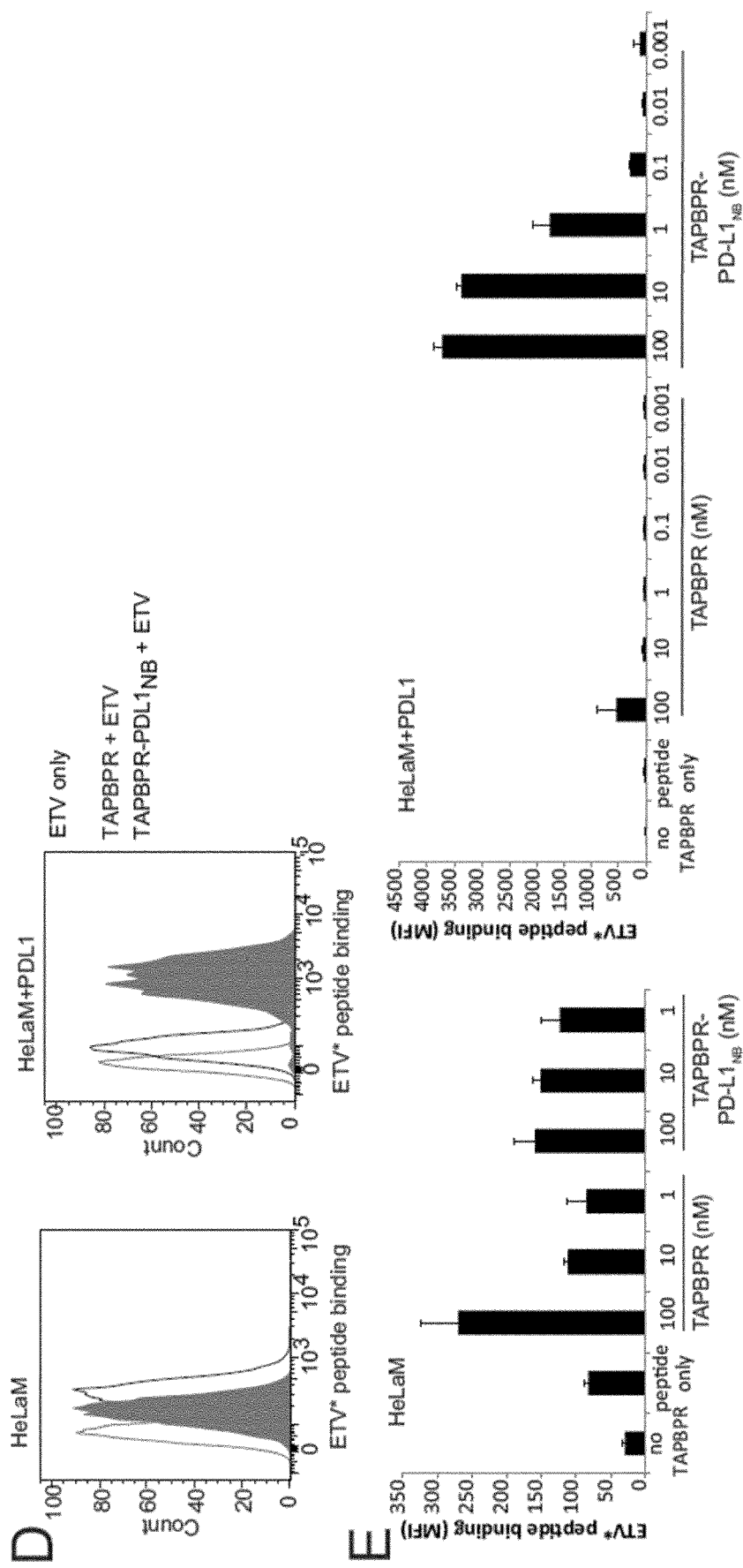

We have also produced recombinant TAPBPR linked to a PD-L1 specific nanobody (FIG. 20). This was also shown to target TAPBPR binding to tumours in a PD-L1 dependent manner (FIGS. 20B & 20C), and to load immunogenic peptides onto a tumour cell line (FIGS. 20D & 20E).

2.13 Steric Hindrance Using the TAPBPR-Antibody Fusion Fragments

We have observed that the TAPBPR-antibody fusion proteins appear to be unable to bind to MHC class I, and consequently unable to mediate peptide exchange, in the absence of the ligand for the antibody. Our findings suggest that the MHC class I binding site on TAPBPR is masked by the antibody fragment (either a nanobody or scFV) in the non-plasma membrane bound state, but is subsequently exposed upon the antibody binding its ligand on the cell surface. Data supporting steric hindrance by the antibody fusion fragment in the non-bound state can found for the TAPBPR-GFP-nanobody fusion protein in FIG. 8 (on HeLa cells i.e not expressing surface GFP) and for the TAPBPR-Her2-scFv fusion protein in FIG. 12 (on the HeLa cell in which Her2 has been knocked out). In both FIGS. 8 and 12 we observed that while soluble TAPBPR alone bound well to MHC class I expressed on HeLa/HeLa-Her2KO cells, the TAPBPR-antibody fusions were unable to bind to HLA molecules expressed on these cells (FIGS. 8B & C on HeLa, FIGS. 12B & C on HeLa-Her2KO cells). However, when the ligand for the antibody was present on the cells, the TAPBPR fusion proteins were able to bind extremely well to the cells (FIGS. 8B & C on HeLa+GFP, FIGS. 12B & C on HeLa). Similarly, when we tested the ability of the TAPBPR-antibody fusion proteins to mediate exogenous peptide loading, we observed in both FIGS. 8 and 12 that while soluble TAPBPR alone could efficiently mediate exogenous peptide loading on MHC class I expressed on HeLa/HeLa-Her2KO cells, the TAPBPR-antibody fusions were unable to load peptides on these cells (FIGS. 8B & C on HeLa, FIGS. 12B & C on HeLa-Her2KO cells). Again, when the ligand for the antibody was present on the cells, the TAPBPR fusion proteins were now capable of efficiently mediating exogenous peptide loading (FIGS. 8B & C on HeLa+GFP, FIGS. 12B & C on HeLa). This interesting observation is promising when considering the therapeutic application of TAPBPR-fusion proteins, as it suggests that such products would be highly selective for chosen target and would have limited effects on healthy cells only expressing MHC class I.

2.14 Viral Peptides Loaded onto Tumour Cells

TAPBPR-Her2-svFc was shown to load viral peptides onto HeLa cells expressing HLA-A2 (FIG. 13a-d). In addition, the T cell receptor (TCR) was shown to recognise the loaded cells (FIG. 13e). This shows that the TAPBPR-Her2-svFc is functional and the resultant peptide/MHC class I complexes are accessible for the T cell to bind.

2.15 Exogenous Mouse TAPBPR can Also be Utilised to Load Immunogenic Peptide onto Human MHC Class I Molecules.

Figure 15:
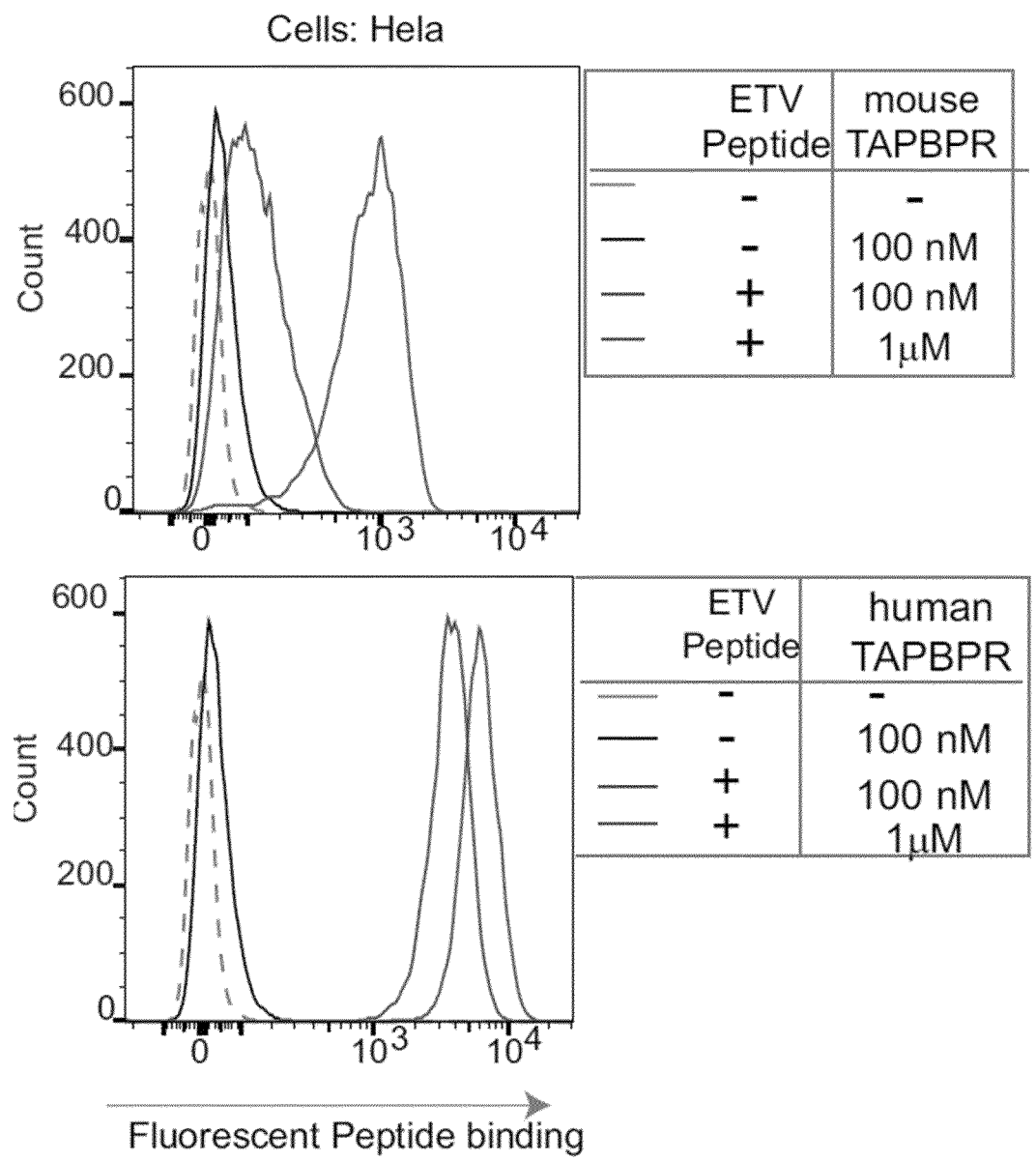
FIG. 15 shows that exogenous mouse TAPBPR can load immunogenic peptide onto human MHC class I. Top panel shows the binding of a fluorescent exogenous neoantigen peptide ETVSK*QSNV (ETV*) to HLA-A68 (MHC class I) expressed on HeLa cells in the absence and presence of mouse TAPBPR. Bottom panel shows the same experiment performed with human TAPBPR for comparison.

The luminal domains of mouse TAPBPR were shown to load fluorescent human neoantigen peptide ETVSK*QSNV (ETV*) to HLA-A68 (MHC class I) expressed on HeLa cells (FIG. 15). These results demonstrate that exogenous mouse TAPBPR can also be utilised in the same way as human TAPBPR to load immunogenic peptide onto human MHC class I molecule. Although less efficient than human TAPBPR, mouse TAPBPR is still capable of loading enough immunogenic peptide that would trigger T cell responses.

2.16 Removal of Cytoplasmic Tail Targets TAPBPR to the Cell Surface

Figure 16:
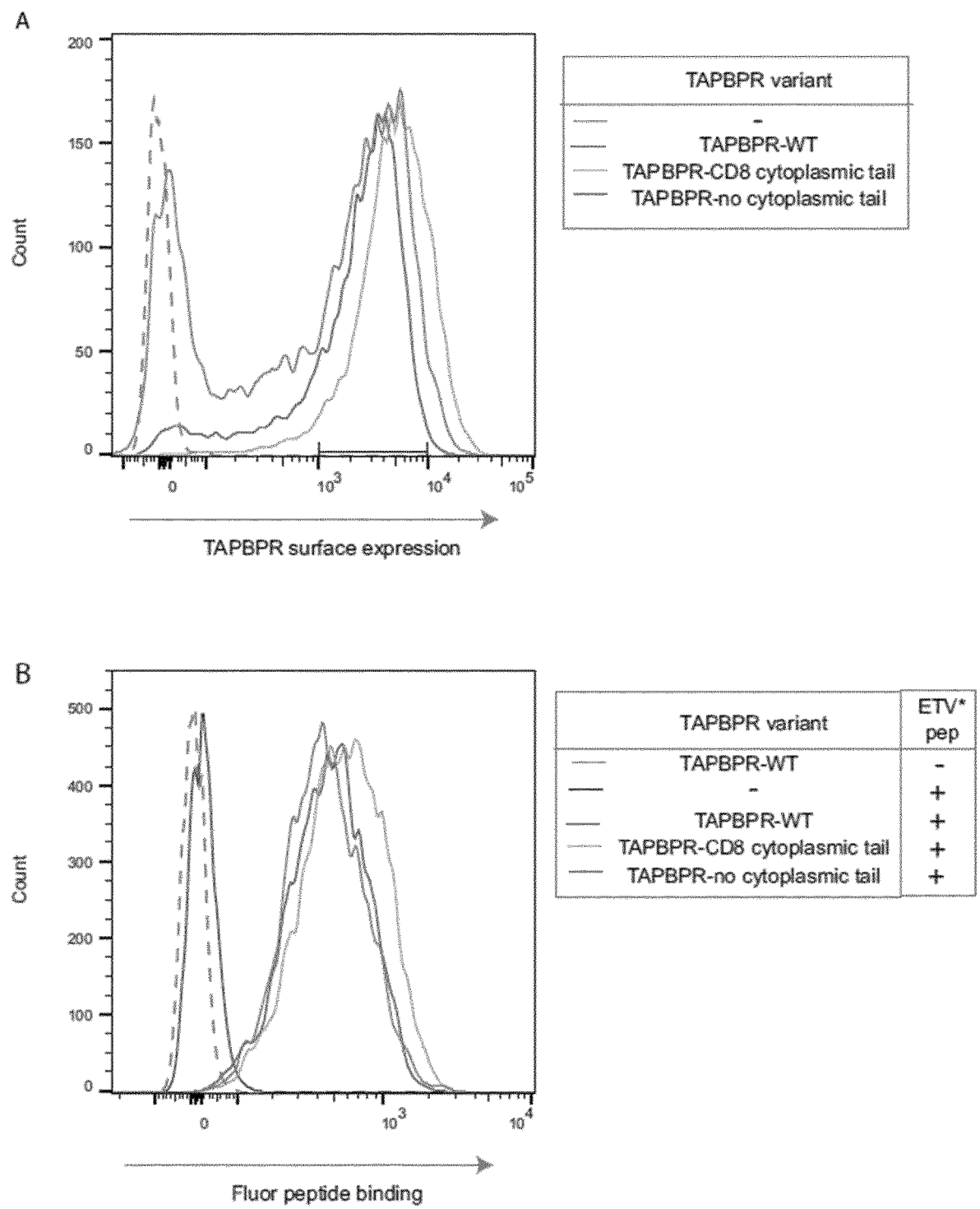
FIG. 16 show expression levels and peptide editing functionality of TAPBPR with alterations to its cytoplasmic tail. (A) Shows the surface detection of TAPBPR and (B) show the binding of fluorescent peptide ETVSK*QSNV (ETV*) when cells are transduced with TAPBPR$^{WT}$, TAPBPR$^{tailless}$ which has the TMD of TAPBPR but lacks the cytoplasmic tail and TAPBPR$^{CD8tail}$ in which its cytoplasmic tail has been replaced with CD8. Staining on non-transduced cells are included as a control.

Cells transduced with TAPBPR$^{WT}$, TAPBPR$^{tailless}$ which has the TMD of TAPBPR but lacks the cytoplasmic tail and TAPBPR$^{CD8tail}$ in which its cytoplasmic tail has been replaced with CD8, were shown to express TAPBPR on the cell surface (FIG. 16A) and bind fluorescent peptide ETVSK*QSNV (ETV*) (FIG. 16B) relative to cells not transduced with TAPBPR. The results in FIG. 16 demonstrate that TAPBPR lacking any cytoplasmic tail is efficiently expressed at the cell surface (Note: Cells expressing TAPBPR$^{CD8tail}$ have a lower level of transduction but the addition of the CD8 cytoplasmic tail onto TAPBPR allows for more efficient surface expression at the lower transduction efficiency). When TAPBPR expressing cells are gated on equivalent population (see gate on A), all TAPBPR variants are capable of a similar degree of peptide editing (B).

2.17 Soluble TAPBPR Induces Tumour Cell Killing by CD8+ T Lymphocytes

Figure 19:
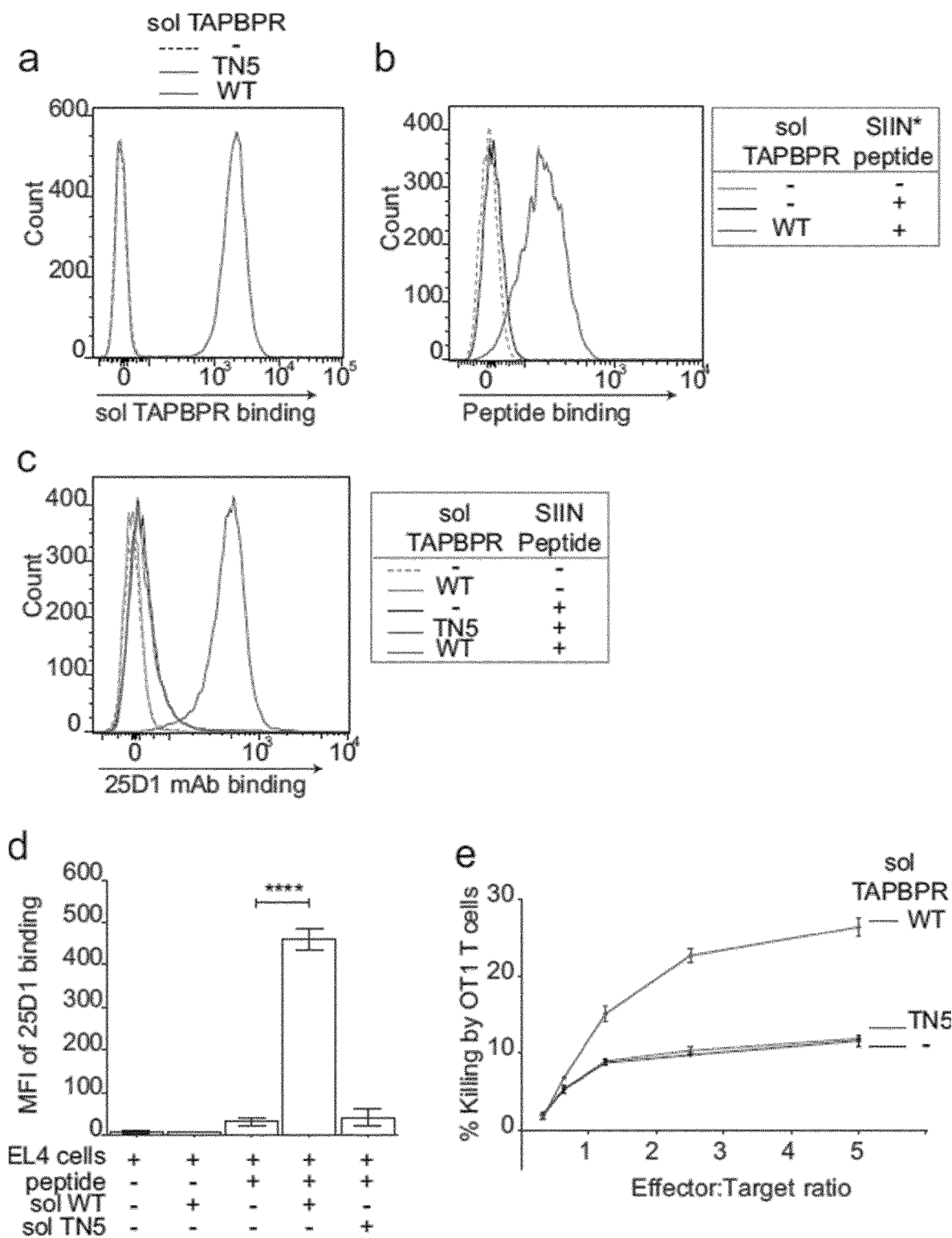
FIG. 19 shows that soluble TAPBPR enhances T cell killing of tumour cells EL4 cells were incubated −/+1 μM soluble TAPBPR$^{WT}$ or TAPBPR$^{TN5}$ for 15 min at 37° C., followed by (19a) detection of surface bound TAPBPR using PeTe-4, (19b) incubation −/+1 nM SIINFEK*L for 30 min at 37° C. or (19c) incubation −/+1 nM non-labelled SIINFEKL peptide for 30 min, followed by staining with the 25-D1.16 mAb (recognises SIINFEKL/H-2K$^b$ complexes). Histograms are representative of three independent experiments. (19d) Bar graphs show the MFI of 25-D1.16−/+SD from three independent experiments. (19e) OT1 killing of EL4 cells treated −/+1 μM soluble TAPBPR$^{WT}$ or TAPBPR$^{TN5}$, followed by incubation with 1 nM SIINFEKL peptide. Error bars−/+s.e.m from triplicate wells. Data is representative of three independent experiments. Note: surface expressed H-2K$^b$ are relatively more peptide receptive compared to human MHC I molecules. At 10 nM SIINFEKL, some exogenous peptide binding was observed in the absence of soluble TAPBPR$^{WT}$. As OT1 T cells are highly efficient cytotoxic cells, killing 80-100% of targets after 1-4 hours, we decreased the concentration of SIINFEKL used in these experiments to 1 nM in order to differentiate between TAPBPR-mediated and background peptide binding, otherwise we would not observe an additive effect of soluble TAPBPR on target cell killing.

Although the results above provide indication that soluble TAPBPR could be utilised to decorate target cells with immunogenic peptides and enhance T cell responses against tumours, we next determined whether this could result in enhanced killing of tumour cells. We assessed killing of murine EL4 tumour cells by OT1 T cells in the presence of human TAPBPR and very low concentrations of SIINFEKL peptide. Soluble human TAPBPR$^{WT}$ bound to EL4 cells (FIG. 19a) and significantly enhanced the loading of SIINFEKL onto H-2K$^b$ expressed on EL4 (FIGS. 19b, 19c & 19d). When we tested the ability of OT1 cytotoxic T cells, which recognise SIINFEKL in the context of H-2K$^b$, to lyse peptide-pulsed EL4 target cells, we observed a significant enhancement in killing in the presence of soluble human TAPBPR$^{WT}$, but not in the presence of TAPBPR$^{TN5}$ (FIG. 19e). These results demonstrate that TAPBPR can be utilised to enhance the killing of tumours by peptide-specific CD8+ T lymphocytes.

Although TAPBPR usually functions as a peptide editor intracellular within cells, we reveal that when given access to the surface pool of MHC class I molecules, either through targeting membrane-bound TAPBPR to plasma membrane or by adding exogenous soluble TAPBPR to cells, TAPBPR retains its function as a peptide exchange catalyst. While, tapasin targeted to the plasma membrane also appeared to assist in the loading of exogenous peptide, the level of peptide binding achieved were significantly lower than TAPBPR. Therefore, this may be due to tapasin dragging a small pool of peptide-receptive molecules with it though the secretory pathway, rather than retaining its peptide-editing activity on the cell surface. A few known factors may help explain why extracellular TAPBPR is the superior peptide editor on surface MHC class I. First, unlike tapasin[18,19], TAPBPR is able to bind to MHC class I in the absence of any other co-factors or leucine zippering[8,9], a finding verified in the recent crystal structures of the TAPBPR:MHC class I complex[20,21]. Second, TAPBPR has higher affinity for MHC class I than tapasin[9]. Third, TAPBPR can also interact with MHC class I in a glycan-independent manner, thus broadening the species of MHC class I it can bind, including those on the cell surface, compared to tapasin.

By initially exploring the artefactual expression of surface expressed TAPBPR, we have developed a novel cellular based peptide-exchange assay, in addition to those already established[18,19], which may help us better define both the mechanism of peptide editing and the peptide selection criteria exerted by TAPBPR. However, the most exciting implications of our discoveries relates to the potential translational opportunities of utilising TAPBPR to load immunogenic peptides onto cells to target their recognition by the immune system.

Although exogenous peptide alone can bind to MHC class I in a passive manner, the presence of extracellular TAPBPR permits peptide loading in an active mechanism, speeding up the process so that it is almost instantaneously and permitting it to occur at very low peptide concentration. Therefore, extracellular TAPBPR has the potential to enable us to override natural peptide selection processes that occur within cells via the MHC class I antigen processing and pathway. This could be beneficial in a number of clinical situation which is it desirable to induce T cells responses. First, targeting TAPBPR to the surface of professional antigen presenting cells, such as dendritic cells, may prove useful in combination with peptide-based vaccination strategies, to boast the pool of pathogen or tumour-specific lymphocytes in the circulation. Second, targeting TAPBPR to tumours could be utilised to boast the level of tumour antigens including neoantigens displayed directly on the tumour thus improve the recognition of tumours by the pre-existing tumour specific lymphocytes. Third, TAPBPR could be used to load immunogenic peptides derived from pathogens such as viruses onto the surface of tumours permitting pathogen-specific T cells to mediate an antitumour immune response. Fourth, the loading immunogenic peptides onto cells harbouring latent/persistent pathogens via TAPBPR may prove beneficial in infection control.

TAPBPR may also remove peptides which are the targets in CD8+ T cell immune-mediate inflammatory diseases. The ability to switch the exogenous immunogenic peptide displayed on the surface of a cell in the face of immunoediting or immune evasion may be a major advance for future of immunotherapy.

REFERENCES

1. Sharma, P et al Cell 168, 707-723, doi:10.1016/j.cell.2017.01.017 (2017).
2. Pardoll, D. M. *Cancer* 12, 252-264, doi: 10.1038/nrc3239 (2012).
3. Rizvi, N. A. et al. *Science* 348, 124-128, doi:10.1126/science.aaa1348 (2015).
4. Snyder, A. et al. *The New England journal of medicine* 371, 2189-2199, doi:10.1056/NEJMoa1406498 (2014).
5. Van Allen, E. M. et al. *Science* 350, 207-211, doi:10.1126/science.aad0095 (2015).

6. Lauss, M. et al., *Nature Communications* 8, 1738, doi: 10.1038/s41467-017-01460-0 (2017).
7. Mittal, D et al. *Curr Opin Immunol* 27, 16-25, doi: 10.1016/j.coi.2014.01.004 (2014).
8. Hermann, C. et al. *eLife* 4, e09617, doi:10.7554/eLife.09617 (2015).
9. Morozov, G. I. et al. *Proc Natl Acad Sci USA* 113, E1006-1015, doi:10.1073/pnas.1519894113 (2016).
10. Neerincx, A. et al. *eLife* 6, doi:10.7554/eLife.23049 (2017).
11. Boyle, L. H. et al. *Proc Natl Acad Sci USA* 110, 3465-3470, doi:10.1073/pnas.1222342110 1222342110 [pii] (2013).
12. Nilsson, T et al. *Cell* 58, 707-718 (1989).
13. Li, S., et al. *Proc Natl Acad Sci USA* 94, 8708-8713 (1997).
14. Ortmann, B. et al. *Science* 277, 1306-1309 (1997).
15. Hermann, C., et al *J Immunol* 191, 5743-5750, doi: 10.4049/jimmunol.1300929 (2013).
16. Wills, M. R. et al. *J Virol* 70, 7569-7579 (1996).
17. Sim, A. C. et al. *Scientific reports* 3, 3232, doi:10.1038/srep03232 (2013).
18. Wearsch, P. A. et al *Nat Immunol* 8, 873-881, doi: ni1485 [pii] 10.1038/ni1485 (2007).
19. Chen, M. et al *EMBO J* 26, 1681-1690, doi: 7601624 [pii] 10.1038/sj.emboj.7601624 (2007).
20. Jiang, J. et al. *Science* 358, 1064-1068, doi:10.1126/science.aao5154 (2017).
21. Thomas, C. et al. *Science* 358, 1060-1064, doi:10.1126/science.aao6001 (2017).
22. Li, Z et al. *Proc Natl Acad Sci USA* 110, 5004-5009, doi:10.1073/pnas.1218620110 (2013).
23. Tiwari, R. K. et al *EMBO J* 6, 3373-3378 (1987).
24. Barnstable, C. J. et al. *Cell* 14, 9-20 (1978).
25. Stam, N. J. et al *Journal of Immunology* 137, 2299-2306 (1986).
26. Perosa, F. et al. *J Immunol* 171, 1918-1926 (2003).
27. Hogan, K. T. et al. *Cancer research* 58, 5144-5150 (1998).
28. Parkhurst M R, et al. (1996) *J Immunol* 157(6):2539-2548.
29. Valmori D, et al. (1998) *J Immunol* 160(4):1750-1758.
30. Theobald M, et al. (1995) *Proc Natl Acad Sci USA* 92(26):11993-11997.
31. Kawashima I, et al. (1998) *Hum Immunol* 59(1):1-14.

```
Sequences
nucleotide sequence encoding TAPBPR lumina! domain (mature sequence
without 21 aa leader sequence)
                                                         SEQ ID NO: 1
aagccccacccagcagaggggcagtggcgggcagtggacgtggtcctagactgtttcctggtgaaggacggtgcgca ccgtggagctctcgccagcagtgaggacagggcaagggcctcccttgtgctgaagcaggtgccagtgctggacgatg gctccctggaggacttcaccgatttccaaggggggcacactggcccaagatgacccacctattatctttgaggcctca gtggacctggtccagattcccagccgaggccttgctccatgctgactgcagtgggaaggaggtgacctgtgagat ctcccgctactttctccagatgacagagaccactgttaagacagcagcttggttcatggccaacgtgcaggtctctg gagggggacctagcatctccttggtgatgaagactcccagggtcgccaagaatgaggtgctctggcacccaacgctg aacttgccactgagcccccaggggactgtgcgaactgcagtggagttccaggtgatgacacagacccaatccctgag cttcctgctggggtcctcagcctccttggactgtggcttctccatggcaccgggcttggacctcatcagtgtggagt ggcgactgcagcacaagggcaggggtcagttggtgtacagctggaccgcagggcaggggcaggctgtgcggaagggc gctaccctggagcctgcacaactgggcatggccagggatgcctccctcaccctgcccggcctcactatacaggacga ggggacctacatttgccagatcaccacctctctgtaccgagctcagcagatcatccagctcaacatccaagcttccc ctaaagtacgactgagcttggcaaacgaagctctgctgcccaccctcatctgcgacattgctggctattaccctctg gatgtggtggtgacgtggacccgagaggagctgggtggtccccagcccaagtctctggtgcctccttctccagcct caggcaaagcgtggcaggcacctacagcatctcctcctctctcaccgcagaacctggctctgcaggtgccacttaca cctgccaggtcacacacatctctctggaggagcccttggggccagcacccaggttgtcccaccagagcggaga TAPBPR luminal domain (mature sequence without 21 aa leader sequence)
                                                         SEQ ID NO: 2
KPHPAEGQWRAVDVVLDCFLVKDGAHRGALASSEDRARASLVLKQVPVLDDGSLEDFTDFQGGTLAQDDPPIIFEAS

VDLVQIPQAEALLHADCSGKEVTCEISRYFLQMTETTVKTAAWFMANVQVSGGGPSISLVMKTPRVAKNEVLWHPTL

NLPLSPQGTVRTAVEFQVMTQTQSLSFLLGSSASLDCGFSMAPGLDLISVEWRLQHKGRGQLVYSWTAGQGQAVRKG

ATLEPAQLGMARDASLTLPGLTIQDEGTYICQITTSLYRAQQIIQLNIQASPKVRLSLANEALLPTLICDIAGYYPL

DVVVTWTREELGGSPAQVSGASFSSLRQSVAGTYSISSSLTAEPGSAGATYTCQVTHISLEEPLGASTQVVPPERR nucleotide sequence encoding TAPBPR-LONG-FcIgG1
                                                         SEQ ID NO: 3
atgggcacacaggagggctggtgcctgctgctctgcctggctctatctggagcagcagaaaccaagcccacccagc agaggggcagtggcgggcagtggacgtggtcctagactgtttcctggtgaaggacggtgcgcaccgtggagctctcg
```

-continued

```
ccagcagtgaggacagggcaagggcctcccttgtgctgaagcaggtgccagtgctggacgatggctccctggaggac
ttcaccgatttccaaggggggcacactggcccaagatgacccacctattatctttgaggcctcagtggacctggtcca
gattccccaggccgaggccttgctccatgctgactgcagtgggaaggaggtgacctgtgagatctcccgctactttc
tccagatgacagagaccactgttaagacagcagcttggttcatggccaacgtgcaggtctctggaggggacctagc
atctccttggtgatgaagactcccagggtcgccaagaatgaggtgctctggcacccaacgctgaacttgccactgag
cccccagggactgtgcgaactgcagtggagttccaggtgatgacacagacccaatccctgagcttcctgctgggt
cctcagcctccttggactgtggcttctccatggcacgggcttggacctcatcagtgtggagtggcgactgcagcac
aagggcagggtcagttggtgtacagctggaccgcagggcagggcaggctgtgcggaagggcgctaccctggagcc
tgcacaactgggcatggccagggatgcctccctcaccctgcccggcctcactatacaggacgaggggacctacattt
gccagatcaccacctctctgtaccgagctcagcagatcatccagctcaacatccaagcttcccctaaagtacgactg
agcttggcaaacgaagctctgctgcccaccctcatctgcgacattgctggctattaccctctggatgtggtggtgac
gtggacccgagaggagctggtgggtccccagcccaagtctctggtgcctccttctccagcctcaggcaaagcgtgg
caggcacctacagcatctcctcctctctcaccgcagaacctggctctgcaggtgccacttacacctgccaggtcaca
cacatctctctggaggagccccttggggccagcacccaggttgtcccaccagagcggagacacgtgggtggcggtgg
ctccggtggcggtggctccggtggcggtggctccactagtgacaaaactcacacatgcccaccgtgcccagcacctg
aactcctggggggaccgtcagtcttcctcttccccccaaaacccaaggacaccctcatgatctcccggacccctgag
gtcacatgcgtggtggtggacgtgagccacgaagaccctgaggtcaagttcaactggtacgtggacggcgtggaggt
gcataatgccaagacaaagccgcgggaggagcagtacaacagcacgtaccgtgtggtcagcgtcctcaccgtcctgc
accaggactggctgaatggcaaggagtacaagtgcaaggtctccaacaaagccctcccagcccccatcgagaaaacc
atctccaaagccaaagggcagccccgagaaccacaggtgtacaccctgcccccatcccgggatgagctgaccaagaa
ccaggtcagcctgacctgcctggtcaaaggcttctatcccagcgacatcgccgtggagtgggagagcaatgggcagc
cggagaacaactacaagaccacgcctcccgtgctggactccgacggctccttcttcctctacagcaagctcaccgtg
gacaagagcaggtggcagcaggggaacgtcttctcatgctccgtgatgcatgaggctctgcacaaccactacacgca
gaagagcctctccctgtctccgggtaaaggcggaggaggatct
```

TAPBPR-LONG-FcIgG1 (mature TAPBPR domain underlined)

SEQ ID NO: 4

MGTQEGWCLLLCLALSGAAET<u>KPHPAEGQWRAVDVVLDCFLVKDGAHRGALASSEDRARASLVLKQVPVLDDGSLED
FTDFQGGTLAQDDPPIIFEASVDLVQIPQAEALLHADCSGKEVTCEISRYFLQMTETTVKTAAWFMANVQVSGGGPS
ISLVMKTPRVAKNEVLWHPTLNLPLSPQGTVRTAVEFQVMTQTQSLSFLLGSSASLDCGFSMAPGLDLISVEWRLQH
KGRGQLVYSWTAGQGQAVRKGATLEPAQLGMARDASLTLPGLTIQDEGTYICQITTSLYRAQQIIQLNIQASPKVRL
SLANEALLPTLICDIAGYYPLDVVVTWTREELGGSPAQVSGASFSSLRQSVAGTYSISSSLTAEPGSAGATYTCQVT
HISLEEPLGASTQVVPPERRHVGGGGSGGGGSGGGGSTSDKTHTCPPCPAPELLGGPSVFLFPPKPKDTLMISRTPE</u>
VTCVVVDVSHEDPEVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGKGGGGS nucleotide sequence encoding sTAPBPR-sPD1

SEQ ID NO: 5

```
atgggcacacaggagggctggtgcctgctgctctgcctggctctatctggagcagcagaaaccaagccccacccagc
agaggggcagtggcgggcagtggacgtggtcctagactgtttcctggtgaaggacggtgcgcaccgtggagctctcg
ccagcagtgaggacagggcaagggcctcccttgtgctgaagcaggtgccagtgctggacgatggctccctggaggac
ttcaccgatttccaaggggggcacactggcccaagatgacccacctattatctttgaggcctcagtggacctggtcca
gattccccaggccgaggccttgctccatgctgactgcagtgggaaggaggtgacctgtgagatctcccgctactttc
tccagatgacagagaccactgttaagacagcagcttggttcatggccaacgtgcaggtctctggaggggacctagc
```

```
atctccttggtgatgaagactcccagggtcgccaagaatgaggtgctctggcacccaacgctgaacttgccactgag
ccccaggggactgtgcgaactgcagtggagttccaggtgatgacacagacccaatccctgagcttcctgctgggt
cctcagcctccttggactgtggcttctccatggcaccgggcttggacctcatcagtgtggagtggcgactgcagcac
aagggcaggggtcagttggtgtacagctggaccgcagggcaggggcaggctgtgcggaagggcgctaccctggagcc
tgcacaactgggcatggccagggatgcctccctcaccctgcccggcctcactatacaggacgaggggacctacattt
gccagatcaccacctctctgtaccgagctcagcagatcatccagctcaacatccaagcttcccctaaagtacgactg
agcttggcaaacgaagctctgctgcccaccctcatctgcgacattgctggctattaccctctggatgtggtggtgac
gtggacccgagaggagctgggtgggtcccagcccaagtctctggtgcctccttctccagcctcaggcaaagcgtgg
caggcacctacagcatctcctcctctcaccgcagaacctggctctgcaggtgccacttacacctgccaggtcaca
cacatctctctggaggagccccttggggccagcacccaggttgtcccaccagagcggagacacgtgggtggcggtgg
ctccggtggcggtggctccggtggcggtggctccactagtgactccccagacaggccctggaaccccccaccttct
tcccagccctgctcgtggtgaccgaaggggacaacgccaccttcacctgcagcttctccaacacatcggagagcttc
cacgtgatctggcaccgcgagagccccagcggccagacggacaccctggccgccttccccgaggaccgcagccagcc
cggccaggactgccgcttccgtgtcacacaactgcccaacgggcgtgacttccacatgagcgtggtcagggcccggc
gcaatgacagcggcacctacgtgtgtggggtgatctccctggcccccaagatccagatcaaagagagcctg sTAPBPR-sPD1 (mature TAPBPR domain underlined)
                                                                    SEQ ID NO: 6
MGTQEGWCLLLCLALSGAAET<u>KPHPAEGQWRAVDVVLDCFLVKDGAHRGALASSEDRARASLVLKQVPVLDDGSLED
FTDFQGGTLAQDDPPIIFEASVDLVQIPQAEALLHADCSGKEVTCEISRYFLQMTETTVKTAAWFMANVQVSGGGPS
ISLVMKTPRVAKNEVLWHPTLNLPLSPQGTVRTAVEFQVMTQTQSLSFLLGSSASLDCGFSMAPGLDLISVEWRLQH
KGRGQLVYSWTAGQGQAVRKGATLEPAQLGMARDASLTLPGLTIQDEGTYICQITTSLYRAQQIIQLNIQASPKVRL
SLANEALLPTLICDIAGYYPLDVVVTWTREELGGSPAQVSGASFSSLRQSVAGTYSISSSLTAEPGSAGATYTCQVT
HISLEEPLGASTQVVPPERR</u>HVGGGGSGGGGSGGGGSTSDSPDRPWNPPTFFPALLVVTEGDNATFTCSFSNTSESF
HVIWHRESPSGQTDTLAAFPEDRSQPGQDCRFRVTQLPNGRDFHMSVVRARRNDSGTYVCGVISLAPKIQIKESL* nucleotide sequence encoding TAPBPR-Her2scFv
                                                                    SEQ ID NO: 7
atgggcacacaggagggctggtgcctgctgctctgcctggctctatctggagcagcagaaaccaagccccacccagc
agaggggcagtggcgggcagtggacgtggtcctagactgtttcctggtgaaggacggtgcgcaccgtggagctctcg
ccagcagtgaggacagggcaagggcctcccttgtgctgaagcaggtgccagtgctggacgatggctccctggaggac
ttcaccgatttccaaggggggcacactggcccaagatgacccacctattatctttgaggcctcagtggacctggtcca
gattccccaggccgaggccttgctccatgctgactgcagtgggaaggaggtgacctgtgagatctcccgctactttc
tccagatgacagagaccactgttaagacagcagcttggttcatggccaacgtgcaggtctctggagggggacctagc
atctccttggtgatgaagactcccagggtcgccaagaatgaggtgctctggcacccaacgctgaacttgccactgag
ccccaggggactgtgcgaactgcagtggagttccaggtgatgacacagacccaatccctgagcttcctgctgggt
cctcagcctccttggactgtggcttctccatggcaccgggcttggacctcatcagtgtggagtggcgactgcagcac
aagggcaggggtcagttggtgtacagctggaccgcagggcaggggcaggctgtgcggaagggcgctaccctggagcc
tgcacaactgggcatggccagggatgcctccctcaccctgcccggcctcactatacaggacgaggggacctacattt
gccagatcaccacctctctgtaccgagctcagcagatcatccagctcaacatccaagcttcccctaaagtacgactg
agcttggcaaacgaagctctgctgcccaccctcatctgcgacattgctggctattaccctctggatgtggtggtgac
gtggacccgagaggagctgggtgggtcccagcccaagtctctggtgcctccttctccagcctcaggcaaagcgtgg
caggcacctacagcatctcctcctctcaccgcagaacctggctctgcaggtgccacttacacctgccaggtcaca
cacatctctctggaggagccccttggggccagcacccaggttgtcccaccagagcggagacacgtgggtggcggtgg
```

-continued ctccggtggcggtggctccggtggcggtggctccactagtgcggatcttggatcccgggccatggcccaggtgcagc
tggtgcagtctggggcagaggtgaaaaagcccggggagtctctgaagatctcctgtaagggttctggatacagcttt
accagctactggatcgcctgggtgcgccagatgcccgggaaaggcctggagtacatgggctcatctatcctggtga
ctctgacaccaaatacagcccgtccttccaaggccaggtcaccatctcagtcgacaagtccgtcagcactgcctact
tgcaatggagcagtctgaagccctcggacagcgccgtgtattttgtgcgagacatgacgtgggatattgcagtagt
tccaactgcgcaaagtggcctgaatacttccagcattggggccagggcaccctggtcaccgtctcctcaggtggagg
cggttcaggcggaggtggctctggcggtggcggatcgcagtctgtgttgacgcagccgccctcagtgtctgcggcc
caggacagaaggtcaccatctcctgctctggaagcagctccaacattgggaataattatgtatcctggtaccagcag
ctcccaggaacagcccccaaactcctcatctatgatcacaccaatcggcccgcagggtccctgaccgattctctgg
ctccaagtctggcacctcagcctccctggccatcagtgggttccggtccgaggatgaggctgattattactgtgcct
cctgggactacaccctctcgggctgggtgttcggcggaggaaccaagctgaccgtcctaggtgcggccgccggcgga
ggaggatct TAPBPR-Her2scFv (mature TAPBPR domain underlined)
SEQ ID NO: 8
MGTQEGWCLLLCLALSGAAETKPHPAEGQWRAVDVVLDCFLVKDGAHRGALASSEDRARASLVLKQVPVLDDGSLED
FTDFQGGTLAQDDPPIIFEASVDLVQIPQAEALLHADCSGKEVTCEISRYFLQMTETTVKTAAWFMANVQVSGGGPS
ISLVMKTPRVAKNEVLWHPTLNLPLSPQGTVRTAVEFQVMTQTQSLSFLLGSSASLDCGFSMAPGLDLISVEWRLQH
KGRGQLVYSWTAGQGQAVRKGATLEPAQLGMARDASLTLPGLTIQDEGTYICQITTSLYRAQQIIQLNIQASPKVRL
SLANEALLPTLICDIAGYYPLDVVVTWTREELGGSPAQVSGASFSSLRQSVAGTYSISSSLTAEPGSAGATYTCQVT
HISLEEPLGASTQVVPPERRHVGGGGSGGGGSGGGGSTSADLGSRAMAQVQLVQSGAEVKKPGESLKISCKGSGYSF
TSYWIAWVRQMPGKGLEYMGLIYPGDSDTKYSPSFQGQVTISVDKSVSTAYLQWSSLKPSDSAVYFCARHDVGYCSS
SNCAKWPEYFQHWGQGTLVTVSSGGGGSGGGGSGGGGSQSVLTQPPSVSAAPGQKVTISCSGSSSNIGNNYVSWYQQ
LPGTAPKLLIYDHTNRPAGVPDRFSGSKSGTSASLAISGFRSEDEADYYCASWDYTLSGWVFGGGTKLTVLGAAAGG
GGS* nucleotide sequence encoding TAPBPR-GFP-NB
SEQ ID NO: 9
atgggcacacaggagggctggtgcctgctgctctgcctggctctatctggagcagcagaaaccaagcccacccagc
agagggggcagtggcgggcagtggacgtggtcctagactgttttcctggtgaaggacggtgcgcaccgtggagctctcg
ccagcagtgaggacagggcaagggcctcccttgtgctgaagcaggtgccagtgctggacgatggctccctggaggac
ttcaccgatttccaagggggcacactggcccaagatgacccacctattatctttgaggcctcagtggacctggtcca
gattccccaggccgaggccttgctccatgctgactgcagtgggaaggaggtgacctgtgagatctcccgctactttc
tccagatgacagagaccactgttaagacagcagcttggttcatggccaacgtgcaggtctctggaggggggacctagc
atctccttggtgatgaagactcccagggtcgccaagaatgaggtgctctggcacccaacgctgaacttgccactgag
ccccaggggactgtgcgaactgcagtggagttccaggtgatgacacagacccaatccctgagcttcctgctgggt
cctcagcctccttggactgtgcttctccatggcaccgggcttggacctcatcagtgtggagtggcgactgcagcac
aagggcaggggtcagttggtgtacagctggaccgcagggcaggggcaggctgtgcggaagggcgctaccctggagcc
tgcacaactgggcatgccagggatgcctccctcaccctgcccggcctcactatacaggacgaggggacctacattt
gccagatcaccacctctctgtaccgagctcagcagatcatccagctcaacatccaagcttcccctaaagtacgactg
agcttggcaaacgaagctctgctgccaccctcatctgcgacattgctggctattaccctctggatgtggtggtgac
gtggacccgagaggagctgggtgggtccccagcccaagtctctggtgcctccttctccagcctcaggcaaagcgtgg
caggcacctacagcatctcctcctctctcaccgcagaacctggctctgcaggtgccacttacacctgccaggtcaca
cacatctctctggaggagccccttggggccagcacccaggttgtcccaccagagcggagacacgtgggtggcggtgg
ctccggtggcggtggctccggtggcggtggctccactagtcaggttcagctggttgaaagcggtggtgcactggttc -continued

```
agcctggtggtagcctgcgtctgagctgtgcagcaagcggttttccggttaatcgttatagcatgcgttggtatcgt caggcaccgggtaaagaacgtgaatgggttgcaggtatgagcagtgccggtgatcgtagcagctatgaagatagcgt taaaggtcgttttaccatcagccgtgatgatgcacgtaataccgtttatctgcaaatgaatagcctgaaaccggaag ataccgcagtgtattattgcaatgttaacgtgggctttgaatattggggtcagggcacccaggttaccgttagcagc aaa
```

TAPBPR-GFP-NB (mature TAPBPR domain underlined)

SEQ ID NO: 10

MGTQEGWCLLLCLALSGAAET<u>KPHPAEGQWRAVDVVLDCFLVKDGAHRGALASSEDRARASLVLKQVPVLDDGSLED</u>

<u>FTDFQGGTLAQDDPPIIFEASVDLVQIPQAEALLHADCSGKEVTCEISRYFLQMTETTVKTAAWFMANVQVSGGGPS</u>

<u>ISLVMKTPRVAKNEVLWHPTLNLPLSPQGTVRTAVEFQVMTQTQSLSFLLGSSASLDCGFSMAPGLDLISVEWRLQH</u>

<u>KGRGQLVYSWTAGQGQAVRKGATLEPAQLGMARDASLTLPGLTIQDEGTYICQITTSLYRAQQIIQLNIQASPKVRL</u>

<u>SLANEALLPTLICDIAGYYPLDVVVTWTREELGGSPAQVSGASFSSLRQSVAGTYSISSSLTAEPGSAGATYTCQVT</u>

<u>HISLEEPLGASTQVVPPERRH</u>VGGGGSGGGGSGGGGSTSQVQLVESGGALVQPGGSLRLSCAASGFPVNRYSMRWYR

QAPGKEREWVAGMSSAGDRSSYEDSVKGRFTISRDDARNTVYLQMNSLKPEDTAVYYCNVNVGFEYWGQGTQVTVSS

K* nucleotide sequence encoding sTAPBPR-LONG-PD-L1-NB1

SEQ ID NO: 11

```
atgggcacacaggagggctggtgcctgctgctctgcctggctctatctggagcagcagaaaccaagccccacccagc agaggggcagtggcgggcagtggacgtggtcctagactgtttcctggtgaaggacggtgcgcaccgtggagctctcg ccagcagtgaggacagggcaagggcctcccttgtgctgaagcaggtgccagtgctggacgatggctccctggaggac ttcaccgatttccaaggggcacactggcccaagatgacccacctattatctttgaggcctcagtggacctggtcca gattccccaggccgaggccttgctccatgctgactgcagtgggaaggaggtgacctgtgagatctcccgctactttc tccagatgacagagaccactgttaagacagcagcttggttcatggccaacgtgcaggtctctggaggggggacctagc atctccttggtgatgaagactcccagggtcgccaagaatgaggtgctctggcacccaacgctgaacttgccactgag cccccaggggactgtgcgaactgcagtggagttccaggtgatgacacagacccaatccctgagcttcctgctggggt cctcagcctccttggactgtggcttctccatggcaccgggcttggacctcatcagtgtggagtggcgactgcagcac aagggcaggggtcagttggtgtacagctggaccgcagggcaggggcaggctgtgcggaagggcgctaccctggagcc tgcacaactgggcatggccagggatgcctccctcaccctgccggcctcactatacaggacgagggacctacattt gccagatcaccacctctctgtaccgagctcagcagatcatccagctcaacatccaagcttcccctaaagtacgactg agcttggcaaacgaagctctgctgccaccctcatctgcgacattgctggctatttaccctctggatgtggtggtgac gtggacccgagaggagctgggtgggtccccagcccaagtctctggtgcctccttctccagcctcaggcaaagcgtgg caggcacctacagcatctcctcctctctcaccgcagaacctggctctgcaggtgccacttacacctgccaggtcaca cacatctctctggaggagcccttggggccagcacccaggttgtcccaccagagcggagacacgtgggtggcggtgg ctccggtggcggtggctccggtggcggtggctccactagtgaggtgcagctggtggagagcggcggcggcctggtgc agccccggcggcagcctgagactgagctgcgccgccagcggcttcaccctggactactacgccatcggctggttcaga caggcccccggcaaggagagagtgggccagcagcatcagcagcagcgacggcagcacctactacgccgacagcgt gaagggcagattcaccatcagcagagacaacgccaagaacaccgtgttcctgcagatgaacagcctgaagcccgagg acaccgccgtgtacagctgcgccgccagccaggcccccatcaccatcgccaccatgatgaagcccttctacgactac tggggccagggcacccaggtgaccgtgagcagcggcggaggaggatct
``` sTAPBPR-LONG-PD-L1-NB1 (mature TAPBPR domain underlined)

SEQ ID NO: 12

MGTQEGWCLLLCLALSGAAET<u>KPHPAEGQWRAVDVVLDCFLVKDGAHRGALASSEDRARASLVLKQVPVLDDGSLED</u>

<u>FTDFQGGTLAQDDPPIIFEASVDLVQIPQAEALLHADCSGKEVTCEISRYFLQMTETTVKTAAWFMANVQVSGGGPS</u>

ISLVMKTPRVAKNEVLWHPTLNLPLSPQGTVRTAVEFQVMTQTQSLSFLLGSSASLDCGFSMAPGLDLISVEWRLQH

KGRGQLVYSWTAGQGQAVRKGATLEPAQLGMARDASLTLPGLTIQDEGTYICQITTSLYRAQQIIQLNIQASPKVRL

SLANEALLPTLICDIAGYYPLDVVVTWTREELGGSPAQVSGASFSSLRQSVAGTYSISSSLTAEPGSAGATYTCQVT

HISLEEPLGASTQVVPPERRHVGGGSGGGGSGGGGSTSEVQLVESGGGLVQPGGSLRLSCAASGFTLDYYAIGWFR

QAPGKEREWASSISSSDGSTYYADSVKGRFTISRDNAKNTVFLQMNSLKPEDTAVYSCAASQAPITIATMMKPFYDY

WGQGTQVTVSSGGGGS* nucleotide sequence encoding sTAPBPR-LONG-PD-L1-NB2
SEQ ID NO: 13 atgggcacacaggagggctggtgcctgctgctctgcctggctctatctggagcagcagaaaccaagccccacccagc agaggggcagtggcgggcagtggacgtggtcctagactgtttcctggtgaaggacggtgcgcaccgtggagctctcg ccagcagtgaggacagggcaagggcctcccttgtgctgaagcaggtgccagtgctggacgatggctccctggaggac ttcaccgatttccaaggggcacactggcccaagatgacccacctattatctttgaggcctcagtggacctggtcca gattccccaggccgaggccttgctccatgctgactgcagtgggaaggaggtgacctgtgagatctcccgctactttc tccagatgacagagaccactgttaagacagcagcttggttcatggccaacgtgcaggtctctggaggggacctagc atctccttggtgatgaagactcccagggtcgccaagaatgaggtgctctggcacccaacgctgaacttgccactgag ccccaggggactgtgcgaactgcagtggagttccaggtgatgacacagacccaatccctgagcttcctgctggggt cctcagcctccttggactgtggcttctccatggcaccgggcttggacctcatcagtgtggagtggcgactgcagcac aagggcaggggtcagttggtgtacagctggaccgcagggcaggggcaggctgtgcggaagggcgctaccctggagcc tgcacaactgggcatggccagggatgcctccctcaccctgcccggcctcactatacaggacgaggggacctacattt gccagatcaccacctctctgtaccgagctcagcagatcatccagctcaacatccaagcttcccctaaagtacgactg agcttggcaaacgaagctctgctgcccaccctcatctgcgacattgctggctataccctctggatgtggtggtgac gtggaccccgagaggagctgggtgggtcccagcccaagtctctggtgcctccttctccagcctcaggcaaagcgtgg caggcacctacagcatctcctcctctctcaccgcagaacctggctctgcaggtgccacttacacctgccaggtcaca cacatctctctggaggagcccttggggcagcacccaggttgtcccaccagagcggagacacgtgggtggcggtgg ctccggtggcggtggctccggtggcggtggctccactagtgaggtgcagctggtggagagcggcggcggcctggtgc agcccggcggcagcctgagactgagctgcgccgcagcggcttcaccctggactactacgccaagtgctggttcaga caggccccggcaaggagagagtgggtgagctgcatcagcagcagcgacggcagcacctactacgccgacagcgt gaagggcagattcaccatcagcagagacaacgccaagaacaccgtgtacctgcagatgaacagcctgaagcccgagg acaccgccgtgtacttctgcgccgccagacacggcggccccctgaccgtggagtacttcttcgactactggggccag ggcacccaggtgaccgtgagcagcggcggaggaggatct sTAPBPR-LONG-PD-L1-NB2 (mature TAPBPR domain underlined)
SEQ ID NO: 14

MGTQEGWCLLLCLALSGAAETKPHPAEGQWRAVDVVLDCFLVKDGAHRGALASSEDRARASLVLKQVPVLDDGSLED

FTDFQGGTLAQDDPPIIFEASVDLVQIPQAEALLHADCSGKEVTCEISRYFLQMTETTVKTAAWFMANVQVSGGGPS

ISLVMKTPRVAKNEVLWHPTLNLPLSPQGTVRTAVEFQVMTQTQSLSFLLGSSASLDCGFSMAPGLDLISVEWRLQH

KGRGQLVYSWTAGQGQAVRKGATLEPAQLGMARDASLTLPGLTIQDEGTYICQITTSLYRAQQIIQLNIQASPKVRL

SLANEALLPTLICDIAGYYPLDVVVTWTREELGGSPAQVSGASFSSLRQSVAGTYSISSSLTAEPGSAGATYTCQVT

HISLEEPLGASTQVVPPERRHVGGGSGGGGSGGGGSTSEVQLVESGGGLVQPGGSLRLSCAASGFTLDYYAKCWFR

QAPGKEREWVSCISSSDGSTYYADSVKGRFTISRDNAKNTVYLQMNSLKPEDTAVYFCAARHGGPLTVEYFFDYWGQ

GTQVTVSSGGGGS* nucleotide sequence encoding sTAPBPR-LONG-PD-L1-NB4
SEQ ID NO: 15 atgggcacacaggagggctggtgcctgctgctctgcctggctctatctggagcagcagaaaccaagccccacccagc agaggggcagtggcgggcagtggacgtggtcctagactgtttcctggtgaaggacggtgcgcaccgtggagctctcg -continued

```
ccagcagtgaggacagggcaagggcctcccttgtgctgaagcaggtgccagtgctggacgatggctccctggaggac ttcaccgatttccaaggggcacactggcccaagatgacccacctattatctttgaggcctcagtggacctggtcca gattccccaggccgaggccttgctccatgctgactgcagtgggaaggaggtgacctgtgagatctcccgctactttc tccagatgacagagaccactgttaagacagcagcttggttcatggccaacgtgcaggtctctggaggggacctagc atctccttggtgatgaagactcccagggtcgccaagaatgaggtgctctggcacccaacgctgaacttgccactgag cccccaggggactgtgcgaactgcagtggagttccaggtgatgacacagacccaatccctgagcttcctgctgggt cctcagcctccttggactgtggcttctccatggcacgggcttggacctcatcagtgtggagtggcgactgcagcac aagggcaggggtcagttggtgtacagctggaccgcagggcagggcaggctgtgcggaagggcgctaccctggagcc tgcacaactgggcatggccagggatgcctccctcaccctgcccggcctcactatacaggacgaggggacctacattt gccagatcaccacctctctgtaccgagctcagcagatcatccagctcaacatccaagcttcccctaaagtacgactg agcttggcaaacgaagctctgctgcccaccctcatctgcgacattgctggctattaccctctggatgtggtggtgac gtggaccccgagaggagctgggtgggtccccagcccaagtctctggtgcctccttctccagcctcaggcaaagcgtgg caggcacctacagcatctcctcctctctcaccgcagaacctggctctgcaggtgccacttacacctgccaggtcaca cacatctctctggaggagcccttggggccagcacccaggttgtcccaccagagcggagacacgtgggtggcggtgg ctccggtggcggtggctccggtggcggtggctccactagtgaggtgcagctggtggagagcggcggcggcctggtgc aggccggcggcagcctgagactgagctgcgccgcagcggcagccttcagccagtacgacgtgggctggtacaga caggcccccggcaagcagagagagctggtggccttcagcagcagcggcggcagaaccatctaccccgacagcgtgaa gggcagattcaccttcagcagagacaacaccaagaacaccgtgtacctgcagatgaccagcctgaagcccgaggaca ccgccgtgtactactgcaagatcgactggtacctgaacagctactggggccagggcacccaggtgaccgtgagcagc ggcggaggaggatct
``` sTAPBPR-LONG-PD-L1-NB4 (mature TAPBPR domain underlined)

SEQ ID NO: 16

MGTQEGWCLLLCLALSGAAET<u>KPHPAEGQWRAVDVVLDCFLVKDGAHRGALASSEDRARASLVLKQVPVLDDGSLED</u>
<u>FTDFQGGTLAQDDPPIIFEASVDLVQIPQAEALLHADCSGKEVTCEISRYFLQMTETTVKTAAWFMANVQVSGGGPS</u>
<u>ISLVMKTPRVAKNEVLWHPTLNLPLSPQGTVRTAVEFQVMTQTQSLSFLLGSSASLDCGFSMAPGLDLISVEWRLQH</u>
<u>KGRGQLVYSWTAGQGQAVRKGATLEPAQLGMARDASLTLPGLTIQDEGTYICQITTSLYRAQQIIQLNIQASPKVRL</u>
<u>SLANEALLPTLICDIAGYYPLDVVVTWTREELGGSPAQVSGASFSSLRQSVAGTYSISSSLTAEPGSAGATYTCQVT</u>
<u>HISLEEPLGASTQVVPPERRH</u>VGGGSGGGGSGGGGSTSEVQLVESGGGLVQAGGSLRLSCAASGSTFSQYDVGWYR
QAPGKQRELVAFSSSGGRTIYPDSVKGRFTFSRDNTKNTVYLQMTSLKPEDTAVYYCKIDWYLNSYWGQGTQVTVSS
GGGGS* nucleotide sequence encoding hTAPBPR full length (with TMD and cytoplasmic
tail) (V41_G151_V169 polymorphisms as used in our studies)

SEQ ID NO: 17

```
atgggcacacaggagggctggtgcctgctgctctgcctggctctatctggagcagcagaaaccaagcccacccagc agaggggcagtggcgggcagtggacgtggtcctagactgtttcctggtgaaggacggtgcgcaccgtggagctctcg ccagcagtgaggacagggcaagggcctcccttgtgctgaagcaggtgccagtgctggacgatggctccctggaggac ttcaccgatttccaaggggcacactggcccaagatgacccacctattatctttgaggcctcagtggacctggtcca gattccccaggccgaggccttgctccatgctgactgcagtgggaaggaggtgacctgtgagatctcccgctactttc tccagatgacagagaccactgttaagacagcagcttggttcatggccaacgtgcaggtctctggaggggacctagc atctccttggtgatgaagactcccagggtcgccaagaatgaggtgctctggcacccaacgctgaacttgccactgag cccccaggggactgtgcgaactgcagtggagttccaggtgatgacacagacccaatccctgagcttcctgctgggt cctcagcctccttggactgtggcttctccatggcacgggcttggacctcatcagtgtggagtggcgactgcagcac aagggcaggggtcagttggtgtacagctggaccgcagggcaggggcaggctgtgcggaagggcgctaccctggagcc
```

-continued

```
tgcacaactgggcatggccagggatgcctccctcaccctgcccggcctcactatacaggacgagggacctacattt gccagatcaccacctctctgtaccgagctcagcagatcatccagctcaacatccaagcttcccctaaagtacgactg agcttggcaaacgaagctctgctgcccaccctcatctgcgacattgctggctattaccctctggatgtggtggtgac gtggaccccgagaggagctgggtgggtccccagcccaagtctctggtgcctccttctccagcctcaggcaaagcgtgg caggcacctacagcatctcctcctctctcaccgcagaacctggctctgcaggtgccacttacacctgccaggtcaca cacatctctctggaggagccccttggggccagcacccaggttgtcccaccagagcggagaacagccttgggagtcat ctttgccagcagtctcttccttcttgcactgatgttcctggggcttcagagacggcaagcacctacaggacttgggc tgcttcaggctgaacgctgggagaccacttcctgtgctgacacacagagctcccatctccatgaagaccgcacagcg cgtgtaagccagcccagctga
``` hTAPBPR full length (with TMD and cytoplasmic tail) (V41_G151_V169 polymorphisms as used herein) (mature TAPBPR domain full underline; TMD italics; cytoplasmic tail dotted underline)
SEQ ID NO: 18

MGTQEGWCLLLCLALSGAAET<u>KPHPAEGQWRAVDVVLDCFLVKDGAHRGALASSEDRARASLVLKQVPVLDDGSLED
FTDFQGGTLAQDDPPIIFEASVDLVQIPQAEALLHADCSGKEVTCEISRYFLQMTETTVKTAAWFMANVQVSGGGPS
ISLVMKTPRVAKNEVLWHPTLNLPLSPQGTVRTAVEFQVMTQTQSLSFLLGSSASLDCGFSMAPGLDLISVEWRLQH
KGRGQLVYSWTAGQGQAVRKGATLEPAQLGMARDASLTLPGLTIQDEGTYICQITTSLYRAQQIIQLNIQASPKVRL
SLANEALLPTLICDIAGYYPLDVVVTWTREELGGSPAQVSGASFSSLRQSVAGTYSISSSLTAEPGSAGATYTCQVT
HISLEEPLGASTQVVPPERR</u>TALGVIFASSLFLLALMFLGLQRRQAPTGLLLQAERWETTSCADTQSSHLHEDRTA
RVSQPS* nucleotide sequence encoding mouse TAPBPR full length
SEQ ID NO: 19

```
atgggcttggagcccagctggtatctgctgctctgtttggctgtctctggggcagcagggactgaccctcccacagc gcccaccacagcagaaagacagcggcagcccacggacatcatcttagactgcttcttggtgacagaagacaggcacc gcggggcttttgccagcagtggggacagggagagggccttgcttgtgctgaagcaggtaccagtgctggatgatggc tccctggaaggcatcacagatttccaggggagcactgagaccaaacaggattcacctgttatctttgaggcctcagt ggacttggtacagattccccaggcagaggcgttgctccatgctgactgcagcgggaaggcagtgacctgcgagatct ccaagtatttcctccaggcagacaagaggccacttttgagaaagcacattggttcatcagcaacatgcaggtttct agaggtggcccccagtgtctccatggtgatgaagactctaagagatgctgaagttggagctgtccggcaccctacact gaacctacctctgagtgcccagggcacagtgaagactcaagtggagttccaggtgacatcagagacccaaaccctga accacctgctggggtcctctgtctccctgcactgcagtttctccatggcaccagacctggacctcactggcgtggag tggcggctgcagcataaaggcagcggccagctggtgtacagctggaagacagggcaggggcaggccaagcgcaaggg cgctacactggagcctgaggagctactcagggctggaaacgcctctctcaccttacccaacctcactctaaaggatg aggggacctacatctgccagatctccacctctctgtatcaagctcaacgatcatgccacttaacatcctggctccc cccaaagtacaactgcacttggcaaacaaggaccctctgccttccctcgtctgcagcattgccggctactatcctct ggatgtgggagtgacgtggattcgagaggagctgggtggaattccagcccaagtctctggtgcctccttctccagcc tcaggcagagcacgatgggaacctacagcatttcttccacggtgatggctgacccaggccccacaggtgccacttat acctgccaagtcgcccacgtctccctggaggagccccttacaaccagcatgagggttttgccaaatccagagcagag aggaaccttgggagtcatctttgccagcatcatcttcctttctgcgctgttgttgtttctgggacttcacagacagc aagcttcttcgtcaaggtccaccaggcctatgaggcattctgggtga
``` mouse TAPBPR full length
SEQ ID NO: 20

MGLEPSWYLLLCLAVSGAAGTDPPTAPTTAERQRQPTDIILDCFLVTEDRHRGAFASSGDRERALLVLKQVPVLDDG
SLEGITDFQGSTETKQDSPVIFEASVDLVQIPQAEALLHADCSGKAVTCEISKYFLQARQEATFEKAHWFISNMQVS

-continued

```
RGGPSVSMVMKTLRDAEVGAVRHPTLNLPLSAQGTVKTQVEFQVTSETQTLNHLLGSSVSLHCSFSMAPDLDLTGVE

WRLQHKGSGQLVYSWKTGQGQAKRKGATLEPEELLRAGNASLTLPNLTLKDEGTYICQISTSLYQAQQIMPLNILAP

PKVQLHLANKDPLPSLVCSIAGYYPLDVGVTWIREELGGIPAQVSGASFSSLRQSTMGTYSISSTVMADPGPTGATY

TCQVAHVSLEEPLTTSMRVLPNPEQRGTLGVIFASIIFLSALLLFLGLHRQQASSSRSTRPMRHSG*
``` nucleotide sequence encoding luminal domains of mouse TAPBPR

SEQ ID NO: 21

```
gaccctcccacagcgcccaccacagcagaaagacagcggcagcccacggacatcatcttagactgcttcttggtgac agaagacaggcaccgcggggcttttgccagcagtggggacagggagagggccttgcttgtgctgaagcaggtaccag tgctggatgatggctccctggaaggcatcacagatttccaggggagcactgagaccaaacaggattcacctgttatc tttgaggcctcagtggacttggtacagattccccaggcagaggcgttgctccatgctgactgcagcgggaaggcagt gacctgcgagatctccaagtatttcctccaggccagacaagaggccacttttgagaaagcacattggttcatcagca acatgcaggtttctagaggtggccccagtgtctccatggtgatgaagactctaagagatgctgaagttggagctgtc cggcacccctacactgaacctacctctgagtgcccagggcacagtgaagactcaagtggagttccaggtgacatcaga gacccaaaccctgaaccacctgctggggtcctctgtctcccctgcactgcagtttctccatggcaccagacctggacc tcactggcgtggagtggcggctgcagcataaaggcagcggccagctggtgtacagctggaagacagggcaggggcag gccaagcgcaagggcgctacactggagcctgaggagctactcagggctgaaacgcctctctcaccttacccaacct cactctaaaggatgagggacctacatctgccagatctccacctctctgtatcaagctcaacagatcatgccactta acatcctggctcccccaaagtacaactgcacttggcaaacaaggaccctctgccttccctcgtctgcagcattgcc ggctactatcctctggatgtgggagtgacgtggattcgagaggagctgggtggaattccagcccaagtctctggtgc ctccttctccagcctcaggcagagcacgatgggaacctacagcatttcttccacggtgatggctgacccaggcccca caggtgccacttatacctgccaagtcgcccacgtctccctggaggagcccttacaaccagcatgagggttttgcca aatccagagcagagaggaacc
``` luminal domains of mouse TAPBPR

SEQ ID NO: 22

```
DPPTAPTTAERQRQPTDIILDCFLVTEDRHRGAFASSGDRERALLVLKQVPVLDDGSLEGITDFQGSTETKQDSPVI

FEASVDLVQIPQAEALLHADCSGKAVTCEISKYFLQARQEATFEKAHWFISNMQVSRGGPSVSMVMKTLRDAEVGAV

RHPTLNLPLSAQGTVKTQVEFQVTSETQTLNHLLGSSVSLHCSFSMAPDLDLTGVEWRLQHKGSGQLVYSWKTGQGQ

AKRKGATLEPEELLRAGNASLTLPNLTLKDEGTYICQISTSLYQAQQIMPLNILAPPKVQLHLANKDPLPSLVCSIA

GYYPLDVGVTWIREELGGIPAQVSGASFSSLRQSTMGTYSISSTVMADPGPTGATYTCQVAHVSLEEPLTTSMRVLP

NPEQRGT*
```

Anti-HER2 svFc

SEQ ID NO: 23

```
ADLGSRAMAQVQLVQSGAEVKKPGESLKISCKGSGYSFTSYWIAWVRQMPGKGLEYMGLIYPGDSDTKYSPSFQGQV

TISVDKSVSTAYLQWSSLKPSDSAVYFCARHDVGYCSSSNCAKWPEYFQHWGQGTLVTVSSGGGGSGGGGSGGGGSQ

SVLTQPPSVSAAPGQKVTISCSGSSSNIGNNYVSWYQQLPGTAPKLLIYDHTNRPAGVPDRFSGSKSGTSASLAISG

FRSEDEADYYCASWDYTLSGWVFGGGTKLTVLGAAA
```

Anti-HER2 (trastuzumab) Light chain

SEQ ID NO: 24

```
DIQMTQSPSSLSASVGDRVTITCRASQDVNTAVAWYQQKPGKAPKLLIYSASFLYSGVPSRFSGSRSGTDFTLTISS

LQPEDFATYYCQQHYTTPPTFGQGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC
```

Anti-HER2 (trastuzumab) Heavy chain

SEQ ID NO: 25

```
EVQLVESGGGLVQPGGSLRLSCAASGFNIKDTYIHWVRQAPGKGLEWVARIYPTNGYTRYADSVKGRFTISADTSKN

TAYLQMNSLRAEDTAVYYCSRWGGDGFYAMDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNVNHKPSNTKVDKKVEPPKSCDKTHTCP
```

PCPAPELLGGPSVFLFPPKPKDTLMISRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSPGK

Anti-PDL1 nanobody
SEQ ID NO: 26
EVQLVESGGGLVQPGGSLRLSCAASGFTLDYYAIGWFRQAPGKEREWASSISSSDGSTYYADSVKGRFTISRDNAKN

TVFLQMNSLKPEDTAVYSCAASQAPITIATMMKPFYDYWGQGTQVTVSS

Anti-PDL1 nanobody
SEQ ID NO: 27
EVQLVESGGGLVQPGGSLRLSCAASGFTLDYYAKCWFRQAPGKEREWVSCISSSDGSTYYADSVKGRFTISRDNAKN

TVYLQMNSLKPEDTAVYFCAARHGGPLTVEYFFDYWGQGTQVTVSS

Anti-PDL1 nanobody
SEQ ID NO: 28
EVQLVESGGGLVQPGGSLRLSCAASGFTFDYYAIGWFRQAPGKAREGVSCISGGDNSTYYADSVKGRFTISRDNAKN

TVYLQMNSLKPEDTAVYYCATGGWKYCSGYDPEYIYWGQGTQVTVSS

Anti-PDL1 nanobody
SEQ ID NO: 29
EVQLVESGGGLVQAGGSLRLSCAASGSTFSQYDVGWYRQAPGKQRELVAFSSSGGRTIYPDSVKGRFTFSRDNTKNT

VYLQMTSLKPEDTAVYYCKIDWYLNSYWGQGTQVTVSS

Anti-PDL1 nanobody
SEQ ID NO: 30
EVQLVESGGGLVQAGGSLRLSCAASGVDASNSAMGWYRQAPGKQREWVARITGGGLIAYTDSVKGRFTISRDNAKST

VYLQMWSLEPEDTAVYYCNTINSRDGWGQGTQVTVSS

Anti-PDL1 nanobody
SEQ ID NO: 31
EVQLVESGGGLVQAGGSLTISCAASGITFSDSIVSWYRRARGKQREWVAGISNGGTTKYAESVLGRFTISRDNAKNM

VYLQMWGLNPEDTAVYLCKVRQYWGQGTQVTVSS

Human TAPBPR TMD
SEQ ID NO: 32
TALGVIFASSLFLLALMFLGL nucleotide sequence encoding hTAPBPR-CD8 cytoplasmic tail
SEQ ID NO: 33
atgggcacacaggagggctggtgcctgctgctctgcctggctctatctggagcagcagaaaccaagccccacccagc agaggggcagtggcgggcagtggacgtggtcctagactgtttcctggtgaaggacggtgcgcaccgtggagctctcg ccagcagtgaggacagggcaagggcctcccttgtgctgaagcaggtgccagtgctggacgatggctccctggaggac ttcaccgatttccaagggggcacactggcccaagatgacccacctattatctttgaggcctcagtggacctggtcca gattccccaggccgaggccttgctccatgctgactgcagtgggaaggaggtgacctgtgagatctcccgctactttc tccagatgacagagaccactgttaagacagcagcttggttcatggccaacgtgcaggtctctggaggggggacctagc atctccttggtgatgaagactcccagggtcgccaagaatgaggtgctctggcacccaacgctgaacttgccactgag cccccaggggactgtgcgaactgcagtggagttccaggtgatgacacagacccaatccctgagcttcctgctgggt cctcagcctccttggactgtggcttctccatggcaccgggcttggacctcatcagtgtggagtggcgactgcagcac aagggcaggggtcagttggtgtacagctggaccgcagggcaggggcaggctgtgcggaagggcgctaccctggagcc tgcacaactgggcatggccagggatgcctccctcaccctgcccggcctcactatacaggacgaggggacctacattt gccagatcaccacctctctgtaccgagctcagcagatcatccagctcaacatccaagcttcccctaaagtacgactg agcttggcaaacgaagctctgctgcccaccctcatctgcgacattgctggctataccctctggatgtggtggtgac gtggaccccgagaggagctgggtgggtcccagcccaagtctctggtgcctccttctccagcctcaggcaaagcgtgg caggcacctacagcatctcctcctctctcaccgcagaacctggctctgcaggtgccacttacacctgccaggtcaca cacatctctctggaggagcccttggggccagcacccaggttgtcccaccagagcggagaacagccttgggagtcat ctttgccagcagtctcttccttcttgcactgatgttcctggggcttcagagacgaagacgtgtttgcaaatgtcccc ggcctgtggtcaaatcgggagacaagcccagcctttcggcgagatacgtctaa TAPBPR-CD8 cytoplasmic tail

SEQ ID NO: 34

MGTQEGWCLLLCLALSGAAETKPHPAEGQWRAVDVVLDCFLVKDGAHRGALASSEDRARASLVLKQVPVLDDGSLED
FTDFQGGTLAQDDPPIIFEASVDLVQIPQAEALLHADCSGKEVTCEISRYFLQMTETTVKTAAWFMANVQVSGGGPS
ISLVMKTPRVAKNEVLWHPTLNLPLSPQGTVRTAVEFQVMTQTQSLSFLLGSSASLDCGFSMAPGLDLISVEWRLQH
KGRGQLVYSWTAGQGQAVRKGATLEPAQLGMARDASLTLPGLTIQDEGTYICQITTSLYRAQQIIQLNIQASPKVRL
SLANEALLPTLICDIAGYYPLDVVVTWTREELGGSPAQVSGASFSSLRQSVAGTYSISSSLTAEPGSAGATYTCQVT
HISLEEPLGASTQVVPPERRTALGVIFASSLFLLALMFLGLQRRRRVCKCPRPVVKSGDKPSLSARYV*

The invention claimed is:

1. An isolated peptide-exchange protein consisting of:
a fragment of TAP-binding protein-related (TAPBPR), said fragment consisting of the TAPBPR luminal domain, wherein the TAPBPR fragment consists of an amino acid sequence having at least 95% sequence identity over its full length to the full-length sequence of SEQ ID NO: 2 or SEQ ID NO: 22; and
a targeting domain comprising an antibody antigen-binding domain that specifically binds to the surface of target cells, wherein the targeting domain is a whole antibody or an antigen binding fragment thereof comprising a Fab fragment, an Fv fragment, a single domain antibody, a F(ab')2 fragment, an scFv, a bispecific single chain Fv dimer, or a diabody,
wherein the peptide exchange protein is capable of catalyzing peptide exchange on major histocompatibility complex (MHC) class I molecules at the surface of the target cells.

2. The isolated peptide-exchange protein according to claim 1, wherein the target cells are cancer cells, pathogen infected cells or antigen presenting cells.

3. An isolated peptide-exchange protein according to claim 1 wherein the TAPBPR fragment consists of SEQ ID NO: 2 or SEQ ID NO: 22.

4. An isolated peptide-exchange protein comprising the amino acid sequence of SEQ ID NO: 4, SEQ ID NO: 6, SEQ ID NO: 8, SEQ ID NO: 10, SEQ ID NO: 12, SEQ ID NO: 14, or SEQ ID NO: 16.

* * * * *